(12) United States Patent
Gurney et al.

(10) Patent No.: US 9,168,300 B2
(45) Date of Patent: Oct. 27, 2015

(54) MET-BINDING AGENTS AND USES THEREOF

(71) Applicant: OncoMed Pharmaceuticals, Inc., Redwood City, CA (US)

(72) Inventors: Austin L. Gurney, San Francisco, CA (US); Ming-Hong Xie, Foster City, CA (US); Christopher John Bond, San Mateo, CA (US)

(73) Assignee: OncoMed Pharmaceuticals, Inc., Redwood City, CA (US)

( * ) Notice: Subject to any disclaimer, the term of this patent is extended or adjusted under 35 U.S.C. 154(b) by 0 days.

(21) Appl. No.: 14/212,177

(22) Filed: Mar. 14, 2014

(65) Prior Publication Data

US 2014/0286951 A1    Sep. 25, 2014

Related U.S. Application Data

(60) Provisional application No. 61/783,552, filed on Mar. 14, 2013.

(51) Int. Cl.
*A61K 39/395*    (2006.01)
*C07K 14/71*    (2006.01)
*C07K 16/28*    (2006.01)
*A61K 39/00*    (2006.01)

(52) U.S. Cl.
CPC .......... *A61K 39/39558* (2013.01); *C07K 14/71* (2013.01); *C07K 16/2863* (2013.01); *A61K 2039/505* (2013.01); *C07K 2317/35* (2013.01); *C07K 2317/64* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,109,496 A | 8/1978 | Allemann et al. |
| 4,323,546 A | 4/1982 | Crockford et al. |
| 4,411,990 A | 10/1983 | Salmon et al. |
| 4,612,282 A | 9/1986 | Schlom et al. |
| 4,670,393 A | 6/1987 | Seeburg |
| 4,873,191 A | 10/1989 | Wagner et al. |
| 4,968,103 A | 11/1990 | McNab et al. |
| 4,981,785 A | 1/1991 | Nayak |
| 5,019,497 A | 5/1991 | Olsson |
| 5,034,506 A | 7/1991 | Summerton et al. |
| 5,061,620 A | 10/1991 | Tsukamoto et al. |
| 5,087,570 A | 2/1992 | Weissman et al. |
| 5,223,409 A | 6/1993 | Ladner et al. |
| 5,225,539 A | 7/1993 | Winter |
| 5,283,317 A | 2/1994 | Saifer et al. |
| 5,358,691 A | 10/1994 | Clark et al. |
| 5,489,677 A | 2/1996 | Sanghvi et al. |
| 5,534,617 A | 7/1996 | Cunningham et al. |
| 5,538,848 A | 7/1996 | Livak et al. |
| 5,539,082 A | 7/1996 | Nielsen et al. |
| 5,565,332 A | 10/1996 | Hoogenboom et al. |
| 5,589,376 A | 12/1996 | Anderson et al. |
| 5,599,677 A | 2/1997 | Dowell et al. |
| 5,602,240 A | 2/1997 | De Mesmaeker et al. |
| 5,614,396 A | 3/1997 | Bradley et al. |
| 5,631,169 A | 5/1997 | Lakowicz et al. |
| 5,639,606 A | 6/1997 | Willey |
| 5,643,741 A | 7/1997 | Tsukamoto et al. |
| 5,643,765 A | 7/1997 | Willey |
| 5,646,036 A | 7/1997 | Schwall et al. |
| 5,648,464 A | 7/1997 | Artavanis-Tsakonas et al. |
| 5,650,317 A | 7/1997 | Chang et al. |
| 5,654,183 A | 8/1997 | Anderson et al. |
| 5,672,499 A | 9/1997 | Anderson et al. |
| 5,674,739 A | 10/1997 | Shyjan |
| 5,686,292 A | 11/1997 | Schwall et al. |
| 5,688,666 A | 11/1997 | Bass et al. |
| 5,693,482 A | 12/1997 | Anderson et al. |
| 5,705,188 A | 1/1998 | Junichi et al. |
| 5,707,624 A | 1/1998 | Nickoloff et al. |
| 5,714,331 A | 2/1998 | Buchardt et al. |
| 5,719,262 A | 2/1998 | Buchardt et al. |
| 5,739,277 A | 4/1998 | Presta et al. |
| 5,750,376 A | 5/1998 | Weiss et al. |
| 5,753,229 A | 5/1998 | Mordoh et al. |
| 5,753,506 A | 5/1998 | Johe |
| 5,780,300 A | 7/1998 | Artavanis-Tsakonas et al. |

(Continued)

FOREIGN PATENT DOCUMENTS

| | | |
|---|---|---|
| CN | 1176659 A | 3/1998 |
| CN | 1511850 A | 7/2004 |

(Continued)

OTHER PUBLICATIONS

Barbas, III, C., et al., "In vitro evolution of a neutralizing human antibody to human immunodeficiency virus type 1 to enhance affinity and broaden strain cross-reactivity," *Proc. Nat. Acad. Sci. USA* 91:3809-3813, National Academy of Sciences, United States (1994).
Bloom, J., et al., "Intrachain disulfide bond in the core hinge region of human IgG4," *Protein Science* 6:407-415, Cambridge University Press, United States (1997).
Boerner, P., et al., "Production of Antigen-Specific Human Monoclonal Antibodies From In Vitro-Primed Human Splenocytes," *J. Immunol.* 147:86-95, The American Association of Immunologists, United States (1991).
Brennan, M., et al., "Preparation of Bispecific Antibodies by Chemical Recombination of Monoclonal Immunoglobin $G_1$ Fragments," *Science* 229: 81-83, National Academy of Sciences, United States (1985).
Carter, P., et al., "Humanization of an anti-p185$^{HER2}$ antibody for human cancer therapy," *Proc. Natl. Acad. Sci. USA* 89:4285-4289, Academy of Sciences, United States (1992).

(Continued)

*Primary Examiner* — Sheela J Huff
(74) *Attorney, Agent, or Firm* — Sterne, Kessler, Goldstein & Fox P.L.L.C.

(57) ABSTRACT

The present invention relates to binding agents that specifically bind human MET, binding agents that specifically bind one or more components of the WNT pathway, bispecific agents that bind both human MET and one or more components of the WNT pathway, and methods of using the agents for treating diseases such as cancer.

21 Claims, 8 Drawing Sheets

(56) References Cited

U.S. PATENT DOCUMENTS

Figure 1A:
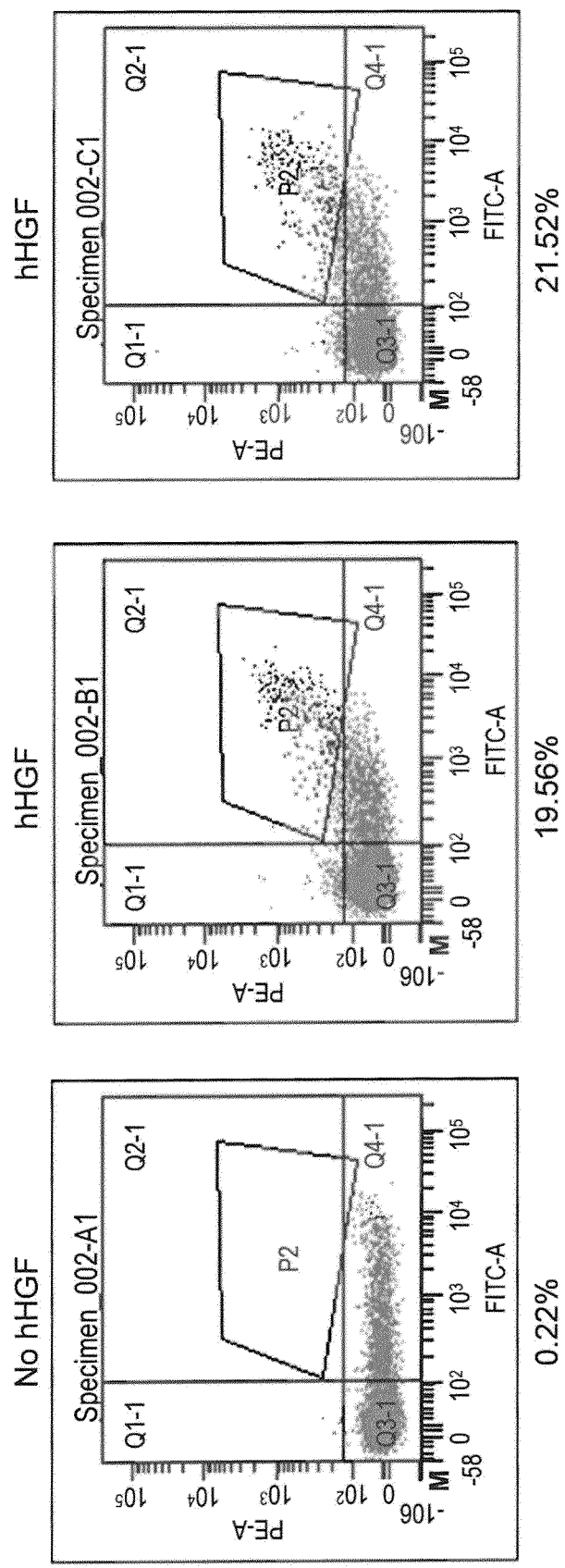
Figure 1B:
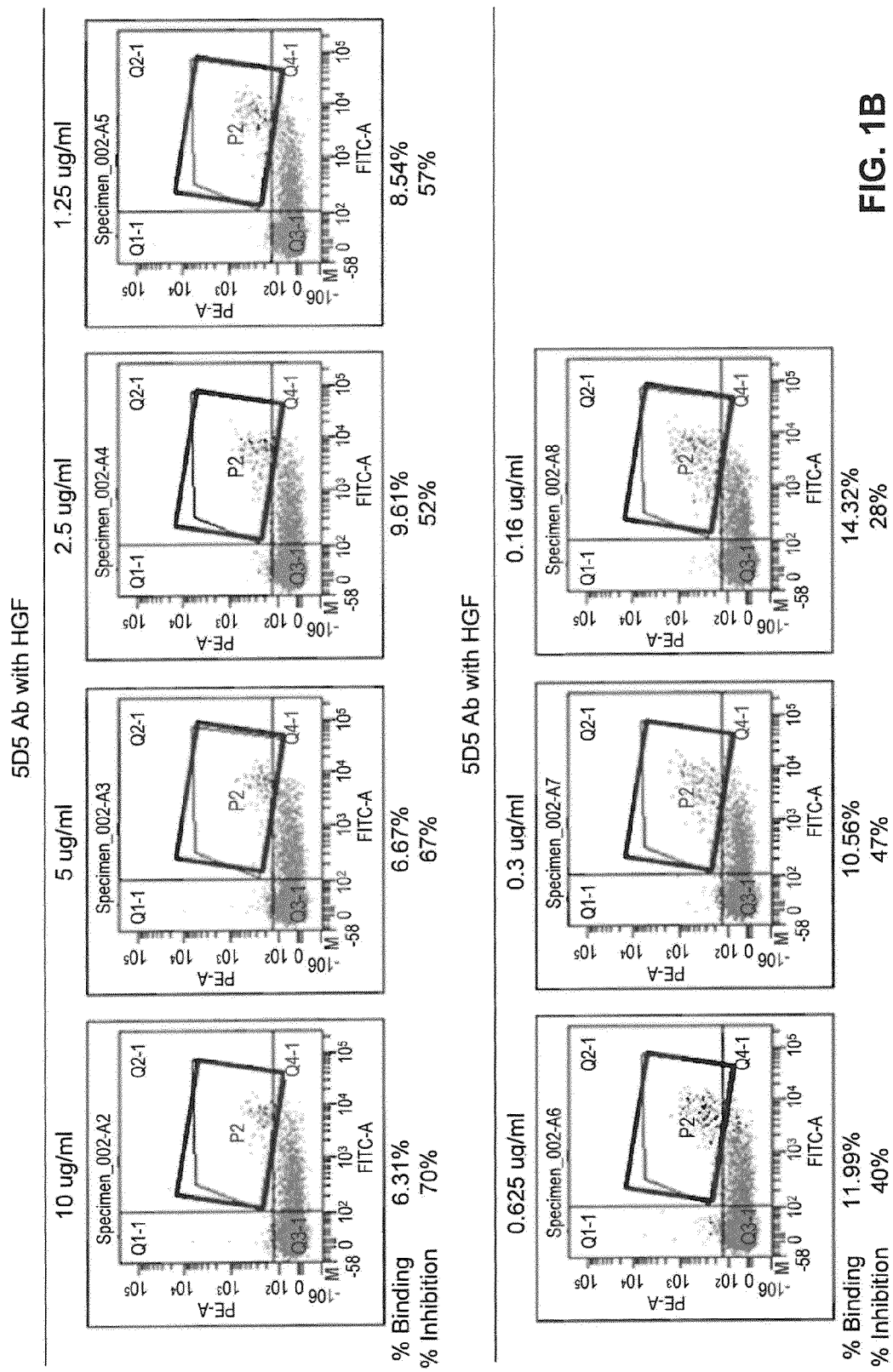
Figure 1C:
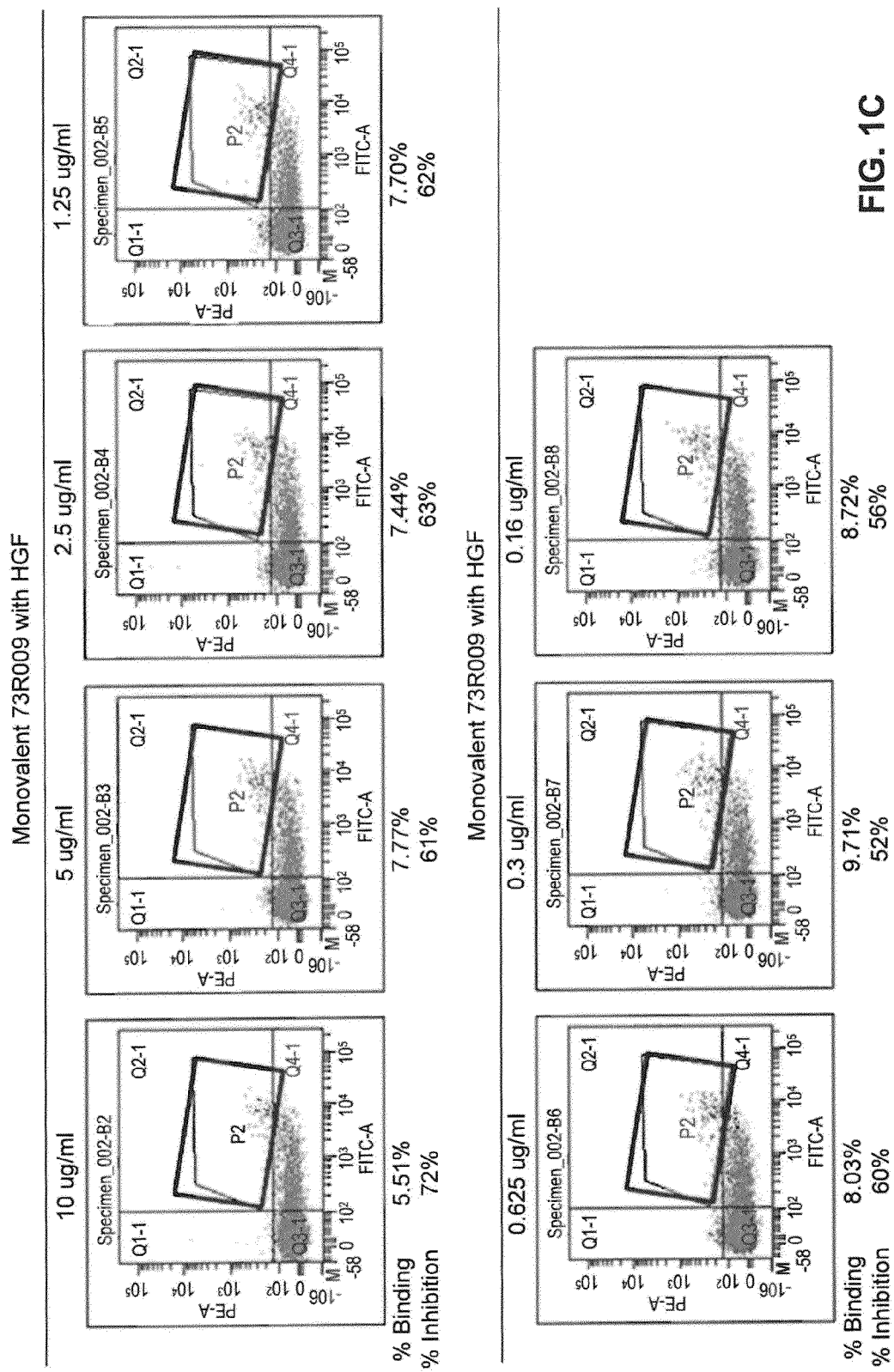
Figure 1D:
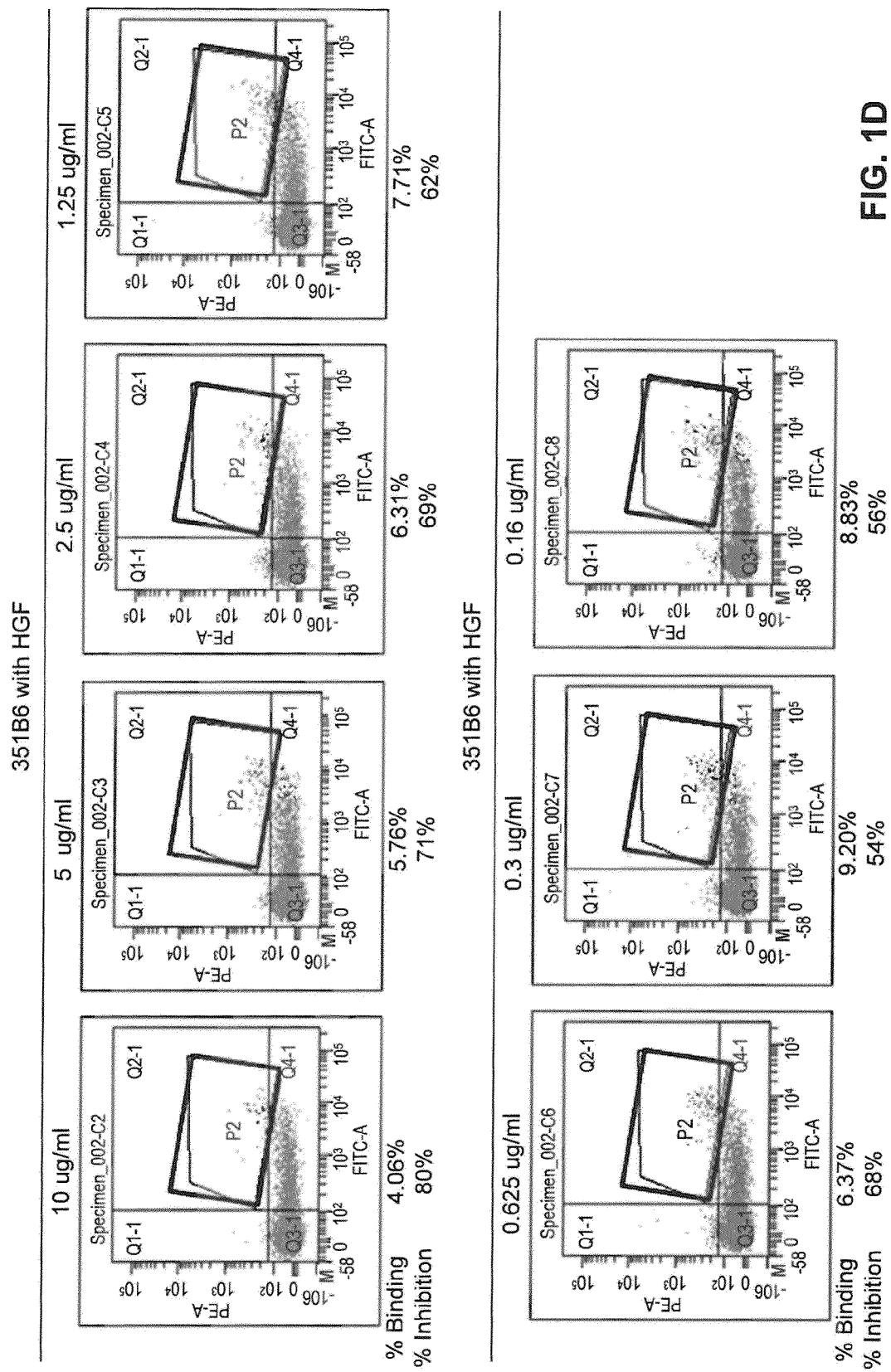

| | | |
|---|---|---|
| 5,786,158 A | 7/1998 | Artavanis-Tsakonas et al. |
| 5,789,195 A | 8/1998 | Artavanis-Tsakonas et al. |
| 5,814,511 A | 9/1998 | Chang et al. |
| 5,821,108 A | 10/1998 | Akashi et al. |
| 5,824,489 A | 10/1998 | Anderson et al. |
| 5,824,544 A | 10/1998 | Armentano et al. |
| 5,830,730 A | 11/1998 | German et al. |
| 5,834,598 A | 11/1998 | Lowman et al. |
| 5,849,535 A | 12/1998 | Cunningham et al. |
| 5,849,553 A | 12/1998 | Anderson et al. |
| 5,849,869 A | 12/1998 | Artavanis-Tsakonas et al. |
| 5,854,026 A | 12/1998 | Cunningham et al. |
| 5,856,441 A | 1/1999 | Artavanis-Tsakonas et al. |
| 5,859,535 A | 1/1999 | Liu |
| 5,861,832 A | 1/1999 | Nagaraj |
| 5,869,282 A | 2/1999 | Ish-Horowicz et al. |
| 5,872,154 A | 2/1999 | Wilson et al. |
| 5,876,978 A | 3/1999 | Willey et al. |
| 5,885,530 A | 3/1999 | Babson et al. |
| 5,885,808 A | 3/1999 | Spooner et al. |
| 5,914,108 A | 6/1999 | Tsukamoto et al. |
| 5,935,792 A | 8/1999 | Rubin et al. |
| 5,942,225 A | 8/1999 | Bruder et al. |
| 5,981,225 A | 11/1999 | Kochanek et al. |
| 5,986,170 A | 11/1999 | Subjeck |
| 5,994,106 A | 11/1999 | Kovesdi et al. |
| 5,994,128 A | 11/1999 | Fallaux et al. |
| 5,994,132 A | 11/1999 | Chamberlain et al. |
| 5,994,617 A | 11/1999 | Dick et al. |
| 6,001,557 A | 12/1999 | Wilson et al. |
| 6,004,528 A | 12/1999 | Bergstein |
| 6,004,924 A | 12/1999 | Ish-Horowicz et al. |
| 6,019,978 A | 2/2000 | Ertl et al. |
| 6,022,711 A | 2/2000 | Cunningham et al. |
| 6,033,908 A | 3/2000 | Bout et al. |
| 6,054,297 A | 4/2000 | Carter et al. |
| 6,080,912 A | 6/2000 | Bremel et al. |
| 6,083,904 A | 7/2000 | Artavanis-Tsakonas |
| 6,090,922 A | 7/2000 | Artavanis-Tsakonas et al. |
| 6,099,841 A | 8/2000 | Hillan et al. |
| 6,117,985 A | 9/2000 | Thomas et al. |
| 6,121,045 A | 9/2000 | McCarthy et al. |
| 6,127,526 A | 10/2000 | Blank |
| 6,135,653 A | 10/2000 | Aichi |
| 6,136,952 A | 10/2000 | Li et al. |
| 6,143,523 A | 11/2000 | Cunningham et al. |
| 6,149,902 A | 11/2000 | Artavanis-Tsakonas et al. |
| 6,156,305 A | 12/2000 | Brauker et al. |
| 6,159,750 A | 12/2000 | Edmonds |
| 6,180,370 B1 | 1/2001 | Queen et al. |
| 6,190,876 B1 | 2/2001 | Rubin et al. |
| 6,197,523 B1 | 3/2001 | Rimm et al. |
| 6,198,107 B1 | 3/2001 | Seville |
| 6,207,147 B1 | 3/2001 | Hiserodt et al. |
| 6,207,152 B1 | 3/2001 | Schwall et al. |
| 6,214,344 B1 | 4/2001 | Schwall et al. |
| 6,218,166 B1 | 4/2001 | Ravindranath et al. |
| 6,252,050 B1 | 6/2001 | Ashkenazi et al. |
| 6,262,025 B1 | 7/2001 | Ish-Horowicz et al. |
| 6,353,150 B1 | 3/2002 | Dick et al. |
| 6,379,925 B1 | 4/2002 | Kitajewski et al. |
| 6,380,362 B1 | 4/2002 | Watson et al. |
| 6,429,186 B1 | 8/2002 | Fuh et al. |
| 6,433,138 B1 | 8/2002 | Zimrin et al. |
| 6,433,155 B1 | 8/2002 | Umansky et al. |
| 6,448,229 B2 | 9/2002 | Teall et al. |
| 6,468,529 B1 | 10/2002 | Schwall et al. |
| 6,506,559 B1 | 1/2003 | Fire et al. |
| 6,537,775 B1 | 3/2003 | Tournier-Lasserve et al. |
| 6,583,115 B1 | 6/2003 | Kopchick et al. |
| 6,632,620 B1 | 10/2003 | Makarovskiy |
| 6,660,843 B1 | 12/2003 | Feige et al. |
| 6,664,098 B1 | 12/2003 | Sakano |
| 6,683,091 B2 | 1/2004 | Asberom et al. |
| 6,689,744 B2 | 2/2004 | Gao et al. |
| 6,703,221 B1 | 3/2004 | Chan et al. |
| 6,703,489 B1 | 3/2004 | Ish-Horowicz et al. |
| 6,713,206 B2 | 3/2004 | Markoski et al. |
| 6,716,974 B1 | 4/2004 | Maciag et al. |
| 6,756,511 B2 | 6/2004 | Castro Pineiro et al. |
| 6,833,441 B2 | 12/2004 | Wang et al. |
| 6,894,522 B2 | 5/2005 | Averill et al. |
| 6,984,522 B2 | 1/2006 | Clarke et al. |
| 6,995,677 B2 | 2/2006 | Aronstam et al. |
| 7,091,321 B2 | 8/2006 | Gillies et al. |
| 7,091,323 B2 | 8/2006 | Pan et al. |
| 7,115,360 B2 | 10/2006 | Clarke et al. |
| 7,115,653 B2 | 10/2006 | Baxter et al. |
| 7,118,853 B2 | 10/2006 | Botstein et al. |
| 7,138,370 B2 | 11/2006 | Oliner et al. |
| 7,211,404 B2 | 5/2007 | Lagasse et al. |
| 7,238,786 B2 | 7/2007 | Gold et al. |
| 7,361,336 B1 | 4/2008 | Bergstein |
| 7,381,408 B2 | 6/2008 | Mezo et al. |
| 7,404,956 B2 | 7/2008 | Peters et al. |
| 7,413,873 B2 | 8/2008 | Waterman et al. |
| 7,425,328 B2 | 9/2008 | Wang |
| 7,442,778 B2 | 10/2008 | Gegg et al. |
| 7,476,724 B2 | 1/2009 | Dennis et al. |
| 7,507,406 B2 | 3/2009 | Gillies et al. |
| 7,608,453 B2 | 10/2009 | Cattaneo et al. |
| 7,615,529 B2 | 11/2009 | Kong-Beltran et al. |
| 7,628,986 B2 | 12/2009 | Weber et al. |
| 7,635,530 B2 | 12/2009 | Kenis et al. |
| 7,659,116 B2 | 2/2010 | Buehring et al. |
| 7,662,931 B2 | 2/2010 | Gegg et al. |
| 7,682,607 B2 | 3/2010 | Rhee et al. |
| 7,713,526 B2 | 5/2010 | Rhee et al. |
| 7,723,477 B2 | 5/2010 | Gurney et al. |
| 7,803,370 B2 | 9/2010 | Nakamura et al. |
| 7,803,783 B2 | 9/2010 | Lee et al. |
| 7,803,913 B2 | 9/2010 | Dimitrov et al. |
| 7,867,705 B2 | 1/2011 | Wands et al. |
| 7,879,322 B2 | 2/2011 | Kneissel et al. |
| 7,892,770 B2 | 2/2011 | Cao et al. |
| 7,947,277 B2 | 5/2011 | Ernst et al. |
| 7,982,013 B2 | 7/2011 | Gurney et al. |
| 8,017,559 B2 | 9/2011 | Etzerodt et al. |
| 8,133,867 B2 | 3/2012 | Otsuka et al. |
| 8,158,761 B2 | 4/2012 | Wands et al. |
| 8,309,315 B2 | 11/2012 | Cao et al. |
| 8,410,061 B2 | 4/2013 | Williams et al. |
| 8,431,532 B2 | 4/2013 | Brennan et al. |
| 8,507,442 B2 | 8/2013 | Gurney et al. |
| 8,536,118 B2 | 9/2013 | Kong-Beltran et al. |
| 8,551,789 B2 | 10/2013 | Gurney |
| 8,562,985 B2 | 10/2013 | Michaud et al. |
| 8,637,027 B2 | 1/2014 | Hultberg et al. |
| 8,703,135 B2 | 4/2014 | Beste et al. |
| 8,765,917 B2 | 7/2014 | Deckert et al. |
| 8,809,287 B2 | 8/2014 | Bafico et al. |
| 2002/0119565 A1 | 8/2002 | Clarke et al. |
| 2002/0137129 A1 | 9/2002 | Barnes et al. |
| 2002/0151487 A1 | 10/2002 | Nickoloff et al. |
| 2002/0169300 A1 | 11/2002 | Waterman et al. |
| 2002/0187502 A1 | 12/2002 | Waterman et al. |
| 2003/0032184 A1 | 2/2003 | Lagasse et al. |
| 2003/0044409 A1 | 3/2003 | Carson et al. |
| 2003/0064384 A1 | 4/2003 | Hung et al. |
| 2003/0086934 A1 | 5/2003 | Botstein et al. |
| 2003/0114387 A1 | 6/2003 | Castro et al. |
| 2003/0119029 A1 | 6/2003 | Glick et al. |
| 2003/0135044 A1 | 7/2003 | Asberom et al. |
| 2003/0139457 A1 | 7/2003 | Baxter et al. |
| 2003/0162709 A1 | 8/2003 | Rossi et al. |
| 2003/0165500 A1 | 9/2003 | Rhee et al. |
| 2003/0166543 A1 | 9/2003 | Williams et al. |
| 2003/0175877 A1 | 9/2003 | Baker et al. |
| 2003/0180784 A1 | 9/2003 | McCarthy et al. |
| 2003/0185829 A1 | 10/2003 | Koller et al. |
| 2003/0229023 A1 | 12/2003 | Oliner et al. |
| 2004/0023244 A1 | 2/2004 | Griffin et al. |
| 2004/0037815 A1 | 2/2004 | Clarke et al. |
| 2004/0038876 A1 | 2/2004 | Pepinsky et al. |

(56) References Cited

U.S. PATENT DOCUMENTS

| | | |
|---|---|---|
| 2004/0048249 A1 | 3/2004 | Tang et al. |
| 2004/0058217 A1 | 3/2004 | Ohlsen et al. |
| 2004/0058443 A1 | 3/2004 | Artavanis-Tsakonas et al. |
| 2004/0105862 A1 | 6/2004 | Pan et al. |
| 2004/0127474 A1 | 7/2004 | Dudek et al. |
| 2004/0171559 A1 | 9/2004 | Weissman et al. |
| 2004/0203003 A1 | 10/2004 | Rhee et al. |
| 2004/0214186 A1 | 10/2004 | Engelberg et al. |
| 2004/0219579 A1 | 11/2004 | Aziz et al. |
| 2004/0247593 A1 | 12/2004 | He et al. |
| 2005/0123900 A1 | 6/2005 | Dimitrov et al. |
| 2005/0130199 A1 | 6/2005 | Carson et al. |
| 2005/0272063 A1 | 12/2005 | Nakamura et al. |
| 2005/0288864 A1 | 12/2005 | Cattaneo et al. |
| 2006/0019256 A1 | 1/2006 | Clarke et al. |
| 2006/0019320 A1 | 1/2006 | Civenni et al. |
| 2006/0040883 A1 | 2/2006 | You et al. |
| 2006/0210867 A1 | 9/2006 | Kenis et al. |
| 2007/0072238 A1 | 3/2007 | Bhat |
| 2007/0116701 A1 | 5/2007 | Gurney et al. |
| 2007/0117751 A1 | 5/2007 | Gurney et al. |
| 2007/0237770 A1 | 10/2007 | Lai et al. |
| 2007/0238658 A1 | 10/2007 | Levin et al. |
| 2008/0038272 A1 | 2/2008 | Buehring et al. |
| 2008/0044423 A1 | 2/2008 | Cochrane et al. |
| 2008/0063635 A1 | 3/2008 | Takahashi et al. |
| 2008/0075714 A1 | 3/2008 | Lee et al. |
| 2008/0118432 A1 | 5/2008 | Bergstein et al. |
| 2008/0194457 A1 | 8/2008 | Wands et al. |
| 2008/0299136 A1 | 12/2008 | Ernst et al. |
| 2009/0023905 A1 | 1/2009 | Askew et al. |
| 2009/0042906 A1 | 2/2009 | Huang et al. |
| 2009/0074777 A1 | 3/2009 | Wands et al. |
| 2009/0130113 A1 | 5/2009 | Kneissel et al. |
| 2009/0163407 A1 | 6/2009 | Bafico et al. |
| 2009/0186010 A1 | 7/2009 | Li et al. |
| 2009/0234104 A1 | 9/2009 | Gegg et al. |
| 2009/0263400 A1 | 10/2009 | Urdea et al. |
| 2009/0304695 A1 | 12/2009 | He et al. |
| 2010/0015133 A1 | 1/2010 | Igawa et al. |
| 2010/0055099 A1 | 3/2010 | Filvaroff et al. |
| 2010/0062441 A1 | 3/2010 | Salgia |
| 2010/0104574 A1 | 4/2010 | Gurney et al. |
| 2010/0169025 A1 | 7/2010 | Arthur et al. |
| 2011/0020326 A1 | 1/2011 | Kreidberg et al. |
| 2011/0020368 A1 | 1/2011 | Hynes |
| 2011/0092452 A1 | 4/2011 | Simeone et al. |
| 2011/0104166 A1 | 5/2011 | Stankovic et al. |
| 2011/0123532 A1 | 5/2011 | Gurney et al. |
| 2011/0200596 A1 | 8/2011 | Huang et al. |
| 2011/0224243 A1 | 9/2011 | Rethore |
| 2011/0237514 A1 | 9/2011 | Kakitani et al. |
| 2011/0262436 A1 | 10/2011 | Bender et al. |
| 2011/0287003 A1 | 11/2011 | Patel et al. |
| 2011/0318341 A1 | 12/2011 | Gurney et al. |
| 2012/0003222 A1 | 1/2012 | Brennan et al. |
| 2012/0027778 A1 | 2/2012 | Gurney |
| 2012/0064090 A1 | 3/2012 | Yano et al. |
| 2012/0171210 A1 | 7/2012 | Kong-Beltran et al. |
| 2012/0237524 A1 | 9/2012 | Boccaccio et al. |
| 2012/0321628 A1 | 12/2012 | Schwall et al. |
| 2013/0029357 A1 | 1/2013 | Ise et al. |
| 2013/0089557 A1 | 4/2013 | Cheong et al. |
| 2013/0102494 A1 | 4/2013 | Jouhanneaud |
| 2013/0143813 A1 | 6/2013 | Kirchhofer et al. |
| 2013/0171063 A1 | 7/2013 | Johns et al. |
| 2013/0209365 A1 | 8/2013 | Wu et al. |
| 2013/0216548 A1 | 8/2013 | Neijssen et al. |
| 2013/0252326 A1 | 9/2013 | Gurney et al. |
| 2013/0295105 A1 | 11/2013 | Gurney et al. |
| 2013/0295106 A1 | 11/2013 | Gurney et al. |
| 2014/0105917 A1 | 4/2014 | Gurney |
| 2014/0134159 A1 | 5/2014 | Stagg et al. |
| 2014/0193431 A1 | 7/2014 | Park et al. |

FOREIGN PATENT DOCUMENTS

| | | |
|---|---|---|
| CN | 1558916 A | 12/2004 |
| EP | 1 004 669 A1 | 5/1998 |
| EP | 0 861 894 A1 | 9/1998 |
| EP | 0 662 827 A1 | 4/2002 |
| EP | 0662827 B1 | 4/2002 |
| EP | 1 576 119 | 9/2005 |
| EP | 1 805 221 B1 | 4/2006 |
| EP | 1 805 519 | 7/2007 |
| EP | 1805221 A1 | 7/2007 |
| EP | 0 805 203 B1 | 8/2007 |
| EP | 2 019 116 A1 | 1/2009 |
| EP | 1 641 828 B1 | 4/2010 |
| EP | 1 718 677 B1 | 4/2012 |
| WO | WO 90/08832 A1 | 8/1990 |
| WO | WO 92/19734 A1 | 11/1992 |
| WO | WO 94/07474 A1 | 4/1994 |
| WO | WO 94/10300 A1 | 5/1994 |
| WO | WO 97/01571 A1 | 1/1997 |
| WO | WO 97/30731 A2 | 8/1997 |
| WO | WO 97/37004 A1 | 10/1997 |
| WO | WO 98/05775 A1 | 2/1998 |
| WO | WO 98/45434 A1 | 10/1998 |
| WO | WO 98/51799 A1 | 11/1998 |
| WO | WO 98/57621 A1 | 12/1998 |
| WO | WO 99/02685 A1 | 1/1999 |
| WO | WO 00/06726 A2 | 2/2000 |
| WO | WO 00/09675 A1 | 2/2000 |
| WO | WO 00/12738 A1 | 3/2000 |
| WO | WO 00/52143 A2 | 9/2000 |
| WO | WO-0102568 A2 | 1/2001 |
| WO | WO 01/07483 A1 | 2/2001 |
| WO | WO 01/26643 A1 | 4/2001 |
| WO | WO 01/98354 A2 | 12/2001 |
| WO | WO 01/98537 A2 | 12/2001 |
| WO | WO 02/00576 A1 | 1/2002 |
| WO | WO 02/12447 A2 | 2/2002 |
| WO | WO 02/18544 A2 | 3/2002 |
| WO | WO 02/078704 A1 | 10/2002 |
| WO | WO-02078703 A1 | 10/2002 |
| WO | WO 02/088081 A2 | 11/2002 |
| WO | WO 02/092635 A2 | 11/2002 |
| WO | WO 02/102978 A2 | 12/2002 |
| WO | WO 03/000893 A2 | 1/2003 |
| WO | WO 03/004045 A2 | 1/2003 |
| WO | WO 03/042246 A2 | 5/2003 |
| WO | WO 03/047316 A1 | 6/2003 |
| WO | WO 03/050502 A2 | 6/2003 |
| WO | WO 03/062273 A2 | 7/2003 |
| WO | WO 03/088964 A1 | 10/2003 |
| WO | WO 2004/001004 A2 | 12/2003 |
| WO | WO 2004/020668 A2 | 3/2004 |
| WO | WO 2004/032838 A2 | 4/2004 |
| WO | WO 2004/042028 A2 | 5/2004 |
| WO | WO 2004/053069 A2 | 6/2004 |
| WO | WO 2004/065545 A2 | 8/2004 |
| WO | WO 2004/073657 A2 | 9/2004 |
| WO | WO 2004/101739 A2 | 11/2004 |
| WO | WO 2005/001025 A2 | 1/2005 |
| WO | WO 2005/004912 A1 | 1/2005 |
| WO | WO 2005/005601 A2 | 1/2005 |
| WO | WO 2006/034328 A2 | 3/2006 |
| WO | WO 2006/036173 A2 | 4/2006 |
| WO | WO 2006/036175 A2 | 4/2006 |
| WO | WO 2006/040163 A1 | 4/2006 |
| WO | WO 2006/055635 A2 | 5/2006 |
| WO | WO 2006/056340 A2 | 6/2006 |
| WO | WO 2006/130076 A1 | 12/2006 |
| WO | WO 2007/053577 A2 | 5/2007 |
| WO | WO 2007/096149 A1 | 8/2007 |
| WO | WO 2007/133250 A2 | 11/2007 |
| WO | WO 2007/134876 A2 | 11/2007 |
| WO | WO 2007/142711 A2 | 12/2007 |
| WO | WO 2007/148417 A1 | 12/2007 |
| WO | WO 2008/031009 A2 | 3/2008 |
| WO | WO-2008039071 A2 | 4/2008 |
| WO | WO 2008/057459 A2 | 5/2008 |
| WO | WO 2008/061020 A2 | 5/2008 |

(56) References Cited

FOREIGN PATENT DOCUMENTS

| WO | WO 2009/042971 A2 | 4/2009 |
|---|---|---|
| WO | WO 2009/118300 A1 | 10/2009 |
| WO | WO 2010/031979 A1 | 3/2010 |
| WO | WO 2010/037041 A2 | 4/2010 |
| WO | WO 2010/038756 A1 | 8/2010 |
| WO | WO-2011088123 A2 | 7/2011 |
| WO | WO-2011101409 A1 | 8/2011 |
| WO | WO-2011112678 A1 | 9/2011 |
| WO | WO 2011/123785 A3 | 10/2011 |
| WO | WO 2012/003189 A1 | 1/2012 |
| WO | WO 2012/006027 A1 | 1/2012 |
| WO | WO-2012058393 A2 | 5/2012 |
| WO | WO 2012/165925 A2 | 12/2012 |
| WO | WO-2014121196 A1 | 8/2014 |

OTHER PUBLICATIONS

Chothia, C., et al., "Domain Association in Immunoglobin Molecules: The Packing of Variable Domains," *J. Mol. Biol.* 186:651-663, Academic Press, United Kingdom (1985).

Chothia, C. and Lesk, A., "Canonical Structures for the Hypervariable Regions of Immunoglobulins," *J. Mol. Biol.* 196:901-917, Academic Press Limited, United States (1987).

Chowdhury, P. and Pastan, I., "Improving antibody affinity by mimicking somatic hypermutation in vitro," *Nat.Biotechnol.* 17:568-572, Nature Publishing Co., United States (1999).

Cole, S., et al., "The EBV-Hybridoma Technique and Its Application to Human Lung Cancer," pp. 77-96, Monoclonal Antibodies and Cancer Therapy, Proceedings of the Roche-UCLA Symposium, Park City, Utah, USA, Alan R. Liss, Inc., Jan. 26-Feb. 2, 1985.

Deisenhofer, J., "Crystallagraphic Refinement and Atomic Models of a Human Fc Fragment and Its Complex with Fragment B of Protein A from *Staphyloccocus aureus* at 2.9 and 2.8-A Resolution," *Biochemistry* 20:2361-2370, The American Chemical Society, United States (1981).

Dreher, M., et al., "Colony assays for antibody fragments expressed in bacteria," *J. Immunol. Methods* 139:197-205, Elsevier Science Publishers B.V., Netherlands (1991).

Eppstein, D., et al., "Biological activity of liposome-encapsulated murine interferon γ is mediated by a cell membrane receptor," *Proc. Natl. Acad. Sci. USA* 82:3688-3692, National Academy of Sciences, United States (1985).

Gruber, M., et al., "Efficient Tumor Cell Lysis Mediated by a Bispecific Single Chain Antibody Expressed in *Escherichia coli,*" *J. Immunol.* 152:5368-5374, The American Association of Immunologists, United States (1994).

Harlow, E. and Lane, D., eds., " Chapter 14: Immunoassays," in *Antibodies: A Laboratory Manual*, pp. 553-612, Cold Spring Harbor Laboratory, Cold Spring Harbor, NY (1988).

Harris, W., "Therapeutic Monoclonals," *Biochem. Soc. Transactions* 23:1035-1038, Industrial Biochemistry and Biotechnology Group Colloquium, University of Manchester, United Kingdom (1995).

Hawkins, R., et al., "Selection of Phage Antibodies by Binding Affinity Mimicking Affinity Maturation," *J. Mol. Biol.* 226:889-896, Academic Press Limited, United States (1992).

Hermentin, P. and Seiler, F., "Investigations with Monoclonal Antibody Drug (Anthracycline) Conjugates," *Behring Inst. Mitt.* 82:197-215, Die Medizinische Verlagsgesellschaft mbH, W. Germany (1988).

Hoogenboom, H. and Winter, G., "By-passing Immunisation: Human Antibodies from Synthetic Repertoires of Germline $V_H$ Gene Segments Rearranged in Vitro," *J. Mol. Biol.* 227:381-388, Academic Press Limited, United States (1992).

Humphreys, D., et al., "Formation of dimeric Fabs in *Escherichia coli*: effect of hinge size and isotype, presence of interchain disulphide bond, Fab' expression levels, tail piece sequences and growth conditions," *J. Immunol. Methods* 209:193-202, Elsevier Science B.V., Netherlands (1997).

Hurle, M. and Gross, M., "Protein engineering techniques for antibody humanization," *Curr. Opin. Biotech.* 5:428-433, Current Biology Ltd., United States (1994).

Hwang, K., et al., "Hepatic uptake and degradation of unilamellar sphingomyelin/cholesterol liposomes: A kinetic study," *Proc. Natl. Acad. Sci. USA* 77:4030-4034, National Academy of Sciences, United States (1980).

Jackson, J., et al., "In Vitro Antibody Maturation," *J. Immunol.* 154:3310-3319, The American Association of Immunologists, United States (1995).

Jones, P., et al., "Replacing the complementarity-determining regions in a human antibody with those from a mouse," *Nature* 321:522-525, Nature Publishing Group, United Kingdom (1986).

Kingsman, A., et al., "Replication in *Saccharomyces cerevisiae* of Plasmid pBR313 Carrying DNA From the Yeast trp 1 Region," *Gene* 7:141-152, Elsevier/North-Holland Biomedical Press, Netherlands (1979).

Kostelny, S., et al., "Formation of a Bispecific Antibody by the Use of Leucine Zippers," *J. Immunol.* 148:1547-1553, The American Association of Immunologists, United States (1992).

Lee, H., et al., "Generation of characterization of a novel single-gene-encoded single-chain immunoglobulin molecular with antigen binding activity and effector functions," *Mol. Immunol.* 36:61-71, Elsevier Science Ltd., Netherlands (1999).

Maeda, H., et al., "Construction of reshaped human antibodies with HIV-neutralizing activity," *Hum. Antibod. Hybridomas* 2:124-134, Butterworth-Heinemann, United Kingdom (1991).

Marks, J., et al., "By-passing Immunization: Human Antibodies from V-gene Libraries Displayed on Phage," *J. Mol. Biol.* 222:581-597, Academic Press Limited, United Kingdom (1991).

Marks, J., et al., "By-Passing Immunization: Building High Affinity Human Antibodies by Chain Shuffling," *Bio/Technology* 10:779-783, Nature Publishing Co., United States (1992).

Milstein, C., et al., "Hybrid hybridomas and their use in immunohistochemistry," *Nature* 305:537-539, Nature Publishing Group, United Kingdom (1983).

Morimoto, K., et al., "Single-step purification of F(ab')$_2$ fragments of mouse monoclonal antibodies (immunoglobulins G1) by hydrophobic interaction high performance liquid chromatography using TSKgel Phenyl-5PW," *J. Biochem. Biophys. Methods* 24:107 -117 , Elsevier Science Publishers B.V., Netherlands (1993).

Morrison, S., et al., "Chimeric human antibody molecules: Mouse antigen-binding domains with human constant region domains," *Proc. Natl. Acad. Sci. USA* 81:6851-6855, National Academy of Sciences, United States (1984).

Nohaile, M., et al., "Altering dimerization specificity by changes in surface electrostatics," *Proc. Natl. Acad. Sci. U.S.A.* 98:3109-3114, United States National Academy of Sciences, United States (2001).

Novotny, J. and Haber, E., "Structural invariants of antigen binding: Comparison of immunoglobin $V_L$-$V_H$ and $V_L$-$V_L$ domain dimers," *Proc. Natl. Acad. Sci. USA* 82:4592-4596, National Academy of Sciences, United States (1985).

Presta, L., et al., "Humanization of an Antibody Directed Against IgE," *J. Immunol.* 151:2623-2632, The American Association of Immunologists, United States (1993).

Riechmann, L., et al., "Reshaping human antibodies for therapy," *Nature* 332:323-329, Nature Publishing Group, United States (1988).

Sal-Man, N., et al., "Arginine mutations within a transmembrane domain of Tar, an *Escherichia coli* aspartate receptor, can drive homodimer dissociation and heterodimer association in vivo," *Biochem. J.* 385:29-36, Portland Press, United Kingdom (2005).

Schier, R., et al., "Identification of function and structural amino-acid residues by parsimonious mutagenesis," *Gene* 169:147-155, Elsevier Science B.V., Netherlands (1996).

Shalaby, M., et al., "Development of Humanized Bispecitic Antibodies Reactive with Cytotoxic Lymphocytes and Tumor Cells Overexpressing the HER2 Protooncogene," *J. Exp. Med.* 175:217-225, The Rockefeller University Press, United States (1992).

Sheets, M., et al., "Efficient construction of a large nonimmune phage antibody library: The production of high-affinity human single-chain antibodies to protein antigens," *Proc. Natl. Acad. Sci. USA* 95:6157-6162, National Academy of Sciences, United States (1998).

(56) References Cited

OTHER PUBLICATIONS

Sims, M., et al., "A Humanized CD18 Antibody Can Block Function without Cell Destruction," *J. Immunol.*151:2296-2308, The American Association of Immunologists, United States (1993).
Stinchcomb, D., et al., "Isolation and characterisation of a yeast chromosomal replicator," *Nature* 282:39-43, Nature Publishing Group, United Kingdom (1979).
Suresh, M., et al., "Bispecitic Monoclonal Antibodies from Hybrid Hybridomas," *Methods Enzymol.* 121:210-228, Academic Press Inc., United Kingdom (1986).
Traunecker, A., et al., "Bispecific single chain molecules (Janusins) target cytotoxic lymphocytes on HIV infected cells," *EMBO J.*10:3655-3659, Oxford University Press, United Kingdom (1991).
Tutt, A., et al., "Trispecific F(ab')$_3$ Derivatives That Use Cooperative Signaling Via the TCR/CD3 Complex and CD2 to Activate and Redirect Resting Cytotoxic T Cells," *J. Immunol.* 147:60-69, The American Association of Immunologists, United States (1991).
Urlaub, G. and Chasin, L., "Isolation of Chinese hamster cell mutants deficient in dihydrofolate reductase activity," *Proc. Natl. Acad. Sci. USA* 77: 4216-4220, National Academy of Sciences, United States (1980).
Vaswani, S. and Hamilton, R., "Humanized antibodies as potential therapeutic drugs," *Ann. Allergy Asthma Immunol.* 81:105-119, American College of Allergy, Asthma, & Immunology, United States (1998).
Vaughan, T., et al., "Human Antibodies with Sub-nanomolar Affinities Isolated from a Large Non-immunized Phage Display Library," *Nat. Biotech.*14:309-314, Nature Publishing Co., United States (1996).
Verhoeyen, M., et al., "Reshaping Human Antibodies: Grafting an Antilysozyme Activity," *Science* 239:1534-1536, American Association for the Advancement of Science, United States (1988).
Ward, E., "Antibody Engineering Using *Escherichia coli* as Host," *Adv. Pharmacol.* 24:1-20, Academic Press, Inc., United Kingdom (1993).
Wu, C., et al., "Simultaneous targeting of multiple disease mediators by a dual-variable-domain immunoglobulin," *Nat. Biotech.* 25:1290-1297, Nature Publishing Co., United States (2007).
Yelton, D., et al., "Affinity Maturation of the BR96 Anti-Carcinoma Antibody by Codon-Based Mutagenesis," *J. Immunol.* 155:1994-2004, The American Association of Immunologists, United States (1995).
International Search Report with the Written Opinion of the International Searching Authority for International application No. PCT/US10/32625, mailed on Dec. 17, 2010, United States Patent and Trademark Office, United States, 12 pages.
English language Abstract of Chinese Patent No. CN 1511850 A, European Patent Office, espacenet database—Worldwide, (2004) (Listed as document FP10 on the accompanying form PTO/SB/08A).
Yan, Wei, "The Design and Engineering of Fc Heterodimers for the Production of Bispecific Antibodies," Symposium Abstract, Eleventh Annual Phage Display of Antibodies and Peptides, Approaches for $2^{nd}$ Generation Biologics, Apr. 6-Apr. 7, 2009, Boston, Massachusetts.
Yan, Wei, "Design and Engineering of Fc Heterodimers for the Production of Bispecific Antibodies," Symposium Abstract, Keystone Symposia on Molecular and Cellular Biology, Accelerating Life Science Discovery, Mar. 27-Apr. 1, 2009, Whistler, British Columbia.
Yan, Wei, "The Design and Engineering of Fc Heterodimers for the Production of Bispecific Antibodies and Other Heterodimer Fusion Proteins," Symposium Abstract, $20^{th}$ Annual International Conference, Antibody Engineering, Antibody Engineering and Immunotherapeutics for the $21^{st}$ Century, Dec. 6-10, 2009, San Diego, California.
Austin, T.W., et al., "A role for the Wnt gene family in hematopoiesis: expansion of multilineage progenitor cells," *Blood* 89:3624-3635 (1997).
Ayyanan, A., et al., "Increased Wnt signaling triggers oncogenic conversion of human breast epithelial cells by a Notch-dependent mechanism," *PNAS* 103:3799-3804, The National Academy of Sciences, Washington, DC, U.S.A. (2006).
Bafico, A., et al., "An autocrine mechanism for constitutive Wnt pathway activation in human cancer cells," *Cancer Cell* 6:497-506 (2004).
Bafico, A., et al., "Interaction of Frizzled Related Protein (FRP) with Wnt Ligands and the Frizzled Receptor Suggests Alternative Mechanisms for FRP Inhibition of Wnt Signaling," *J. Biol. Chem.* 274:16180-16187, The American Society for Biochemistry and Molecular Biology, Inc., Bethesda, MD, U.S.A. (1999).
Barker, N. and Clevers, H., "Mining the Wnt pathway for cancer therapeutics," *Nature Reviews/Drug Discovery* 5:997-1014, Nature Publishing Group, New York, NY, U.S.A. (2006).
Battula, V.L., et al., "Prospective isolation and characterization of mesenchymal stem cells from human placenta using a frizzled-9-specific monoclonal antibody," *Differentiation* 76:326-336, International Society of Differentiation, Higgannum, CT, U.S.A. (2008).
Benhamouche, S., et al.,"Apc Tumor Suppressor Gene Is the "Zonation-Keeper" of Mouse Liver," *Developmental Cell* 10:759-770, Elsevier Inc., Amsterdam, The Netherlands (2006).
Bhanot, P., et al., "A new member of the frizzled family from *Drosophila* functions as a Wingless receptor," *Nature* 382:225-230, Nature Publishing Group, New York, NY, U.S.A. (1996).
Bienz, M., "β-Catenin: A Pivot between Cell Adhesion and Wnt Signalling," *Current Biology* 15:R64-R67, Cell Press, St. Louis, MO, U.S.A. (2004).
Booy, E.P., et al., "Monoclonal and bispecific antibodies as novel therapeutics," *Arch. Immunol. Ther. Exp.* 54:85-101, Birkhauser publications, Basel, Switzerland (2006).
Brabletz, T., et al., "Variable β-catenin expression in colorectal cancers indicates tumor progression driven by the tumor environment," *PNAS* 98(18):10356-10361 (2001).
Brennan, K.R. and Brown, A.M.C., "Wnt Proteins in Mammary Development and Cancer," *J. Mammary Gland Biol. Neoplasia* 9(2):119-131, Kluwer Academic/Plenum Publishers (2004).
Burgess, W.H., et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," *J. Cell Bio.* 111:2129-2138, The Rockefeller University Press, New York, NY, U.S.A. (1990).
Cadigan, K.M. and Nusse, R., "Wnt signaling: a common theme in animal development," *Genes & Development* 11:3286-3305, Cold Spring Harbor Laboratory Press (1997).
Caldwell, G.M., et al., "The Wnt Antagonist sFRP1 in Colorectal Tumorigenesis," *Cancer Res* 64:883-888, American Association for Cancer Research, Philadelphia, PA, U.S.A. (2004).
Chan, E. F., et al., "A common human skin tumour is caused by activating mutations in β-catenin, "*Nature Genetics* 21(4): 410-413 (1999).
Chen, Y., et al., "Selection and Analysis of an Optimized Anti-VEGF Antibody: Crystal Structure of an Affinity-matured Fab in Complex with Antigen," *Journal of Molecular Biology* 293(4): 865-881, Academic Press, England (1999).
Clevers, H., "Axin and hepatocellular carcinomas," *Nature Genetics* 24:206-208, Nature Publishing Group, New York, NY, U.S.A. (2000).
Daniel, C., et al., "Mapping of Linear Antigenic Sites on the S Glycoprotein of a Neurotropic Murine Coronavirus with Synthetic Peptides: A Combination of Nine Prediction Algorithms Fails to Identify Relevant Episodes and Peptide Immunogenicity Is Drastically Influenced by the Nature of the Protein Carrier," *Virology* 202(2):540-549, Elsevier Inc., The Netherlands (1994).
Dann, C.E., et al., "Insights into Wnt binding and signalling from the structures of two Frizzled cysteine-rich domains," *Nature* 412:86-90, Nature Publishing Group, New York, NY, U.S.A. (2001).
Datta, D.V., "Viral Hepatitis," *Jr. Asso. Phys. Ind.* 25(5):325-330, Association of Physicians of India, Mumbai, India (1977).
Davidson, G., et al., "Casein kinase 1γ couples Wnt receptor activation to cytoplasmic signal transduction," *Nature* 438:867-872, Nature Publishing Group, U.S.A. (2005).
De Lau, W. and Clevers, H., "LEF1 turns over a new leaf," *Nature Genetics* 28:3-4, Nature Publishing Group, NY, U.S.A. (2001).

(56) References Cited

OTHER PUBLICATIONS

De Pascalis, R., et al., "Grafting of Abbreviated Complementarity-Determining Regions Containing Specificity-Determining Residues Essential for Ligand Contact to Engineer a Less Immunogenic Humanized Monoclonal Antibody," *Journal of Immunology* 169:3076-3084 (2002).
Dealmeida, V.I., et al., "The Soluble Wnt Receptor Frizzled8CRD-hFc Inhibits the Growth of Teratocarcinomas In vivo," *Cancer Res* 67(1 I):5371-5379, American Association for Cancer Research (Jun. 1, 2007).
Dorvillius, Mylene et al., "Targeting of Human Brest Cancer by a Bispecific Antibody Directed against Two Tumour-Associated Antigens: ErbB-2 and Carcinoembryonic Antigen," *Tumor Biology*, Nov. 2002, pp. 337-347, vol. 23, No. 6, S. Karger Medical and Scientific Publishers, Basel.
Fillmore et al., "Human breast cancer cell lines contain stem-like cells that self-renew, give rise to phenotypically diverse progeny and survive chemotherapy" Breast Cancer Res, 2008, voi10R25: 1-13.
Finch, P.W., et al., "Purification and molecular cloning of a secreted, Frizzled-related antagonist of Wnt action," *PNAS* 94:6770-6775, the National Academy of Sciences, Washington, DC, U.S.A. (1997).
Fogel, M. et al., "L1 expression as a predictor of progression and survival in patients with uterine and ovarian carcinomas," *The Lancet* 362:869-875, Elsevier Inc., Amsterdam, The Netherlands (2003).
Fukukawa, C., et al., "Radioimmunothcrapy of human synovial sarcoma using a monoclonal antibody against FZD10," *Cancer Sci.* 99:432-440, Wiley-Blackwell, Hoboken, NJ, U.S.A. (2008).
Gavert, N. et al., "L1, a novel target of β-catenin signaling, transforms cells and is expressed at the invasive front of colon cancers," *Journal of Cell Biology* 168(4):633-642, The Rockefeller University Press (Feb. 14, 2005).
Gazit, A., et al., "Human frizzles 1 interacts with transforming Wnts to transducer a TCF dependent transcriptional response," *Ocogene* 18:5959-5966, Stockton Press (1999).
Golan, T., et al., "The Human Frizzled 6 (HFz6) Acts as a Negative Regulator of the Canonical Wnt. β-Catenin Signaling Cascade," *J. Biol. Chem.* 279:14879-14888, American Society for Biochemistry and Molecular Biology (Apr. 2004).
Greenspan, N.S. and Di Cera, E., "Defining epitopes: It's not as easy as it seems," *Nature Biotechnology* 17:936-937, Nature Publishing Group, United States (1999).
Gregorieff, A., et al., "Expression Pattern of Wnt Signaling Components in the Adult Intestine," *Gastroenterology* 129:626-638, American Gastroenterological Association (Aug. 2005).
Greiner, D.L., et al., "SCID Mouse Models of Human Stem Cell Engraftment," *Stem Cells* 16:166-177, AlphaMed Press (1998).
Guo, H.H., et al., "Protein tolerance to random amino acid change," *PNAS*, 101:9205-9210, The National Academy of Sciences, Washington, DC, U.S.A. (2004).
Harada, N., et al., "Intestinal polyposis in mice with a dominant stable mutation of the β-catenin gene," *EMBO J.* 18:5931-5942, Oxford University Press, New York, NY U.S.A. (1999).
He, X. and Axelrod, J.D., "A WNTer wonderland in Snowbird," *Development* 133:2597-2603, The Company of Biologists, Cambridge, UK, U.S.A. (2006).
Hering, H., et al., "Direct interaction of Frizzled-1, -2, -4 and -7 with PDZ domains of PSD-95" *FEBS Letters* 521:185-189, Elsevier, Netherlands (2002).
Hicks, et al., "Fringe differentially modulates Jagged1 and Delta1 signalling through Notch1 and Notch2" *Nat Cell Bioi.* (8):515-520 (2000).
Hill, R. P., "Identifying cancer stem cells in solid tumors: case not proven" *Cancer Research* 66:1891-1896, American Association for Cancer Research (2006).
Holcombe, R.F., et al., "Expression of Wnt ligands and Frizzled receptors in colonic mucosa and in colon carcinoma," *J. Clin. Pathol: Mol. Pathol.* 55:220-226, BMJ Publishing Group (2002).
Holmes, E.H., "PSMA specific antibodies and their diagnostic and therapeutic use," *Exp. Opin. Invest. Drugs* 10:511-519, Informa Pharmaceutical Science, London, UK (2001).
Hsieh, A.C. and Moasser, M.M., "Targeting HER proteins in cancer therapy and the role of the non-target HER3," *British J. Cancer* 97:453-457, Cancer Research UK, England (2007).
Hsieh, J-C., et al., "Biochemical characterization of Wnt-Frizzled interactions using a soluble, biologically active vertebrate Wnt protein," *Proc. Natl. Acad. Sci. U.S.A.* 96(7):3546-3551, National Academy of Sciences, United States (Mar. 1999).
Huang, H-C. and Klein, P.S., "The Frizzled family: receptors for multiple signal transduction pathways," *Genome Biol.* 5:234.1-234.7, BioMed Central Ltd. (Jun. 2004).
Ilyas, M., Wnt signalling and the mechanistic basis of tumour development, *J Pathology* 205:130-144 (2005).
International Search Report for International Patent Application No. PCT/US11/30950, ISA/US, Alexandria, Virginia 22313-1450, mailed on Oct. 18, 2011.
Ishikawa, T., et al., "Mouse Wnt receptor gene Fzd5 is essential for yolk sac and placental angiogenesis," *Development* 128:25-33, Company of Biologists Limited (2001).
Ishitani, T., et al., "The TAK1-NLK Mitogen-Activated Protein Kinase Cascade Functions in the Wnt-5a/Ca$^{2+}$ Pathway to Antagonize Wnt/β-Catenin Signaling," *Mol. Cell. Biol.* 23:131-139, American Society for Microbiology (2003).
Jamieson, C.H.M., et al., "Granulocyte-Macrophage Progenitors as Candidate Leukemic Stem Cells in Blast-Crisis CML," *N. Engl. J. Med.* 351:657-667, Massachusetts Medical Society, Waltham, MA, U.S.A. (2004).
Janssens, N., et al., "Alteration of Frizzled Expression in Renal Cell Carcinoma," *Tumor Biol.* 25:161-171, Karger (Jul. 2004).
Jiang, B., et al., "A Novel Peptide Isolated from a Phage Display Peptide Library with Trastuzumab Can Mimic Antigen Epitope of HER-2," *J. Biol. Chem.* 280:4656-4662, The American Society for Biochemistry and Molecular Biology, Inc., Bethesda, MD, U.S.A. (2005).
Joesting, M.S., et al., "Identification of SFRP1 as a Candidate Mediator of Stromal-to-Epithelial Signaling in Prostate Cancer," *Cancer Res.* 65:10423-10430, the American Association for Cancer Research, Philadelphia, PA, U.S.A. (2005).
Johnson, M.L., et al., "LRP5 and Wnt Signaling: A Union Made for Bone," *J. Bone Mineral Res.* 19:1749-1757, American Society for Bone and Mineral Research, Washington DC, U.S.A. (2004).
Jones, D.T., "Critically assessing the state-of-the-art in protein structure prediction," *Pharmacogenomics Journal* 1:126-134, Nature Publishing Group, New York, NY, U.S.A. (2001).
Jonsson, M., et al., "Involvement of adenomatous polyposis coli (APC)/β-catenin signalling in human breast cancer," *Eur. J. Cancer* 36: 242-248 (2000).
Katoh, M. and Katoh, M., "WNT Signaling Pathway and Stem Cell Signaling Network," *Clin. Cancer Res.* 13:4042-4045, the American Association for Cancer Research, Philadelphia, PA, U.S.A. (2007).
Katoh, M. and Katoh, M., "STAT3-induced WNT5A signaling loop in embryonic stem cells, adult normal tissues, chronic persistent inflammation, rheumatoid arthritis and cancer (Review)," *Int. J. Mol. Med.* 19:273-278, D.A. Spandidos (Feb. 2007).
Katoh, M., "Molecular Cloning and Characterization of MFRP, a Novel Gene Encoding a Membrane-Type Frizzled-Related Protein," *Biochemical and Biophysical Research Communications* 282:116-123, Academic Press, United States (2001).
Kawakami, Y., et al., "Involvement of Frizzled-10 in Wnt-7a signaling during chick limb development," *Dev. Growth Differ.* 42:561-569, Blackwell Publishing (2000).
Kawano, Y. and Kypta, R., "Secreted antagonists of the Wnt signaling pathway," *Journal of Cell Science* 116:2627-2634, The Company of Biologists Ltd, London, UK (2003).
Kirikoshi et al., "Expression of WNT10A in human cancer," *Int J Oncology* 19:997-1001 (2001).
Kirikoshi, H., et al., "Expression profiles of 10 members of Frizzled gene family in human gastric cancer," *Int. J. Oncol.* 19:767-771, D.A. Spandidos (2001).
Kirikoshi, H., et al., "Molecular Cloning and Characterization of Human Frizzled-4 on Chromosome 11q14-q21," *Biochem. Biophys. Res. Commun.* 264:955-961, Academic Press (1999).
Kirikoshi, H., et al., "Up-regulation of Frizzled-7 (FZD7) in human gastric cancer," *Int. J. Oncol.* 19:111-115, D.A. Spandidos (2001).

(56) References Cited

OTHER PUBLICATIONS

Kirikoshi, H., et al., "Molecular Cloning and Genomic Structure of Human Frizzled-3 at Chromosome 8p21," *Biochemical and Biophysical Research Communications* 271:8-14, Academic Press, United States (2000).

Kirkin, A.F., et al., "Melanoma-associated antigens recognized by cytotoxic T lymphocytes," *APMIS* 106:665-679, AMPIS, Denmark (1998).

Klaus, A. and Birchmeier, W., "Wnt signaling and its impact on development and cancer," *Nature Reviews/Cancer* 8:387-398, Nature Publishing Group, New York, NY, U.S.A. (May 2008).

Kobielak, A. and Fuchs, E., "α-Catenin: at the junction of intercelullar adhesion and actin dynamics," *Nat Rev Mol Cell Bioi.* 5:614-25 (2004).

Koike, J., et al., "Molecular Cloning of Frizzled-10, a Novel Member of the Frizzled Gene Family," *Biochem. Biophys. Res. Commun.* 262:39-43, Academic Press (1999).

Korinek, V., et al., "Two Members of the Tcf Family Implicated in Wnt/β-catenin Signaling during Embryogenesis in the Mouse," *Mol Cell Bioi* 18: 1248-1256, American Society for Microbiology, United States (1998).

Kuhnert, F., et al., "Essential requirement for Wnt signaling in proliferation of adult small intestine and colon revealed by adenoviral expression of Dickkopf-1," *PNAS* 101:266-271, the National Academy of Sciences, Washington, DC, U.S.A. (2004).

Lazar, E., et al., "Transforming Growth Factor α: Mutation of Aspartic Acid 47 and Leucine 48 Results in Different Biological Activities," *Mol. Cell. Bio.* 8:1247-1252, American Society for Microbiology, Washington, DC, U.S.A. (1988).

Lee, H.X., et al., "Embryonic Dorsal-Ventral Signaling: Secreted Frizzled-related Proteins as inhibitors of Tolloid Proteinases," *Cell* 124:147-159, Elsevier inc., Amsterdam, The Netherlands (Jan. 13, 2006).

Li, Y., et al., "LRP6 expression promotes cancer cell proliferation and tumorigenesis by altering β-catenin subcellular distribution," *Oncogene* 23:9129-9135, Nature Publishing Group, New York, NY, U.S.A. (2004).

Li, Y., et al., "The Gene for Autosomal Dominant Familial Exudative Vitreoretinopathy (Criswick-Schepens) on the Long Arm of Chromosome 11," *Am. J. Opthamol.* 113:712-713, Elsevier Inc., Amsterdam, The Netherlands (1992).

Lin, S.Y., et al., "β-catenin, a novel prognostic marker for breast cancer: its roles in cyclin D1 expression and cancer progression," *Proc. Natl. Acad. Sci. USA* 97:4262-4266, (2000).

Liu, S., et al., "Interaction of hedgehog and notch pathways, and Bmi-1 in the regulation of human breast stem cell self-renewal" *Proc Amer Associ Cancer Res* 46: Apr. 2005.

Li, Y., et al., "Evidence that transgenes encoding components of the Wnt signaling pathway preferentially induce mammary cancers from progenitor cells." Proc. Nail. Acad. Sci. USA, 100:15853-8 (2003).

Lo, P.-K., et al., "Epigenetic Suppression of Secreted Frizzled Related Protein 1 (SFRP1) Expression in Human Breast Cancer," *Cancer Biology & Therapy* 5:e1-e6, Landes Bioscience, Austin, TX, U.S.A. (2006).

Lodygin, D., et al., "Functional Epigenomics Identifies Genes Frequently Silenced in Prostate Cancer," *Cancer Res.* 65:4218-4227, the American Association for Cancer Research, Philadelphia, PA, U.S.A. (2005).

Lu, D., et al., "Repression of β-catenin function in malignant cells by nonsteroidal antiinflammatory drugs," *PNAS* 102:18567-18571, the National Academy of Sciences, Washington, DC, U.S.A. (Dec. 20, 2005).

Lyons, J.P., et al., "Wnt-4 activates the canonical β-catenin-mediated Wnt pathway and binds Frizzled-6 CRD: functional implications of Wnt/β-catenin activity in kidney epithelial cells," *Exp. Cell Res.* 298:369-387, Elsevier Inc., United States (2004).

Mazieres, J., et al., "Wnt signaling in lung cancer," *Cancer Letters* 222:1-10, Elsevier Inc., Amsterdam, The Netherlands (2005).

Miller, J.R., et al., "Mechanism and function of signal transduction by the Wnt/β-catenin and Wnt/$Ca^2$ pathways," *Oncogene* 18:7860-7872, Nature Publishing Group (1999).

Milovanovic, T., et al., "Expression of Wnt genes and frizzled 1 and 2 receptors in normal breast epithelium and infiltrating breast carcinoma," *Int. J. Oncol.* 25:1337-1342, D.A. Spandidos (Nov. 2004).

Moon, R.T., "Wnt/β-Catenin Pathway," *Sci. STKE* 271:1-3, American Association for the Advancement of Science, Washington, DC, 20005 (2005).

Morrell, N.T., et al., "Liposomal Packaging Generates Wnt protein with In Vivo Biological Activity," *PLoS ONE* 3:1-9, e2930, Public Library of Science (PLoS), San Francisco, CA, U.S.A. (Aug. 2008).

Murdoch, B., et al., "Wnt-5A augments repopulating capacity and primitive hemaropoietic development of human blood stem cells in vivo," *PNAS* 100:3422-3427, the National Academy of Sciences, Washington, DC, U.S.A. (2003).

Nagayama, S., et al., "Therapeutic potential of antibodies against FZD10, a cell-surface protein, for synovial sarcomas," *Oncogene* 24:6201-6212, Nature Publishing Group (Sep. 2005).

Nunnally, A.P. and Parr, B.A., "Analysis of Fz10 expression in mouse embryos," *Dev. Genes Evol.* 214:144-148, Springer-Verlag (Mar. 2004).

Nusse, R., et al., A new nomenclature for int-1 and related genes: the Wnt gene family. Cell 64, 231 (1991).

Nusse, R., "The Wnt gene family in tumorigenesis and in normal development," *Journal of Steroid Biochemistry & Molecular Biology* 43: 9-12 (1992).

Olson, D.J. and Gibo, D.M., "Antisense wnt-5a Mimics wnt-1-Mediated C57MG Mammary Epithelial Cell Transformation," *Exp. Cell Res.* 241:134-141, Elsevier Inc., Amsterdam, The Netherlands (1998).

Oshima, H., et al., Morphological and Molecular Processes of Polyp Formation in $Apc^{\Delta 716}$ Knockout Mice, *Cancer Res.* 57:1644-1649, The American Association for Cancer Research, Philadelphia, PA, U.S.A. (1997).

Patel, S., et al., "Glycogen synthase kinase-3 in insulin and Wnt signalling: a double-edged sword?" *Biochemical Society Transactions* 32:803-808, Portland Press Ltd., London, UK (2004).

Pinto, D. and Clevers, H., "Wnt control of stem cells and differentiation in the intestinal epithelium," *Experimental Cell Research* 306:357-363, Elsevier Inc., Amsterdam, The Netherlands (2005).

Polakis, P., "Wnt signaling and cancer," *Genes & Development* 14:1837-1851, Cold Spring Harbor Laboratory Press, Woodbury NY, U.S.A. (2000).

Radtke, F. and Clevers, H., "Self-Renewal and Cancer of the Gut: Two Sides of a Coin," *Science* 307:1904-1909, The Company of Biologists Ltd, London, UK (2005).

Reya, T., et al., "Wnt Signaling Regulates B Lymphocyte Proliferation through a LEF-1 Dependent Mechanism," *Immunity* 13:15-24 (2000).

Reya T., et al., "Stem cells, cancer, and cancer stem cells." *Nature* 414(6859):105-111, Nature Publishing Group, England (2001).

Reya, T. and Clevers, H., "Wnt signalling in stem cells and cancer," *Nature* 434:843-850, Nature Publishing Group, New York, NY, U.S. A. (2005).

Reya, T., et al., "A role for Wnt signalling in self-renewal of haematopoietic stem cells," *Nature* 423:409-414, Nature Publishing Group, New York, NY, U.S.A. (2003).

Rhee, C.S., et al., "Wnt and frizzled receptors as potential targets for immunotherapy in head and neck squamous cell carcinomas," *Oncogene* 21:6598-6605, Nature Publishing Group (2002).

Sagara, N., et al., "Molecular Cloning, Differential Expression, and Chromosomal Localization of Human Frizzled-1, Frizzled-2, and Frizzled-7," *Biochem. Biophys. Res. Commun.* 252:117-122, Academic Press (1998).

Saitoh, T., et al., "Frequent up-regulation of WNT5A mRNA in primary gastric cancer" *Inti J Mol Med* 9:515-519 (2002).

Saitoh, T., et al., "Molecular cloning and characterization of human Frizzled-8 gene on chromosome 10p11.2," *Int. J. Oncol.* 18:991-996, D.A. Spandidos (2001).

Saitoh, T., et al., "Up-regulation of Frizzled-10 (FZD10) by β-estradiol in MCF-7 cells and by retinoic acid in NT2 cells," *Int. J. Oncol.* 20:117-120, D.A. Spandidos (2002).

(56) References Cited

OTHER PUBLICATIONS

Sala, C.F., et al., "Identification, Gene Structure, and Expression of Human Frizzled-3 (FZD3)," *Biochem. Biophys. Res. Commun.* 273:27-34, Academic Press (2000).

Saldanha, J., et al., "Identification of a Frizzled-like cysteine rich domain in the extracellular region of developmental receptor tyrosine kinases," *Protein Science* 7:1632-1635, The Protein Society, United States (1998).

Saneyoshi, T., et al., "The Wnt/calcium pathway activates NF-AT and promotes ventral cell fate in *Xenopus* embryos," *Nature* 417:295-299, Nature Publishing Group, New York, NY, U.S.A. (2002).

Sagara, N., et al., "FZD4S, a Splicing Variant of Frizzled-4, Encodes a SolubleType Positive Regulator of the WNT Signaling Pathway," *Biochem. Biophys. Res. Commun.* 282:750-756, Academic Press, United States (2001).

Schweizer, L. and Varmus, H., "Wnt/Wingless signaling through β-catenin requires the function of both LRP/Arrow and frizzled classes of receptors," *BMC Cell Biology* 4, 11 pages, BioMed Central Ltd., London, UK (2003).

Semënov, M., et al., "SOST Is a Ligand for LRP5/LRP6 and a Wnt Signaling Inhibitor," *The Journal of Biological Chemistry* 280:26770-26775, American Society for Biochemistry and Molecular Biology, Bethesda, MD, U.S.A. (2005).

Sen, M., et al., "Blockade of Wnt-5A/Frizzled 5 Signaling Inhibits Rheumatoid Synoviocyte Activation," *Arthritis Rheum.* 44:772-781, Wiley-Liss, Inc. (2001).

Shalaby, M.R., et al., "Bispecific HER X CD3 Antibodies Enhance T-Cell Cytotoxicity in Vitro and Localize to HER2-Overexpressing Xenografts in Nude Mice," *Clin. Imm. and Immunopath*, 74:185-192, Elsevier Inc., Amsterdam, The Netherlands 1995.

Skolnick, J. and Fetrow, J.S., "From genes to protein structure and function: novel applications of computational approaches in the genomic era," *Trends in Biotechnology* 18:34-39, Elsevier Inc., Amsterdam, The Netherlands (2000).

Sperger, J.M., et al., "Gene expression patterns in human embryonic stem cells and human pluripotent germ cell tumors," *PNAS* 23:13350-13355, The National Academy of Sciences of the USA, United States (2003).

Suresh, M.R., et al., "Advantages of bispecific hybridomas in one-step immunocytochemistry and immunoassays," *Neurobiology, Proceedings of the National Academy of Sciences of the United States of America*, Oct. 1986, pp. 7989-7993, vol. 83, USA.

Suzuki, H., et al., "A genomic screen for genes unregulated by demethylation and histone deacetylase inhibition in human colorectal cancer," *Nature Genetics* 31:141-149, Nature Publishing Group, New York, NY, U.S.A. (Jun. 2002).

Suzuki, H., et al., "Epigenetic inactivation of SFRP genes allows constitutive WNT signaling in colorectal cancer," *Nature Genetics* 36:417-422, Nature Publishing Group, New York, NY, U.S.A. (Apr. 2004).

Suzuki, H., et al., "Frequent epigenetic inactivation of Wnt antagonist genes in breast cancer," *British Journal of Cancer* 98:1147-1156, Nature Publishing Group, New York, NY, U.S.A. (2008).

Tanaka, S., et al., "A novel frizzled gene identified in human esophageal carcinoma mediates APC/β-catenin signals," *Proc. Natl. Acad. Sci. U.S.A.* 95:10164-10169, National Academy of Sciences (1998).

Terasaki, H., et al., "Frizzled-10, up-regulated in primary colorectal cancer, is a positive regulator of the WNT—β-catenin—TCF signaling pathway," *Int. J Mol. Med.* 9:107-112, D.A. Spandidos (2002).

Tokuhara, M., et al., "Molecular Cloning of Human Frizzled-6," *Biochem. Biophys. Res. Commun.* 243:622-627, Academic Press (1998).

Topol, L., et al., "Wnt-5a inhibits the canonical Wnt pathway by promoting GSK-3-independent β-catenin degradation," *J. Cell Biol.* 162:899-908, The Rockefeller University Press, New York, NY, U.S.A. (2003).

Tosatto, S.C.E. and Toppo, S., Large-Scale Prediction of Protein Structure and Function from Sequence, *Current Pharmaceutical Design* 12:2067-2086, Bentham Science Publishers, Oak Park, IL, U.S.A. (2006).

Townsend, A. and Trowsdale, J., "The transporters associates with antigen presentation" *Seminars in Cell Biology* 4:53-61, Academic Press Limited, United States (1993).

Toyofuku, T., et al., "Wnt/frizzled-2 Signaling Induces Aggregation and Adhesion among Cardiac Myocytes by Increased Cadherin-β-Catenin Complex," *J. Cell. Biol.* 150:225-241, Rockefeller University Press (2000).

Umbhauer, M., et al., "The C-terminal cytoplasmic Lys-thr-X-X-X-Trp motif in frizzled receptors mediates Wnt/β-catenin signalling," *The EMBO Journal* 19:4944-4954, Oxford University Press, New York, NY, U.S.A. (2000).

Unkeless, J.C., "Characterization of a Monoclonal Antibody Directed Against Mouse Macrophage and Lymphocyte Fc Receptors," *J. Exp. Med.* 150:580-596, The Rockefeller University Press, New York, NY, U.S.A. (Sep. 1979).

Unknown Author, "Purified Rat Anti-Mouse CD16/CD32 (Mouse BD Fc BlockTM)," Technical Data Sheet 553142 Rev. 16, 2 pages, BD Biosciences (date unknown), URL:http://www.bdbiosciences.com/external_files/pm/doc/tds/mouse/live/web_enabled/01241D_553142.pdf.

Uren, A., et al., "Secreted Frizzled-related Protein-1 Binds Directly to Wingless and Is a Biphasic Modulator of Wnt Signaling," *The Journal of Biological Chemistry* 275:4374-4382, American Society for Biochemistry and Molecular Biology, Bethesda, MD, U.S.A. (2000).

Uyttendaele, H., et al., "Notch4 and Wnt-1 Proteins Function to Regulate Branching Morphogeneses of Mammary Epithelial Cells in an Opposing Fashion" *Dev. Bioi.* 196:204-217, Elsevier Inc., The Netherlands (1998).

Van De Vijver, M., et al., "A gene-expression signature as a predictor of survival in breast cancer" *N Eng. J Med* 347:1999-2009 (2002).

Van De Wetering, M., et al., "The β-catenin/TCF-4 complex imposes a crypt progenitor phenotype on colorectal cancer cells," *Cell* 111: 241-259, Cell Press, United States (2002).

Van Den Berg, D.J., et al., "Role of Members of the Wnt Gene Family in Human Hematopoiesis," *Blood* 92:3189-3202, The American Society of Hematology, Washington, DC, U.S.A. (1998).

Van Es, J.H. and Clevers, H., "Notch and Wnt inhibitors as potential new drugs for intestinal neoplastic disease," *Trends Mol. Med.* 11:496-502, Elsevier Inc., The Netherlands (2005).

Van't Veer, L.J., et al., "Gene expression profiling predicts clinical outcome of breast cancer" *Nature* 415:530-6 (2002).

Veeman, M.T., et al., "A Second Canon: Functions and Mechanisms of β-Catenin-Independent Wnt Signaling," *Dev. Cell* 5:367-377, Elsevier Inc., Amsterdam, The Netherlands (2003).

Vincan, E., et al., "Frizzled-7 receptor ectodomain expression in a colon cancer cell line induces morphological change and attenuates tumor growth," *Differentiation* 73:142-153, Blackwell (Apr. 2005).

Voronkov, A., et al., "Molecular Model of the Wnt Protein Binding Site on the Surface of Dimeric CRD Domain of the hFzd8 Receptor," Doklady Biochemistry and Biophysics 419:75-78, Pleiades Publishing Ltd., Russia (2008).

Wang, Y., et al., "A Large Family of Putative Transmembrane Receptors Homologous to the Product of the *Drosophila* Tissue Polarity Gene frizzled," *J. Biol. Chem.* 271:4468-4476, American Society for Biochemistry and Molecular Biology (1996).

Wang, Y-K., et al., "Characterization and Expression Pattern of the frizzled Gene Fzd9, the Mouse Homolog of FZD9 which Is Deleted in Williams-Beuren Syndrome," *Genomics* 57:235-248, Academic Press (1999).

Wang, Z., et al., "Wnt7b Activates Canonical Signaling in Epithelial and Vascular Smooth Muscle Cells through Interactions with Fzd1, Fzd10, and LRP5," *Mol. Cell. Biol.* 25:5022-5030, American Society for Microbiology (2005).

Webb, T., "Work on Breast Cancer Stem Cells Raises Questions About Treatment Strategies," *Journal of the National Cancer Institute.* 95(11): 774-775, Jun. 4, 2003, printed online, pp. 1-5.

(56) References Cited

OTHER PUBLICATIONS

Weeraratna, A.T., et al., "Wnt5a signaling directly affects cell motility and invasion of metastatic melanoma," *Cancer Cell* 1:279-288, Cell Press (2002).
Willert, K. and Jones, K.A., "Wnt signaling: is the party in the nucleus?" *Genes & Development* 20:1394-1404, Cold Spring Harbor Laboratory Press, Cold Spring Harbor, NY, U.S.A. (2006).
Willert, K., et al., "Wnt proteins are lipid-modified and can act as stem cell growth factors," *Nature* 423:448-452, Nature Publishing Group, New York, NY, U.S.A. (2003).
Wnt-3a COPE, (Online 201 0), accessed on Oct. 1, 2010, accessed from http://www.copewithcytokines.de/cope.cgi?key=Wnt-3a.paras 2 and 5.
Wong, N.A.C.S. and Pignatelli, M., "β-catenin—A Linchpin in Colorectal Carcinogenesis?," *Am. J. Pathol.* 160:389-401, American Society for Investigative Pathology (2002).
Wong, S.C.C., et al., "Expression of frizzled-related protein and Wnt-signalling molecules in invasive human breast tumours," *J. Pathol.* 196:145-253 (2002).
Woodward, W.A., et al., "Wnt/β-caten in mediates radiation resistance of mouse mammary progenitor cells," *PNAS* 104:618-623, the National Academy of Sciences, Washington, DC, U.S.A. (2007).
Wu, C-H. and Nusse, R., "Ligand Receptor Interactions in the Wnt Signaling Pathway in *Drosophila*," *J. Biol. Chem.* 277:41762-41769, American Society for Biochemistry and Molecular Biology (2002).
Yamashita, J.K., et al., Prospective identification of cardiac progenitors by a novel single cell-based cardiomyocyte induction, *The FASEB Journal*, 29 pages (Published online Jul. 20, 2005).
Yang, P., et al., "Study design considerations in clinical outcome research of lung cancer using microarray analysis" 2004 Lung Cancer 46:215-226.
Yang-Snyder, J., et al., "A frizzled homolog functions in a vertebrate Wnt signaling pathway," *Curr. Biol.* 6:1302-1306, Cell Press (1996).
Zeng, X., et al., "A dual-kinase mechanism for Wnt co-receptor phosphorylation and activation," *Nature* 438:873-877 (Dec. 8, 2005).
Zhao, Z., et al., "A Human Homologue of the *Drosophila* Polarity Gene frizzled Has Been Identified and Mapped to 17q21.1," *Genomics* 27:370-373, Academic Press (1995).
Zhu, A.J.Z., et al., "β-Catenin signaling modulates proliferative potential of human epidermal keratinocytes independently of intracellular adhesion," *Development* 126: 2285-2298, The Company of Biologists Limited, Great Britin (1999).
English language Abstract of German Patent Publication No. WO 02/00576 A1, European Patent Office, espacenet database (2002).
Lepourcelet, M., et al., "Small-molecule antagonists of the oncogenic Tcf/β-catenin protein complex," *Cancer Cell* 5:91-102, Cell Press, U.S.A. (2004).
International Search Report for International Application No. PCT/US09/58635, ISA/US, Alexandria, VA, mailed on Nov. 19, 2010.
Written Opinion for International Application No. PCT/US09/58635, ISA/US, Alexandria, VA, mailed on Nov. 19, 2010.
Lu, C., et al., "The Binding Sites for Competitive Antagonistic, Allosteric Antagonistic, and Agonistic Antibodies to the I Domain of Integrin LFA-1," *J. Immunol.* 173:3972-3978, American Society of Immunologists, Inc., United States (2004).
Wood, V., et al., "The genome sequence of *Schizosaccharomyces pombe*," *Nature* 415:871-880, Nature Publishing Group, United Kingdom (2002).
Decypher ClustalW Multiple Alignment, Stanford University (online, Sep. 2006), accessed on Sep. 30, 2010, accessed from http://web.archive.org/web/20060912071608/http://www2.stanford.edu/~rnusse/genealigns/mhfzalign.html>.
Polakis, P., "Evidence for Wnt Signaling in Cancers lacking Genetic Defects," PowerPoint NYAS Presentation and transcript, presented on Oct. 25, 2005, 71 pages.
International Search Report of the International Searching Authority for International Application No. PCT/US07/005443, mailed on Oct. 30, 2008, United States Patent and Trademark Office, United States, 4 pages.
Written Opinion for the International Searching Authority for International Application No. PC/US07/05443, mailed on Oct. 30, 2008, The International Bureau of WIPO, Switzerland, 4 pages.
Guyre, P.M., et al., "Increased potency of Fc-receptor-targeted antigens," *Cancer Immunol. Immunother.* 45:146-148, 1997.
Fredriksson, R., et al., "The G-Protein-Coupled Receptors in the Human Genome Form Five Main Families. Phylogenetic Analysis, Paralogon Groups, and Fingerprints" *Mol. Pharmacol.* 63:1256-1272, The American Society for Pharmacology and Experimental Therapeutics, United States (2003).
De Gruijl, T. and Curiel, D.T., "Cancer vaccine strategies get bigger and better," *Nat. Med.* 5(10):1124-1125, Nature Publishing Company, United States (1999).
Vajdos, F.F., et al., "Comprehensive functional maps of the antigen binding site of an anti-ErbB2 antibody obtained with shotgun scanning mutagenesis," *J. Mol. Biol.* 320:415-428, Elsevier, England (2002).
Lee, K-H., et al., "Increased vaccine specific T cell frequency after peptide based vaccination correlates with increased susceptibility to in vitro stimulation but does not lead to tumor regression," *J. Immunol.* 163(11):6292-300, Williams & Wilkins, United States (1999).
Bodey, B., et al., "Failure of cancer vaccines: the significant limitations of this approach to immunotherapy," *Anticancer Res.* 20(4):2665-2676, International Institute of Anticancer Research, Greece (2000).
MacCallum, R.M., et al., "Antibody antigen interactions: contact analysis and binding site topography," *J. Mol. Biol.* 262(5):732-745, Elsevier, England (1996).
Casset, F., et al., "A peptide mimetic of an anti-CD4 monoclonal antibody by rational design," *Biochem. Biophys. Res. Comm.* 37:198-205, Academic Press, United States (2003).
Holm, P., et al., "Functional mapping and single chain construction of the anti-cytokeratin 8 monoclonal antibody TS1," *Mol. Immunol.* 44:1075-1084, Pergamon Press, England (2007).
Donnelly, J., "Cancer vaccine targets leukemia," *Nat. Med.* 9(11):1354-6, Nature Publishing Company, United States (2003).
Wu, H., et al., "Humanization of a murine monoclonal antibody by simultaneous optimization of framework and CDR residues," *J. Mol. Biol.* 294:151-162, Elsevier, England (1999).
Ezzel, C., "Cancer 'Vaccines': An Idea Whose Time Has Come?" *Journal of NIH Research* 7:46-49, National Institutes of Health, United States (1995).
Forni, G., et al., "Immunoprevention of Cancer: Is the Time Ripe?" *Cancer Res* 60(10):2571-2575, American Association for Cancer Research, United States (2000).
Chatterjee, M.B., et al., "Idiotypic antibody immunotherapy of cancer," *Cancer Immunol. Immunother.* 38(2):75-82, Springer International, Germany (1994).
Rudikoff, S., et al., "Single amino acid substitution altering antigen binding specificity," *Proc. Natl. Acad. Sci.* 79(6):1979-83, National Academy of Sciences, United States (1982).
International Search Report of the International Searching Authority for International Application No. PCT/US11/20994, mailed on Aug. 15, 2011, United States Patent and Trademark Office, United States, 4 pages.
Written Opinion for the International Searching Authority for International Application No. PCT/US11/20994, mailed on Aug. 15, 2011, International Searching Authority, United States, 6 pages.
Unknown Author, "Biotinylated Anti-mouse Fzd-2 Antibody," 1 page, R&D Systems, dated Feb. 11, 2004, URL:http://www.rndsystems.com/pdf/baf1307.pdf, downloaded Sep. 27, 2012.
Schulte, G. and Bryja, V., "The Frizzled family of unconventional G-protein-coupled receptors," *Trends Pharmacol Sci.* 28(10):518-25, Elsevier in Association With The International Union of Pharmacology, England (2007).
Aruffo, A., et al., "CD44 is the principal cell surface receptor for hyaluronate," *Cell* 61(7):1303-13, Cell Press, United States (1990).
"Frizzled 8 precursor (Frizled 8) (Fz-8) (hFz8)." [online], Sep. 2005, Accession Q9H461, Retrieved on Feb. 1, 2013 from http://www.ncbi.nlm.nih.gov/protein/17433053?sat=34&satkey=5096022.

(56) References Cited

OTHER PUBLICATIONS

"Frizzled 4 precursor (Frizled-4) (Fz-4) (hFz4) (FzE4)." [online], Sep. 2005, Accession Q9ULV1, Retrieved on Feb. 1, 2013 from http://www.ncbi.nlm.nih.gov/protein/62298045?sat=34&satkey=4861841.

Macleod, R.J., et al., "Wnt5a secretion stimulated by extracellular calcium-sensing receptor inhibits defective Wnt signaling in colon cancer cells," *Am. J. Physiol. Gastrointest. Liver. Physiol.* 293(1):G403-G411, American Physiological Society, United States (2007).

Khan, N.I., et al., "Activation of Wnt/beta-catenin pathway mediates growth and survival in B-cell progenitor acute lymphoblastic leukaemia," *Br. J Haematol.* 138(3):338-348, Wiley-Blackwell, England (2007).

You, L., et al.,"Wnt-1 signal as a potential cancer therapeutic target," *Drug News Perspect.* 19(1):27-31, Thomson Reuters, United States (2006).

Katoh, Y. and Katoh, M., "Comparative genomics on Fzd8 orthologs," *Oncol. Rep.* 13(15):993-997, D.A. Spandidos, Greece (2005).

Merle, P., et al., "Functional consequences of frizzled-7 receptor overexpression in human hepatocellular carcinoma," *Gastroenterology* 127 (4):1110-1122, W.B. Saunders, United States (2004).

Gurney, A., et al., "Wnt pathway inhibition via the targeting of Frizzled receptors results in decreased growth and tumorigenicity of human tumors," *Proc. Natl. Acad. Sci. USA* 109(29):11717-22, National Academy of Sciences, United States (Jul. 17, 2012).

Luu, H.H., et al., "Wnt/β-Catenin Signaling Pathway as Novel Cancer Drug Targets," *Curr. Cancer Drug Targets* 4:653-671, Bentham Science Publishers, Netherlands (2004).

Ueno, K., et al., "Frizzled homolog proteins, microRNAs and Wnt Signaling in cancer," *Int. J. Cancer* 132:1731-1740, Wiley-Liss, United States (Apr. 15, 2013).

Bourhis, E., et al., "Reconstitution of a Frizzled8.Wnt3a.LRP6 Signaling Complex Reveals Multiple Wnt and Dkk1 Binding Sites on LRP6," *J. Biol. Chem.* 285(12):9172-9179, American Society for Biochemistry and Molecular Biology, United States (Jan. 21, 2010).

Accession No. UNITPROT: A6CA06, EBI database, accessed Sep. 4, 2013, 4 pages.

Accession No. GSP: AVA85292, EBI database , accessed Jul. 18, 2013, 1 page.

Accession No. GSP: ARJ99386, EBI database, accessed Jul. 18, 2013, 1 page.

International Search Report of the International Searching Authority for International Application No. PCT/US13/66087 mailed on Jan. 16, 2014, United States Patent and Trademark Office, United States, 4 pages.

Written Opinion for the International Searching Authority for International Application No. PCT/US13/66087 mailed on Jan. 16, 2014 The International Bureau of WIPO, Switzerland, 4 pages.

International Search Report and Written Opinion for International Application No. PCT/US14/24258, ISA/US, Alexandria, Virginia, United States, mailed Aug. 25, 2014.

Accession No. UNITPROT: A6CA06, EBI database (Jul. 24, 2007).

Al-Hajj, M., et al., "Prospective Identification of Tumorigenic Breast Cancer Cells," Proceedings of the National Academy of Sciences 100(7):3983-3988, The National Academy of Sciences, United States (2003).

Caricasole, A., et al., "Functional Characterization of WNT7A Signaling in PC12 Cells," The Journal of Biological Chemistry 278(39):37024-37031, The American Society for Biochemistry and Molecular Biology, United States (2003).

Cong, F., et al., "Wnt Signals across the Plasma Membrane to Activate the Beta-catenin Pathway by Forming Oligomers Containing its Receptors, Frizzled and LRP," Development 131(20):5130-5115, Company of Biologists, England (2004).

"frizzled Antibody (H-300): sc-9169" accessed at http://scbt.com/datasheet-9169-frizzled-h-300-antibody.html, accessed on Mar. 20, 2015, 6 pages.

Gaudio, A., et al., "Increased Sclerostin Serum Levels Associated with Bone Formation and Resorption Markers in Patients with Immobilization-Induced Bone Loss," The Journal of Clinical Endocrinology and Metabolism 95(5):2248-2253, The Endocrine Society, United States (2010).

Gore, L., et al., "Safety, pharmacokinetics, and pharmacodynamics results from a phase I trial of BAY 86/9766 (RDEA119), a MEK inhibitor, in patients with advanced cancer," J Clin Oncol 29:2 pages, presented at the 2011 ASCO Annual Meeting, American Society of Clinical Oncology, United States (2011) (Abstract 3007).

International Search Report for International Application No. PCT/US14/68097, United States Patent and Trademark Office, United States, mailed on Apr. 30, 2015, 10 pages.

International Search Report for International Application No. PCT/US2012/068351, US Patent Office, Virginia, mailed on May 24, 2013, 7 pages.

International Search Report for International Application No. PCT/US2014/014443, United States Patent and Trademark Office, United States, mailed on Apr. 15, 2014, 4 pages.

Jimeno, A., et al., "A first-in-human phase 1 study of anticancer stem cell agent OMP-54F28 (FZD-Fc), decoy receptor for WNT ligands, in patient with advanced solid tumors," 2014 ASCO Annual Meeting, Abstract 2505, 2 pages (2014).

Kabacik, S., et al., "Gene Expression Following Ionising Radiation: Identification of Biomarkers for Dose Estimation and Prediction of Individual Response," International Journal of Radiation Biology 67(2):115-129, Informa Healthcare, England (2011).

Lin, S.Y. et al., "β-catenin, a novel prognostic marker for breast cancer: its roles in cyclin D1 expression and cancer progression," Proceedings of the National Academy of Sciences of the United States of America 97(8):4262-4266, National Academy of Sciences, United States (2000).

Miele, L. and Osborne, B., "Arbiter of Differentiation and Death: Notch Signaling Meets Apoptosis," Journal of Cellular Physiology 181(3):393-409, Wiley-Liss, Inc., United States (1999).

OncoMed Pharmaceuticals Press Release, "OncoMed Announces Abstracts Accepted at the 2014 ASCO Meeting," Apr. 23, 2014, 2 pages.

OncoMed Pharmaceuticals Press Release, "OncoMed Pharmaceuticals Announces FDA Clearance to Commence Phase 1 Testing of Anti-Cancer Stem Cell Therapeutic OMP-18R5," Apr. 28, 2011, 2 pages.

OncoMed Pharmaceuticals Press Release, "OncoMed Pharmaceuticals Commences Third Phase 1b Clinical Trial for OMP-54F28 (Fzd8-Fc) With Carboplatin and Paclitaxel in Ovarian Cancer," Feb. 20, 2014, 3 pages.

OncoMed Pharmaceuticals Press Release, "OncoMed Pharmaceuticals Initiates First Phase 1b Clinical Trial of First-in-Class WNT-Pathway-Targeting Antibody Vantictumab (OMP-18R5) With Paclitaxel in Breast Cancer," Oct. 29, 2013, 3 pages.

OncoMed Pharmaceuticals Press Release, "OncoMed Pharmaceuticals Initiates First Phase 1b Clinical Trial of OMP-54F28 (Fzd8-Fc) With Nab-Paclitaxel (Abraxane(R)) and Gemcitabine in Pancreatic Cancer," Jan. 13, 2014, 3 pages.

OncoMed Pharmaceuticals Press Release, "OncoMed Pharmaceuticals Initiates Phase I Clinical Trial of Anti-Cancer Stem Cell Therapeutic OMP-54F28 (Fzd8-Fc)," Jul. 12, 2012, 2 pages.

OncoMed Pharmaceuticals Press Release, "OncoMed Pharmaceuticals Initiates Second Phase 1b Clinical Trial for OMP-54F28 (Fzd8-Fc) With Sorafenib (Nexavar (R)) in Hepatocellular Cancer," Feb. 18, 2014, 3 pages.

OncoMed Pharmaceuticals Press Release, "OncoMed Pharmaceuticals Initiates Second Phase 1b Clinical Trial of First-in-Class WNT Pathway-Targeting Antibody Vantictumab (OMP-18R5) With Docetaxel in Non-Small Lung Cancer (NSCLC)," Nov. 15, 2013, 3 pages.

OncoMed Pharmaceuticals Press Release, "OncoMed Pharmaceuticals Initiates Third Phase 1b Clinical Trial of First-in-Class WNT Pathway-Targeting Antibody Vantictumab (OMP-18R5) With Nab-Paclitaxel (Abraxane®) and Gemcitabine in Stage IV Pancreatic Cancer," Dec. 4, 2013, 3 pages.

OncoMed Pharmaceuticals Press Release, "OncoMed Pharmaceuticals Presents Data From Clinical Trials of Four Novel Anti-Cancer

(56) References Cited

OTHER PUBLICATIONS

Stem Cell (Anti-CSC) Therapeutics at the AACR-NCI-EORTC International Conference on Molecular Targets and Cancer Therapeutics in Boston, Oct. 19-23, 2013," Oct. 21, 2013, 4 pages.
OncoMed Pharmaceuticals Press Release, "OncoMed Pharmaceuticals Presents Phase 1 Data in Solid Tumor Patients for the First-in-Class Wnt Pathway Targeting Antibody Vantictumab (OMP-18R5) at ASCO," Jun. 3, 2013, 2 pages.
OncoMed Pharmaceuticals Press Release, "OncoMed Pharmaceuticals Presents Updated Phase 1a Data in Advanced Solid Tumor Patients for the First-in-Class WNT-Pathway-Targeting Antibody Vantictumab (OMP-18R5) at the European Cancer Congress 2013," Sep. 29, 2013, 3 pages.
OncoMed Pharmaceuticals Press Release, "OncoMed Pharmaceuticals Recaps New Data Presented at AACR," Apr. 3, 2012, 2 pages.
OncoMed Pharmaceuticals Press Release, "OncoMed Pharmaceuticals to Present Data From Clinical Trials of Four Novel Anti-Cancer Stem Cell (Anti-CSC) Therapeutics in Five Posters at the AACR-NCI-EORTC International Conference on Molecular Targets and Cancer Therapeutics in Boston, Oct. 19-23, 2013," Oct. 14, 2013, 4 pages.
OncoMed Pharmaceuticals Press Release, "OncoMed Pharmaceuticals to Present Phase 1a Data in Advanced Solid Tumor Patients for the First-in-Class WNT-Pathway-Targeting Antibody Vantictumab (OMP-18R5) at the European Cancer Congress 2013 (ECC 2013)," Sep. 23, 2013, 2 pages.
OncoMed Pharmaceuticals Press Release, "OncoMed Presents Data on Multiple Anti-Cancer Stem Cell Programs at American Association for Cancer Research Annual Meeting," Apr. 8, 2014, 4 pages.
OncoMed Pharmaceuticals Press Release, "OncoMed Presents New Data in Six Anti-Cancer Stem Cell Programs at AACR," Apr. 9, 2013, 3 pages.
OncoMed Pharmaceuticals Press Release, "OncoMed Provides Update on FZD8-Fc (OMP-54F28) Phase I Clinical Trials," Jun. 18, 2014, 2 pages.
OncoMed Pharmaceuticals Press Release, "OncoMed to Present Data From Three Clinical Studies at the 2014 ASCO Annual Meeting," May 14, 2014, 4 pages.
OncoMed Pharmaceuticals Press Release, "OncoMed to Present New Data in Six Anti-Cancer Stem Cell Programs at AACR," Apr. 2, 2013, 2 pages.
OncoMed Pharmaceuticals Press Release, "PNAS Publishes OncoMed Data Demonstrating Potent Anti-Cancer Activity for Novel Wnt Pathway Antibody OMP-18R5," Jul. 3, 2012, 2 pages.
Smith, D.C., et al., "A first-in-human Phase 1 study of anti-cancer stem cell (CSC) agent OMP-54F28 (FZD8-Fc) targeting the WNT pathway in patients with advanced solid tumors," AACR-NCI-EORTC International Conference on Molecular Targets and Cancer Therapeutics, Oct. 19-23, 2013, Abstract B79, 1 page (2013).
Smith, D.C., et al., "Biomarker analysis in the first-in-human Phase 1a study for vantictumab (OMP-18R5; anti-Frizzled) demonstrates pharmacodynamics (PD) modulation of the Wnt pathway in patients with advanced solid tumors," AACR-NCI-EORTC International Conference on Molecular Targets and Cancer Therapeutics in Boston, Oct. 19-23, 2013, Poster 823, 1 page (2013).
Wheater, G., et al., "The clinical utility of bone marker measurements in osteoporosis," Journal of Translational Medicine 11(201):11 pages, BioMed Central Ltd, England (2013).
Written Opinion for International Application No. PCT/US14/68097, United States Patent and Trademark Office, United States, mailed on Apr. 30, 2015, 25 pages.
Yen, W-C., et al., "Enhanced anti-tumor effect of WNT pathway antagonists in combination with taxanes," AACR Annual Meeting Apr. 5-9, 2014, Abstract 4547, 1 page (2014).
Yeung, P. et al., "Wnt pathway antagonist OMP-54F28 (FZD8-Fc) inhibits tumor growth and reduces tumor-initiating cell frequency in patient-derived hepatocellular carcinoma and ovarian cancer xenograft models," AACR Annual Meeting Apr. 5-9, 2014, Abstract 1907, 1 page (2014).
Zhang, C., et al., "Predictive biomarker identification for response to vantictumab (OMP-18R5; anti-Frizzled) by mining gene expression data of human breast cancer xenografts," AACR Annual Meeting, Apr. 5-9, Abstract 2830, 1 page (2014).
US 5,962,233, 10/1999, Livak (withdrawn)

SEQUENCE LISTING

<160> NUMBER OF SEQ ID NOS: 93

<210> SEQ ID NO 1
<211> LENGTH: 6
<212> TYPE: PRT
<213> ORGANISM: Artificial Sequence
<220> FEATURE:
<223> OTHER INFORMATION: 73R009 Heavy chain CDR1

<400> SEQUENCE: 1

Ala Ser Tyr Ala Trp Ser
1               5

<210> SEQ ID NO 2
<211> LENGTH: 16
<212> TYPE: PRT
<213> ORGANISM: Artificial Sequence
<220> FEATURE:
<223> OTHER INFORMATION: 73R009 Heavy chain CDR2

<400> SEQUENCE: 2

Tyr Ile Ser Tyr Ser Gly Gly Thr Asp Tyr Asn Pro Ser Leu Lys Ser
1               5                   10                  15

<210> SEQ ID NO 3
<211> LENGTH: 4
<212> TYPE: PRT
<213> ORGANISM: Artificial Sequence
<220> FEATURE:
<223> OTHER INFORMATION: 73R009 Heavy chain CDR3

<400> SEQUENCE: 3

Lys Gly Ala Tyr
1

<210> SEQ ID NO 4
<211> LENGTH: 12
<212> TYPE: PRT
<213> ORGANISM: Artificial Sequence
<220> FEATURE:
<223> OTHER INFORMATION: 73R009 Light chain CDR1

<400> SEQUENCE: 4

Ser Ala Ser Ser Ser Val Ser Ser Ser Tyr Leu Tyr
1               5                   10

<210> SEQ ID NO 5

```
<211> LENGTH: 7
<212> TYPE: PRT
<213> ORGANISM: Artificial Sequence
<220> FEATURE:
<223> OTHER INFORMATION: 73R009 Light chain CDR2

<400> SEQUENCE: 5

Ser Thr Ser Asn Leu Ala Ser
1               5

<210> SEQ ID NO 6
<211> LENGTH: 9
<212> TYPE: PRT
<213> ORGANISM: Artificial Sequence
<220> FEATURE:
<223> OTHER INFORMATION: 73R009 Light chain CDR3

<400> SEQUENCE: 6

His Gln Trp Ser Ser Tyr Pro Tyr Thr
1               5

<210> SEQ ID NO 7
<211> LENGTH: 113
<212> TYPE: PRT
<213> ORGANISM: Artificial Sequence
<220> FEATURE:
<223> OTHER INFORMATION: 73R009 Heavy chain variable region amino acid
      sequence

<400> SEQUENCE: 7

Gln Val Gln Leu Gln Glu Ser Gly Pro Gly Leu Val Lys Pro Ser Glu
1               5                   10                  15

Thr Leu Ser Leu Thr Cys Thr Val Thr Gly Thr Thr Ile Thr Ala Ser
                20                  25                  30

Tyr Ala Trp Ser Trp Ile Arg Gln Pro Pro Gly Lys Gly Leu Glu Trp
            35                  40                  45

Met Gly Tyr Ile Ser Tyr Ser Gly Gly Thr Asp Tyr Asn Pro Ser Leu
    50                  55                  60

Lys Ser Arg Ile Thr Ile Ser Arg Asp Thr Phe Lys Asn Gln Phe Ser
65                  70                  75                  80

Leu Lys Leu Ser Ser Val Thr Ala Ala Asp Thr Ala Thr Tyr Tyr Cys
                85                  90                  95

Ala Arg Lys Gly Ala Tyr Trp Gly Gln Gly Thr Leu Val Thr Val Ser
            100                 105                 110

Ser

<210> SEQ ID NO 8
<211> LENGTH: 108
<212> TYPE: PRT
<213> ORGANISM: Artificial Sequence
<220> FEATURE:
<223> OTHER INFORMATION: 73R009 Light chain variable region amino acid
      sequence

<400> SEQUENCE: 8

Asp Ile Val Leu Thr Gln Ser Pro Ala Thr Leu Ser Ala Ser Pro Gly
1               5                   10                  15

Glu Lys Val Thr Leu Thr Cys Ser Ala Ser Ser Ser Val Ser Ser Ser
                20                  25                  30

Tyr Leu Tyr Trp Tyr Gln Gln Lys Pro Gly Gln Ala Pro Lys Leu Leu
            35                  40                  45

Ile Tyr Ser Thr Ser Asn Leu Ala Ser Gly Val Pro Ala Arg Phe Ser
```

```
                 50                  55                  60
Gly Ser Gly Ser Gly Thr Ser Tyr Ser Leu Thr Ile Ser Ser Leu Glu
 65                  70                  75                  80

Pro Glu Asp Phe Ala Thr Tyr Tyr Cys His Gln Trp Ser Ser Tyr Pro
                     85                  90                  95

Tyr Thr Phe Gly Gly Gly Thr Lys Leu Glu Ile Lys
                100                 105

<210> SEQ ID NO 9
<211> LENGTH: 458
<212> TYPE: PRT
<213> ORGANISM: Artificial Sequence
<220> FEATURE:
<223> OTHER INFORMATION: 73R009 Heavy chain amino acid sequence with
      predicted signal sequence

<400> SEQUENCE: 9

Met Lys His Leu Trp Phe Phe Leu Leu Leu Val Ala Ala Pro Arg Trp
  1               5                  10                  15

Val Leu Ser Gln Val Gln Leu Gln Glu Ser Gly Pro Gly Leu Val Lys
                 20                  25                  30

Pro Ser Glu Thr Leu Ser Leu Thr Cys Thr Val Thr Gly Thr Thr Ile
             35                  40                  45

Thr Ala Ser Tyr Ala Trp Ser Trp Ile Arg Gln Pro Pro Gly Lys Gly
 50                  55                  60

Leu Glu Trp Met Gly Tyr Ile Ser Tyr Ser Gly Gly Thr Asp Tyr Asn
 65                  70                  75                  80

Pro Ser Leu Lys Ser Arg Ile Thr Ile Ser Arg Asp Thr Phe Lys Asn
                 85                  90                  95

Gln Phe Ser Leu Lys Leu Ser Ser Val Thr Ala Ala Asp Thr Ala Thr
            100                 105                 110

Tyr Tyr Cys Ala Arg Lys Gly Ala Tyr Trp Gly Gln Gly Thr Leu Val
            115                 120                 125

Thr Val Ser Ser Ala Ser Thr Lys Gly Pro Ser Val Phe Pro Leu Ala
130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Asn Phe
            195                 200                 205

Gly Thr Gln Thr Tyr Thr Cys Asn Val Asp His Lys Pro Ser Asn Thr
        210                 215                 220

Lys Val Asp Lys Thr Val Glu Arg Lys Cys Cys Val Glu Cys Pro Pro
225                 230                 235                 240

Cys Pro Ala Pro Pro Val Ala Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Gln Phe Asn Trp
            275                 280                 285

Tyr Val Asp Gly Val Glu Val His Asn Ala Lys Thr Lys Pro Arg Glu
        290                 295                 300
```

```
Glu Gln Phe Asn Ser Thr Phe Arg Val Val Ser Val Leu Thr Val Val
305                 310                 315                 320

His Gln Asp Trp Leu Asn Gly Lys Glu Tyr Lys Cys Lys Val Ser Asn
            325                 330                 335

Lys Gly Leu Pro Ala Pro Ile Glu Lys Thr Ile Ser Lys Thr Lys Gly
        340                 345                 350

Gln Pro Arg Glu Pro Gln Val Tyr Thr Leu Pro Pro Ser Arg Glu Glu
    355                 360                 365

Met Thr Lys Asn Gln Val Ser Leu Thr Cys Leu Val Lys Gly Phe Tyr
370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Met Leu Asp Ser Asp Gly Ser Phe Phe
            405                 410                 415

Leu Tyr Ser Lys Leu Thr Val Asp Lys Ser Arg Trp Gln Gln Gly Asn
        420                 425                 430

Val Phe Ser Cys Ser Val Met His Glu Ala Leu His Asn His Tyr Thr
    435                 440                 445

Gln Lys Ser Leu Ser Leu Ser Pro Gly Lys
    450                 455

<210> SEQ ID NO 10
<211> LENGTH: 458
<212> TYPE: PRT
<213> ORGANISM: Artificial Sequence
<220> FEATURE:
<223> OTHER INFORMATION: 73R009 (13A variant) Heavy chain amino acid
      sequence with predicted signal sequence

<400> SEQUENCE: 10

Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Thr Gly Thr Thr Ile
        35                  40                  45

Thr Ala Ser Tyr Ala Trp Ser Trp Ile Arg Gln Pro Pro Gly Lys Gly
    50                  55                  60

Leu Glu Trp Met Gly Tyr Ile Ser Tyr Ser Gly Gly Thr Asp Tyr Asn
65                  70                  75                  80

Pro Ser Leu Lys Ser Arg Ile Thr Ile Ser Arg Asp Thr Phe Lys Asn
            85                  90                  95

Gln Phe Ser Leu Lys Leu Ser Ser Val Thr Ala Ala Asp Thr Ala Thr
        100                 105                 110

Tyr Tyr Cys Ala Arg Lys Gly Ala Tyr Trp Gly Gln Gly Thr Leu Val
    115                 120                 125

Thr Val Ser Ser Ala Ser Thr Lys Gly Pro Ser Val Phe Pro Leu Ala
130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
            165                 170                 175

Ala Leu Thr Ser Gly Val His Thr Phe Pro Ala Val Leu Gln Ser Ser
        180                 185                 190

Gly Leu Tyr Ser Leu Ser Ser Val Val Thr Val Pro Ser Ser Asn Phe
    195                 200                 205
```

Gly Thr Gln Thr Tyr Thr Cys Asn Val Asp His Lys Pro Ser Asn Thr
    210                 215                 220

Lys Val Asp Lys Thr Val Glu Arg Lys Cys Cys Val Glu Cys Pro Pro
225                 230                 235                 240

Cys Pro Ala Pro Pro Val Ala Gly Pro Ser Val Phe Leu Phe Pro Pro
            245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Gln Phe Asn Trp
        275                 280                 285

Tyr Val Asp Gly Val Glu Val His Asn Ala Lys Thr Lys Pro Arg Glu
        290                 295                 300

Glu Gln Phe Asn Ser Thr Phe Arg Val Val Ser Val Leu Thr Val Val
305                 310                 315                 320

His Gln Asp Trp Leu Asn Gly Lys Glu Tyr Lys Cys Lys Val Ser Asn
                325                 330                 335

Lys Gly Leu Pro Ala Pro Ile Glu Lys Thr Ile Ser Lys Thr Lys Gly
            340                 345                 350

Gln Pro Arg Glu Pro Gln Val Tyr Thr Leu Pro Pro Ser Arg Glu Lys
        355                 360                 365

Met Thr Lys Asn Gln Val Ser Leu Thr Cys Leu Val Lys Gly Phe Tyr
370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Met Leu Lys Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455

<210> SEQ ID NO 11
<211> LENGTH: 234
<212> TYPE: PRT
<213> ORGANISM: Artificial Sequence
<220> FEATURE:
<223> OTHER INFORMATION: 73R009 Light chain amino acid sequence with
      predicted signal sequence

<400> SEQUENCE: 11

Met Lys His Leu Trp Phe Phe Leu Leu Val Ala Ala Pro Arg Trp
1               5                   10                  15

Val Leu Ser Asp Ile Val Leu Thr Gln Ser Pro Ala Thr Leu Ser Ala
            20                  25                  30

Ser Pro Gly Glu Lys Val Thr Leu Thr Cys Ser Ala Ser Ser Ser Val
        35                  40                  45

Ser Ser Ser Tyr Leu Tyr Trp Tyr Gln Gln Lys Pro Gly Gln Ala Pro
    50                  55                  60

Lys Leu Leu Ile Tyr Ser Thr Ser Asn Leu Ala Ser Gly Val Pro Ala
65                  70                  75                  80

Arg Phe Ser Gly Ser Gly Ser Gly Thr Ser Tyr Ser Leu Thr Ile Ser
                85                  90                  95

Ser Leu Glu Pro Glu Asp Phe Ala Thr Tyr Tyr Cys His Gln Trp Ser

```
                100               105                 110
Ser Tyr Pro Tyr Thr Phe Gly Gly Gly Thr Lys Leu Glu Ile Lys Arg
            115                 120                 125

Thr Val Ala Ala Pro Ser Val Phe Ile Phe Pro Pro Ser Asp Glu Gln
        130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 12
<211> LENGTH: 439
<212> TYPE: PRT
<213> ORGANISM: Artificial Sequence
<220> FEATURE:
<223> OTHER INFORMATION: 73R009 Heavy chain amino acid sequence without
      predicted signal sequence

<400> SEQUENCE: 12

Gln Val Gln Leu Gln Glu Ser Gly Pro Gly Leu Val Lys Pro Ser Glu
1               5                   10                  15

Thr Leu Ser Leu Thr Cys Thr Val Thr Gly Thr Thr Ile Thr Ala Ser
            20                  25                  30

Tyr Ala Trp Ser Trp Ile Arg Gln Pro Pro Gly Lys Gly Leu Glu Trp
        35                  40                  45

Met Gly Tyr Ile Ser Tyr Ser Gly Gly Thr Asp Tyr Asn Pro Ser Leu
    50                  55                  60

Lys Ser Arg Ile Thr Ile Ser Arg Asp Thr Phe Lys Asn Gln Phe Ser
65                  70                  75                  80

Leu Lys Leu Ser Ser Val Thr Ala Ala Asp Thr Ala Thr Tyr Tyr Cys
                85                  90                  95

Ala Arg Lys Gly Ala Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Asn Phe Gly Thr Gln
            180                 185                 190

Thr Tyr Thr Cys Asn Val Asp His Lys Pro Ser Asn Thr Lys Val Asp
        195                 200                 205

Lys Thr Val Glu Arg Lys Cys Cys Val Glu Cys Pro Pro Cys Pro Ala
    210                 215                 220
```

```
Pro Pro Val Ala Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
            245                 250                 255

Asp Val Ser His Glu Asp Pro Glu Val Gln Phe Asn Trp Tyr Val Asp
        260                 265                 270

Gly Val Glu Val His Asn Ala Lys Thr Lys Pro Arg Glu Glu Gln Phe
    275                 280                 285

Asn Ser Thr Phe Arg Val Val Ser Val Leu Thr Val Val His Gln Asp
290                 295                 300

Trp Leu Asn Gly Lys Glu Tyr Lys Cys Lys Val Ser Asn Lys Gly Leu
305                 310                 315                 320

Pro Ala Pro Ile Glu Lys Thr Ile Ser Lys Thr Lys Gly Gln Pro Arg
                325                 330                 335

Glu Pro Gln Val Tyr Thr Leu Pro Pro Ser Arg Glu Glu Met Thr Lys
            340                 345                 350

Asn Gln Val Ser Leu Thr Cys Leu Val Lys Gly Phe Tyr Pro Ser Asp
        355                 360                 365

Ile Ala Val Glu Trp Glu Ser Asn Gly Gln Pro Glu Asn Asn Tyr Lys
    370                 375                 380

Thr Thr Pro Pro Met Leu Asp Ser Asp Gly Ser Phe Phe Leu Tyr Ser
385                 390                 395                 400

Lys Leu Thr Val Asp Lys Ser Arg Trp Gln Gln Gly Asn Val Phe Ser
                405                 410                 415

Cys Ser Val Met His Glu Ala Leu His Asn His Tyr Thr Gln Lys Ser
            420                 425                 430

Leu Ser Leu Ser Pro Gly Lys
            435

<210> SEQ ID NO 13
<211> LENGTH: 439
<212> TYPE: PRT
<213> ORGANISM: Artificial Sequence
<220> FEATURE:
<223> OTHER INFORMATION: 73R009 (13A variant) Heavy chain amino acid
      sequence without predicted signal sequence

<400> SEQUENCE: 13

Gln Val Gln Leu Gln Glu Ser Gly Pro Gly Leu Val Lys Pro Ser Glu
1               5                   10                  15

Thr Leu Ser Leu Thr Cys Thr Val Thr Gly Thr Thr Ile Thr Ala Ser
            20                  25                  30

Tyr Ala Trp Ser Trp Ile Arg Gln Pro Pro Gly Lys Gly Leu Glu Trp
        35                  40                  45

Met Gly Tyr Ile Ser Tyr Ser Gly Gly Thr Asp Tyr Asn Pro Ser Leu
    50                  55                  60

Lys Ser Arg Ile Thr Ile Ser Arg Asp Thr Phe Lys Asn Gln Phe Ser
65                  70                  75                  80

Leu Lys Leu Ser Ser Val Thr Ala Ala Asp Thr Ala Thr Tyr Tyr Cys
                85                  90                  95

Ala Arg Lys Gly Ala Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140
```

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
            165                 170                 175

Ser Leu Ser Ser Val Val Thr Val Pro Ser Ser Asn Phe Gly Thr Gln
        180                 185                 190

Thr Tyr Thr Cys Asn Val Asp His Lys Pro Ser Asn Thr Lys Val Asp
    195                 200                 205

Lys Thr Val Glu Arg Lys Cys Cys Val Glu Cys Pro Pro Cys Pro Ala
210                 215                 220

Pro Pro Val Ala Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser His Glu Asp Pro Glu Val Gln Phe Asn Trp Tyr Val Asp
            260                 265                 270

Gly Val Glu Val His Asn Ala Lys Thr Lys Pro Arg Glu Glu Gln Phe
        275                 280                 285

Asn Ser Thr Phe Arg Val Val Ser Val Leu Thr Val Val His Gln Asp
290                 295                 300

Trp Leu Asn Gly Lys Glu Tyr Lys Cys Lys Val Ser Asn Lys Gly Leu
305                 310                 315                 320

Pro Ala Pro Ile Glu Lys Thr Ile Ser Lys Thr Lys Gly Gln Pro Arg
                325                 330                 335

Glu Pro Gln Val Tyr Thr Leu Pro Pro Ser Arg Glu Lys Met Thr Lys
            340                 345                 350

Asn Gln Val Ser Leu Thr Cys Leu Val Lys Gly Phe Tyr Pro Ser Asp
        355                 360                 365

Ile Ala Val Glu Trp Glu Ser Asn Gly Gln Pro Glu Asn Asn Tyr Lys
370                 375                 380

Thr Thr Pro Pro Met Leu Lys Ser Asp Gly Ser Phe Phe Leu Tyr Ser
385                 390                 395                 400

Lys Leu Thr Val Asp Lys Ser Arg Trp Gln Gln Gly Asn Val Phe Ser
                405                 410                 415

Cys Ser Val Met His Glu Ala Leu His Asn His Tyr Thr Gln Lys Ser
            420                 425                 430

Leu Ser Leu Ser Pro Gly Lys
        435

<210> SEQ ID NO 14
<211> LENGTH: 215
<212> TYPE: PRT
<213> ORGANISM: Artificial Sequence
<220> FEATURE:
<223> OTHER INFORMATION: 73R009 Light chain amino acid sequence without
      predicted signal sequence

<400> SEQUENCE: 14

Asp Ile Val Leu Thr Gln Ser Pro Ala Thr Leu Ser Ala Ser Pro Gly
1               5                   10                  15

Glu Lys Val Thr Leu Thr Cys Ser Ala Ser Ser Val Ser Ser
            20                  25                  30

Tyr Leu Tyr Trp Tyr Gln Gln Lys Pro Gly Gln Ala Pro Lys Leu Leu
            35                  40                  45

Ile Tyr Ser Thr Ser Asn Leu Ala Ser Gly Val Pro Ala Arg Phe Ser

```
                    50                  55                  60
Gly Ser Gly Ser Gly Thr Ser Tyr Ser Leu Thr Ile Ser Ser Leu Glu
 65                  70                  75                  80

Pro Glu Asp Phe Ala Thr Tyr Tyr Cys His Gln Trp Ser Ser Tyr Pro
                 85                  90                  95

Tyr Thr Phe Gly Gly Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 15
<211> LENGTH: 1374
<212> TYPE: DNA
<213> ORGANISM: Artificial Sequence
<220> FEATURE:
<223> OTHER INFORMATION: 73R009 Heavy chain nucleotide sequence
<220> FEATURE:
<221> NAME/KEY: misc_feature
<222> LOCATION: (1104)..(1104)
<223> OTHER INFORMATION: R = A or G
<220> FEATURE:
<221> NAME/KEY: misc_feature
<222> LOCATION: (1230)..(1230)
<223> OTHER INFORMATION: Y = C or T

<400> SEQUENCE: 15
atgaagcatc tgtggttttt cctgctgctc gtggctgctc cccggtgggt cctgtctcag     60
gtccaattgc aagagtcagg accagggctt gtgaagccct cagagactct gtcactcact    120
tgtaccgtga ccggaactac catcactgcc tcctacgcct ggagctggat caggcagcct    180
ccgggaaaag gcctggaatg gatgggttac atctcctatt caggcggaac cgactacaat    240
cctagcctga gtctcgcat caccatttca cgcgatacct tcaagaacca attcagcctt    300
aaactctcca gcgtgaccgc tgcagacact gccacctact actgcgcaag aaagggagcc    360
tattggggtc aggggaccct tgtgaccgtg agctcagcct ctaccaaggg cccatcggtc    420
ttccctctgg ccccctgctc ccggtccacc agcgagagca cagccgccct gggctgcctg    480
gtcaaggact acttccccga acctgtgaca gtgtcctgga actccggcgc tctgaccagc    540
ggcgtgcaca ccttcccagc tgtcctccag tcctccggac tctactccct cctccgtgtg    600
gtgacagtgc cctcctccaa cttcggcacc cagacctaca cctgcaacgt cgatcacaag    660
cccagcaaca ccaaggttga taagacagtt gagcgcaaat gttgtgtcga gtgccctcct    720
tgcccagccc ctcctgtggc tggaccttcc gtcttcctct cccccctaa acccaaagac    780 accctcatga tctcccggac ccctgaggtc acatgcgtgg tggtggacgt gagccacgaa    840
gaccccgagg tccagttcaa ctggtatgtg gacggcgtgg aggtgcataa tgccaagaca    900
```

```
aagccacggg aggagcagtt caacagcaca ttccgggtgg tcagcgtcct caccgttgtg    960
caccaggact ggctgaacgg caaggagtac aagtgcaaag tctccaacaa aggcctccct   1020
gcccccatcg agaaaccat ctccaaaacc aagggcagc ccagggaacc acaggtgtac     1080
accctgcccc cttcccggga ggaratgacc aagaaccaag tcagcctgac ctgcctggtc   1140
aaaggcttct accccctccga catcgccgtg gagtgggaga gcaatgggca gcctgagaac  1200
aactacaaga ccacacctcc catgctggay tccgacggct ccttcttcct ctactccaaa  1260
ctcaccgtgg acaagagcag gtggcagcag gggaacgtct tctcctgctc cgtgatgcat  1320
gaggctctgc acaaccacta cacacagaag tccctctccc tgtctcctgg aaaa        1374
```

<210> SEQ ID NO 16
<211> LENGTH: 1374
<212> TYPE: DNA
<213> ORGANISM: Artificial Sequence
<220> FEATURE:
<223> OTHER INFORMATION: 73R009 (13A variant) Heavy chain nucleotide
      sequence

<400> SEQUENCE: 16

```
atgaagcatc tgtggttttt cctgctgctc gtggctgctc cccggtgggt cctgtctcag     60
gtccaattgc aagagtcagg accagggctt gtgaagccct cagagactct gtcactcact   120
tgtaccgtga ccggaactac catcactgcc tcctacgcct ggagctggat caggcagcct    180
ccgggaaaag gcctggaatg gatgggttac atctcctatt caggcggaac cgactacaat    240
cctagcctga agtctcgcat caccatttca cgcgatacct tcaagaacca attcagcctt   300
aaactctcca gcgtgaccgc tgcagacact gccacctact actgcgcaag aaagggagcc    360
tattggggtc aggggaccct tgtgaccgtg agctcagcct ctaccaaggg ccctagcgtc    420
ttccctctgg cccctgctc ccggtccacc agcgagagca cagccgccct gggctgcctg    480
gtcaaggact acttccccga acctgtgaca gtgtcctgga actccggcgc tctgaccagc   540
ggcgtgcaca ccttcccagc tgtcctccag tcctccggac tctactccct ctcctccgtg   600
gtgacagtgc cctcctccaa cttcggcacc cagacctaca cctgcaacgt cgatcacaag   660
cccagcaaca ccaaggttga taagacagtt gagcgcaaat gttgtgtcga gtgccctcct   720
tgcccagccc ctcctgtggc tggaccttcc gtcttcctct ccccccctaa acccaaagac   780
accctcatga tctcccggac ccctgaggtc acatgcgtgg tggtggacgt gagccacgaa    840
gaccccgagg tccagttcaa ctggtatgtg gacggcgtgg aggtgcataa tgccaagaca   900
aagccacggg aggagcagtt caacagcaca ttccgggtgg tcagcgtcct caccgttgtg    960
caccaggact ggctgaacgg caaggagtac aagtgcaaag tctccaacaa aggcctccct   1020
gcccccatcg agaaaccat ctccaaaacc aagggcagc ccagggaacc acaggtgtac     1080
accctgcccc cttcccggga gaagatgacc aagaaccaag tcagcctgac ctgcctggtc   1140
aaaggcttct accccctccga catcgccgtg gagtgggaga gcaatgggca gcctgagaac  1200
aactacaaga ccacacctcc catgctgaag tccgacggct ccttcttcct ctactccaaa  1260
ctcaccgtgg acaagagcag gtggcagcag gggaacgtct tctcctgctc cgtgatgcat  1320
gaggctctgc acaaccacta cacacagaag tccctctccc tgtctcctgg aaaa        1374
```

<210> SEQ ID NO 17
<211> LENGTH: 1317
<212> TYPE: DNA
<213> ORGANISM: Artificial Sequence
<220> FEATURE:
<223> OTHER INFORMATION: 73R009 Heavy chain nucleotide sequence without
      predicted signal sequence
<220> FEATURE:
<221> NAME/KEY: misc_feature
<222> LOCATION: (1047)..(1047)
<223> OTHER INFORMATION: R=A or G
<220> FEATURE:
<221> NAME/KEY: misc_feature
<222> LOCATION: (1173)..(1173)
<223> OTHER INFORMATION: Y = C or T

<400> SEQUENCE: 17
caggtccaat tgcaagagtc aggaccaggg cttgtgaagc cctcagagac tctgtcactc    60
acttgtaccg tgaccggaac taccatcact gcctcctacg cctggagctg gatcaggcag   120
cctccgggaa aaggcctgga atggatgggt tacatctcct attcaggcgg aaccgactac   180
aatcctagcc tgaagtctcg catcaccatt tcacgcgata ccttcaagaa ccaattcagc   240
cttaaactct ccagcgtgac cgctgcagac actgccacct actactgcgc aagaaaggga   300
gcctattggg gtcaggggac ccttgtgacc gtgagctcag cctctaccaa gggccctagc   360
gtcttccctc tggccccctg ctcccggtcc accagcgaga gcacagccgc cctgggctgc   420
ctggtcaagg actacttccc cgaacctgtg acagtgtcct ggaactccgg cgctctgacc   480
agcggcgtgc acaccttccc agctgtcctc cagtcctccg gactctactc cctctcctcc   540
gtggtgacag tgccctcctc caacttcggc acccagacct acacctgcaa cgtcgatcac   600
aagcccagca acaccaaggt tgataagaca gttgagcgca atgttgtgt cgagtgccct   660 ccttgcccag cccctcctgt ggctggacct tccgtcttcc tcttcccccc taaacccaaa   720
gacaccctca tgatctcccg gacccctgag gtcacatgcg tggtggtgga cgtgagccac   780 gaagacccg aggtccagtt caactggtat gtggacggcg tggaggtgca taatgccaag   840
acaaagccac gggaggagca gttcaacagc acattccggg tggtcagcgt cctcaccgtt   900
gtgcaccagg actggctgaa cggcaaggag tacaagtgca aagtctccaa caaaggcctc   960
cctgccccca tcgagaaaac catctccaaa accaaaggc agcccaggga accacaggtg   1020
tacaccctgc cccttcccg ggaggaratg accaagaacc aagtcagcct gacctgcctg   1080
gtcaaaggct tctaccccc cgacatcgcc gtggagtggg agagcaatgg gcagcctgag   1140
aacaactaca agaccacacc tcccatgctg gaytccgacg gctccttctt cctctactcc   1200
aaactcaccg tggacaagag caggtggcag caggggaacg tcttctcctg ctccgtgatg   1260
catgaggctc tgcacaacca ctacacacag aagtccctct ccctgtctcc tggaaaa     1317

<210> SEQ ID NO 18
<211> LENGTH: 1317
<212> TYPE: DNA
<213> ORGANISM: Artificial Sequence
<220> FEATURE:
<223> OTHER INFORMATION: 73R009 (13A variant) Heavy chain nucleotide
      sequence without predicted signal sequence

<400> SEQUENCE: 18
caggtccaat tgcaagagtc aggaccaggg cttgtgaagc cctcagagac tctgtcactc    60
acttgtaccg tgaccggaac taccatcact gcctcctacg cctggagctg gatcaggcag   120
cctccgggaa aaggcctgga atggatgggt tacatctcct attcaggcgg aaccgactac   180
aatcctagcc tgaagtctcg catcaccatt tcacgcgata ccttcaagaa ccaattcagc   240
cttaaactct ccagcgtgac cgctgcagac actgccacct actactgcgc aagaaaggga   300

```
gcctattggg gtcaggggac ccttgtgacc gtgagctcag cctctaccaa gggccctagc      360
gtcttccctc tggccccctg ctcccggtcc accagcgaga gcacagccgc cctgggctgc      420
ctggtcaagg actacttccc cgaacctgtg acagtgtcct ggaactccgg cgctctgacc      480
agcggcgtgc acaccttccc agctgtcctc cagtcctccg gactctactc cctctcctcc      540
gtggtgacag tgccctcctc caacttcggc acccagacct acacctgcaa cgtcgatcac      600
aagcccagca acaccaaggt tgataagaca gttgagcgca aatgttgtgt cgagtgccct      660
ccttgcccag cccctcctgt ggctggacct tccgtcttcc tcttcccccc taaacccaaa      720
gacaccctca tgatctcccg gacccctgag gtcacatgcg tggtggtgga cgtgagccac      780 gaagacccg aggtccagtt caactggtat gtggacggcg tggaggtgca taatgccaag      840
acaaagccac gggaggagca gttcaacagc acattccggg tggtcagcgt cctcaccgtt      900
gtgcaccagg actggctgaa cggcaaggag tacaagtgca agtctccaa caaaggcctc      960 cctgccccca tcgagaaaac catctccaaa accaaagggc agcccaggga accacaggtg     1020
tacaccctgc cccttcccg ggagaagatg accaagaacc aagtcagcct gacctgcctg     1080
gtcaaaggct tctaccctc cgacatcgcc gtggagtggg agagcaatgg gcagcctgag     1140
aacaactaca agaccacacc tcccatgctg aagtccgacg gctccttctt cctctactcc     1200
aaactcaccg tggacaagag caggtggcag caggggaacg tcttctcctg ctccgtgatg     1260
catgaggctc tgcacaacca ctacacacag aagtccctct cctgtctcc tggaaaa       1317
```

<210> SEQ ID NO 19
<211> LENGTH: 702
<212> TYPE: DNA
<213> ORGANISM: Artificial Sequence
<220> FEATURE:
<223> OTHER INFORMATION: 73R009 Light chain nucleotide sequence

<400> SEQUENCE: 19

```
atgaagcacc tctggttctt ccttcttctt gtggccgctc ccgctgggt cctcagcgat       60 atcgtgctga cccagtcacc cgccaccctc tcagcttcac ctggcgagaa ggtcactctg      120
acttgctctg cctcatctag cgtgtcatct tcatatctgt actggtatca gcaaaaaccg      180
ggacaagccc cgaagctcct gatctacagc accagcaacc ttgcatccgg agtgcctgcc      240
aggtttagcg gtccgggtc cggtacctca tattcactga ccattcttc tcttgaaccc      300 gaagatttcg ctacctacta ctgtcatcag tggtctagct acccatacac tttcggcgga      360
ggaaccaaac tggagattaa gcgtacggtg gcagccct ctgtctttat cttccctcca      420
tccgacgagc agctcaaatc aggaaccgct tctgtcgtgt gcctgcttaa caatttctac      480
ccacgggaag ccaaggtgca gtggaaggtg acaatgccc tgcaatcagg taattcccaa      540
gagtcagtga ctgaacagga tagcaaggac agcacctatt cactctccag cactctgacc      600
ctgtccaagg ctgactacga aaagcataag gtgtacgcat gcgaggtgac ccaccagggt      660
ctgagcagcc ccgtcaccaa gtctttcaac agagggagt gt                          702
```

<210> SEQ ID NO 20
<211> LENGTH: 645
<212> TYPE: DNA
<213> ORGANISM: Artificial Sequence
<220> FEATURE:
<223> OTHER INFORMATION: 73R009 Light chain nucleotide sequence without
      predicted signal sequence

<400> SEQUENCE: 20

```
gatatcgtgc tgacccagtc acccgccacc ctctcagctt cacctggcga aaggtcact      60 ctgacttgct ctgcctcatc tagcgtgtca tcttcatatc tgtactggta tcagcaaaaa     120
ccgggacaag ccccgaagct cctgatctac agcaccagca accttgcatc cggagtgcct     180
gccaggttta gcgggtccgg gtccggtacc tcatattcac tgaccatttc ttctcttgaa     240
cccgaagatt tcgctaccta ctactgtcat cagtggtcta gctacccata cactttcggc     300
ggaggaacca aactggagat taagcgtacg gtggcagccc cttctgtctt tatcttccct     360
ccatccgacg agcagctcaa atcaggaacc gcttctgtcg tgtgcctgct aacaatttc      420 tacccacggg aagccaaggt gcagtggaag gtggacaatg ccctgcaatc aggtaattcc     480
caagagtcag tgactgaaca ggatagcaag gacagcacct attcactctc cagcactctg     540
accctgtcca aggctgacta cgaaaagcat aaggtgtacg catgcgaggt gacccaccag     600
ggtctgagca gccccgtcac caagtctttc aacagagggg agtgt                     645
```

<210> SEQ ID NO 21
<211> LENGTH: 151
<212> TYPE: PRT
<213> ORGANISM: Homo sapiens
<400> SEQUENCE: 21

```
Gln Gln Pro Pro Pro Pro Gln Gln Gln Gln Ser Gly Gln Gln Tyr
1               5                   10                  15

Asn Gly Glu Arg Gly Ile Ser Val Pro Asp His Gly Tyr Cys Gln Pro
                20                  25                  30

Ile Ser Ile Pro Leu Cys Thr Asp Ile Ala Tyr Asn Gln Thr Ile Met
            35                  40                  45

Pro Asn Leu Leu Gly His Thr Asn Gln Glu Asp Ala Gly Leu Glu Val
        50                  55                  60

His Gln Phe Tyr Pro Leu Val Lys Val Gln Cys Ser Ala Glu Leu Lys
65                  70                  75                  80

Phe Phe Leu Cys Ser Met Tyr Ala Pro Val Cys Thr Val Leu Glu Gln
                85                  90                  95

Ala Leu Pro Pro Cys Arg Ser Leu Cys Glu Arg Ala Arg Gln Gly Cys
            100                 105                 110

Glu Ala Leu Met Asn Lys Phe Gly Phe Gln Trp Pro Asp Thr Leu Lys
        115                 120                 125

Cys Glu Lys Phe Pro Val His Gly Ala Gly Glu Leu Cys Val Gly Gln
    130                 135                 140

Asn Thr Ser Asp Lys Gly Thr
145                 150
```

<210> SEQ ID NO 22
<211> LENGTH: 136
<212> TYPE: PRT
<213> ORGANISM: Homo sapiens
<400> SEQUENCE: 22

```
Gln Phe His Gly Glu Lys Gly Ile Ser Ile Pro Asp His Gly Phe Cys
1               5                   10                  15

Gln Pro Ile Ser Ile Pro Leu Cys Thr Asp Ile Ala Tyr Asn Gln Thr
                20                  25                  30

Ile Met Pro Asn Leu Leu Gly His Thr Asn Gln Glu Asp Ala Gly Leu
            35                  40                  45

Glu Val His Gln Phe Tyr Pro Leu Val Lys Val Gln Cys Ser Pro Glu
        50                  55                  60
```

```
Leu Arg Phe Phe Leu Cys Ser Met Tyr Ala Pro Val Cys Thr Val Leu
 65                  70                  75                  80

Glu Gln Ala Ile Pro Pro Cys Arg Ser Ile Cys Glu Arg Ala Arg Gln
                 85                  90                  95

Gly Cys Glu Ala Leu Met Asn Lys Phe Gly Phe Gln Trp Pro Glu Arg
            100                 105                 110

Leu Arg Cys Glu His Phe Pro Arg His Gly Ala Glu Gln Ile Cys Val
        115                 120                 125

Gly Gln Asn His Ser Glu Asp Gly
    130                 135

<210> SEQ ID NO 23
<211> LENGTH: 121
<212> TYPE: PRT
<213> ORGANISM: Homo sapiens

<400> SEQUENCE: 23

His Ser Leu Phe Ser Cys Glu Pro Ile Thr Leu Arg Met Cys Gln Asp
 1               5                  10                  15

Leu Pro Tyr Asn Thr Thr Phe Met Pro Asn Leu Leu Asn His Tyr Asp
                 20                  25                  30

Gln Gln Thr Ala Ala Leu Ala Met Glu Pro Phe His Pro Met Val Asn
             35                  40                  45

Leu Asp Cys Ser Arg Asp Phe Arg Pro Phe Leu Cys Ala Leu Tyr Ala
        50                  55                  60

Pro Ile Cys Met Glu Tyr Gly Arg Val Thr Leu Pro Cys Arg Arg Leu
 65                  70                  75                  80

Cys Gln Arg Ala Tyr Ser Glu Cys Ser Lys Leu Met Glu Met Phe Gly
                 85                  90                  95

Val Pro Trp Pro Glu Asp Met Glu Cys Ser Arg Phe Pro Asp Cys Asp
            100                 105                 110

Glu Pro Tyr Pro Arg Leu Val Asp Leu
        115                 120

<210> SEQ ID NO 24
<211> LENGTH: 131
<212> TYPE: PRT
<213> ORGANISM: Homo sapiens

<400> SEQUENCE: 24

Phe Gly Asp Glu Glu Arg Arg Cys Asp Pro Ile Arg Ile Ser Met Cys
 1               5                  10                  15

Cys Gln Asn Leu Gly Tyr Asn Val Thr Lys Met Pro Asn Leu Val Gly
                 20                  25                  30

His Glu Leu Gln Thr Asp Ala Glu Leu Gln Leu Thr Thr Phe Thr Pro
             35                  40                  45

Leu Ile Gln Tyr Gly Cys Ser Ser Gln Leu Gln Phe Phe Leu Cys Ser
        50                  55                  60

Val Tyr Val Pro Met Cys Thr Glu Lys Ile Asn Ile Pro Ile Gly Pro
 65                  70                  75                  80

Cys Gly Gly Met Cys Leu Ser Val Lys Arg Arg Cys Glu Pro Val Leu
                 85                  90                  95

Lys Glu Phe Gly Phe Ala Trp Pro Glu Ser Leu Asn Cys Ser Lys Phe
            100                 105                 110

Pro Pro Gln Asn Asp His Asn His Met Cys Met Glu Gly Pro Gly Asp
        115                 120                 125
```

Glu Glu Val
    130

<210> SEQ ID NO 25
<211> LENGTH: 131
<212> TYPE: PRT
<213> ORGANISM: Homo sapiens

<400> SEQUENCE: 25

Ala Ser Lys Ala Pro Val Cys Gln Glu Ile Thr Val Pro Met Cys Arg
1               5                   10                  15

Gly Ile Gly Tyr Asn Leu Thr His Met Pro Asn Gln Phe Asn His Asp
            20                  25                  30

Thr Gln Asp Glu Ala Gly Leu Glu Val His Gln Phe Trp Pro Leu Val
        35                  40                  45

Glu Ile Gln Cys Ser Pro Asp Leu Arg Phe Phe Leu Cys Ser Met Tyr
    50                  55                  60

Thr Pro Ile Cys Leu Pro Asp Tyr His Lys Pro Leu Pro Pro Cys Arg
65                  70                  75                  80

Ser Val Cys Glu Arg Ala Lys Ala Gly Cys Ser Pro Leu Met Arg Gln
                85                  90                  95

Tyr Gly Phe Ala Trp Pro Glu Arg Met Ser Cys Asp Arg Leu Pro Val
            100                 105                 110

Leu Gly Arg Asp Ala Glu Val Leu Cys Met Asp Tyr Asn Arg Ser Glu
        115                 120                 125

Ala Thr Thr
    130

<210> SEQ ID NO 26
<211> LENGTH: 127
<212> TYPE: PRT
<213> ORGANISM: Homo sapiens

<400> SEQUENCE: 26

His Ser Leu Phe Thr Cys Glu Pro Ile Thr Val Pro Arg Cys Met Lys
1               5                   10                  15

Met Ala Tyr Asn Met Thr Phe Phe Pro Asn Leu Met Gly His Tyr Asp
            20                  25                  30

Gln Ser Ile Ala Ala Val Glu Met Glu His Phe Leu Pro Leu Ala Asn
        35                  40                  45

Leu Glu Cys Ser Pro Asn Ile Glu Thr Phe Leu Cys Lys Ala Phe Val
    50                  55                  60

Pro Thr Cys Ile Glu Gln Ile His Val Val Pro Pro Cys Arg Lys Leu
65                  70                  75                  80

Cys Glu Lys Val Tyr Ser Asp Cys Lys Lys Leu Ile Asp Thr Phe Gly
                85                  90                  95

Ile Arg Trp Pro Glu Glu Leu Glu Cys Asp Arg Leu Gln Tyr Cys Asp
            100                 105                 110

Glu Thr Val Pro Val Thr Phe Asp Pro His Thr Glu Phe Leu Gly
        115                 120                 125

<210> SEQ ID NO 27
<211> LENGTH: 138
<212> TYPE: PRT
<213> ORGANISM: Homo sapiens

<400> SEQUENCE: 27

-continued

Gln Pro Tyr His Gly Glu Lys Gly Ile Ser Val Pro Asp His Gly Phe
1               5                   10                  15

Cys Gln Pro Ile Ser Ile Pro Leu Cys Thr Asp Ile Ala Tyr Asn Gln
            20                  25                  30

Thr Ile Leu Pro Asn Leu Leu Gly His Thr Asn Gln Glu Asp Ala Gly
        35                  40                  45

Leu Glu Val His Gln Phe Tyr Pro Leu Val Lys Val Gln Cys Ser Pro
50                  55                  60

Glu Leu Arg Phe Phe Leu Cys Ser Met Tyr Ala Pro Val Cys Thr Val
65                  70                  75                  80

Leu Asp Gln Ala Ile Pro Pro Cys Arg Ser Leu Cys Glu Arg Ala Arg
            85                  90                  95

Gln Gly Cys Glu Ala Leu Met Asn Lys Phe Gly Phe Gln Trp Pro Glu
            100                 105                 110

Arg Leu Arg Cys Glu Asn Phe Pro Val His Gly Ala Gly Glu Ile Cys
        115                 120                 125

Val Gly Gln Asn Thr Ser Asp Gly Ser Gly
    130                 135

<210> SEQ ID NO 28
<211> LENGTH: 131
<212> TYPE: PRT
<213> ORGANISM: Homo sapiens

<400> SEQUENCE: 28

Ala Ser Ala Lys Glu Leu Ala Cys Gln Glu Ile Thr Val Pro Leu Cys
1               5                   10                  15

Lys Gly Ile Gly Tyr Asn Tyr Thr Tyr Met Pro Asn Gln Phe Asn His
            20                  25                  30

Asp Thr Gln Asp Glu Ala Gly Leu Glu Val His Gln Phe Trp Pro Leu
        35                  40                  45

Val Glu Ile Gln Cys Ser Pro Asp Leu Lys Phe Phe Leu Cys Ser Met
50                  55                  60

Tyr Thr Pro Ile Cys Leu Glu Asp Tyr Lys Lys Pro Leu Pro Pro Cys
65                  70                  75                  80

Arg Ser Val Cys Glu Arg Ala Lys Ala Gly Cys Ala Pro Leu Met Arg
            85                  90                  95

Gln Tyr Gly Phe Ala Trp Pro Asp Arg Met Arg Cys Asp Arg Leu Pro
            100                 105                 110

Glu Gln Gly Asn Pro Asp Thr Leu Cys Met Asp Tyr Asn Arg Thr Asp
        115                 120                 125

Leu Thr Thr
    130

<210> SEQ ID NO 29
<211> LENGTH: 129
<212> TYPE: PRT
<213> ORGANISM: Homo sapiens

<400> SEQUENCE: 29

Ala Ser Ala Lys Glu Leu Ala Cys Gln Glu Ile Thr Val Pro Leu Cys
1               5                   10                  15

Lys Gly Ile Gly Tyr Asn Tyr Thr Tyr Met Pro Asn Gln Phe Asn His
            20                  25                  30

Asp Thr Gln Asp Glu Ala Gly Leu Glu Val His Gln Phe Trp Pro Leu
        35                  40                  45

Val Glu Ile Gln Cys Ser Pro Asp Leu Lys Phe Phe Leu Cys Ser Met
 50                  55                  60

Tyr Thr Pro Ile Cys Leu Glu Asp Tyr Lys Lys Pro Leu Pro Pro Cys
 65                  70                  75                  80

Arg Ser Val Cys Glu Arg Ala Lys Ala Gly Cys Ala Pro Leu Met Arg
                 85                  90                  95

Gln Tyr Gly Phe Ala Trp Pro Asp Arg Met Arg Cys Asp Arg Leu Pro
                100                 105                 110

Glu Gln Gly Asn Pro Asp Thr Leu Cys Met Asp Tyr Asn Arg Thr Asp
            115                 120                 125

Leu

<210> SEQ ID NO 30
<211> LENGTH: 137
<212> TYPE: PRT
<213> ORGANISM: Homo sapiens

<400> SEQUENCE: 30

Leu Glu Ile Gly Arg Phe Asp Pro Glu Arg Gly Arg Gly Ala Ala Pro
 1               5                  10                  15

Cys Gln Ala Val Glu Ile Pro Met Cys Arg Gly Ile Gly Tyr Asn Leu
                 20                  25                  30

Thr Arg Met Pro Asn Leu Leu Gly His Thr Ser Gln Gly Glu Ala Ala
             35                  40                  45

Ala Glu Leu Ala Glu Phe Ala Pro Leu Val Gln Tyr Gly Cys His Ser
 50                  55                  60

His Leu Arg Phe Phe Leu Cys Ser Leu Tyr Ala Pro Met Cys Thr Asp
 65                  70                  75                  80

Gln Val Ser Thr Pro Ile Pro Ala Cys Arg Pro Met Cys Glu Gln Ala
                 85                  90                  95

Arg Leu Arg Cys Ala Pro Ile Met Glu Gln Phe Asn Phe Gly Trp Pro
                100                 105                 110

Asp Ser Leu Asp Cys Ala Arg Leu Pro Thr Arg Asn Asp Pro His Ala
            115                 120                 125

Leu Cys Met Glu Ala Pro Glu Asn Ala
        130                 135

<210> SEQ ID NO 31
<211> LENGTH: 134
<212> TYPE: PRT
<213> ORGANISM: Homo sapiens

<400> SEQUENCE: 31

Ile Ser Ser Met Asp Met Glu Arg Pro Gly Asp Gly Lys Cys Gln Pro
 1               5                  10                  15

Ile Glu Ile Pro Met Cys Lys Asp Ile Gly Tyr Asn Met Thr Arg Met
                 20                  25                  30

Pro Asn Leu Met Gly His Glu Asn Gln Arg Glu Ala Ala Ile Gln Leu
             35                  40                  45

His Glu Phe Ala Pro Leu Val Glu Tyr Gly Cys His Gly His Leu Arg
 50                  55                  60

Phe Phe Leu Cys Ser Leu Tyr Ala Pro Met Cys Thr Glu Gln Val Ser
 65                  70                  75                  80

Thr Pro Ile Pro Ala Cys Arg Val Met Cys Glu Gln Ala Arg Leu Lys
                 85                  90                  95

Cys Ser Pro Ile Met Glu Gln Phe Asn Phe Lys Trp Pro Asp Ser Leu

```
                100             105             110
Asp Cys Arg Lys Leu Pro Asn Lys Asn Asp Pro Asn Tyr Leu Cys Met
            115                 120                 125
Glu Ala Pro Asn Asn Gly
            130

<210> SEQ ID NO 32
<211> LENGTH: 112
<212> TYPE: PRT
<213> ORGANISM: Homo sapiens

<400> SEQUENCE: 32

Cys Gln Pro Ile Ser Ile Pro Leu Cys Thr Asp Ile Ala Tyr Asn Gln
1               5                   10                  15
Thr Ile Met Pro Asn Leu Leu Gly His Thr Asn Gln Glu Asp Ala Gly
            20                  25                  30
Leu Glu Val His Gln Phe Tyr Pro Leu Val Lys Val Gln Cys Ser Ala
            35                  40                  45
Glu Leu Lys Phe Phe Leu Cys Ser Met Tyr Ala Pro Val Cys Thr Val
        50                  55                  60
Leu Glu Gln Ala Leu Pro Pro Cys Arg Ser Leu Cys Glu Arg Ala Arg
65                  70                  75                  80
Gln Gly Cys Glu Ala Leu Met Asn Lys Phe Gly Phe Gln Trp Pro Asp
                85                  90                  95
Thr Leu Lys Cys Glu Lys Phe Pro Val His Gly Ala Gly Glu Leu Cys
                100                 105                 110

<210> SEQ ID NO 33
<211> LENGTH: 112
<212> TYPE: PRT
<213> ORGANISM: Homo sapiens

<400> SEQUENCE: 33

Cys Gln Pro Ile Ser Ile Pro Leu Cys Thr Asp Ile Ala Tyr Asn Gln
1               5                   10                  15
Thr Ile Met Pro Asn Leu Leu Gly His Thr Asn Gln Glu Asp Ala Gly
            20                  25                  30
Leu Glu Val His Gln Phe Tyr Pro Leu Val Lys Val Gln Cys Ser Pro
            35                  40                  45
Glu Leu Arg Phe Phe Leu Cys Ser Met Tyr Ala Pro Val Cys Thr Val
        50                  55                  60
Leu Glu Gln Ala Ile Pro Pro Cys Arg Ser Ile Cys Glu Arg Ala Arg
65                  70                  75                  80
Gln Gly Cys Glu Ala Leu Met Asn Lys Phe Gly Phe Gln Trp Pro Glu
                85                  90                  95
Arg Leu Arg Cys Glu His Phe Pro Arg His Gly Ala Glu Gln Ile Cys
                100                 105                 110

<210> SEQ ID NO 34
<211> LENGTH: 106
<212> TYPE: PRT
<213> ORGANISM: Homo sapiens

<400> SEQUENCE: 34

Cys Glu Pro Ile Thr Leu Arg Met Cys Gln Asp Leu Pro Tyr Asn Thr
1               5                   10                  15
Thr Phe Met Pro Asn Leu Leu Asn His Tyr Asp Gln Gln Thr Ala Ala
            20                  25                  30
```

```
Leu Ala Met Glu Pro Phe His Pro Met Val Asn Leu Asp Cys Ser Arg
        35                  40                  45

Asp Phe Arg Pro Phe Leu Cys Ala Leu Tyr Ala Pro Ile Cys Met Glu
 50                  55                  60

Tyr Gly Arg Val Thr Leu Pro Cys Arg Arg Leu Cys Gln Arg Ala Tyr
 65                  70                  75                  80

Ser Glu Cys Ser Lys Leu Met Glu Met Phe Gly Val Pro Trp Pro Glu
                 85                  90                  95

Asp Met Glu Cys Ser Arg Phe Pro Asp Cys
                100                 105

<210> SEQ ID NO 35
<211> LENGTH: 114
<212> TYPE: PRT
<213> ORGANISM: Homo sapiens

<400> SEQUENCE: 35

Cys Asp Pro Ile Arg Ile Ser Met Cys Gln Asn Leu Gly Tyr Asn Val
 1               5                  10                  15

Thr Lys Met Pro Asn Leu Val Gly His Glu Leu Gln Thr Asp Ala Glu
                 20                  25                  30

Leu Gln Leu Thr Thr Phe Thr Pro Leu Ile Gln Tyr Gly Cys Ser Ser
        35                  40                  45

Gln Leu Gln Phe Phe Leu Cys Ser Val Tyr Val Pro Met Cys Thr Glu
 50                  55                  60

Lys Ile Asn Ile Pro Ile Gly Pro Cys Gly Gly Met Cys Leu Ser Val
 65                  70                  75                  80

Lys Arg Arg Cys Glu Pro Val Leu Lys Glu Phe Gly Phe Ala Trp Pro
                 85                  90                  95

Glu Ser Leu Asn Cys Ser Lys Phe Pro Pro Gln Asn Asp His Asn His
                100                 105                 110

Met Cys

<210> SEQ ID NO 36
<211> LENGTH: 115
<212> TYPE: PRT
<213> ORGANISM: Homo sapiens

<400> SEQUENCE: 36

Cys Gln Glu Ile Thr Val Pro Met Cys Arg Gly Ile Gly Tyr Asn Leu
 1               5                  10                  15

Thr His Met Pro Asn Gln Phe Asn His Asp Thr Gln Asp Glu Ala Gly
                 20                  25                  30

Leu Glu Val His Gln Phe Trp Pro Leu Val Glu Ile Gln Cys Ser Pro
        35                  40                  45

Asp Leu Arg Phe Phe Leu Cys Ser Met Tyr Thr Pro Ile Cys Leu Pro
 50                  55                  60

Asp Tyr His Lys Pro Leu Pro Pro Cys Arg Ser Val Cys Glu Arg Ala
 65                  70                  75                  80

Lys Ala Gly Cys Ser Pro Leu Met Arg Gln Tyr Gly Phe Ala Trp Pro
                 85                  90                  95

Glu Arg Met Ser Cys Asp Arg Leu Pro Val Leu Gly Arg Asp Ala Glu
                100                 105                 110

Val Leu Cys
        115
```

<210> SEQ ID NO 37
<211> LENGTH: 106
<212> TYPE: PRT
<213> ORGANISM: Homo sapiens

<400> SEQUENCE: 37

Cys Glu Pro Ile Thr Val Pro Arg Cys Met Lys Met Ala Tyr Asn Met
1               5                   10                  15

Thr Phe Phe Pro Asn Leu Met Gly His Tyr Asp Gln Ser Ile Ala Ala
            20                  25                  30

Val Glu Met Glu His Phe Leu Pro Leu Ala Asn Leu Glu Cys Ser Pro
        35                  40                  45

Asn Ile Glu Thr Phe Leu Cys Lys Ala Phe Val Pro Thr Cys Ile Glu
    50                  55                  60

Gln Ile His Val Val Pro Pro Cys Arg Lys Leu Cys Glu Lys Val Tyr
65                  70                  75                  80

Ser Asp Cys Lys Lys Leu Ile Asp Thr Phe Gly Ile Arg Trp Pro Glu
                85                  90                  95

Glu Leu Glu Cys Asp Arg Leu Gln Tyr Cys
            100                 105

<210> SEQ ID NO 38
<211> LENGTH: 112
<212> TYPE: PRT
<213> ORGANISM: Homo sapiens

<400> SEQUENCE: 38

Cys Gln Pro Ile Ser Ile Pro Leu Cys Thr Asp Ile Ala Tyr Asn Gln
1               5                   10                  15

Thr Ile Leu Pro Asn Leu Leu Gly His Thr Asn Gln Glu Asp Ala Gly
            20                  25                  30

Leu Glu Val His Gln Phe Tyr Pro Leu Val Lys Val Gln Cys Ser Pro
        35                  40                  45

Glu Leu Arg Phe Phe Leu Cys Ser Met Tyr Ala Pro Val Cys Thr Val
    50                  55                  60

Leu Asp Gln Ala Ile Pro Pro Cys Arg Ser Leu Cys Glu Arg Ala Arg
65                  70                  75                  80

Gln Gly Cys Glu Ala Leu Met Asn Lys Phe Gly Phe Gln Trp Pro Glu
                85                  90                  95

Arg Leu Arg Cys Glu Asn Phe Pro Val His Gly Ala Gly Glu Ile Cys
            100                 105                 110

<210> SEQ ID NO 39
<211> LENGTH: 114
<212> TYPE: PRT
<213> ORGANISM: Homo sapiens

<400> SEQUENCE: 39

Cys Gln Glu Ile Thr Val Pro Leu Cys Lys Gly Ile Gly Tyr Asn Tyr
1               5                   10                  15

Thr Tyr Met Pro Asn Gln Phe Asn His Asp Thr Gln Asp Glu Ala Gly
            20                  25                  30

Leu Glu Val His Gln Phe Trp Pro Leu Val Glu Ile Gln Cys Ser Pro
        35                  40                  45

Asp Leu Lys Phe Phe Leu Cys Ser Met Tyr Thr Pro Ile Cys Leu Glu
    50                  55                  60

Asp Tyr Lys Lys Pro Leu Pro Pro Cys Arg Ser Val Cys Glu Arg Ala

```
                65                  70                  75                  80
Lys Ala Gly Cys Ala Pro Leu Met Arg Gln Tyr Gly Phe Ala Trp Pro
                    85                  90                  95

Asp Arg Met Arg Cys Asp Arg Leu Pro Glu Gln Gly Asn Pro Asp Thr
                100                 105                 110

Leu Cys

<210> SEQ ID NO 40
<211> LENGTH: 114
<212> TYPE: PRT
<213> ORGANISM: Homo sapiens

<400> SEQUENCE: 40

Cys Gln Ala Val Glu Ile Pro Met Cys Arg Gly Ile Gly Tyr Asn Leu
1               5                   10                  15

Thr Arg Met Pro Asn Leu Leu Gly His Thr Ser Gln Gly Glu Ala Ala
                20                  25                  30

Ala Glu Leu Ala Glu Phe Ala Pro Leu Val Gln Tyr Gly Cys His Ser
            35                  40                  45

His Leu Arg Phe Phe Leu Cys Ser Leu Tyr Ala Pro Met Cys Thr Asp
        50                  55                  60

Gln Val Ser Thr Pro Ile Pro Ala Cys Arg Pro Met Cys Glu Gln Ala
65                  70                  75                  80

Arg Leu Arg Cys Ala Pro Ile Met Glu Gln Phe Asn Phe Gly Trp Pro
                85                  90                  95

Asp Ser Leu Asp Cys Ala Arg Leu Pro Thr Arg Asn Asp Pro His Ala
                100                 105                 110

Leu Cys

<210> SEQ ID NO 41
<211> LENGTH: 114
<212> TYPE: PRT
<213> ORGANISM: Homo sapiens

<400> SEQUENCE: 41

Cys Gln Pro Ile Glu Ile Pro Met Cys Lys Asp Ile Gly Tyr Asn Met
1               5                   10                  15

Thr Arg Met Pro Asn Leu Met Gly His Glu Asn Gln Arg Glu Ala Ala
                20                  25                  30

Ile Gln Leu His Glu Phe Ala Pro Leu Val Glu Tyr Gly Cys His Gly
            35                  40                  45

His Leu Arg Phe Phe Leu Cys Ser Leu Tyr Ala Pro Met Cys Thr Glu
        50                  55                  60

Gln Val Ser Thr Pro Ile Pro Ala Cys Arg Val Met Cys Glu Gln Ala
65                  70                  75                  80

Arg Leu Lys Cys Ser Pro Ile Met Glu Gln Phe Asn Phe Lys Trp Pro
                85                  90                  95

Asp Ser Leu Asp Cys Arg Lys Leu Pro Asn Lys Asn Asp Pro Asn Tyr
                100                 105                 110

Leu Cys

<210> SEQ ID NO 42
<211> LENGTH: 227
<212> TYPE: PRT
<213> ORGANISM: Homo sapiens

<400> SEQUENCE: 42
```

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys
225

<210> SEQ ID NO 43
<211> LENGTH: 227
<212> TYPE: PRT
<213> ORGANISM: Artificial Sequence
<220> FEATURE:
<223> OTHER INFORMATION: Human IgG1 Fc region variant

<400> SEQUENCE: 43

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125
```

```
Tyr Thr Leu Pro Pro Ser Arg Glu Glu Met Thr Lys Asn Gln Val Ser
            130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys
225

<210> SEQ ID NO 44
<211> LENGTH: 224
<212> TYPE: PRT
<213> ORGANISM: Homo sapiens

<400> SEQUENCE: 44

Cys Val Glu Cys Pro Pro Cys Pro Ala Pro Pro Val Ala Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Gln Phe Asn Trp Tyr Val Asp Gly Val Glu Val His Asn Ala
    50                  55                  60

Lys Thr Lys Pro Arg Glu Glu Gln Phe Asn Ser Thr Phe Arg Val Val
65                  70                  75                  80

Ser Val Leu Thr Val Val His Gln Asp Trp Leu Asn Gly Lys Glu Tyr
                85                  90                  95

Lys Cys Lys Val Ser Asn Lys Gly Leu Pro Ala Pro Ile Glu Lys Thr
            100                 105                 110

Ile Ser Lys Thr Lys Gly Gln Pro Arg Glu Pro Gln Val Tyr Thr Leu
        115                 120                 125

Pro Pro Ser Arg Glu Glu Met Thr Lys Asn Gln Val Ser Leu Thr Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Met Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly Lys
    210                 215                 220

<210> SEQ ID NO 45
<211> LENGTH: 235
<212> TYPE: PRT
<213> ORGANISM: Homo sapiens

<400> SEQUENCE: 45
```

-continued

```
Thr Lys Val Asp Lys Thr Val Glu Arg Lys Cys Val Glu Cys Pro
1               5                   10                  15

Pro Cys Pro Ala Pro Pro Val Ala Gly Pro Ser Val Phe Leu Phe Pro
            20                  25                  30

Pro Lys Pro Lys Asp Thr Leu Met Ile Ser Arg Thr Pro Glu Val Thr
            35                  40                  45

Cys Val Val Val Asp Val Ser His Glu Asp Pro Glu Val Gln Phe Asn
            50                  55                  60

Trp Tyr Val Asp Gly Val Glu Val His Asn Ala Lys Thr Lys Pro Arg
65              70                  75                  80

Glu Glu Gln Phe Asn Ser Thr Phe Arg Val Val Ser Val Leu Thr Val
                85                  90                  95

Val His Gln Asp Trp Leu Asn Gly Lys Glu Tyr Lys Cys Lys Val Ser
                100                 105                 110

Asn Lys Gly Leu Pro Ala Pro Ile Glu Lys Thr Ile Ser Lys Thr Lys
                115                 120                 125

Gly Gln Pro Arg Glu Pro Gln Val Tyr Thr Leu Pro Pro Ser Arg Glu
                130                 135                 140

Glu Met Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Met Leu Asp Ser Asp Gly Ser Phe
                180                 185                 190

Phe Leu Tyr Ser Lys Leu Thr Val Asp Lys Ser Arg Trp Gln Gln Gly
                195                 200                 205

Asn Val Phe Ser Cys Ser Val Met His Glu Ala Leu His Asn His Tyr
                210                 215                 220

Thr Gln Lys Ser Leu Ser Leu Ser Pro Gly Lys
225                 230                 235

<210> SEQ ID NO 46
<211> LENGTH: 235
<212> TYPE: PRT
<213> ORGANISM: Artificial Sequence
<220> FEATURE:
<223> OTHER INFORMATION: Human IgG2 Fc region variant

<400> SEQUENCE: 46

Thr Lys Val Asp Lys Thr Val Glu Arg Lys Ser Cys Val Glu Cys Pro
1               5                   10                  15

Pro Cys Pro Ala Pro Pro Val Ala Gly Pro Ser Val Phe Leu Phe Pro
            20                  25                  30

Pro Lys Pro Lys Asp Thr Leu Met Ile Ser Arg Thr Pro Glu Val Thr
            35                  40                  45

Cys Val Val Val Asp Val Ser His Glu Asp Pro Glu Val Gln Phe Asn
            50                  55                  60

Trp Tyr Val Asp Gly Val Glu Val His Asn Ala Lys Thr Lys Pro Arg
65              70                  75                  80

Glu Glu Gln Phe Asn Ser Thr Phe Arg Val Val Ser Val Leu Thr Val
                85                  90                  95

Val His Gln Asp Trp Leu Asn Gly Lys Glu Tyr Lys Cys Lys Val Ser
                100                 105                 110

Asn Lys Gly Leu Pro Ala Pro Ile Glu Lys Thr Ile Ser Lys Thr Lys
                115                 120                 125
```

```
Gly Gln Pro Arg Glu Pro Gln Val Tyr Thr Leu Pro Pro Ser Arg Glu
            130                 135                 140

Glu Met Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Met Leu Asp Ser Asp Gly Ser Phe
            180                 185                 190

Phe Leu Tyr Ser Lys Leu Thr Val Asp Lys Ser Arg Trp Gln Gln Gly
        195                 200                 205

Asn Val Phe Ser Cys Ser Val Met His Glu Ala Leu His Asn His Tyr
            210                 215                 220

Thr Gln Lys Ser Leu Ser Leu Ser Pro Gly Lys
225                 230                 235

<210> SEQ ID NO 47
<211> LENGTH: 224
<212> TYPE: PRT
<213> ORGANISM: Artificial Sequence
<220> FEATURE:
<223> OTHER INFORMATION: Human IgG2 Fc region (Variant 13A)

<400> SEQUENCE: 47

Cys Val Glu Cys Pro Pro Cys Pro Ala Pro Pro Val Ala Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Gln Phe Asn Trp Tyr Val Asp Gly Val Glu Val His Asn Ala
    50                  55                  60

Lys Thr Lys Pro Arg Glu Glu Gln Phe Asn Ser Thr Phe Arg Val Val
65                  70                  75                  80

Ser Val Leu Thr Val Val His Gln Asp Trp Leu Asn Gly Lys Glu Tyr
                85                  90                  95

Lys Cys Lys Val Ser Asn Lys Gly Leu Pro Ala Pro Ile Glu Lys Thr
            100                 105                 110

Ile Ser Lys Thr Lys Gly Gln Pro Arg Glu Pro Gln Val Tyr Thr Leu
        115                 120                 125

Pro Pro Ser Arg Glu Lys Met Thr Lys Asn Gln Val Ser Leu Thr Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Met Leu Lys
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly Lys
    210                 215                 220

<210> SEQ ID NO 48
<211> LENGTH: 224
<212> TYPE: PRT
<213> ORGANISM: Artificial Sequence
```

```
<220> FEATURE:
<223> OTHER INFORMATION: Human IgG2 Fc region (Variant 13B)

<400> SEQUENCE: 48

Cys Val Glu Cys Pro Pro Cys Pro Ala Pro Pro Val Ala Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Gln Phe Asn Trp Tyr Val Asp Gly Val Glu Val His Asn Ala
    50                  55                  60

Lys Thr Lys Pro Arg Glu Glu Gln Phe Asn Ser Thr Phe Arg Val Val
65                  70                  75                  80

Ser Val Leu Thr Val Val His Gln Asp Trp Leu Asn Gly Lys Glu Tyr
                85                  90                  95

Lys Cys Lys Val Ser Asn Lys Gly Leu Pro Ala Pro Ile Glu Lys Thr
            100                 105                 110

Ile Ser Lys Thr Lys Gly Gln Pro Arg Glu Pro Gln Val Tyr Thr Leu
        115                 120                 125

Pro Pro Ser Arg Glu Glu Met Thr Lys Asn Gln Val Ser Leu Thr Cys
    130                 135                 140

Leu Val Glu Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Met Leu Asp
                165                 170                 175

Ser Asp Gly Ser Phe Phe Leu Tyr Ser Glu Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly Lys
    210                 215                 220

<210> SEQ ID NO 49
<211> LENGTH: 235
<212> TYPE: PRT
<213> ORGANISM: Artificial Sequence
<220> FEATURE:
<223> OTHER INFORMATION: Human IgG2 Fc region (Variant 13A)

<400> SEQUENCE: 49

Thr Lys Val Asp Lys Thr Val Glu Arg Lys Cys Cys Val Glu Cys Pro
1               5                   10                  15

Pro Cys Pro Ala Pro Pro Val Ala Gly Pro Ser Val Phe Leu Phe Pro
            20                  25                  30

Pro Lys Pro Lys Asp Thr Leu Met Ile Ser Arg Thr Pro Glu Val Thr
        35                  40                  45

Cys Val Val Val Asp Val Ser His Glu Asp Pro Glu Val Gln Phe Asn
    50                  55                  60

Trp Tyr Val Asp Gly Val Glu Val His Asn Ala Lys Thr Lys Pro Arg
65                  70                  75                  80

Glu Glu Gln Phe Asn Ser Thr Phe Arg Val Val Ser Val Leu Thr Val
                85                  90                  95

Val His Gln Asp Trp Leu Asn Gly Lys Glu Tyr Lys Cys Lys Val Ser
            100                 105                 110

Asn Lys Gly Leu Pro Ala Pro Ile Glu Lys Thr Ile Ser Lys Thr Lys
```

```
                115                 120                 125
Gly Gln Pro Arg Glu Pro Gln Val Tyr Thr Leu Pro Pro Ser Arg Glu
            130                 135                 140

Lys Met Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Met Leu Lys Ser Asp Gly Ser Phe
            180                 185                 190

Phe Leu Tyr Ser Lys Leu Thr Val Asp Lys Ser Arg Trp Gln Gln Gly
                195                 200                 205

Asn Val Phe Ser Cys Ser Val Met His Glu Ala Leu His Asn His Tyr
            210                 215                 220

Thr Gln Lys Ser Leu Ser Leu Ser Pro Gly Lys
225                 230                 235

<210> SEQ ID NO 50
<211> LENGTH: 235
<212> TYPE: PRT
<213> ORGANISM: Artificial Sequence
<220> FEATURE:
<223> OTHER INFORMATION: Human IgG2 Fc region variant (Variant 13A)

<400> SEQUENCE: 50

Thr Lys Val Asp Lys Thr Val Glu Arg Lys Ser Cys Val Glu Cys Pro
1               5                   10                  15

Pro Cys Pro Ala Pro Pro Val Ala Gly Pro Ser Val Phe Leu Phe Pro
            20                  25                  30

Pro Lys Pro Lys Asp Thr Leu Met Ile Ser Arg Thr Pro Glu Val Thr
                35                  40                  45

Cys Val Val Val Asp Val Ser His Glu Asp Pro Glu Val Gln Phe Asn
            50                  55                  60

Trp Tyr Val Asp Gly Val Glu Val His Asn Ala Lys Thr Lys Pro Arg
65                  70                  75                  80

Glu Glu Gln Phe Asn Ser Thr Phe Arg Val Val Ser Val Leu Thr Val
                85                  90                  95

Val His Gln Asp Trp Leu Asn Gly Lys Glu Tyr Lys Cys Lys Val Ser
            100                 105                 110

Asn Lys Gly Leu Pro Ala Pro Ile Glu Lys Thr Ile Ser Lys Thr Lys
                115                 120                 125

Gly Gln Pro Arg Glu Pro Gln Val Tyr Thr Leu Pro Pro Ser Arg Glu
            130                 135                 140

Lys Met Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Met Leu Lys Ser Asp Gly Ser Phe
            180                 185                 190

Phe Leu Tyr Ser Lys Leu Thr Val Asp Lys Ser Arg Trp Gln Gln Gly
                195                 200                 205

Asn Val Phe Ser Cys Ser Val Met His Glu Ala Leu His Asn His Tyr
            210                 215                 220

Thr Gln Lys Ser Leu Ser Leu Ser Pro Gly Lys
225                 230                 235
```

```
<210> SEQ ID NO 51
<211> LENGTH: 235
<212> TYPE: PRT
<213> ORGANISM: Artificial Sequence
<220> FEATURE:
<223> OTHER INFORMATION: Human IgG2 Fc region (Variant 13B)

<400> SEQUENCE: 51

Thr Lys Val Asp Lys Thr Val Glu Arg Lys Cys Cys Val Glu Cys Pro
1               5                   10                  15

Pro Cys Pro Ala Pro Pro Val Ala Gly Pro Ser Val Phe Leu Phe Pro
            20                  25                  30

Pro Lys Pro Lys Asp Thr Leu Met Ile Ser Arg Thr Pro Glu Val Thr
        35                  40                  45

Cys Val Val Val Asp Val Ser His Glu Asp Pro Glu Val Gln Phe Asn
    50                  55                  60

Trp Tyr Val Asp Gly Val Glu Val His Asn Ala Lys Thr Lys Pro Arg
65                  70                  75                  80

Glu Glu Gln Phe Asn Ser Thr Phe Arg Val Val Ser Val Leu Thr Val
                85                  90                  95

Val His Gln Asp Trp Leu Asn Gly Lys Glu Tyr Lys Cys Lys Val Ser
            100                 105                 110

Asn Lys Gly Leu Pro Ala Pro Ile Glu Lys Thr Ile Ser Lys Thr Lys
        115                 120                 125

Gly Gln Pro Arg Glu Pro Gln Val Tyr Thr Leu Pro Pro Ser Arg Glu
    130                 135                 140

Glu Met Thr Lys Asn Gln Val Ser Leu Thr Cys Leu Val Glu Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Met Leu Asp Ser Asp Gly Ser Phe
            180                 185                 190

Phe Leu Tyr Ser Glu Leu Thr Val Asp Lys Ser Arg Trp Gln Gln Gly
        195                 200                 205

Asn Val Phe Ser Cys Ser Val Met His Glu Ala Leu His Asn His Tyr
    210                 215                 220

Thr Gln Lys Ser Leu Ser Leu Ser Pro Gly Lys
225                 230                 235

<210> SEQ ID NO 52
<211> LENGTH: 235
<212> TYPE: PRT
<213> ORGANISM: Artificial Sequence
<220> FEATURE:
<223> OTHER INFORMATION: Human IgG2 Fc region variant (Variant 13B)

<400> SEQUENCE: 52

Thr Lys Val Asp Lys Thr Val Glu Arg Lys Ser Cys Val Glu Cys Pro
1               5                   10                  15

Pro Cys Pro Ala Pro Pro Val Ala Gly Pro Ser Val Phe Leu Phe Pro
            20                  25                  30

Pro Lys Pro Lys Asp Thr Leu Met Ile Ser Arg Thr Pro Glu Val Thr
        35                  40                  45

Cys Val Val Val Asp Val Ser His Glu Asp Pro Glu Val Gln Phe Asn
    50                  55                  60

Trp Tyr Val Asp Gly Val Glu Val His Asn Ala Lys Thr Lys Pro Arg
65                  70                  75                  80
```

```
Glu Glu Gln Phe Asn Ser Thr Phe Arg Val Ser Val Leu Thr Val
                85                  90                  95

Val His Gln Asp Trp Leu Asn Gly Lys Glu Tyr Lys Cys Lys Val Ser
            100                 105                 110

Asn Lys Gly Leu Pro Ala Pro Ile Glu Lys Thr Ile Ser Lys Thr Lys
            115                 120                 125

Gly Gln Pro Arg Glu Pro Gln Val Tyr Thr Leu Pro Pro Ser Arg Glu
130             135                 140

Glu Met Thr Lys Asn Gln Val Ser Leu Thr Cys Leu Val Glu Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Met Leu Asp Ser Asp Gly Ser Phe
            180                 185                 190

Phe Leu Tyr Ser Glu Leu Thr Val Asp Lys Ser Arg Trp Gln Gln Gly
            195                 200                 205

Asn Val Phe Ser Cys Ser Val Met His Glu Ala Leu His Asn His Tyr
            210                 215                 220

Thr Gln Lys Ser Leu Ser Leu Ser Pro Gly Lys
225                 230                 235

<210> SEQ ID NO 53
<211> LENGTH: 363
<212> TYPE: PRT
<213> ORGANISM: Artificial Sequence
<220> FEATURE:
<223> OTHER INFORMATION: FZD8-Fc variant 54F28 amino acid sequence
      without predicted signal sequence

<400> SEQUENCE: 53

Ala Ser Ala Lys Glu Leu Ala Cys Gln Glu Ile Thr Val Pro Leu Cys
1               5                   10                  15

Lys Gly Ile Gly Tyr Asn Tyr Thr Tyr Met Pro Asn Gln Phe Asn His
            20                  25                  30

Asp Thr Gln Asp Glu Ala Gly Leu Glu Val His Gln Phe Trp Pro Leu
        35                  40                  45

Val Glu Ile Gln Cys Ser Pro Asp Leu Lys Phe Phe Leu Cys Ser Met
    50                  55                  60

Tyr Thr Pro Ile Cys Leu Glu Asp Tyr Lys Lys Pro Leu Pro Pro Cys
65                  70                  75                  80

Arg Ser Val Cys Glu Arg Ala Lys Ala Gly Cys Ala Pro Leu Met Arg
                85                  90                  95

Gln Tyr Gly Phe Ala Trp Pro Asp Arg Met Arg Cys Asp Arg Leu Pro
            100                 105                 110

Glu Gln Gly Asn Pro Asp Thr Leu Cys Met Asp Tyr Asn Arg Thr Asp
            115                 120                 125

Leu Thr Thr Glu Pro Lys Ser Ser Asp Lys Thr His Thr Cys Pro Pro
130                 135                 140

Cys Pro Ala Pro Glu Leu Leu Gly Gly Pro Ser Val Phe Leu Phe Pro
145                 150                 155                 160

Pro Lys Pro Lys Asp Thr Leu Met Ile Ser Arg Thr Pro Glu Val Thr
                165                 170                 175

Cys Val Val Val Asp Val Ser His Glu Asp Pro Glu Val Lys Phe Asn
            180                 185                 190

Trp Tyr Val Asp Gly Val Glu Val His Asn Ala Lys Thr Lys Pro Arg
            195                 200                 205
```

```
Glu Gln Tyr Asn Ser Thr Tyr Arg Val Val Ser Val Leu Thr Val
    210                 215                 220

Leu His Gln Asp Trp Leu Asn Gly Lys Glu Tyr Lys Cys Lys Val Ser
225                 230                 235                 240

Asn Lys Ala Leu Pro Ala Pro Ile Glu Lys Thr Ile Ser Lys Ala Lys
                245                 250                 255

Gly Gln Pro Arg Glu Pro Gln Val Tyr Thr Leu Pro Pro Ser Arg Asp
                260                 265                 270

Glu Leu Thr Lys Asn Gln Val Ser Leu Thr Cys Leu Val Lys Gly Phe
            275                 280                 285

Tyr Pro Ser Asp Ile Ala Val Glu Trp Glu Ser Asn Gly Gln Pro Glu
            290                 295                 300

Asn Asn Tyr Lys Thr Thr Pro Pro Val Leu Asp Ser Asp Gly Ser Phe
305                 310                 315                 320

Phe Leu Tyr Ser Lys Leu Thr Val Asp Lys Ser Arg Trp Gln Gln Gly
                325                 330                 335

Asn Val Phe Ser Cys Ser Val Met His Glu Ala Leu His Asn His Tyr
                340                 345                 350

Thr Gln Lys Ser Leu Ser Leu Ser Pro Gly Lys
            355                 360

<210> SEQ ID NO 54
<211> LENGTH: 390
<212> TYPE: PRT
<213> ORGANISM: Artificial Sequence
<220> FEATURE:
<223> OTHER INFORMATION: FZD8-Fc variant 54F28 amino acid sequence with
      signal sequence

<400> SEQUENCE: 54

Met Glu Trp Gly Tyr Leu Leu Glu Val Thr Ser Leu Leu Ala Ala Leu
1               5                   10                  15

Leu Leu Leu Gln Arg Ser Pro Phe Val His Ala Ala Ser Ala Lys Glu
                20                  25                  30

Leu Ala Cys Gln Glu Ile Thr Val Pro Leu Cys Lys Gly Ile Gly Tyr
            35                  40                  45

Asn Tyr Thr Tyr Met Pro Asn Gln Phe Asn His Asp Thr Gln Asp Glu
50                  55                  60

Ala Gly Leu Glu Val His Gln Phe Trp Pro Leu Val Glu Ile Gln Cys
65                  70                  75                  80

Ser Pro Asp Leu Lys Phe Phe Leu Cys Ser Met Tyr Thr Pro Ile Cys
                85                  90                  95

Leu Glu Asp Tyr Lys Lys Pro Leu Pro Pro Cys Arg Ser Val Cys Glu
            100                 105                 110

Arg Ala Lys Ala Gly Cys Ala Pro Leu Met Arg Gln Tyr Gly Phe Ala
        115                 120                 125

Trp Pro Asp Arg Met Arg Cys Asp Arg Leu Pro Glu Gln Gly Asn Pro
    130                 135                 140

Asp Thr Leu Cys Met Asp Tyr Asn Arg Thr Asp Leu Thr Thr Glu Pro
145                 150                 155                 160

Lys Ser Ser Asp Lys Thr His Thr Cys Pro Pro Cys Pro Ala Pro Glu
                165                 170                 175

Leu Leu Gly Gly Pro Ser Val Phe Leu Phe Pro Pro Lys Pro Lys Asp
            180                 185                 190

Thr Leu Met Ile Ser Arg Thr Pro Glu Val Thr Cys Val Val Val Asp
```

```
                    195                 200                 205
        Val Ser His Glu Asp Pro Glu Val Lys Phe Asn Trp Tyr Val Asp Gly
            210                 215                 220

Val Glu Val His Asn Ala Lys Thr Lys Pro Arg Glu Glu Gln Tyr Asn
        225                 230                 235                 240

Ser Thr Tyr Arg Val Val Ser Val Leu Thr Val Leu His Gln Asp Trp
                        245                 250                 255

Leu Asn Gly Lys Glu Tyr Lys Cys Lys Val Ser Asn Lys Ala Leu Pro
                    260                 265                 270

Ala Pro Ile Glu Lys Thr Ile Ser Lys Ala Lys Gly Gln Pro Arg Glu
                275                 280                 285

Pro Gln Val Tyr Thr Leu Pro Pro Ser Arg Asp Glu Leu Thr Lys Asn
        290                 295                 300

Gln Val Ser Leu Thr Cys Leu Val Lys Gly Phe Tyr Pro Ser Asp Ile
        305                 310                 315                 320

Ala Val Glu Trp Glu Ser Asn Gly Gln Pro Glu Asn Asn Tyr Lys Thr
                        325                 330                 335

Thr Pro Pro Val Leu Asp Ser Asp Gly Ser Phe Phe Leu Tyr Ser Lys
                    340                 345                 350

Leu Thr Val Asp Lys Ser Arg Trp Gln Gln Gly Asn Val Phe Ser Cys
                355                 360                 365

Ser Val Met His Glu Ala Leu His Asn His Tyr Thr Gln Lys Ser Leu
            370                 375                 380

Ser Leu Ser Pro Gly Lys
        385                 390

<210> SEQ ID NO 55
<211> LENGTH: 393
<212> TYPE: PRT
<213> ORGANISM: Artificial Sequence
<220> FEATURE:
<223> OTHER INFORMATION: FZD8-Fc variant (13B variant) amino acid
      sequence with signal sequence

<400> SEQUENCE: 55

Met Glu Trp Gly Tyr Leu Leu Glu Val Thr Ser Leu Leu Ala Ala Leu
1               5                   10                  15

Leu Leu Leu Gln Arg Ser Pro Ile Val His Ala Ala Ser Ala Lys Glu
            20                  25                  30

Leu Ala Cys Gln Glu Ile Thr Val Pro Leu Cys Lys Gly Ile Gly Tyr
        35                  40                  45

Asn Tyr Thr Tyr Met Pro Asn Gln Phe Asn His Asp Thr Gln Asp Glu
    50                  55                  60

Ala Gly Leu Glu Val His Gln Phe Trp Pro Leu Val Glu Ile Gln Cys
65                  70                  75                  80

Ser Pro Asp Leu Lys Phe Phe Leu Cys Ser Met Tyr Thr Pro Ile Cys
                85                  90                  95

Leu Glu Asp Tyr Lys Lys Pro Leu Pro Pro Cys Arg Ser Val Cys Glu
            100                 105                 110

Arg Ala Lys Ala Gly Cys Ala Pro Leu Met Arg Gln Tyr Gly Phe Ala
        115                 120                 125

Trp Pro Asp Arg Met Arg Cys Asp Arg Leu Pro Glu Gln Gly Asn Pro
    130                 135                 140

Asp Thr Leu Cys Met Asp Tyr Asn Arg Thr Asp Leu Thr Thr Thr Lys
145                 150                 155                 160
```

```
Val Asp Lys Thr Val Glu Arg Lys Ser Cys Val Glu Cys Pro Pro Cys
            165                 170                 175

Pro Ala Pro Val Ala Gly Pro Ser Val Phe Leu Phe Pro Pro Lys
            180                 185                 190

Pro Lys Asp Thr Leu Met Ile Ser Arg Thr Pro Glu Val Thr Cys Val
            195                 200                 205

Val Val Asp Val Ser His Glu Asp Pro Glu Val Gln Phe Asn Trp Tyr
210                 215                 220

Val Asp Gly Val Glu Val His Asn Ala Lys Thr Lys Pro Arg Glu Glu
225                 230                 235                 240

Gln Phe Asn Ser Thr Phe Arg Val Val Ser Val Leu Thr Val Val His
            245                 250                 255

Gln Asp Trp Leu Asn Gly Lys Glu Tyr Lys Cys Lys Val Ser Asn Lys
            260                 265                 270

Gly Leu Pro Ala Pro Ile Glu Lys Thr Ile Ser Lys Thr Lys Gly Gln
            275                 280                 285

Pro Arg Glu Pro Gln Val Tyr Thr Leu Pro Pro Ser Arg Glu Glu Met
            290                 295                 300

Thr Lys Asn Gln Val Ser Leu Thr Cys Leu Val Glu Gly Phe Tyr Pro
305                 310                 315                 320

Ser Asp Ile Ala Val Glu Trp Glu Ser Asn Gly Gln Pro Glu Asn Asn
            325                 330                 335

Tyr Lys Thr Thr Pro Pro Met Leu Asp Ser Asp Gly Ser Phe Phe Leu
            340                 345                 350

Tyr Ser Glu Leu Thr Val Asp Lys Ser Arg Trp Gln Gln Gly Asn Val
            355                 360                 365

Phe Ser Cys Ser Val Met His Glu Ala Leu His Asn His Tyr Thr Gln
            370                 375                 380

Lys Ser Leu Ser Leu Ser Pro Gly Lys
385                 390

<210> SEQ ID NO 56
<211> LENGTH: 366
<212> TYPE: PRT
<213> ORGANISM: Artificial Sequence
<220> FEATURE:
<223> OTHER INFORMATION: FZD8-Fc variant (13B variant) amino acid
      sequence without signal sequence

<400> SEQUENCE: 56

Ala Ser Ala Lys Glu Leu Ala Cys Gln Glu Ile Thr Val Pro Leu Cys
1               5                   10                  15

Lys Gly Ile Gly Tyr Asn Tyr Thr Tyr Met Pro Asn Gln Phe Asn His
            20                  25                  30

Asp Thr Gln Asp Glu Ala Gly Leu Glu Val His Gln Phe Trp Pro Leu
            35                  40                  45

Val Glu Ile Gln Cys Ser Pro Asp Leu Lys Phe Phe Leu Cys Ser Met
    50                  55                  60

Tyr Thr Pro Ile Cys Leu Glu Asp Tyr Lys Lys Pro Leu Pro Pro Cys
65                  70                  75                  80

Arg Ser Val Cys Glu Arg Ala Lys Ala Gly Cys Ala Pro Leu Met Arg
                85                  90                  95

Gln Tyr Gly Phe Ala Trp Pro Asp Arg Met Arg Cys Asp Arg Leu Pro
            100                 105                 110

Glu Gln Gly Asn Pro Asp Thr Leu Cys Met Asp Tyr Asn Arg Thr Asp
            115                 120                 125
```

```
Leu Thr Thr Thr Lys Val Asp Lys Thr Val Glu Arg Lys Ser Cys Val
        130                 135                 140

Glu Cys Pro Pro Cys Pro Ala Pro Pro Val Ala Gly Pro Ser Val Phe
145                 150                 155                 160

Leu Phe Pro Pro Lys Pro Lys Asp Thr Leu Met Ile Ser Arg Thr Pro
                165                 170                 175

Glu Val Thr Cys Val Val Val Asp Val Ser His Glu Asp Pro Glu Val
            180                 185                 190

Gln Phe Asn Trp Tyr Val Asp Gly Val Glu Val His Asn Ala Lys Thr
        195                 200                 205

Lys Pro Arg Glu Glu Gln Phe Asn Ser Thr Phe Arg Val Val Ser Val
210                 215                 220

Leu Thr Val Val His Gln Asp Trp Leu Asn Gly Lys Glu Tyr Lys Cys
225                 230                 235                 240

Lys Val Ser Asn Lys Gly Leu Pro Ala Pro Ile Glu Lys Thr Ile Ser
                245                 250                 255

Lys Thr Lys Gly Gln Pro Arg Glu Pro Gln Val Tyr Thr Leu Pro Pro
                260                 265                 270

Ser Arg Glu Glu Met Thr Lys Asn Gln Val Ser Leu Thr Cys Leu Val
                275                 280                 285

Glu Gly Phe Tyr Pro Ser Asp Ile Ala Val Glu Trp Glu Ser Asn Gly
290                 295                 300

Gln Pro Glu Asn Asn Tyr Lys Thr Thr Pro Pro Met Leu Asp Ser Asp
305                 310                 315                 320

Gly Ser Phe Phe Leu Tyr Ser Glu Leu Thr Val Asp Lys Ser Arg Trp
                325                 330                 335

Gln Gln Gly Asn Val Phe Ser Cys Ser Val Met His Glu Ala Leu His
                340                 345                 350

Asn His Tyr Thr Gln Lys Ser Leu Ser Leu Ser Pro Gly Lys
                355                 360                 365

<210> SEQ ID NO 57
<211> LENGTH: 83
<212> TYPE: PRT
<213> ORGANISM: Homo sapiens

<400> SEQUENCE: 57

Asp Leu Val Tyr Phe Glu Lys Ser Pro Asn Phe Cys Thr Tyr Ser Gly
1               5                   10                  15

Arg Leu Gly Thr Ala Gly Thr Ala Gly Arg Ala Cys Asn Ser Ser Ser
            20                  25                  30

Pro Ala Leu Asp Gly Cys Glu Leu Leu Cys Cys Gly Arg Gly His Arg
        35                  40                  45

Thr Arg Thr Gln Arg Val Thr Glu Arg Cys Asn Cys Thr Phe His Trp
    50                  55                  60

Cys Cys His Val Ser Cys Arg Asn Cys Thr His Thr Arg Val Leu His
65                  70                  75                  80

Glu Cys Leu

<210> SEQ ID NO 58
<211> LENGTH: 94
<212> TYPE: PRT
<213> ORGANISM: Homo sapiens

<400> SEQUENCE: 58
```

Asp Leu Val Tyr Phe Glu Asn Ser Pro Asp Tyr Cys Ile Arg Asp Arg
1               5                   10                  15

Glu Ala Gly Ser Leu Gly Thr Ala Gly Arg Val Cys Asn Leu Thr Ser
            20                  25                  30

Arg Gly Met Asp Ser Cys Glu Val Met Cys Cys Gly Arg Gly Tyr Asp
        35                  40                  45

Thr Ser His Val Thr Arg Met Thr Lys Cys Gly Cys Lys Phe His Trp
    50                  55                  60

Cys Cys Ala Val Arg Cys Gln Asp Cys Leu Glu Ala Leu Asp Val His
65                  70                  75                  80

Thr Cys Lys Ala Pro Lys Asn Ala Asp Trp Thr Thr Ala Thr
                85                  90

<210> SEQ ID NO 59
<211> LENGTH: 94
<212> TYPE: PRT
<213> ORGANISM: Homo sapiens

<400> SEQUENCE: 59

Asp Leu Val Tyr Phe Asp Asn Ser Pro Asp Tyr Cys Val Leu Asp Lys
1               5                   10                  15

Ala Ala Gly Ser Leu Gly Thr Ala Gly Arg Val Cys Ser Lys Thr Ser
            20                  25                  30

Lys Gly Thr Asp Gly Cys Glu Ile Met Cys Cys Gly Arg Gly Tyr Asp
        35                  40                  45

Thr Thr Arg Val Thr Arg Val Thr Gln Cys Glu Cys Lys Phe His Trp
    50                  55                  60

Cys Cys Ala Val Arg Cys Lys Glu Cys Arg Asn Thr Val Asp Val His
65                  70                  75                  80

Thr Cys Lys Ala Pro Lys Lys Ala Glu Trp Leu Asp Gln Thr
                85                  90

<210> SEQ ID NO 60
<211> LENGTH: 83
<212> TYPE: PRT
<213> ORGANISM: Homo sapiens

<400> SEQUENCE: 60

Asp Leu Val Tyr Tyr Glu Asn Ser Pro Asn Phe Cys Glu Pro Asn Pro
1               5                   10                  15

Glu Thr Gly Ser Phe Gly Thr Arg Asp Arg Thr Cys Asn Val Thr Ser
            20                  25                  30

His Gly Ile Asp Gly Cys Asp Leu Leu Cys Cys Gly Arg Gly His Asn
        35                  40                  45

Thr Arg Thr Glu Lys Arg Lys Glu Lys Cys His Cys Ile Phe His Trp
    50                  55                  60

Cys Cys Tyr Val Ser Cys Gln Glu Cys Ile Arg Ile Tyr Asp Val His
65                  70                  75                  80

Thr Cys Lys

<210> SEQ ID NO 61
<211> LENGTH: 83
<212> TYPE: PRT
<213> ORGANISM: Homo sapiens

<400> SEQUENCE: 61

Asp Leu Val Tyr Tyr Glu Ala Ser Pro Asn Phe Cys Glu Pro Asn Pro
1               5                   10                  15

```
Glu Thr Gly Ser Phe Gly Thr Arg Asp Arg Thr Cys Asn Val Ser Ser
                20                  25                  30

His Gly Ile Asp Gly Cys Asp Leu Leu Cys Cys Gly Arg Gly His Asn
        35                  40                  45

Ala Arg Ala Glu Arg Arg Glu Lys Cys Arg Cys Val Phe His Trp
 50                  55                  60

Cys Cys Tyr Val Ser Cys Gln Glu Cys Thr Arg Val Tyr Asp Val His
 65                  70                  75                  80

Thr Cys Lys
```

<210> SEQ ID NO 62
<211> LENGTH: 83
<212> TYPE: PRT
<213> ORGANISM: Homo sapiens

<400> SEQUENCE: 62

```
Asp Leu Val Tyr Ile Glu Lys Ser Pro Asn Tyr Cys Glu Glu Asp Pro
 1               5                  10                  15

Val Thr Gly Ser Val Gly Thr Gln Gly Arg Ala Cys Asn Lys Thr Ala
                20                  25                  30

Pro Gln Ala Ser Gly Cys Asp Leu Met Cys Cys Gly Arg Gly Tyr Asn
        35                  40                  45

Thr His Gln Tyr Ala Arg Val Trp Gln Cys Asn Cys Lys Phe His Trp
 50                  55                  60

Cys Cys Tyr Val Lys Cys Asn Thr Cys Ser Glu Arg Thr Glu Met Tyr
 65                  70                  75                  80

Thr Cys Lys
```

<210> SEQ ID NO 63
<211> LENGTH: 83
<212> TYPE: PRT
<213> ORGANISM: Homo sapiens

<400> SEQUENCE: 63

```
Asp Leu Val Tyr Ile Glu Lys Ser Pro Asn Tyr Cys Glu Glu Asp Ala
 1               5                  10                  15

Ala Thr Gly Ser Val Gly Thr Gln Gly Arg Leu Cys Asn Arg Thr Ser
                20                  25                  30

Pro Gly Ala Asp Gly Cys Asp Thr Met Cys Cys Gly Arg Gly Tyr Asn
        35                  40                  45

Thr His Gln Tyr Thr Lys Val Trp Gln Cys Asn Cys Lys Phe His Trp
 50                  55                  60

Cys Cys Phe Val Lys Cys Asn Thr Cys Ser Glu Arg Thr Glu Val Phe
 65                  70                  75                  80

Thr Cys Lys
```

<210> SEQ ID NO 64
<211> LENGTH: 108
<212> TYPE: PRT
<213> ORGANISM: Homo sapiens

<400> SEQUENCE: 64

```
Glu Leu Ile Phe Leu Glu Glu Ser Pro Asp Tyr Cys Thr Cys Asn Ser
 1               5                  10                  15

Ser Leu Gly Ile Tyr Gly Thr Glu Gly Arg Glu Cys Leu Gln Asn Ser
                20                  25                  30
```

```
His Asn Thr Ser Arg Trp Glu Arg Arg Ser Cys Gly Arg Leu Cys Thr
            35                  40                  45

Glu Cys Gly Leu Gln Val Glu Glu Arg Lys Thr Glu Val Ile Ser Ser
 50                  55                  60

Cys Asn Cys Lys Phe Gln Trp Cys Cys Thr Val Lys Cys Asp Gln Cys
 65                  70                  75                  80

Arg His Val Val Ser Lys Tyr Tyr Cys Ala Arg Ser Pro Gly Ser Ala
                 85                  90                  95

Gln Ser Leu Gly Arg Val Trp Phe Gly Val Tyr Ile
            100                 105
```

<210> SEQ ID NO 65
<211> LENGTH: 107
<212> TYPE: PRT
<213> ORGANISM: Homo sapiens

<400> SEQUENCE: 65

```
Glu Leu Val His Leu Glu Asp Ser Pro Asp Tyr Cys Leu Glu Asn Lys
 1               5                  10                  15

Thr Leu Gly Leu Leu Gly Thr Glu Gly Arg Glu Cys Leu Arg Arg Gly
             20                  25                  30

Arg Ala Leu Gly Arg Trp Glu Leu Arg Ser Cys Arg Arg Leu Cys Gly
            35                  40                  45

Asp Cys Gly Leu Ala Val Glu Glu Arg Arg Ala Glu Thr Val Ser Ser
 50                  55                  60

Cys Asn Cys Lys Phe His Trp Cys Cys Ala Val Arg Cys Glu Gln Cys
 65                  70                  75                  80

Arg Arg Arg Val Thr Lys Tyr Phe Cys Ser Arg Ala Glu Arg Pro Arg
                 85                  90                  95

Gly Gly Ala Ala His Lys Pro Gly Arg Lys Pro
            100                 105
```

<210> SEQ ID NO 66
<211> LENGTH: 83
<212> TYPE: PRT
<213> ORGANISM: Homo sapiens

<400> SEQUENCE: 66

```
Asp Leu Val Tyr Phe Glu Lys Ser Pro Asp Phe Cys Glu Arg Glu Pro
 1               5                  10                  15

Arg Leu Asp Ser Ala Gly Thr Val Gly Arg Leu Cys Asn Lys Ser Ser
             20                  25                  30

Ala Gly Ser Asp Gly Cys Gly Ser Met Cys Cys Gly Arg Gly His Asn
            35                  40                  45

Ile Leu Arg Gln Thr Arg Ser Glu Arg Cys His Cys Arg Phe His Trp
 50                  55                  60

Cys Cys Phe Val Val Cys Glu Glu Cys Arg Ile Thr Glu Trp Val Ser
 65                  70                  75                  80

Val Cys Lys
```

<210> SEQ ID NO 67
<211> LENGTH: 83
<212> TYPE: PRT
<213> ORGANISM: Homo sapiens

<400> SEQUENCE: 67

```
Glu Leu Val Tyr Phe Glu Lys Ser Pro Asp Phe Cys Glu Arg Asp Pro
 1               5                  10                  15
```

```
Thr Met Gly Ser Pro Gly Thr Arg Gly Arg Ala Cys Asn Lys Thr Ser
            20                  25                  30

Arg Leu Leu Asp Gly Cys Gly Ser Leu Cys Cys Gly Arg Gly His Asn
        35                  40                  45

Val Leu Arg Gln Thr Arg Val Glu Arg Cys His Cys Arg Phe His Trp
    50                  55                  60

Cys Cys Tyr Val Leu Cys Asp Glu Cys Lys Val Thr Glu Trp Val Asn
65                  70                  75                  80

Val Cys Lys

<210> SEQ ID NO 68
<211> LENGTH: 8
<212> TYPE: PRT
<213> ORGANISM: Artificial Sequence
<220> FEATURE:
<223> OTHER INFORMATION: Linker

<400> SEQUENCE: 68

Glu Ser Gly Gly Gly Gly Val Thr
1               5

<210> SEQ ID NO 69
<211> LENGTH: 9
<212> TYPE: PRT
<213> ORGANISM: Artificial Sequence
<220> FEATURE:
<223> OTHER INFORMATION: Linker

<400> SEQUENCE: 69

Leu Glu Ser Gly Gly Gly Gly Val Thr
1               5

<210> SEQ ID NO 70
<211> LENGTH: 6
<212> TYPE: PRT
<213> ORGANISM: Artificial Sequence
<220> FEATURE:
<223> OTHER INFORMATION: Linker

<400> SEQUENCE: 70

Gly Arg Ala Gln Val Thr
1               5

<210> SEQ ID NO 71
<211> LENGTH: 6
<212> TYPE: PRT
<213> ORGANISM: Artificial Sequence
<220> FEATURE:
<223> OTHER INFORMATION: Linker

<400> SEQUENCE: 71

Trp Arg Ala Gln Val Thr
1               5

<210> SEQ ID NO 72
<211> LENGTH: 8
<212> TYPE: PRT
<213> ORGANISM: Artificial Sequence
<220> FEATURE:
<223> OTHER INFORMATION: Linker

<400> SEQUENCE: 72

Ala Arg Gly Arg Ala Gln Val Thr
1               5
```

```
<210> SEQ ID NO 73
<211> LENGTH: 8
<212> TYPE: PRT
<213> ORGANISM: Artificial Sequence
<220> FEATURE:
<223> OTHER INFORMATION: FLAG peptide

<400> SEQUENCE: 73

Asp Tyr Lys Asp Asp Asp Asp Lys
1               5

<210> SEQ ID NO 74
<211> LENGTH: 330
<212> TYPE: PRT
<213> ORGANISM: Homo sapiens

<400> SEQUENCE: 74

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 75
<211> LENGTH: 326
<212> TYPE: PRT
<213> ORGANISM: Homo sapiens

<400> SEQUENCE: 75

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 76

```
<211> LENGTH: 377
<212> TYPE: PRT
<213> ORGANISM: Homo sapiens

<400> SEQUENCE: 76

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
    130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375
```

<210> SEQ ID NO 77
<211> LENGTH: 327
<212> TYPE: PRT
<213> ORGANISM: Homo sapiens

<400> SEQUENCE: 77

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 78
<211> LENGTH: 10
<212> TYPE: PRT
<213> ORGANISM: Artificial Sequence
<220> FEATURE:
<223> OTHER INFORMATION: MET antibody Heavy chain CDR1

<400> SEQUENCE: 78

```
Gly Tyr Thr Phe Thr Ser Tyr Trp Leu His
1               5                   10

<210> SEQ ID NO 79
<211> LENGTH: 18
<212> TYPE: PRT
<213> ORGANISM: Artificial Sequence
<220> FEATURE:
<223> OTHER INFORMATION: MET antibody Heavy chain CDR2

<400> SEQUENCE: 79

Gly Met Ile Asp Pro Ser Asn Ser Asp Thr Arg Phe Asn Pro Asn Phe
1               5                   10                  15

Lys Asp

<210> SEQ ID NO 80
<211> LENGTH: 11
<212> TYPE: PRT
<213> ORGANISM: Artificial Sequence
<220> FEATURE:
<223> OTHER INFORMATION: MET Heavy chain CDR3
<220> FEATURE:
<221> NAME/KEY: MISC_FEATURE
<222> LOCATION: (1)..(1)
<223> OTHER INFORMATION: wherein X is not R

<400> SEQUENCE: 80

Xaa Tyr Gly Ser Tyr Val Ser Pro Leu Asp Tyr
1               5                   10

<210> SEQ ID NO 81
<211> LENGTH: 11
<212> TYPE: PRT
<213> ORGANISM: Artificial Sequence
<220> FEATURE:
<223> OTHER INFORMATION: MET Heavy chain CDR3

<400> SEQUENCE: 81

Thr Tyr Gly Ser Tyr Val Ser Pro Leu Asp Tyr
1               5                   10

<210> SEQ ID NO 82
<211> LENGTH: 11
<212> TYPE: PRT
<213> ORGANISM: Artificial Sequence
<220> FEATURE:
<223> OTHER INFORMATION: MET Heavy chain CDR3

<400> SEQUENCE: 82

Ser Tyr Gly Ser Tyr Val Ser Pro Leu Asp Tyr
1               5                   10

<210> SEQ ID NO 83
<211> LENGTH: 12
<212> TYPE: PRT
<213> ORGANISM: Artificial Sequence
<220> FEATURE:
<223> OTHER INFORMATION: MET Heavy chain CDR3

<400> SEQUENCE: 83

Ala Thr Tyr Gly Ser Tyr Val Ser Pro Leu Asp Tyr
1               5                   10

<210> SEQ ID NO 84
<211> LENGTH: 17
<212> TYPE: PRT
```

```
<213> ORGANISM: Artificial Sequence
<220> FEATURE:
<223> OTHER INFORMATION: MET Light chain CDR1

<400> SEQUENCE: 84

Lys Ser Ser Gln Ser Leu Leu Tyr Thr Ser Ser Gln Lys Asn Tyr Leu
1               5                   10                  15

Ala

<210> SEQ ID NO 85
<211> LENGTH: 7
<212> TYPE: PRT
<213> ORGANISM: Artificial Sequence
<220> FEATURE:
<223> OTHER INFORMATION: MET Light chain CDR2

<400> SEQUENCE: 85

Trp Ala Ser Thr Arg Glu Ser
1               5

<210> SEQ ID NO 86
<211> LENGTH: 9
<212> TYPE: PRT
<213> ORGANISM: Artificial Sequence
<220> FEATURE:
<223> OTHER INFORMATION: MET Light chain CDR3

<400> SEQUENCE: 86

Gln Gln Tyr Tyr Ala Tyr Pro Trp Thr
1               5

<210> SEQ ID NO 87
<211> LENGTH: 366
<212> TYPE: PRT
<213> ORGANISM: Artificial Sequence
<220> FEATURE:
<223> OTHER INFORMATION: FZD8-Fc variant (13A variant) amino acid
      sequence without signal sequence

<400> SEQUENCE: 87

Ala Ser Ala Lys Glu Leu Ala Cys Gln Glu Ile Thr Val Pro Leu Cys
1               5                   10                  15

Lys Gly Ile Gly Tyr Asn Tyr Thr Tyr Met Pro Asn Gln Phe Asn His
                20                  25                  30

Asp Thr Gln Asp Glu Ala Gly Leu Glu Val His Gln Phe Trp Pro Leu
            35                  40                  45

Val Glu Ile Gln Cys Ser Pro Asp Leu Lys Phe Phe Leu Cys Ser Met
    50                  55                  60

Tyr Thr Pro Ile Cys Leu Glu Asp Tyr Lys Lys Pro Leu Pro Pro Cys
65                  70                  75                  80

Arg Ser Val Cys Glu Arg Ala Lys Ala Gly Cys Ala Pro Leu Met Arg
                85                  90                  95

Gln Tyr Gly Phe Ala Trp Pro Asp Arg Met Arg Cys Asp Arg Leu Pro
                100                 105                 110

Glu Gln Gly Asn Pro Asp Thr Leu Cys Met Asp Tyr Asn Arg Thr Asp
            115                 120                 125

Leu Thr Thr Thr Lys Val Asp Lys Thr Val Glu Arg Lys Ser Cys Val
            130                 135                 140

Glu Cys Pro Pro Cys Pro Ala Pro Val Ala Gly Pro Ser Val Phe
145                 150                 155                 160

Leu Phe Pro Pro Lys Pro Lys Asp Thr Leu Met Ile Ser Arg Thr Pro
```

```
            165                 170                 175
Glu Val Thr Cys Val Val Val Asp Val Ser His Glu Asp Pro Glu Val
            180                 185                 190

Gln Phe Asn Trp Tyr Val Asp Gly Val Glu Val His Asn Ala Lys Thr
            195                 200                 205

Lys Pro Arg Glu Glu Gln Phe Asn Ser Thr Phe Arg Val Val Ser Val
            210                 215                 220

Leu Thr Val Val His Gln Asp Trp Leu Asn Gly Lys Glu Tyr Lys Cys
225                 230                 235                 240

Lys Val Ser Asn Lys Gly Leu Pro Ala Pro Ile Glu Lys Thr Ile Ser
            245                 250                 255

Lys Thr Lys Gly Gln Pro Arg Glu Pro Gln Val Tyr Thr Leu Pro Pro
            260                 265                 270

Ser Arg Glu Lys Met Thr Lys Asn Gln Val Ser Leu Thr Cys Leu Val
            275                 280                 285

Lys Gly Phe Tyr Pro Ser Asp Ile Ala Val Glu Trp Glu Ser Asn Gly
            290                 295                 300

Gln Pro Glu Asn Asn Tyr Lys Thr Thr Pro Pro Met Leu Lys Ser Asp
305                 310                 315                 320

Gly Ser Phe Phe Leu Tyr Ser Lys Leu Thr Val Asp Lys Ser Arg Trp
                325                 330                 335

Gln Gln Gly Asn Val Phe Ser Cys Ser Val Met His Glu Ala Leu His
            340                 345                 350

Asn His Tyr Thr Gln Lys Ser Leu Ser Leu Ser Pro Gly Lys
            355                 360                 365

<210> SEQ ID NO 88
<211> LENGTH: 439
<212> TYPE: PRT
<213> ORGANISM: Artificial Sequence
<220> FEATURE:
<223> OTHER INFORMATION: 73R009 (13B variant) Heavy chain amino acid
      sequence without signal sequence

<400> SEQUENCE: 88

Gln Val Gln Leu Gln Glu Ser Gly Pro Gly Leu Val Lys Pro Ser Glu
1               5                   10                  15

Thr Leu Ser Leu Thr Cys Thr Val Thr Gly Thr Thr Ile Thr Ala Ser
            20                  25                  30

Tyr Ala Trp Ser Trp Ile Arg Gln Pro Pro Gly Lys Gly Leu Glu Trp
        35                  40                  45

Met Gly Tyr Ile Ser Tyr Ser Gly Gly Thr Asp Tyr Asn Pro Ser Leu
    50                  55                  60

Lys Ser Arg Ile Thr Ile Ser Arg Asp Thr Phe Lys Asn Gln Phe Ser
65                  70                  75                  80

Leu Lys Leu Ser Ser Val Thr Ala Ala Asp Thr Ala Thr Tyr Tyr Cys
                85                  90                  95

Ala Arg Lys Gly Ala Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
            115                 120                 125

Arg Ser Thr Ser Glu Ser Thr Ala Ala Leu Gly Cys Leu Val Lys Asp
        130                 135                 140

Tyr Phe Pro Glu Pro Val Thr Val Ser Trp Asn Ser Gly Ala Leu Thr
145                 150                 155                 160
```

```
Ser Gly Val His Thr Phe Pro Ala Val Leu Gln Ser Ser Gly Leu Tyr
            165                 170                 175
Ser Leu Ser Ser Val Val Thr Val Pro Ser Ser Asn Phe Gly Thr Gln
        180                 185                 190
Thr Tyr Thr Cys Asn Val Asp His Lys Pro Ser Asn Thr Lys Val Asp
    195                 200                 205
Lys Thr Val Glu Arg Lys Cys Cys Val Glu Cys Pro Pro Cys Pro Ala
210                 215                 220
Pro Pro Val Ala Gly Pro Ser Val Phe Leu Phe Pro Pro Lys Pro Lys
225                 230                 235                 240
Asp Thr Leu Met Ile Ser Arg Thr Pro Glu Val Thr Cys Val Val Val
            245                 250                 255
Asp Val Ser His Glu Asp Pro Glu Val Gln Phe Asn Trp Tyr Val Asp
        260                 265                 270
Gly Val Glu Val His Asn Ala Lys Thr Lys Pro Arg Glu Glu Gln Phe
    275                 280                 285
Asn Ser Thr Phe Arg Val Val Ser Val Leu Thr Val Val His Gln Asp
290                 295                 300
Trp Leu Asn Gly Lys Glu Tyr Lys Cys Lys Val Ser Asn Lys Gly Leu
305                 310                 315                 320
Pro Ala Pro Ile Glu Lys Thr Ile Ser Lys Thr Lys Gly Gln Pro Arg
            325                 330                 335
Glu Pro Gln Val Tyr Thr Leu Pro Pro Ser Arg Glu Glu Met Thr Lys
        340                 345                 350
Asn Gln Val Ser Leu Thr Cys Leu Val Glu Gly Phe Tyr Pro Ser Asp
    355                 360                 365
Ile Ala Val Glu Trp Glu Ser Asn Gly Gln Pro Glu Asn Asn Tyr Lys
370                 375                 380
Thr Thr Pro Pro Met Leu Asp Ser Asp Gly Ser Phe Phe Leu Tyr Ser
385                 390                 395                 400
Glu Leu Thr Val Asp Lys Ser Arg Trp Gln Gln Gly Asn Val Phe Ser
            405                 410                 415
Cys Ser Val Met His Glu Ala Leu His Asn His Tyr Thr Gln Lys Ser
        420                 425                 430
Leu Ser Leu Ser Pro Gly Lys
        435

<210> SEQ ID NO 89
<211> LENGTH: 1182
<212> TYPE: DNA
<213> ORGANISM: Artificial Sequence
<220> FEATURE:
<223> OTHER INFORMATION: FZD8-Fc variant (13B variant) nucleotide
      sequence with signal sequence

<400> SEQUENCE: 89
atggagtggg gttatctttt agaagtgacc tcgctgctag ccgccttgct actgctgcag      60
cgctctccga tcgtgcacgc cgcctcggcc aaggagctgg catgccaaga gatcaccgtg     120
ccgctatgca agggcatcgg ctacaactac acctacatgc caatcaatt caaccacgac     180 acgcaagacg aggcgggcct ggaggtgcac cagttctggc cgctggtgga gatccagtgc     240
tcgcccgatc tcaagttctt cctgtgcagc atgtacacgc ccatctgcct agaggactac     300
aagaagccgc tgccgccctg ccgctcggtg tgcgagcgcg ccaaggccgg ctgcgcgccg     360
ctcatgcgcc agtacggctt cgcctggccc gaccgcatgc gctgcgaccg gctgcccgag     420
```

```
caaggcaacc ctgacacgct gtgcatggac tacaaccgca ccgacctaac caccaccaaa      480
gttgacaaga ctgttgagcg aaagagctgc gttgagtgcc ctccatgtcc tgcacctcct      540
gtggctggcc cttctgtgtt cctgttccct ccaaaaccta agacactct aatgatctct       600 cggactcctg aggtgacttg cgtggttgtg gacgtgtccc acgaggaccc tgaggtgcag      660
tttaattggt acgtggacgg agtcgaggtg cacaatgcaa agaccaagcc tcgggaggaa      720
cagttcaact ccaccttccg ggtggttttct gtgttgaccg ttgtgcacca agactggctg     780
aacggcaaag aatacaagtg caaggtgtcc aacaagggcc tgcctgcccc tatcgaaaag     840
accatcagca agaccaaggg ccagcctcgc gagcctcagg tgtacacccct gcctcccagc    900 cgggaagaaa tgaccaagaa ccaggtgtcc ctgacctgtc tggtggaggg cttctaccct     960
tccgacatcg ccgttgagtg ggagtctaac ggacagccgg agaacaacta caagactacg    1020
cctccaatgc tggactccga cggctccttc ttcctgtact ccgaactgac cgtggacaag    1080
tcccggtggc agcagggcaa cgtgttctca tgctccgtaa tgcacgaagc cttacacaat    1140
cactacactc aaaagtccct atccttatct cctggcaagt ag                       1182
```

<210> SEQ ID NO 90
<211> LENGTH: 1122
<212> TYPE: DNA
<213> ORGANISM: Artificial Sequence
<220> FEATURE:
<223> OTHER INFORMATION: FZD8-Fc variant (13B variant) nucleotide sequence without signal sequence

<400> SEQUENCE: 90

```
cgctctccga tcgtgcacgc cgcctcggcc aaggagctgg catgccaaga gatcaccgtg       60
ccgctatgca agggcatcgg ctacaactac acctacatgc caatcaatt caaccacgac      120 acgcaagacg aggcgggcct ggaggtgcac cagttctggc cgctggtgga gatccagtgc     180
tcgcccgatc tcaagttctt cctgtgcagc atgtacacgc ccatctgcct agaggactac     240
aagaagccgc tgccgccctg ccgctcggtg tgcgagcgcg ccaaggccgg ctgcgcgccg    300
ctcatgcgcc agtacggctt cgcctggccc gaccgcatgc gctgcgaccg gctgcccgag    360
caaggcaacc ctgacacgct gtgcatggac tacaaccgca ccgacctaac caccaccaaa   420
gttgacaaga ctgttgagcg aaagagctgc gttgagtgcc ctccatgtcc tgcacctcct    480
gtggctggcc cttctgtgtt cctgttccct ccaaaaccta agacactct aatgatctct     540 cggactcctg aggtgacttg cgtggttgtg gacgtgtccc acgaggaccc tgaggtgcag   600
tttaattggt acgtggacgg agtcgaggtg cacaatgcaa agaccaagcc tcgggaggaa   660
cagttcaact ccaccttccg ggtggttttct gtgttgaccg ttgtgcacca agactggctg   720
aacggcaaag aatacaagtg caaggtgtcc aacaagggcc tgcctgcccc tatcgaaaag  780
accatcagca agaccaaggg ccagcctcgc gagcctcagg tgtacacccct gcctcccagc   840 cgggaagaaa tgaccaagaa ccaggtgtcc ctgacctgtc tggtggaggg cttctaccct    900
tccgacatcg ccgttgagtg ggagtctaac ggacagccgg agaacaacta caagactacg    960
cctccaatgc tggactccga cggctccttc ttcctgtact ccgaactgac cgtggacaag   1020
tcccggtggc agcagggcaa cgtgttctca tgctccgtaa tgcacgaagc cttacacaat   1080
cactacactc aaaagtccct atccttatct cctggcaagt ag                      1122
```

<210> SEQ ID NO 91
<211> LENGTH: 230
<212> TYPE: PRT

<213> ORGANISM: Homo sapiens

<400> SEQUENCE: 91

```
Lys Ser Ser Asp Lys Thr His Thr Cys Pro Cys Pro Ala Pro Glu
1               5                   10                  15

Leu Leu Gly Gly Pro Ser Val Phe Leu Phe Pro Pro Lys Pro Lys Asp
            20                  25                  30

Thr Leu Met Ile Ser Arg Thr Pro Glu Val Thr Cys Val Val Val Asp
        35                  40                  45

Val Ser His Glu Asp Pro Glu Val Lys Phe Asn Trp Tyr Val Asp Gly
    50                  55                  60

Val Glu Val His Asn Ala Lys Thr Lys Pro Arg Glu Glu Gln Tyr Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Ala Leu Pro
            100                 105                 110

Ala Pro Ile Glu Lys Thr Ile Ser Lys Ala Lys Gly Gln Pro Arg Glu
        115                 120                 125

Pro Gln Val Tyr Thr Leu Pro Pro Ser Arg Asp Glu Leu Thr Lys Asn
130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Lys
            180                 185                 190

Leu Thr Val Asp Lys Ser Arg Trp Gln Gln Gly Asn Val Phe Ser Cys
        195                 200                 205

Ser Val Met His Glu Ala Leu His Asn His Tyr Thr Gln Lys Ser Leu
    210                 215                 220

Ser Leu Ser Pro Gly Lys
225                 230
```

<210> SEQ ID NO 92
<211> LENGTH: 232
<212> TYPE: PRT
<213> ORGANISM: Homo sapiens

<400> SEQUENCE: 92

```
Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
```

```
                115                 120                 125
Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
                180                 185                 190

Ser Lys Leu Thr Val Asp Lys Ser Arg Trp Gln Gln Gly Asn Val Phe
                195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 93
<211> LENGTH: 1390
<212> TYPE: PRT
<213> ORGANISM: Homo sapiens

<400> SEQUENCE: 93

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
                20                  25                  30

Ser Glu Met Asn Val Asn Met Lys Tyr Gln Leu Pro Asn Phe Thr Ala
            35                  40                  45

Glu Thr Pro Ile Gln Asn Val Ile Leu His Glu His His Ile Phe Leu
        50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255
```

-continued

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Asn Val Arg
    370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
        435                 440                 445

Asp Leu Thr Ile Ala Asn Leu Gly Thr Ser Glu Gly Arg Phe Met Gln
    450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
        515                 520                 525

Cys Leu Ser Ala Pro Pro Phe Val Gln Cys Gly Trp Cys His Asp Lys
530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
        595                 600                 605

Ser Cys Thr Leu Thr Leu Ser Glu Ser Thr Met Asn Thr Leu Lys Cys
    610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
            660                 665                 670

Thr Leu Leu Thr Leu Thr Gly Asn Tyr Leu Asn Ser Gly Asn Ser Arg

```
              675                 680                 685
His Ile Ser Ile Gly Gly Lys Thr Cys Thr Leu Lys Ser Val Ser Asn
    690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
            740                 745                 750

Phe Ile Ser Gly Gly Ser Thr Ile Thr Gly Val Gly Lys Asn Leu Asn
        755                 760                 765

Ser Val Ser Val Pro Arg Met Val Ile Asn Val His Glu Ala Gly Arg
    770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
            820                 825                 830

Leu Ile Tyr Val His Asn Pro Val Phe Lys Pro Phe Glu Lys Pro Val
        835                 840                 845

Met Ile Ser Met Gly Asn Glu Asn Val Leu Glu Ile Lys Gly Asn Asp
    850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                885                 890                 895

Pro Asn Asp Leu Leu Lys Leu Asn Ser Glu Leu Asn Ile Glu Trp Lys
            900                 905                 910

Gln Ala Ile Ser Ser Thr Val Leu Gly Lys Val Ile Val Gln Pro Asp
        915                 920                 925

Gln Asn Phe Thr Gly Leu Ile Ala Gly Val Val Ser Ile Ser Thr Ala
    930                 935                 940

Leu Leu Leu Leu Leu Gly Phe Phe Leu Trp Leu Lys Lys Arg Lys Gln
945                 950                 955                 960

Ile Lys Asp Leu Gly Ser Glu Leu Val Arg Tyr Asp Ala Arg Val His
                965                 970                 975

Thr Pro His Leu Asp Arg Leu Val Ser Ala Arg Ser Val Ser Pro Thr
            980                 985                 990

Thr Glu Met Val Ser Asn Glu Ser  Val Asp Tyr Arg Ala  Thr Phe Pro
        995                 1000                1005

Glu Asp  Gln Phe Pro Asn Ser  Ser Gln Asn Gly Ser  Cys Arg Gln
    1010                1015                1020

Val Gln  Tyr Pro Leu Thr Asp  Met Ser Pro Ile Leu  Thr Ser Gly
    1025                1030                1035

Asp Ser  Asp Ile Ser Ser Pro  Leu Leu Gln Asn Thr  Val His Ile
    1040                1045                1050

Asp Leu  Ser Ala Leu Asn Pro  Glu Leu Val Gln Ala  Val Gln His
    1055                1060                1065

Val Val  Ile Gly Pro Ser Ser  Leu Ile Val His Phe  Asn Glu Val
    1070                1075                1080

Ile Gly  Arg Gly His Phe Gly  Cys Val Tyr His Gly  Thr Leu Leu
    1085                1090                1095
```

-continued

```
Asp Asn Asp Gly Lys Lys Ile His Cys Ala Val Lys Ser Leu Asn
    1100            1105            1110

Arg Ile Thr Asp Ile Gly Glu Val Ser Gln Phe Leu Thr Glu Gly
    1115            1120            1125

Ile Ile Met Lys Asp Phe Ser His Pro Asn Val Leu Ser Leu Leu
    1130            1135            1140

Gly Ile Cys Leu Arg Ser Glu Gly Ser Pro Leu Val Val Leu Pro
    1145            1150            1155

Tyr Met Lys His Gly Asp Leu Arg Asn Phe Ile Arg Asn Glu Thr
    1160            1165            1170

His Asn Pro Thr Val Lys Asp Leu Ile Gly Phe Gly Leu Gln Val
    1175            1180            1185

Ala Lys Gly Met Lys Tyr Leu Ala Ser Lys Lys Phe Val His Arg
    1190            1195            1200

Asp Leu Ala Ala Arg Asn Cys Met Leu Asp Glu Lys Phe Thr Val
    1205            1210            1215

Lys Val Ala Asp Phe Gly Leu Ala Arg Asp Met Tyr Asp Lys Glu
    1220            1225            1230

Tyr Tyr Ser Val His Asn Lys Thr Gly Ala Lys Leu Pro Val Lys
    1235            1240            1245

Trp Met Ala Leu Glu Ser Leu Gln Thr Gln Lys Phe Thr Thr Lys
    1250            1255            1260

Ser Asp Val Trp Ser Phe Gly Val Leu Leu Trp Glu Leu Met Thr
    1265            1270            1275

Arg Gly Ala Pro Pro Tyr Pro Asp Val Asn Thr Phe Asp Ile Thr
    1280            1285            1290

Val Tyr Leu Leu Gln Gly Arg Arg Leu Leu Gln Pro Glu Tyr Cys
    1295            1300            1305

Pro Asp Pro Leu Tyr Glu Val Met Leu Lys Cys Trp His Pro Lys
    1310            1315            1320

Ala Glu Met Arg Pro Ser Phe Ser Glu Leu Val Ser Arg Ile Ser
    1325            1330            1335

Ala Ile Phe Ser Thr Phe Ile Gly Glu His Tyr Val His Val Asn
    1340            1345            1350

Ala Thr Tyr Val Asn Val Lys Cys Val Ala Pro Tyr Pro Ser Leu
    1355            1360            1365

Leu Ser Ser Glu Asp Asn Ala Asp Asp Glu Val Asp Thr Arg Pro
    1370            1375            1380

Ala Ser Phe Trp Glu Thr Ser
    1385            1390
```

MET-BINDING AGENTS AND USES THEREOF

CROSS-REFERENCE TO RELATED APPLICATIONS

This application claims priority benefit of U.S. Provisional Application No. 61/783,552, filed Mar. 14, 2013, which is hereby incorporated by reference herein in its entirety.

REFERENCE TO A SEQUENCE LISTING SUBMITTED ELECTRONICALLY VIA EFS-WEB

The content of the electronically submitted sequence listing (Name: 22931070004SL.txt, Size: 144 kilobytes; and Date of Creation: Mar. 13, 2014) is herein incorporated by reference in its entirety.

FIELD OF THE INVENTION

The present invention generally relates to antibodies, bispecific agents, and other binding agents that bind MET, one or more components of the WNT pathway, or both MET and one or more components of the WNT pathway, particularly bispecific agents that bind both MET and one or more WNT proteins, as well as to methods of using the binding agents for the treatment of diseases such as cancer.

BACKGROUND OF THE INVENTION

Cancer is one of the leading causes of death in the developed world, with over one million people diagnosed with cancer and 500,000 deaths per year in the United States alone. Overall it is estimated that more than 1 in 3 people will develop some form of cancer during their lifetime. There are more than 200 different types of cancer, four of which—breast, lung, colorectal, and prostate—account for almost half of all new cases (Siegel et al., 2011, *CA: A Cancer J. Clin.* 61:212-236).

Signaling pathways normally connect extracellular signals to the nucleus leading to expression of genes that directly or indirectly control cell growth, differentiation, survival, and death. In a wide variety of cancers, signaling pathways are dysregulated and may be linked to tumor initiation and/or progression. Signaling pathways implicated in human oncogenesis include, but are not limited to, the WNT pathway, the Ras-Raf-MEK-ERK or MAPK pathway, the PI3K-AKT pathway, the MET/HGF pathway, the CDKN2A/CDK4 pathway, the Bcl-2/TP53 pathway, and the NOTCH pathway.

The MET/HGF (hepatocyte growth factor) pathway has been shown to play a critical role in early embryonic development. However, in adult tissues the MET pathway is tightly controlled and primarily quiescent in its growth signaling program, except in processes such as wound repair. Dysregulation of the MET pathway may lead to cell proliferation, protection from apoptosis, angiogenesis, invasion, and metastasis. MET may be dysregulated by a variety of different mechanisms including protein over-expression, constitutive activation, ligand-dependent activation, gene amplification, gene mutation, and/or MET modifications (e.g., phosphorylation). The MET pathway has been shown to be dysregulated in many tumor types, including but not limited to, lung, colorectal, breast, liver, gastric, pancreas, and brain.

The WNT signaling pathway is one of several critical regulators of embryonic pattern formation, post-embryonic tissue maintenance, and stem cell biology. More specifically, WNT signaling plays an important role in the generation of cell polarity and cell fate specification including self-renewal by stem cell populations. Unregulated activation of the WNT pathway is associated with numerous human cancers where it is believed the activation can alter the developmental fate of cells. The activation of the WNT pathway may maintain tumor cells in an undifferentiated state and/or lead to uncontrolled proliferation. Thus, carcinogenesis can proceed by overtaking homeostatic mechanisms that control normal development and tissue repair (reviewed in Reya & Clevers, 2005, Nature, 434:843-50; Beachy et al., 2004, Nature, 432: 324-31).

The MET pathway and the WNT pathway have both been identified as potential targets for cancer therapy. It is one of the objectives of the present invention to provide improved molecules for cancer treatment, particularly bispecific agents that specifically bind human MET and one or more WNT proteins. Another objective of the invention is to use these novel bispecific agents to modulate the MET pathway and the WNT pathway and inhibit tumor growth.

SUMMARY OF THE INVENTION

The present invention provides binding agents, such as antibodies, soluble receptors, or bispecific agents that bind MET, one or more components of the WNT pathway, or both MET and one or more components of the WNT pathway, as well as compositions, such as pharmaceutical compositions, comprising the binding agents. Binding agents that bind MET, bind one or more components of the WNT pathway, or bind both MET and one or more components of the WNT pathway, and pharmaceutical compositions of such binding agents, are also provided. In certain embodiments, the binding agents are novel polypeptides, such as antibodies, antibody fragments, and other polypeptides related to such antibodies. In certain embodiments, the binding agents are novel polypeptides, such as soluble receptors and other polypeptides related to such soluble receptors. In certain embodiments, the binding agents are antibodies that specifically bind human MET. In some embodiments, the binding agents are antibodies that specifically bind one or more human WNT proteins. In some embodiments, the binding agents are antibodies that specifically bind one or more human Frizzled (FZD) proteins. In some embodiments, the binding agents are soluble FZD receptors that specifically bind one or more human WNT proteins. In some embodiments, the binding agents are bispecific agents that specifically bind human MET and one or more components of the WNT pathway. In some embodiments, the binding agents are bispecific agents that specifically bind human MET and one or more human WNT proteins. In some embodiments, the binding agents are bispecific molecules that specifically bind human MET and one or more human FZD proteins. The invention further provides methods of inhibiting the growth of a tumor by administering the binding agents to a subject with a tumor. The invention further provides methods of treating cancer by administering the binding agents to a subject in need thereof. In some embodiments, the methods of treating cancer or inhibiting tumor growth comprise targeting cancer stem cells with the binding agents. In certain embodiments, the methods comprise reducing the frequency of cancer stem cells in a tumor, reducing the number of cancer stem cells in a tumor, reducing the tumorigenicity of a tumor, and/or reducing the tumorigenicity of a tumor by reducing the number or frequency of cancer stem cells in the tumor.

In one aspect, the invention provides a binding agent, such as an antibody, that specifically binds human MET. In some embodiments, the binding agent inhibits binding of MET to hepatocyte growth factor. In certain embodiments, the binding agent (e.g., a bispecific agent) specifically binds one or more components of the human WNT pathway in addition to binding human MET. In certain embodiments, the binding agent (e.g., a bispecific agent) specifically binds one or more human FZD proteins in addition to binding human MET. In certain embodiments, the binding agent (e.g., a bispecific agent) specifically binds one or more human WNT proteins in addition to binding human MET.

In certain embodiments, the binding agent specifically binds the extracellular domain of human MET. In some embodiments, the binding agent specifically binds the Sema domain of human MET. In some embodiments, the binding agent specifically binds within the Sema domain of human MET. In some embodiments, the binding agent specifically binds within amino acids 25-932 of human MET (SEQ ID NO:93). In some embodiments, the binding agent specifically binds within amino acids 25-836 of human MET (SEQ ID NO:93). In some embodiments, the binding agent specifically binds within amino acids 25-515 of human MET (SEQ ID NO:93). In some embodiments, the binding agent specifically binds within amino acids 563-836 of human MET (SEQ ID NO:93).

In some embodiments, the binding agent is an antibody that specifically binds human MET. In some embodiments, the MET-binding agent is an antibody that comprises a heavy chain CDR1 comprising ASYAWS (SEQ ID NO:1), a heavy chain CDR2 comprising YISYSGGTDYNPSLKS (SEQ ID NO:2), and a heavy chain CDR3 comprising KGAY (SEQ ID NO:3); and a light chain CDR1 comprising SASSSVSSSYLY (SEQ ID NO:4), a light chain CDR2 comprising STSNLAS (SEQ ID NO:5), and a light chain CDR3 comprising HQWSSYPYT (SEQ ID NO:6).

In certain embodiments, the MET-binding agent is an antibody that comprises a heavy chain variable region having at least about 80% sequence identity to SEQ ID NO:7; and/or a light chain variable region having at least about 80% sequence identity to SEQ ID NO:8. In certain embodiments, the binding agent comprises a heavy chain variable region having at least about 90% sequence identity to SEQ ID NO:7; and/or a light chain variable region having at least about 90% sequence identity to SEQ ID NO:8. In certain embodiments, the binding agent comprises a heavy chain variable region having at least about 95% sequence identity to SEQ ID NO:7; and/or a light chain variable region having at least about 95% sequence identity to SEQ ID NO:8. In certain embodiments, the binding agent is an antibody that comprises a heavy chain variable region of SEQ ID NO:7; and/or a light chain variable region of SEQ ID NO:8.

In some embodiments, the MET-binding agent is an antibody that comprises a heavy chain of SEQ ID NO:9, SEQ ID NO:10, SEQ ID NO:12, SEQ ID NO:13, or SEQ ID NO:88; and/or a light chain of SEQ ID NO:11 or SEQ ID NO:14.

In some embodiments, the binding agent is antibody 73R009. In some embodiments, the binding agent is a variant of antibody 73R009. In some embodiments, the binding agent is a monovalent version of 73R009.

In another aspect, the invention provides a binding agent that is a bispecific agent, wherein the bispecific agent specifically binds human MET. In some embodiments, the bispecific agent specifically binds human MET and a second target. In some embodiments the bispecific agent binds human MET and one or more components of the human WNT pathway. In some embodiments, the bispecific agent binds both human MET and one or more human WNT proteins. In some embodiments, the bispecific agent is a bispecific antibody. In some embodiments, the bispecific antibody binds both human MET and one or more components of the human WNT pathway. In some embodiments, the bispecific antibody binds both human MET and one or more human WNT proteins. In some embodiments, the bispecific antibody binds both human MET and one or more human FZD proteins. In certain embodiments, the bispecific antibody comprises two identical light chains. In certain embodiments the bispecific antibody is an IgG antibody. In certain embodiments the bispecific antibody is an IgG1 antibody. In certain embodiments the bispecific antibody is an IgG2 antibody In another aspect, the invention provides a bispecific agent that comprises a first arm that comprises a first binding site and a second arm that comprises a second binding site. In some embodiments, the first binding site comprises a first antigen-binding site from a first antibody and the second binding site comprises a second antibody-binding site from a second antibody. In some embodiments, the first binding site comprises an antigen-binding site from an antibody and the second binding site comprises a binding site that is not from an antibody. In some embodiments, the first arm comprises a monovalent antibody and the second arm comprises a soluble receptor.

In some embodiments, the bispecific agent comprises: a first binding site that specifically binds human MET, and a second binding site that specifically binds one or more components of the WNT pathway. In some embodiments, the bispecific agent comprises a first binding site that specifically binds human MET, and a second binding site that specifically binds one or more components of the WNT pathway, wherein the first binding site comprises a heavy chain CDR1 comprising ASYAWS (SEQ ID NO:1), a heavy chain CDR2 comprising YISYSGGTDYNPSLKS (SEQ ID NO:2), and a heavy chain CDR3 comprising KGAY (SEQ ID NO:3). In some embodiments, the bispecific agent further comprises: a light chain CDR1 comprising SASSSVSSSYLY (SEQ ID NO:4), a light chain CDR2 comprising STSNLAS (SEQ ID NO:5), and a light chain CDR3 comprising HQWSSYPYT (SEQ ID NO:6). In some embodiments, the bispecific agent comprises: a first binding site that specifically binds human MET, wherein the first binding site comprises (a) a heavy chain CDR1 comprising ASYAWS (SEQ ID NO:1), a heavy chain CDR2 comprising YISYSGGTDYNPSLKS (SEQ ID NO:2), and a heavy chain CDR3 comprising KGAY (SEQ ID NO:3), and a light chain CDR1 comprising SASSSVSSSYLY (SEQ ID NO:4), a light chain CDR2 comprising STSNLAS (SEQ ID NO:5), and a light chain CDR3 comprising HQWSSY-PYT (SEQ ID NO:6).

In some embodiments, the bispecific agent comprises: a first binding site that specifically binds human MET, and a second binding site that specifically binds one or more components of the WNT pathway. In some embodiments, the bispecific agent comprises a first binding site that specifically binds human MET, and a second binding site that specifically binds one or more components of the WNT pathway, wherein the first binding site comprises a heavy chain CDR1 comprising GYTFTSYWLH (SEQ ID NO:78), a heavy chain CDR2 comprising GMIDPSNSDTRFNPNFKD (SEQ ID NO:79), and a heavy chain CDR3 comprising TYGSYVSPLDY (SEQ ID NO:81), SYGSYVSPLDY (SEQ ID NO:82), ATYGSYVSPLDY (SEQ ID NO:83), or XYGSYVSPLDY (SEQ ID NO:80), wherein X is not R; and a light chain CDR1 comprising KSSQSLLYTSSQKNYLA (SEQ ID NO:84), a light chain CDR2 comprising WASTRES (SEQ ID NO:85), and a light chain CDR3 comprising QQYYAYPWT (SEQ ID NO:86).

In some embodiments, the bispecific agent comprises a first binding site that specifically binds human MET, and a second binding site that specifically binds one or more components of the WNT pathway, wherein the first binding site comprises a first antigen-binding site from a first antibody, and the second binding site comprises a second antigen-binding site from a second antibody. Thus, in some embodiments, the bispecific agent is a bispecific antibody. In some embodiments, the second binding site specifically binds one or more human WNT proteins. In some embodiments, the one or more WNT proteins is selected from the group consisting of: WNT1, WNT2, WNT2b, WNT3, WNT3a, WNT7a, WNT7b, WNT8a, WNT8b, WNT100a, and WNT10b. In some embodiments, the second binding site specifically binds one or more Frizzled (FZD) proteins. In some embodiments, the one or more FZD proteins is selected from the group consisting of: FZD1, FZD2, FZD3, FZD4, FZD5, FZD6, FZD7, FZD8, FZD9, and FZD10. In some embodiments, the one or more FZD proteins is selected from the group consisting of: FZD1, FZD2, FZD5, FZD7, and FZD8.

In some embodiments, the bispecific agent comprises a first binding site that specifically binds human MET, and a second binding site that specifically binds one or more components of the WNT pathway, wherein the second binding site comprises a soluble receptor. In some embodiments, the soluble receptor comprises an extracellular domain (ECD) of a human FZD protein. In some embodiments, the soluble receptor comprises a fragment of an ECD of a human FZD protein. In some embodiments, the soluble receptor comprises a Fri domain of a human FZD protein. In some embodiments, the soluble receptor comprises a Fri domain of a human FZD protein that comprises the Fri domain of FZD1, the Fri domain of FZD2, the Fri domain of FZD3, the Fri domain of FZD4, the Fri domain of FZD5, the Fri domain of FZD6, the Fri domain of FZD7, the Fri domain of FZD8, the Fri domain of FZD9, or the Fri domain of FZD10. In some embodiments, the soluble receptor comprises a Fri domain of a human FZD protein that comprises the Fri domain of FZD8. In some embodiments, the soluble receptor comprises a Fri domain of a human FZD protein that comprises a sequence selected from the group consisting of: SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, and SEQ ID NO:31. In some embodiments, the soluble receptor comprises a minimal core Fri domain of a human FZD protein that comprises a sequence selected from the group consisting of: SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, and SEQ ID NO:41. In some embodiments, the soluble receptor comprises a Fri domain of a human FZD protein of SEQ ID NO:28, SEQ ID NO:29, or SEQ ID NO:39. In some embodiments, the Fri domain of a human FZD protein is directly linked to a heterologous polypeptide. In some embodiments, the Fri domain of a human FZD protein is connected to a heterologous polypeptide by a linker. In some embodiments, the heterologous polypeptide comprises a human Fc region. In some embodiments, the heterologous polypeptide comprises: SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:42, SEQ ID NO:43, SEQ ID NO:91, or SEQ ID NO:92. In some embodiments, the soluble receptor comprises: (a) a first polypeptide of SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, or SEQ ID NO:41; and (b) a second polypeptide of SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:42, SEQ ID NO:43, SEQ ID NO:91, or SEQ ID NO:92, wherein the first polypeptide is directly linked to the second polypeptide. In some embodiments, the soluble receptor comprises: (a) a first polypeptide of SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, or SEQ ID NO:41; and (b) a second polypeptide of SEQ ID NO:44, SEQ ID NO:45. SEQ ID NO:46. SEQ ID NO:47, SEQ ID NO:48, SEQ ID NO:49, SEQ ID NO:50, SEQ ID NO:51, SEQ ID NO:52, SEQ ID NO:42, SEQ ID NO:43, SEQ ID NO:91, or SEQ ID NO:92, wherein the first polypeptide is connected to the second polypeptide by a linker. In some embodiments, the soluble receptor comprises a first polypeptide comprising SEQ ID NO:28. In some embodiments, the soluble receptor comprises a first polypeptide of SEQ ID NO:28. In some embodiments, the soluble receptor comprises a first polypeptide of SEQ ID NO:28, and a second polypeptide of SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments, the soluble receptor comprises a first polypeptide comprising SEQ ID NO:29. In some embodiments, the soluble receptor comprises a first polypeptide of SEQ ID NO:29. In some embodiments, the soluble receptor comprises a first polypeptide of SEQ ID NO:29, and a second polypeptide SEQ ID NO:44, SEQ ID NO:45, SEQ ID NO:46, SEQ ID NO:47, or SEQ ID NO:48, SEQ ID NO:49, SEQ ID NO:50, SEQ ID NO:51, or SEQ ID NO:52. In some embodiments, the soluble receptor comprises SEQ ID NO:52 or SEQ ID NO:50. In some embodiments, the soluble receptor comprises SEQ ID NO:52.

In some embodiments, the bispecific agent comprises a first arm that specifically binds human MET, and a second arm that specifically binds one or more components of the WNT pathway, wherein the first arm comprises a heavy chain CDR1 comprising ASYAWS (SEQ ID NO:1), a heavy chain CDR2 comprising YISYSGGTDYNPSLKS (SEQ ID NO:2), and a heavy chain CDR3 comprising KGAY (SEQ ID NO:3), and a light chain CDR1 comprising SASSSVSSSYLY (SEQ ID NO:4), a light chain CDR2 comprising STSNLAS (SEQ ID NO:5), and a light chain CDR3 comprising HQWSSYPYT (SEQ ID NO:6), and wherein the second arm comprises SEQ ID NO:56 or SEQ ID NO:87.

In some embodiments, a bispecific agent comprises a first binding site that specifically binds human MET, and a second binding site that specifically binds one or more components of the WNT pathway, wherein the first binding site comprises a heavy chain variable region having at least about 90% sequence identity to SEQ ID NO:7 and a light chain variable region having at least about 90% sequence identity to SEQ ID NO:8. In some embodiments, the first antigen-binding site comprises a heavy chain variable region having at least about 95% sequence identity to SEQ ID NO:7 and a light chain variable region have at least about 95% sequence identity to SEQ ID NO:8. In some embodiments, the first antigen-binding site comprises a heavy chain variable region of SEQ ID NO:7 and a light chain variable region of SEQ ID NO:8.

In some embodiments, a bispecific agent comprises a first arm that specifically binds human MET, and a second arm that specifically binds one or more components of the WNT pathway, wherein the first arm comprises a heavy chain variable region having at least about 90% sequence identity to SEQ ID NO:7 and a light chain variable region having at least about 90% sequence identity to SEQ ID NO:8, and wherein the second arm comprises SEQ ID NO:56 or SEQ ID NO:87.

In some embodiments, the bispecific agent comprises (a) a first binding site that binds human MET with a $K_D$ between about 0.1 nM and about 1.0 nM and (b) a second binding site that specifically binds one or more components of the human WNT pathway with a $K_D$ between about 0.1 nM and about 20 nM.

In certain embodiments of each of the aforementioned aspects, as well as other aspects and/or embodiments described elsewhere herein, the binding agent is isolated. In certain embodiments of each of the aforementioned aspects, as well as other aspects and/or embodiments described elsewhere herein, the binding agent is substantially pure.

In another aspect, the invention provides a polypeptide selected from the group consisting of: SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:55, SEQ ID NO:56, SEQ ID NO:87, and SEQ ID NO:88. In some embodiments, the polypeptide is isolated. In certain embodiments, the polypeptide is substantially pure. In certain embodiments, the polypeptide is an antibody or part of an antibody, such as an antibody fragment. In some embodiments, the polypeptide is a soluble receptor or fragment of a soluble receptor. In some embodiments, the polypeptide is a fusion protein.

The invention further provides cells that comprise the bispecific agents, antibodies, or polypeptides described herein. The invention further provides cells that produce the bispecific agents, antibodies, or polypeptides described herein. In some embodiments, the cell is a prokaryotic cell. In some embodiments, the cell is an eukaryotic cell.

In another aspect, the invention provides isolated polynucleotide molecules comprising a polynucleotide that encodes the binding agents and/or polypeptides of each of the aforementioned aspects, as well as other aspects and/or embodiments described herein. In some embodiments, the polynucleotide comprises a polynucleotide sequence that encodes a sequence selected from the group consisting of: SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:55, SEQ ID NO:56, SEQ ID NO:87, and SEQ ID NO:88. In some embodiments, the polynucleotide comprises a sequence selected from the group consisting of: SEQ ID NO:15, SEQ ID NO:16, SEQ ID NO:17, SEQ ID NO:18, SEQ ID NO:19, SEQ ID NO:20, SEQ ID NO:89, and SEQ ID NO:90.

The invention further provides expression vectors that comprise the polynucleotides, as well as cells that comprise the expression vectors and/or the polynucleotides. In some embodiments, the cell is a prokaryotic cell. In some embodiments, the cell is an eukaryotic cell.

Pharmaceutical compositions comprising a binding agent, a bispecific agent, an antibody, or a polypeptide described herein and a pharmaceutically acceptable carrier are further provided.

In another aspect, the invention provides methods of using the binding agents, bispecific agents, antibodies, and/or polypeptides described herein. In some embodiments, a method of inhibiting growth of a tumor comprises contacting the tumor with an effective amount of a bispecific agent or antibody described herein. In some embodiments, a method of inhibiting growth of a tumor in a subject comprises administering to the subject a therapeutically effective amount of a bispecific agent or antibody described herein. In some embodiments, a method of reducing the tumorigenicity of a tumor in a subject by reducing the frequency of cancer stem cells in the tumor comprises administering to the subject a therapeutically effective amount of a bispecific agent or antibody described herein. In some embodiments, a method of reducing the frequency of cancer stem cells in a tumor in a subject comprises administering to the subject a therapeutically effective amount of a bispecific agent or antibody described herein. In some embodiments, a method of inhibiting epithelial-mesenchymal transition (EMT) in a tumor in a subject comprises administering to the subject a therapeutically effective amount of a bispecific agent or antibody described herein. In some embodiments, the tumor is selected from the group consisting of colorectal tumor, colon tumor, ovarian tumor, pancreatic tumor, lung tumor, liver tumor, breast tumor, kidney tumor, prostate tumor, gastrointestinal tumor, melanoma, cervical tumor, bladder tumor, glioblastoma, and head and neck tumor.

In some embodiments, a method of treating cancer in a subject comprises administering to the subject a therapeutically effective amount of a bispecific agent or antibody described herein. The invention also provides a bispecific agent or antibody for use in a method of treating cancer, wherein the bispecific agent or antibody is an agent or antibody described herein. The invention also provides the use of a bispecific agent or antibody described herein for the manufacture of a medicament for the treatment of cancer. In some embodiments, the cancer is selected from the group consisting of colorectal cancer, colon cancer, ovarian cancer, pancreatic cancer, lung cancer, liver cancer, breast cancer, kidney cancer, prostate cancer, gastrointestinal cancer, melanoma, cervical cancer, bladder cancer, glioblastoma, and head and neck cancer. In some embodiments, a method further comprises administering at least one additional therapeutic agent.

The invention also provides a bispecific agent or antibody for use in a method of treating cancer, wherein the bispecific agent or antibody is an agent or antibody described herein. The invention also provides the use of a bispecific agent or antibody described herein for the manufacture of a medicament for the treatment of cancer.

Methods of treatment described herein comprising administering to a subject (e.g., a human) an effective amount of a binding agent, a bispecific agent, an antibody, or a polypeptide described herein as part of a pharmaceutical composition are also provided.

In another aspect, the invention provides a method of identifying a human subject or selecting a human subject for treatment with a binding agent, a bispecific agent, an antibody, or a polypeptide described herein. In some embodiments, the method comprises determining if the subject has a tumor that has an elevated expression level of MET as compared to a reference sample or a pre-determined level. In some embodiments, the method comprises identifying a subject for treatment or selecting a subject for treatment if the tumor has an elevated level of MET expression.

Where aspects or embodiments of the invention are described in terms of a Markush group or other grouping of alternatives, the present invention encompasses not only the entire group listed as a whole, but also each member of the group individually and all possible subgroups of the main group, and also the main group absent one or more of the group members. The present invention also envisages the explicit exclusion of one or more of any of the group members in the claimed invention.

BRIEF DESCRIPTIONS OF THE DRAWINGS

FIG. 1A-1D. Inhibition of binding of hepatocyte growth factor to human MET. HEK-293T cells were transiently transfected with a human MET construct and then subsequently mixed with anti-MET antibody 5D5 (FIG. 1B), monovalent version of anti-MET antibody 73R009 (FIG. 1C), or anti-MET/FZD8-Fc bispecific agent 315B6 (Fig, 1D), and hepatocyte growth factor (HGF). Cells treated with only HGF were used as a positive control and untreated transfected cells were used as a negative control (FIG. 1 A). Specific binding is indicated by the presence of signal within the box overlay on each FACS plot. The percent binding is shown underneath each FACS plot. The percent inhibition of binding as compared to the percent binding of the average of the two positive controls in shown underneath each FACS plot.

Figure 2:
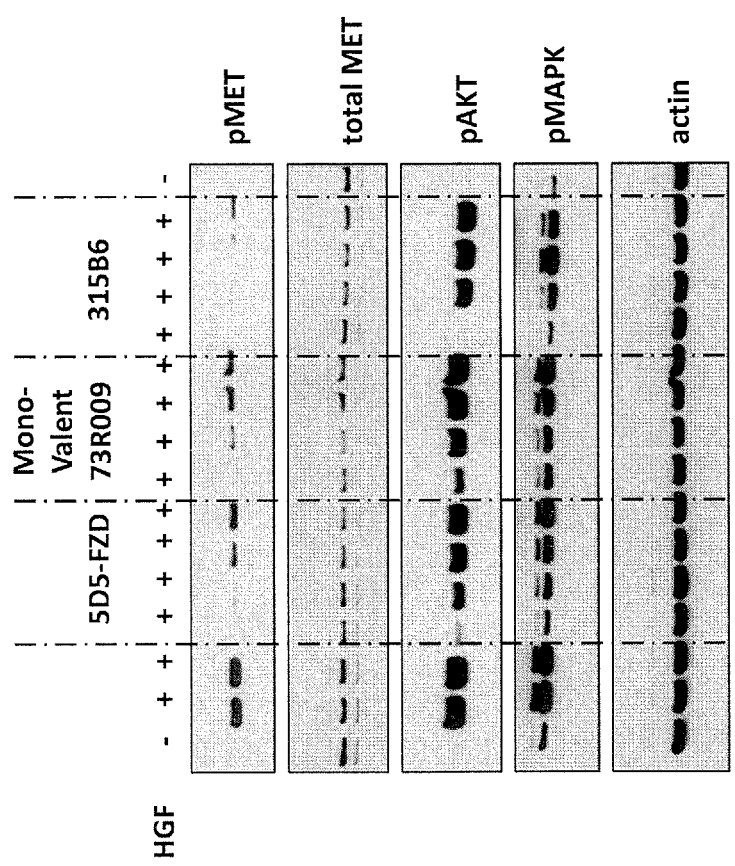

FIG. 2. Inhibition of MET activity induced by hepatocyte growth factor. A549 cells were pre-treated for one hour with monovalent version of anti-MET antibody 73R009, bispecific anti-MET/FZD8 agent 5D5/FZD8-Fc, or bispecific anti-MET/FZD8-Fc agent 315B6 and then stimulated with human hepatocyte growth factor. Cell lysates were analyzed by Western blotting.

Figure 3:
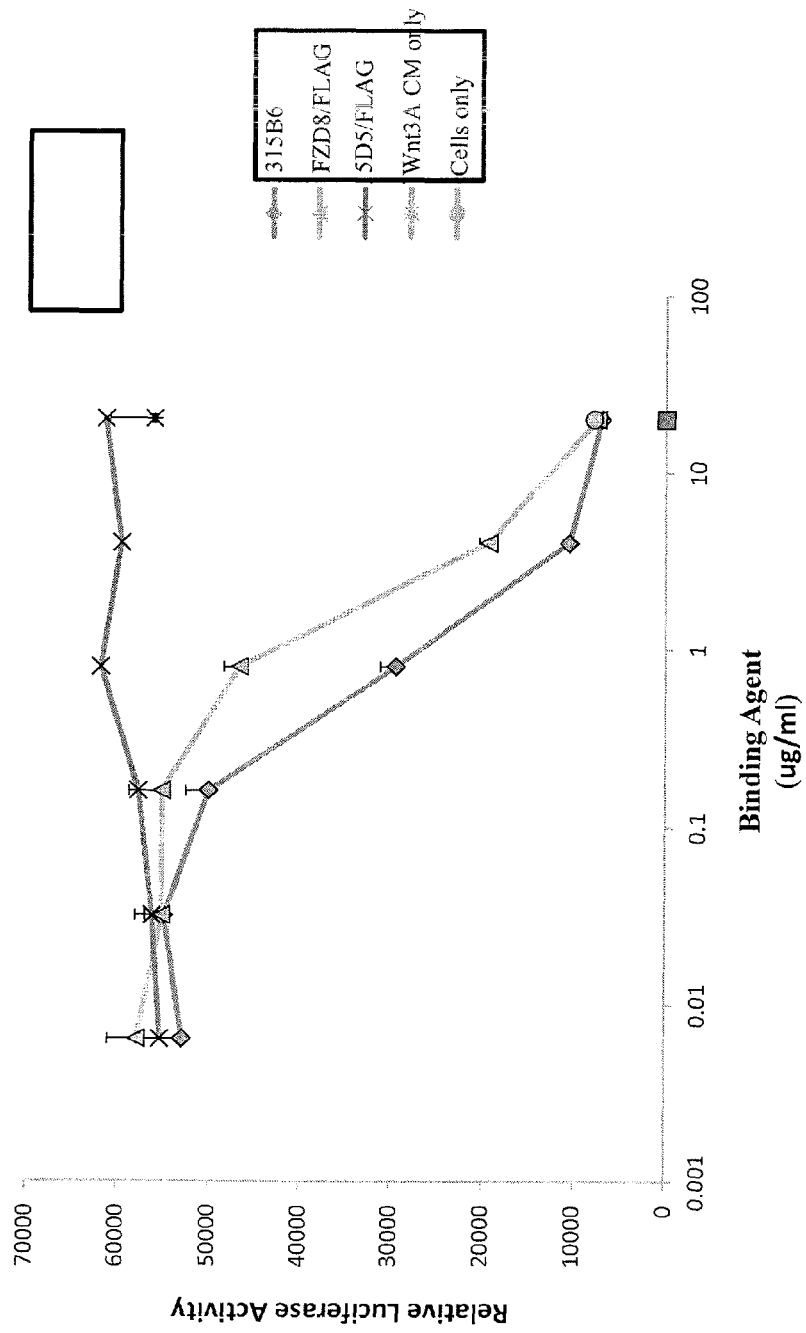

FIG. 3. Inhibition of WNT signaling. A 8×TCF-luciferase reporter assay was used to measure WNT signaling in STF-293 cells. STF-293 cells were treated with anti-MET/FZD8-Fc bispecific agent 315B6 (—♦—) and control binding agents monovalent anti-MET antibody 5D5/FLAG (—X—) and monovalent FZD8-Fc FZD8/FLAG (—▲—). Cells were exposed to medium containing WNT3a L cell-conditioned medium or control medium from cells not over-expressing WNT3a (—●—).

Figure 4A:
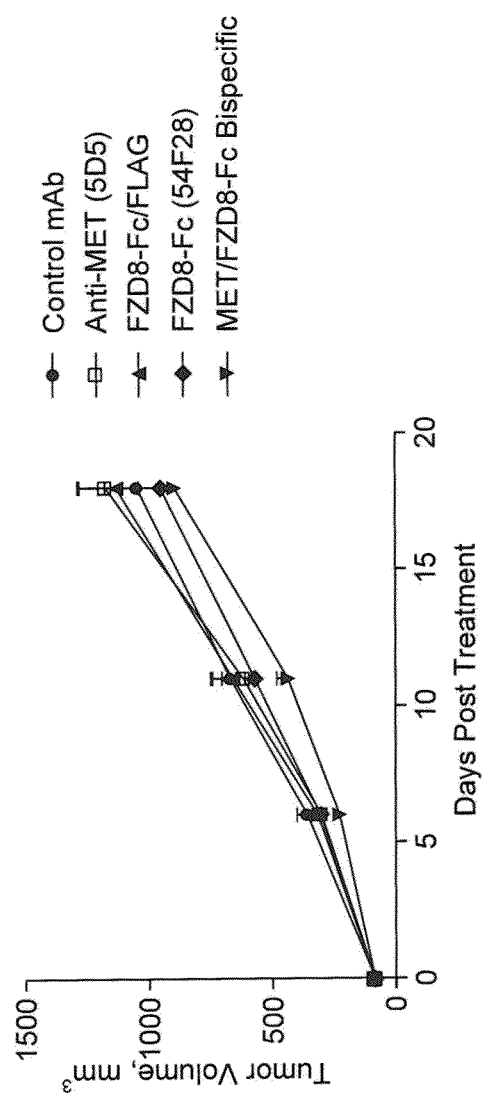
Figure 4B:
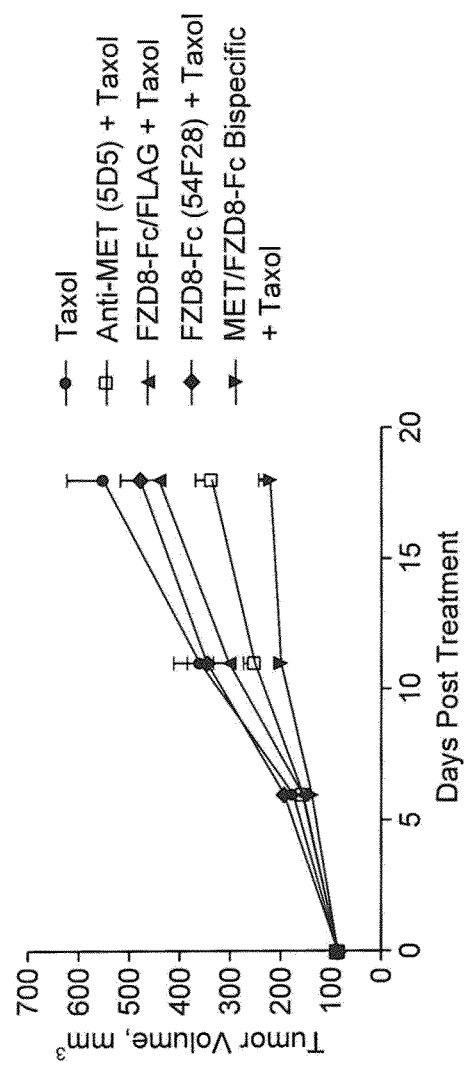

FIG. 4A-4B. Inhibition of OMP-LU45 lung tumor growth. LU45 lung tumor cells were injected subcutaneously into NOD/SCID mice. Mice were treated with a control antibody (—●—), monovalent anti-MET antibody (5D5) (—□—), monovalent FZD8-Fc (—▲—), bivalent FZD8-Fc (54F28) (—♦—), anti-MET/FZD8-Fc bispecific (—▼—) without taxol (FIG. 4A) or in combination with taxol (FIG. 4B). Data is shown as tumor volume ($mm^3$) over days post treatment.

DETAILED DESCRIPTION OF THE INVENTION

The present invention provides novel binding agents that bind MET, bind one or more components of the WNT pathway, or bind both MET and one or more components of the WNT pathway. The phrase "components of the WNT pathway" as used herein, generally refers to one or more WNT proteins and/or one or more FZD proteins. Related polypeptides and polynucleotides, compositions comprising the binding agents, and methods of making the binding agents are also provided. Methods of using the novel binding agents, such as methods of inhibiting tumor growth, methods of treating cancer, methods of reducing tumorigenicity of a tumor, methods of reducing the frequency of cancer stem cells in a tumor, methods of inhibiting EMT, methods of inhibiting angiogenesis, and/or methods of identifying and/or selecting subjects for treatment, are further provided.

A humanized monoclonal antibody that specifically binds human MET has been identified (73R009). This antibody has a binding affinity for human MET of about 1.1 nM and does not bind mouse MET. A monovalent version of the antibody has been generated and has a binding affinity for human MET of 1.4 nM. A bispecific agent that specifically binds human MET and one or more human WNT proteins has been produced, 315B6. Bispecific agent 315B6 has a binding affinity for human MET of 1.8 nM and does not bind mouse MET. Bispecific agent 315B6 inhibits binding of human hepatocyte growth factor (HGF) to human MET (Example 2, FIG. 1). Bispecific agent 315B6 inhibits HGF-induced MET activity (Example 3, FIG. 2). Bispecific agent 315B6 inhibits WNT pathway signaling (Example 4, FIG. 3). A bispecific agent comprising an anti-MET antibody and a FZD8-Fc inhibited growth of a lung tumor when combined with taxol (Example 5, FIG. 4).

I. Definitions

To facilitate an understanding of the present invention, a number of terms and phrases are defined below.

The term "antibody" as used herein refers to an immunoglobulin molecule that recognizes and specifically binds a target, such as a protein, polypeptide, peptide, carbohydrate, polynucleotide, lipid, or combinations of the foregoing, through at least one antigen-binding site within the variable region of the immunoglobulin molecule. As used herein, the term encompasses intact polyclonal antibodies, intact monoclonal antibodies, single chain antibodies, antibody fragments (such as Fab, Fab', F(ab')2, and Fv fragments), single chain Fv (scFv) antibodies, multispecific antibodies such as bispecific antibodies, monospecific antibodies, monovalent antibodies, chimeric antibodies, humanized antibodies, human antibodies, fusion proteins comprising an antigen-binding site of an antibody, and any other modified immunoglobulin molecule comprising an antigen-binding site as long as the antibodies exhibit the desired biological activity. An antibody can be any of the five major classes of immunoglobulins: IgA, IgD, IgE, IgG, and IgM, or subclasses (isotypes) thereof (e.g., IgG1, IgG2, IgG3, IgG4, IgA1, and IgA2), based on the identity of their heavy chain constant domains referred to as alpha, delta, epsilon, gamma, and mu, respectively. The different classes of immunoglobulins have different and well-known subunit structures and three-dimensional configurations. Antibodies can be naked or conjugated to other molecules, including but not limited to, toxins and radioisotopes.

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, single chain antibodies, and multispecific antibodies formed from antibody fragments. "Antibody fragment" as used herein comprises an antigen-binding site or epitope-binding site.

The term "variable region" of an antibody refers to the variable region of an antibody light chain, or the variable region of an antibody heavy chain, either alone or in combination. The variable region of a heavy or light chain each consist of four framework regions (FR) connected by three complementarity determining regions (CDRs), also known as "hypervariable regions". The CDRs in each chain are held together in close proximity by the framework regions and, with the CDRs from the other chain, contribute to the formation of the antigen-binding site(s) of the antibody. There are at least two techniques for determining CDRs: (1) an approach based on cross-species sequence variability (i.e., Kabat et al., 1991, *Sequences of Proteins of Immunological Interest*, 5th Edition, National Institutes of Health, Bethesda, Md.), and (2) an approach based on crystallographic studies of antigen-antibody complexes (Al-Lazikani et al., 1997, *J. Mol. Biol.*, 273:927-948). In addition, combinations of these two approaches are sometimes used in the art to determine CDRs.

The term "monoclonal antibody" as used herein refers to a homogeneous antibody population involved in the highly specific recognition and binding of a single antigenic determinant or epitope. This is in contrast to polyclonal antibodies that typically include a mixture of different antibodies directed against a variety of different antigenic determinants. The term "monoclonal antibody" encompasses both intact and full-length monoclonal antibodies as well as antibody fragments (e.g., Fab, Fab', F(ab')2, Fv), single chain (scFv) antibodies, fusion proteins comprising an antibody portion, and any other modified immunoglobulin molecule comprising an antigen-binding site. Furthermore, "monoclonal antibody" refers to such antibodies made by any number of techniques, including but not limited to, hybridoma production, phage selection, recombinant expression, and transgenic animals.

The term "humanized antibody" as used herein refers to forms of non-human (e.g., murine) antibodies that are specific immunoglobulin chains, chimeric immunoglobulins, or fragments thereof that contain minimal non-human sequences. Typically, humanized antibodies are human immunoglobulins in which residues of the CDRs are replaced by residues from the CDRs of a non-human species (e.g., mouse, rat, rabbit, or hamster) that have the desired specificity, affinity, and/or binding capability (Jones et al., 1986, *Nature,* 321: 522-525; Riechmann et al., 1988, *Nature,* 332:323-327; Verhoeyen et al., 1988, *Science.* 239:1534-1536). In some instances, the Fv framework region residues of a human immunoglobulin are replaced with the corresponding residues in an antibody from a non-human species that has the desired specificity, affinity, and/or binding capability. The humanized antibody can be further modified by the substitution of additional residues either in the Fv framework region and/or within the replaced non-human residues to refine and optimize antibody specificity, affinity, and/or binding capability. In general, the humanized antibody will comprise substantially all of at least one, and typically two, variable domains containing all or substantially all of the CDRs that correspond to the non-human immunoglobulin whereas all or substantially all of the framework regions are those of a human immunoglobulin consensus sequence. The humanized antibody can also comprise at least a portion of an immunoglobulin constant region or domain (Fc), typically that of a human immunoglobulin. Methods used to generate humanized antibodies are well known in the art.

The term "human antibody" as used herein refers to an antibody produced by a human or an antibody having an amino acid sequence corresponding to an antibody produced by a human. A human antibody may be made using any of the techniques known in the art. This definition of a human antibody specifically excludes a humanized antibody comprising non-human CDRs.

The term "chimeric antibody" as used herein refers to an antibody wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc.) with the desired specificity, affinity, and/or binding capability, while the constant regions correspond to sequences in antibodies derived from another species (usually human).

The phrase "affinity-matured antibody" as used herein refers to an antibody with one or more alterations in one or more CDRs thereof that result in an improvement in the affinity of the antibody for antigen, compared to a parent antibody that does not possess those alterations(s). The definition also includes alterations in non-CDR residues made in conjunction with alterations to CDR residues. Preferred affinity-matured antibodies will have nanomolar or even picomolar affinities for the target antigen. Affinity-matured antibodies are produced by procedures known in the art. For example, Marks et al., 1992, *Bio/Technology* 10:779-783, describes affinity maturation by VH and VL domain shuffling. Random mutagenesis of CDR and/or framework residues is described by Barbas et al., 1994, *PNAS,* 91:3809-3813; Schier et al., 1995, *Gene,* 169:147-155; Yelton et al., 1995, *J. Immunol.* 155:1994-2004; Jackson et al., 1995, *J. Immunol.,* 154:3310-9; and Hawkins et al., 1992, *J. Mol. Biol.,* 226:889-896. Site-directed mutagenesis may also be used to obtain affinity-matured antibodies.

The terms "epitope" and "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids (also referred to as linear epitopes) are typically retained upon protein denaturing, whereas epitopes formed by tertiary folding (also referred to as conformational epitopes) are typically lost upon protein denaturing. An epitope typically includes at least 3, and more usually, at least 5 or 8-10 amino acids in a unique spatial conformation.

The terms "heteromultimeric molecule" or "heteromultimer" or "heteromultimeric complex" or "heteromultimeric polypeptide" are used interchangeably herein to refer to a molecule comprising at least a first polypeptide and a second polypeptide, wherein the second polypeptide differs in amino acid sequence from the first polypeptide by at least one amino acid residue. The heteromultimeric molecule can comprise a "heterodimer" or "heterodimeric agent" formed by the first and second polypeptide or can form higher order tertiary structures where additional polypeptides are present.

The terms "antagonist" and "antagonistic" as used herein refer to any molecule that partially or fully blocks, inhibits, reduces, or neutralizes a biological activity of a target and/or signaling pathway (e.g., the WNT pathway or MET pathway). The term "antagonist" is used herein to include any molecule that partially or fully blocks, inhibits, reduces, or neutralizes the activity of a protein. Suitable antagonist molecules specifically include, but are not limited to, antagonist antibodies, antibody fragments, soluble receptors, or fragments of soluble receptors.

The terms "modulation" and "modulate" as used herein refer to a change or an alteration in a biological activity. Modulation includes, but is not limited to, stimulating or inhibiting an activity. Modulation may be an increase or a decrease in activity (e.g., a decrease in pathway signaling), a change in binding characteristics, or any other change in the biological, functional, or immunological properties associated with the activity of a protein, pathway, or other biological point of interest.

The terms "selectively binds" or "specifically binds" mean that a binding agent or an antibody reacts or associates more frequently, more rapidly, with greater duration, with greater affinity, or with some combination of the above to the epitope, protein, or target molecule than with alternative substances, including unrelated or related proteins. In certain embodiments "specifically binds" means, for instance, that an antibody binds a protein with a $K_D$ of about 0.1 mM or less, but more usually less than about 1 µM. In certain embodiments, "specifically binds" means that an antibody binds a target at times with a $K_D$ of at least about 0.1 µM or less, at other times at least about 0.01 µM or less, and at other times at least about 1 nM or less. Because of the sequence identity between homologous proteins in different species, specific binding can include an antibody that recognizes a protein in more than one species (e.g., human MET and mouse MET). Likewise, because of homology within certain regions of polypeptide sequences of different proteins, specific binding can include an antibody (or other polypeptide or binding agent) that recognizes more than one protein (e.g., human WNT1 and human WNT7). It is understood that, in certain embodiments, an antibody or binding agent that specifically binds a first target may or may not specifically bind a second target. As such, "specific binding" does not necessarily require (although it can include) exclusive binding, i.e. binding to a single target. Thus, a binding agent may, in certain embodiments, specifically bind more than one target. In certain embodiments, multiple targets may be bound by the same binding site on the agent or antibody. For example, an antibody may, in certain instances, comprise two identical antigen-binding sites, each of which specifically binds the same epitope on two or more proteins. In certain alternative embodiments, an antibody may be bispecific or multispecific and comprise at least two antigen-binding sites with differing specificities. By way of non-limiting example, a bispecific agent may comprise one binding site that recognizes a target on one protein (e.g., human MET) and further comprise a second, different binding site that recognizes a different target on a second protein (e.g., a human WNT protein). Generally, but not necessarily, reference to binding means specific binding.

The terms "polypeptide" and "peptide" and "protein" are used interchangeably herein and refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids), as well as other modifications known in the art. It is understood that, because the polypeptides of this invention may be based upon antibodies, in certain embodiments, the polypeptides can occur as single chains or associated chains (e.g., dimers).

The terms "polynucleotide" and "nucleic acid" are used interchangeably herein and refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase.

"Conditions of high stringency" may be identified by those that: (1) employ low ionic strength and high temperature for washing, for example 15 mM sodium chloride/1.5 mM sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 in 5×SSC (0.75M NaCl, 75 mM sodium citrate) at 42° C.; or (3) employ during hybridization 50% formamide in 5×SSC, 50 mM sodium phosphate (pH 6.8), 0.1% sodium pyrophosphate, 5×Denhardt's solution, sonicated salmon sperm DNA (50 µ/ml), 0.1% SDS, and 10% dextran sulfate at 42° C., with washes at 42° C. in 0.2×SSC and 50% formamide, followed by a high-stringency wash consisting of 0.1×SSC containing EDTA at 55° C.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity may be measured using sequence comparison software or algorithms or by visual inspection. Various algorithms and software that may be used to obtain alignments of amino acid or nucleotide sequences are well-known in the art. These include, but are not limited to, BLAST, ALIGN, Megalign, BestFit, GCG Wisconsin Package, and variations thereof. In some embodiments, two nucleic acids or polypeptides of the invention are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In some embodiments, identity exists over a region of the sequences that is at least about 10, at least about 20, at least about 40-60 residues, at least about 60-80 residues in length or any integral value therebetween. In some embodiments, identity exists over a longer region than 60-80 residues, such as at least about 80-100 residues, and in some embodiments the sequences are substantially identical over the full length of the sequences being compared, such as the coding region of a nucleotide sequence.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. Preferably, conservative substitutions in the sequences of the polypeptides and antibodies of the invention do not abrogate the binding of the polypeptide or antibody containing the amino acid sequence, to the antigen to which the polypeptide or antibody binds. Methods of identifying nucleotide and amino acid conservative substitutions which do not eliminate antigen binding are well-known in the art.

The term "vector" as used herein means a construct, which is capable of delivering, and usually expressing, one or more gene(s) or sequence(s) of interest in a host cell. Examples of vectors include, but are not limited to, viral vectors, naked DNA or RNA expression vectors, plasmid, cosmid, or phage vectors, DNA or RNA expression vectors associated with cationic condensing agents, and DNA or RNA expression vectors encapsulated in liposomes.

As used herein the term "soluble receptor" refers to an N-terminal extracellular domain (or a fragment thereof) of a receptor protein preceding the first transmembrane domain of the receptor that can be secreted from a cell in soluble form.

As used herein the term "FZD soluble receptor" or "soluble FZD receptor" refers to an N-terminal extracellular fragment of a FZD receptor protein preceding the first transmembrane domain of the receptor that can be secreted from a cell in soluble form. FZD soluble receptors comprising the entire N-terminal extracellular domain (ECD) as well as smaller fragments are encompassed by the term. Thus, FZD soluble receptors comprising a FZD Fri domain are also included in this term.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cells, or compositions include those which have been purified to a degree that they are no longer in a form in which they are found in nature. In some embodiments, a polypeptide, antibody, polynucleotide, vector, cell, or composition which is isolated is substantially pure.

The term "substantially pure" as used herein refers to material which is at least 50% pure (i.e., free from contaminants), at least 90% pure, at least 95% pure, at least 98% pure, or at least 99% pure.

The terms "cancer" and "cancerous" as used herein refer to or describe the physiological condition in mammals in which a population of cells are characterized by unregulated cell growth. Examples of cancer include, but are not limited to, carcinoma, blastoma, sarcoma, and hematologic cancers such as lymphoma and leukemia.

The terms "tumor" and "neoplasm" as used herein refer to any mass of tissue that results from excessive cell growth or proliferation, either benign (non-cancerous) or malignant (cancerous) including pre-cancerous lesions.

The term "metastasis" as used herein refers to the process by which a cancer spreads or transfers from the site of origin to other regions of the body with the development of a similar cancerous lesion at the new location. A "metastatic" or "metastasizing" cell is one that loses adhesive contacts with neighboring cells and migrates (e.g., via the bloodstream or lymph) from the primary site of disease to secondary sites.

The terms "cancer stem cell" and "CSC" and "tumor stem cell" and "tumor initiating cell" are used interchangeably herein and refer to cells from a cancer or tumor that: (1) have extensive proliferative capacity; 2) are capable of asymmetric cell division to generate one or more types of differentiated cell progeny wherein the differentiated cells have reduced and/or limited proliferative or developmental potential; and (3) are capable of symmetric cell divisions for self-renewal or self-maintenance. These properties confer on the cancer stem cells the ability to form or establish a tumor or cancer upon serial transplantation into an immunocompromised host (e.g., a mouse) compared to the majority of tumor cells that fail to form tumors. Cancer stem cells undergo self-renewal versus differentiation in a chaotic manner to form tumors with abnormal cell types that can change over time as mutations occur.

The terms "cancer cell" and "tumor cell" refer to the total population of cells derived from a cancer or tumor or pre-cancerous lesion, including both non-tumorigenic cells, which comprise the bulk of the cancer cell population, and tumorigenic stem cells (cancer stem cells). As used herein, the terms "cancer cell" or "tumor cell" will be modified by the term "non-tumorigenic" when referring solely to those cells lacking the capacity to renew and differentiate to distinguish those tumor cells from cancer stem cells.

The term "tumorigenic" as used herein refers to the functional features of a cancer stem cell including the properties of self-renewal (giving rise to additional tumorigenic cancer stem cells) and proliferation to generate all other tumor cells (giving rise to differentiated and thus non-tumorigenic tumor cells).

The term "tumorigenicity" as used herein refers to the ability of a random sample of cells from the tumor to form palpable tumors upon serial transplantation into immuno-compromised hosts (e.g., mice). This definition also includes enriched and/or isolated populations of cancer stem cells that form palpable tumors upon serial transplantation into immunocompromised hosts (e.g., mice).

The term "subject" refers to any animal (e.g., a mammal), including, but not limited to, humans, non-human primates, canines, felines, rodents, and the like, which is to be the recipient of a particular treatment. Typically, the terms "subject" and "patient" are used interchangeably herein in reference to a human subject.

The term "pharmaceutically acceptable" refers to a product or compound approved (or approvable) by a regulatory agency of the Federal government or a state government or listed in the U.S. Pharmacopeia or other generally recognized pharmacopeia for use in animals, including humans.

The terms "pharmaceutically acceptable excipient, carrier or adjuvant" or "acceptable pharmaceutical carrier" refer to an excipient, carrier or adjuvant that can be administered to a subject, together with at least one binding agent of the present disclosure, and which does not destroy the activity of the binding agent. The excipient, carrier or adjuvant should be non-toxic when administered with a binding agent in doses sufficient to deliver a therapeutic effect.

The terms "effective amount" or "therapeutically effective amount" or "therapeutic effect" refer to an amount of a binding agent, an antibody, polypeptide, polynucleotide, small organic molecule, or other drug effective to "treat" a disease or disorder in a subject or mammal. In the case of cancer, the therapeutically effective amount of a drug (e.g., an antibody) has a therapeutic effect and as such can reduce the number of cancer cells; decrease tumorigenicity, tumorigenic frequency or tumorigenic capacity; reduce the number or frequency of cancer stem cells; reduce the tumor size; reduce the cancer cell population; inhibit and/or stop cancer cell infiltration into peripheral organs including, for example, the spread of cancer into soft tissue and bone; inhibit and/or stop tumor or cancer cell metastasis; inhibit and/or stop tumor or cancer cell growth; relieve to some extent one or more of the symptoms associated with the cancer; reduce morbidity and mortality; improve quality of life; or a combination of such effects. To the extent the agent, for example an antibody, prevents growth and/or kills existing cancer cells, it can be referred to as cytostatic and/or cytotoxic.

The terms "treating" or "treatment" or "to treat" or "alleviating" or "to alleviate" refer to both 1) therapeutic measures that cure, slow down, lessen symptoms of, and/or halt progression of a diagnosed pathologic condition or disorder and 2) prophylactic or preventative measures that prevent or slow the development of a targeted pathologic condition or disorder. Thus those in need of treatment include those already with the disorder, those prone to have the disorder; and those in whom the disorder is to be prevented. In some embodiments, a subject is successfully "treated" according to the methods of the present invention if the patient shows one or more of the following: a reduction in the number of or complete absence of cancer cells; a reduction in the tumor size; inhibition of or an absence of cancer cell infiltration into peripheral organs including the spread of cancer cells into soft tissue and bone; inhibition of or an absence of tumor or cancer cell metastasis; inhibition or an absence of cancer growth; relief of one or more symptoms associated with the specific cancer, reduced morbidity and mortality; improvement in quality of life; reduction in tumorigenicity; reduction in the number or frequency of cancer stem cells; or some combination of effects.

As used in the present disclosure and claims, the singular forms "a", "an" and "the" include plural forms unless the context clearly dictates otherwise.

It is understood that wherever embodiments are described herein with the language "comprising" otherwise analogous embodiments described in terms of "consisting of" and/or "consisting essentially of" are also provided. It is also understood that wherever embodiments are described herein with the language "consisting essentially of" otherwise analogous embodiments described in terms of "consisting of" are also provided.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. Met-Binding Agents

The present invention provides agents that specifically bind human MET. The agents are referred to herein as "MET-binding agents". The phrase "MET-binding agent" encompasses agents that bind only MET and bispecific agents that bind both MET and at least one additional target or antigen. Thus, in some embodiments, the MET-binding agent specifically binds human MET. In some embodiments, the MET-binding agent specifically binds both MET and at least one additional target or antigen. In some embodiments, the MET-binding agent binds both MET and one or more components of the WNT pathway. In some embodiments, the MET-binding agent binds both MET and one or more WNT proteins. In some embodiments, the MET-binding agent binds both MET and one or more FZD proteins. In some embodiments, the MET-binding agent is a polypeptide. In some embodiments, the MET-binding agent is an antibody. In some embodiments, the MET-binding agent is a monovalent antibody. In some embodiments, the MET-binding agent is a heterodimer. In certain embodiments, the MET-binding agent is a bispecific antibody. In certain embodiments, the MET-binding agent is a bispecific agent. In certain embodiments, the MET-binding agent is a bispecific agent comprising a soluble receptor. In certain embodiments, the MET-binding agent is a bispecific agent comprising a monovalent antibody that specifically binds MET. In certain embodiments, the MET-binding agent is a bispecific agent comprising a monovalent antibody that specifically binds MET and a monovalent antibody that specifically binds one or more components of the WNT pathway. In certain embodiments, the MET-binding agent is a bispecific agent (e.g., a heterodimeric agent) comprising a monovalent antibody that specifically binds MET and a soluble receptor that specifically binds one or more WNT proteins.

In certain embodiments, the MET-binding agent specifically binds the extracellular domain of human MET. In some embodiments, the MET-binding agent specifically binds the Sema domain of human MET. In some embodiments, the MET-binding agent specifically binds within the Sema domain of human MET. In some embodiments, the MET-binding agent specifically binds within amino acids 25-932 of human MET (SEQ ID NO:93). In some embodiments, the MET-binding agent specifically binds within amino acids 25-836 of human MET (SEQ ID NO:93). In some embodiments, the MET-binding agent specifically binds within amino acids 25-515 of human MET (SEQ ID NO:93). In some embodiments, the MET-binding agent specifically binds within amino acids 563-836 of human MET (SEQ ID NO:93).

In certain embodiments, the invention provides a MET-binding agent that specifically binds human MET, wherein the MET-binding agent comprises a heavy chain CDR1 comprising ASYAWS (SEQ ID NO:1), a heavy chain CDR2 comprising YISYSGGTDYNPSLKS (SEQ ID NO:2), and a heavy chain CDR3 comprising KGAY (SEQ ID NO:3). In some embodiments, the MET-binding agent further comprises a light chain CDR1 comprising SASSSVSSSYLY (SEQ ID NO:4), a light chain CDR2 comprising STSNLAS (SEQ ID NO:5), and a light chain CDR3 comprising HQWSSYPYT (SEQ ID NO:6). In certain embodiments, the MET-binding agent comprises: (a) a heavy chain CDR1 comprising ASYAWS (SEQ ID NO:1), a heavy chain CDR2 comprising YISYSGGTDYNPSLKS (SEQ ID NO:2), and a heavy chain CDR3 comprising KGAY (SEQ ID NO:3), and (b) a light chain CDR1 comprising SASSSVSSSYLY (SEQ ID NO:4), a light chain CDR2 comprising STSNLAS (SEQ ID NO:5), and a light chain CDR3 comprising HQWSSYPYT (SEQ ID NO:6).

In certain embodiments, the invention provides a MET-binding agent that specifically binds human MET, wherein the MET-binding agent comprises: (a) a heavy chain CDR1 comprising ASYAWS (SEQ ID NO: 1), or a variant thereof comprising 1, 2, 3, or 4 amino acid substitutions; (b) a heavy chain CDR2 comprising YISYSGGTDYNPSLKS (SEQ ID NO:2), or a variant thereof comprising 1, 2, 3, or 4 amino acid substitutions; (c) a heavy chain CDR3 comprising KGAY (SEQ ID NO:3), or a variant thereof comprising 1, 2, 3, or 4 amino acid substitutions; (d) a light chain CDR1 comprising SASSSVSSSYLY (SEQ ID NO:4), or a variant thereof comprising 1, 2, 3, or 4 amino acid substitutions; (e) a light chain CDR2 comprising STSNLAS (SEQ ID NO:5), or a variant thereof comprising 1, 2, 3, or 4 amino acid substitutions; and (f) a light chain CDR3 comprising HQWSSYPYT (SEQ ID NO:6), or a variant thereof comprising 1, 2, 3, or 4 amino acid substitutions. In certain embodiments, the amino acid substitutions are conservative substitutions.

In certain embodiments, the invention provides a MET-binding agent that specifically binds MET, wherein the MET-binding agent comprises a heavy chain variable region having at least about 80% sequence identity to SEQ ID NO:7, and a light chain variable region having at least about 80% sequence identity to SEQ ID NO:8. In certain embodiments, the MET-binding agent comprises a heavy chain variable region having at least about 85%, at least about 90%, at least about 95%, at least about 97%, or at least about 99% sequence identity to SEQ ID NO:7. In certain embodiments, the MET-binding agent comprises a light chain variable region having at least about 85%, at least about 90%, at least about 95%, at least about 97%, or at least about 99% sequence identity to SEQ ID NO:8. In certain embodiments, the MET-binding agent comprises a heavy chain variable region having at least about 95% sequence identity to SEQ ID NO:7 and a light chain variable region having at least about 95% sequence identity to SEQ ID NO:8. In certain embodiments, the MET-binding agent comprises a heavy chain variable region comprising SEQ ID NO:7 and a light chain variable region comprising SEQ ID NO:8. In certain embodiments, the MET-binding agent comprises a heavy chain variable region consisting essentially of SEQ ID NO:7 and a light chain variable region consisting essentially of SEQ ID NO:8. In certain embodiments, the MET-binding agent comprises a heavy chain variable region of SEQ ID NO:7 and a light chain variable region of SEQ ID NO:8.

In some embodiments, the invention provides a MET-binding agent that specifically binds MET, wherein the MET-binding agent comprises a heavy chain comprising SEQ ID NO:12 and a light chain comprising SEQ ID NO:14. In some embodiments, the MET-binding agent comprises a heavy chain of SEQ ID NO:12 and a light chain of SEQ ID NO:14.

In some embodiments, the MET-binding agent comprises a heavy chain comprising SEQ ID NO:13 and a light chain comprising SEQ ID NO:14. In some embodiments, the MET-binding agent comprises a heavy chain of SEQ ID NO: 13 and a light chain of SEQ ID NO:14. In some embodiments, the MET-binding agent comprises a heavy chain comprising SEQ ID NO:88 and a light chain comprising SEQ ID NO: 14. In some embodiments, the MET-binding agent comprises a heavy chain of SEQ ID NO:88 and a light chain of SEQ ID NO:14.

In certain embodiments, the invention provides a MET-binding agent that specifically binds human MET, wherein the MET-binding agent comprises one, two, three, four, five, and/or six of the CDRs of antibody 73R009 (see Table 1). In some embodiments, the MET-binding agent comprises one or more of the CDRs of 73R009, two or more of the CDRs of 73R009, three or more of the CDRs of 73R009, four or more of the CDRs of 73R009, five or more of the CDRs of 73R009, or all six of the CDRs of 73R009.

TABLE 1

| | 73R009 | |
|---|---|---|
| HC CDR1 | ASYAWS | (SEQ ID NO: 1) |
| HC CDR2 | YISYSGGTDYNPSLKS | (SEQ ID NO: 2) |
| HC CDR3 | KGAY | (SEQ ID NO: 3) |
| LC CDR1 | SASSSVSSSYLY | (SEQ ID NO: 4) |
| LC CDR2 | STSNLAS | (SEQ ID NO: 5) |
| LC CDR3 | HQWSSYPYT | (SEQ ID NO: 6) |

In certain embodiments, a MET-binding agent comprises the heavy chain variable region and the light chain variable region of antibody 73R009. In certain embodiments, a MET-binding agent comprises the heavy chain and the light chain of antibody 73R009 (with or without the leader sequence). In certain embodiments, a MET-binding agent comprises the heavy chain and the light chain of antibody 73R009 (with or without the leader sequence) wherein the heavy chain is modified to promote formation of heterodimers (e.g., bispecific agents) or heteromultimers. In certain embodiments, a MET-binding agent is antibody 73R009. In some embodiments, the MET-binding agent comprises a heavy chain variable region encoded by the plasmid deposited with American Type Culture Collection (ATCC), and designated PTA-13609. In some embodiments, the MET-binding agent comprises a light chain variable region encoded by the plasmid deposited with ATCC and designated PTA-13610.

In certain embodiments, a MET-binding agent comprises, consists essentially of, or consists of, antibody 73R009.

In certain embodiments, a MET-binding agent binds the same epitope or essentially the same epitope on MET as a binding agent of the invention. In another embodiment, a MET-binding agent is an antibody or a bispecific agent that binds an epitope on MET that overlaps with the epitope on MET bound by a binding agent of the invention. In certain embodiments, a MET-binding agent binds the same epitope, or essentially the same epitope, on MET as antibody 73R009. In another embodiment, a MET-binding agent is an antibody or a bispecific agent that binds an epitope on MET that overlaps with the epitope on MET bound by antibody 73R009.

In certain embodiments, the MET-binding agent is an antibody. In some embodiments, the antibody is a recombinant antibody. In some embodiments, the antibody is a monoclonal antibody. In some embodiments, the antibody is a chimeric antibody. In some embodiments, the antibody is a humanized antibody. In some embodiments, the antibody is a human antibody. In certain embodiments, the antibody is an IgA, IgD, IgE, IgG, or IgM antibody. In certain embodiments, the antibody is an IgG1 antibody. In certain embodiments, the antibody is an IgG2 antibody. In certain embodiments, the antibody is an antibody fragment comprising an antigen-binding site. In some embodiments, the antibody is a bispecific antibody. In some embodiments, the antibody is a monovalent antibody. In some embodiments, the antibody is monospecific. In some embodiment, the antibody is multispecific.

In some embodiments, the MET-binding agent inhibits binding of MET to hepatocyte growth factor. In some embodiments, the MET-binding agent blocks binding of MET to hepatocyte growth factor. In some embodiments, the MET-binding agent specifically binds MET and facilitates internalization of MET. In some embodiments, the MET-binding agent specifically binds MET and stimulates degradation of MET. In some embodiments, the MET-binding agent specifically binds MET and inhibits dimerization of MET. In some embodiments, the MET-binding agent specifically binds MET and inhibits activation of MET. In some embodiments, the MET-binding agent specifically binds MET and inhibits tumor growth.

In some embodiments, the MET-binding agent binds MET with a $K_D$ of about 100 nM or less. In some embodiments, the MET-binding agent binds MET with a $K_D$ of about 10 nM or less. In some embodiments, the MET-binding agent binds MET with a $K_D$ of about 1 nM or less. In some embodiments, the MET-binding agent binds MET with a $K_D$ of about 0.1 nM or less. In some embodiments, the MET-binding agent binds MET with a $K_D$ of about 0.01 nM or less. In some embodiments, at least one amino acid residue in at least one CDR of the MET-binding agent is substituted with a different amino acid so that the affinity of the MET-binding agent for MET is altered. In some embodiments, the affinity of the MET-binding agent for MET is increased. In some embodiments, the affinity of the MET-binding agent for MET is decreased. In some embodiments, the MET-binding agent binds human MET. In some embodiments, the MET-binding agent binds human MET and mouse MET. In some embodiments, the MET-binding agent binds human MET and does not bind mouse MET.

In certain embodiments, the invention provides a MET-binding agent that is a bispecific agent. In some embodiments, the MET-binding agent is a bispecific agent comprising a first arm and a second arm. In some embodiments, the MET-binding agent is a bispecific agent comprising a first arm and a second arm, wherein the first arm comprises a first binding site that specifically binds MET. In some embodiments, the MET-binding agent is a bispecific agent comprising a first arm and a second arm, wherein the first arm comprises a first binding site that specifically binds MET and the second arm comprises a second binding site that specifically binds a second target or antigen. In some embodiments, the first binding site comprises an antigen-binding site. In some embodiments, the second binding site comprises an antigen-binding site. In some embodiments, the MET-binding agent is a bispecific agent wherein the first arm comprises a first binding site that specifically binds human MET and the second arm comprises a second binding site that binds one or more components of the WNT pathway.

In certain embodiments, the MET-binding agent is a bispecific agent that specifically binds human MET and one or more human FZD proteins. In certain embodiments, the bispecific agent is a bispecific antibody that specifically binds both human MET and one or more human FZD proteins. In some embodiments, the bispecific antibody specifically binds one, two, three, four, five, six, seven, eight, nine, or ten FZD proteins. In some embodiments, the bispecific antibody binds one or more FZD proteins selected from the group consisting of FZD1, FZD2, FZD3, FZD4, FZD5, FZD6, FZD7, FZD8, FZD9, and FZD10. In some embodiments, the bispecific antibody binds one or more FZD proteins comprising FZD1, FZD2, FZD5, FZD7, and/or FZD8. In certain embodiments, the bispecific antibody binds FZD7. In certain embodiments, the bispecific antibody binds FZD5 and/or FZD8. In certain embodiments, the bispecific antibody specifically binds FZD1, FZD2, FZD5, FZD7, and FZD8. Non-limiting examples of FZD-binding agents can be found in U.S. Pat. No. 7,982,013.

In certain embodiments, the bispecific antibody specifically binds MET and the extracellular domain (ECD) of one or more human FZD proteins. In certain embodiments, the bispecific antibody specifically binds MET and a fragment of the extracellular domain (ECD) of one or more human FZD proteins. In certain embodiments, the bispecific antibody specifically binds within the Fri domain (also known as the cysteine-rich domain (CRD)) of one or more human FZD proteins. Sequences of the Fri domain of each of the human FZD proteins are known in the art and are provided as SEQ ID NO:21 (FZD1), SEQ ID NO:22 (FZD2), SEQ ID NO:23 (FZD3), SEQ ID NO:24 (FZD4), SEQ ID NO:25 (FZD5), SEQ ID NO:26 (FZD6), SEQ ID NO:27 (FZD7), SEQ ID NO:28 (FZD8), SEQ ID NO:29 (FZD8), SEQ ID NO:30 (FZD9) and SEQ ID NO:31 (FZD10). Sequences of the predicted minimal Fri domains are provided as SEQ ID NO:32 (FZD1), SEQ ID NO:33 (FZD2), SEQ ID NO:34 (FZD3), SEQ ID NO:35 (FZD4), SEQ ID NO:36 (FZD5), SEQ ID NO:37 (FZD6), SEQ ID NO:38 (FZD7), SEQ ID NO:39 (FZD8), SEQ ID NO:40 (FZD9) and SEQ ID NO:41 (FZD10).

In certain embodiments, the bispecific antibody binds human MET and binds one, two, three, four, five, or more FZD proteins. In some embodiments, the bispecific antibody specifically binds human MET and binds one, two, three, four, or five FZD proteins selected from the group consisting of FZD1, FZD2, FZD5, FZD7, and FZD8. In some embodiments, the bispecific antibody specifically binds MET and binds at least FZD5 and FZD8.

In certain embodiments, the bispecific antibody that binds human MET and one or more human FZD proteins is a FZD antagonist. In certain embodiments, the bispecific antibody is a Wnt pathway antagonist. In certain embodiments, the bispecific antibody inhibits Wnt signaling. In some embodiments, the bispecific antibody inhibits canonical Wnt signaling.

In certain embodiments, the MET-binding agent is a bispecific agent that specifically binds human MET and one or more human WNT proteins. In certain embodiments, the bispecific agent is a bispecific antibody that specifically binds human MET and one or more human WNT proteins. In certain embodiments, the bispecific antibody specifically binds human MET and binds one, two, three, four, five, six, seven, eight, nine, ten, or more WNT proteins. In some embodiments, the bispecific antibody binds human MET and binds one or more human WNT proteins selected from the group consisting of WNT1, WNT2, WNT2b, WNT3, WNT3a, WNT4, WNT5a, WNT5b, WNT6, WNT7a, WNT7b, WNT8a, WNT8b, WNT9a, WNT9b, WNT10a, WNT10b, WNT11, and WNT16. In certain embodiments, the bispecific antibody binds human MET and binds one or more (or two or more, three or more, four or more, five or more, etc.) WNT proteins selected from the group consisting of WNT1, WNT2, WNT2b, WNT3, WNT3a, WNT7a, WNT7b, WNT8a, WNT8b, WNT10a, and WNT10b. In certain embodiments, the one or more (or two or more, three or more, four or more, five or more, etc.) WNT proteins are selected from the group consisting of WNT1, WNT2, WNT2b, WNT3, WNT3a, WNT8a, WNT8b, WNT10a, and WNT10b. Non-limiting examples of WNT-binding agents can be found in International Publication WO 2011/088127.

In certain embodiments, the bispecific antibody specifically binds MET and the C-terminal cysteine rich domain (CRD) of one or more human WNT proteins. In certain embodiments, the bispecific antibody binds a domain within one or more WNT proteins selected from the group consisting of: SEQ ID NO:57 (WNT1), SEQ ID NO:58 (WNT2), SEQ ID NO:59 (WNT2b), SEQ ID NO:60 (WNT3), SEQ ID NO:61 (WNT3a), SEQ ID NO:62 (WNT7a), SEQ ID NO:63 (WNT7b), SEQ ID NO:64 (WNT8a), SEQ ID NO:65 (WNT8b), SEQ ID NO:66 (WNT10a), and SEQ ID NO:67 (WNT10b).

In certain embodiments, the bispecific antibody that binds human MET and one or more WNT proteins is a WNT antagonist. In certain embodiments, the bispecific antibody is a WNT pathway antagonist. In certain embodiments, the bispecific antibody inhibits WNT signaling. In some embodiments, the bispecific antibody inhibits canonical WNT signaling.

In certain embodiments, the MET-binding agent is a bispecific agent that specifically binds human MET and one or more human WNT proteins. In certain embodiments, the bispecific agent that specifically binds human MET and one or more human WNT proteins is a hetcrodimeric agent. In certain embodiments, the bispecific agent that specifically binds human MET and one or more human WNT proteins is a heterodimeric agent comprising a soluble receptor. In certain embodiments, the bispecific agent that specifically binds human MET and one or more human WNT proteins is a heterodimeric agent comprising a fusion protein. In certain embodiments, the bispecific agent that specifically binds human MET and one or more human WNT proteins is a heterodimeric agent comprising a first arm comprising a monovalent antibody and a second arm comprising a soluble receptor. In certain embodiments, the bispecific agent that specifically binds human MET and one or more human WNT proteins is a heterodimeric agent comprising a first arm comprising a monovalent antibody and a second arm comprising a fusion protein.

In certain embodiments, the MET-binding agent is a bispecific agent that specifically binds human MET and one or more human WNT proteins, wherein the bispecific agent comprises the extracellular domain (ECD) of a FZD receptor protein (e.g., a soluble receptor). In certain embodiments, the FZD protein is a human FZD protein. In certain embodiments, the human FZD protein is FZD1, FZD2, FZD3, FZD4, FZD5, FZD6, FZD7, FZD8, FZD9, or FZD10. In certain embodiments, the human FZD protein is FZD8. Non-limiting examples of soluble FZD receptors can be found in U.S. Pat. Nos. 7,723,477 and 7,947,277; and U.S. Patent Publication No. 2011/0305695.

In some embodiments, the bispecific agent comprises a Fri domain of an ECD of a FZD protein. The Fri domains for each of the human FZD1-10 proteins are provided as SEQ ID NOs:21-31. The minimal (or core) Fri domains for each of the human FZD1-10 proteins are provided as SEQ ID NOs:32-41. Those of skill in the art may differ in their understanding of the exact amino acids corresponding to the various Fri domains. Thus, the N-terminus and/or C-terminus of the domains outlined above and herein may extend or be shortened by 1, 2, 3, 4, 5, 6, 7, 8, 9, or even 10 amino acids.

In some embodiments, a soluble receptor comprising a FZD Fri domain can demonstrate altered biological activity (e.g., increased protein half-life) compared to a soluble receptor comprising the entire FZD ECD. In some embodiments, protein half-life can be further increased by covalent modification with polyethylene glycol (PEG) or polyethylene oxide (PEO).

In certain embodiments, the bispecific agent comprises a Fri domain of a human FZD protein, or a fragment or variant of the Fri domain that binds one or more human WNT proteins. In certain embodiments, the human FZD protein is FZD1, FZD2, FZD3, FZD4, FZD5, FZD6, FZD7, FZD8, FZD9, or FZD10. In certain embodiments, the human FZD protein is FZD8. In certain embodiments, the human FZD protein is FZD4. In certain embodiments, the human FZD protein is FZD5. In certain embodiments, the human FZD protein is FZD10. In certain embodiments, the FZD protein is FZD4 and the bispecific agent comprises SEQ ID NO:24. In certain embodiments, the FZD protein is FZD5 and the bispecific agent comprises SEQ ID NO:25. In certain embodiments, the FZD protein is FZD7 and the bispecific agent comprises SEQ ID NO:27. In certain embodiments, the FZD protein is FZD8 and the bispecific agent comprises SEQ ID NO:28 or SEQ ID NO:29. In certain embodiments, the FZD protein is FZD10 and the bispecific agent comprises SEQ ID NO:31.

In some embodiments, the bispecific agent comprises a Fri domain comprising the minimal Fri domain of FZD1 (SEQ ID NO:32), the minimal Fri domain of FZD2 (SEQ ID NO:33), the minimal Fri domain of FZD3 (SEQ ID NO:34), the minimal Fri domain of FZD4 (SEQ ID NO:35), the minimal Fri domain of FZD5 (SEQ ID NO:36), the minimal Fri domain of FZD6 (SEQ ID NO:37), the minimal Fri domain of FZD7 (SEQ ID NO:38), the minimal Fri domain of FZD8 (SEQ ID NO:39), the minimal Fri domain of FZD9 (SEQ ID NO:40), or the minimal Fri domain of FZD10 (SEQ ID NO:41). In some embodiments, the bispecific agent comprises a Fri domain comprising the minimal Fri domain of FZD8 (SEQ ID NO:39).

In some embodiments, the bispecific agent comprises a Fri domain consisting essentially of the Fri domain of FZD1, the Fri domain of FZD2, the Fri domain of FZD3, the Fri domain of FZD4, the Fri domain of FZD5, the Fri domain of FZD6, the Fri domain of FZD7, the Fri domain of FZD8, the Fri domain of FZD9, or the Fri domain of FZD10. In some embodiments, the bispecific agent comprises a Fri domain consisting essentially of the Fri domain of FZD8.

In some embodiments, the bispecific agent comprises a sequence selected from the group consisting of: SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, and SEQ ID NO:41. In some embodiments, the bispecific agent comprises a Fri domain comprising SEQ ID NO:39. In some embodiments, the bispecific agent comprises a Fri domain comprising SEQ ID NO:28. In some embodiments, the bispecific agent comprises a Fri domain of SEQ ID NO:28. In some embodiments, the bispecific agent comprises a Fri domain comprising SEQ ID NO:29. In some embodiments, the bispecific agent comprises a Fri domain of SEQ ID NO:29.

In certain embodiments, the bispecific agent comprises a variant of any one of the aforementioned FZD Fri domain sequences that comprises one or more (e.g., one, two, three, four, five, six, seven, eight, nine, ten, etc.) conservative substitutions and is capable of binding WNT protein(s).

In certain embodiments, a bispecific agent, such as an agent comprising a soluble FZD receptor, further comprises a heterologous polypeptide. In some embodiments, a soluble FZD receptor may include FZD ECD or Fri domains linked to other heterologous functional and structural polypeptides including, but not limited to, a human Fc region, protein tags (e.g., myc, FLAG, GST), other endogenous proteins or protein fragments, or any other useful protein sequence including any linker region between a FZD ECD or Fri domain and a second polypeptide. In certain embodiments, the heterologous polypeptide comprises a human Fc region. The Fc region can be obtained from any of the classes of immunoglobulin, IgG, IgA, IgM, IgL) and IgE. In some embodiments, the Fc region is a human IgG1 Fc region. In some embodiments, the Fc region is a human IgG2 Fc region. In some embodiments, the Fc region is a wild-type Fc region (including Fc region variants found in nature). In some embodiments, the Fc region is a mutated Fc region. In some embodiments, the Fc region is truncated at the N-terminal end by 1, 2, 3, 4, 5, 6, 7, 8, 9, 10, or more amino acids, (e.g., in the hinge domain). In some embodiments, an amino acid in the hinge domain is changed to hinder undesirable disulfide bond formation. In some embodiments, a cysteine is replaced with a serine to hinder or block undesirable disulfide bond formation. In some embodiments, the Fc region is truncated at the C-terminal end by 1, 2, 3, or more amino acids. In some embodiments, the Fc region is truncated at the C-terminal end by 1 amino acid. In certain embodiments, the heterologous polypeptide comprises SEQ ID NO:42, SEQ ID NO:43, SEQ ID NO:44, SEQ ID NO:45, SEQ ID NO:46, SEQ ID NO: 47, SEQ ID NO:48, SEQ ID NO:49, SEQ ID NO:50, SEQ ID NO:51, SEQ ID NO:52, SEQ ID NO:91, or SEQ ID NO:92. In certain embodiments, the heterologous polypeptide is SEQ ID NO:42, SEQ ID NO:43, SEQ ID NO:44, SEQ ID NO:45, SEQ ID NO:46, SEQ ID NO: 47, SEQ ID NO:48, SEQ ID NO:49, SEQ ID NO:50, SEQ ID NO:511, SEQ ID NO:52, SEQ ID NO:91, or SEQ ID NO:92. In certain embodiments, the heterologous polypeptide comprises SEQ ID NO:48, SEQ ID NO:51, or SEQ ID NO:52. In certain embodiments, the heterologous polypeptide is SEQ ID NO:48, SEQ ID NO:51, or SEQ ID NO:52.

In certain embodiments, a bispecific agent comprises a fusion protein comprising at least a minimal Fri domain of a FZD receptor and a Fec region. As used herein, a "fusion protein" is a hybrid protein expressed by a nucleic acid molecule comprising nucleotide sequences of at least two genes. In some embodiments, the C-terminus of the first polypeptide is linked to the N-terminus of the immunoglobulin Fc region. In some embodiments, the first polypeptide (e.g., a FZD Fri domain) is directly linked to the Fc region (i.e. without an intervening linker). In some embodiments, the first polypeptide is linked to the Fc region via a linker.

As used herein, the term "linker" refers to a linker inserted between a first polypeptide (e.g., a FZD component) and a second polypeptide (e.g., a Fc region). In some embodiments, the linker is a peptide linker. Linkers should not adversely affect the expression, secretion, or bioactivity of the polypeptide. Linkers should not be antigenic and should not elicit an immune response. Suitable linkers are known to those of skill in the art and often include mixtures of glycine and serine residues and often include amino acids that are sterically unhindered. Other amino acids that can be incorporated into useful linkers include threonine and alanine residues. Linkers can range in length, for example from 1-50 amino acids in length, 1-22 amino acids in length, 1-10 amino acids in length, 1-5 amino acids in length, or 1-3 amino acids in length. Linkers may include, but are not limited to, SerGly, GGSG, GSGS, GGGS, S(GGS)n where n is 1-7, GRA, poly (Gly), poly(Ala), ESGGGGVT (SEQ ID NO:68), LESGGGGVT (SEQ ID NO:69), GRAQVT (SEQ ID NO:70), WRAQVT (SEQ ID NO:71), and ARGRAQVT (SEQ ID NO:72). As used herein, a linker is an intervening peptide sequence that does not include amino acid residues from either the C-terminus of the first polypeptide (e.g., a FZD Fri domain) or the N-terminus of the second polypeptide (e.g., the Fc region).

In some embodiments, the bispecific agent comprises a FZD Fri domain, a Fc region and a linker connecting the FZD Fri domain to the Fc region. In some embodiments, the FZD Fri domain comprises SEQ ID NO:28, SEQ ID NO:29, or SEQ ID NO:39. In some embodiments, the linker comprises ESGGGGVT (SEQ ID NO:68) or LESGGGGVT (SEQ ID NO:69).

FZD receptors and immunoglobulin proteins contain signal sequences that direct the transport of the proteins. Signal sequences (also referred to as signal peptides or leader sequences) are located at the N-terminus of nascent polypeptides. They target the polypeptide to the endoplasmic reticulum and the proteins are sorted to their destinations, for example, to the inner space of an organelle, to an interior membrane, to the cell's outer membrane, or to the cell exterior via secretion. Most signal sequences are cleaved from the protein by a signal peptidase after the proteins are transported to the endoplasmic reticulum. The cleavage of the signal sequence from the polypeptide usually occurs at a specific site in the amino acid sequence and is dependent upon amino acid residues within the signal sequence. Although there is usually one specific cleavage site, more than one cleavage site may be recognized and/or used by a signal peptidase resulting in a non-homogenous N-terminus of the polypeptide. For example, the use of different cleavage sites within a signal sequence can result in a polypeptide expressed with different N-terminal amino acids. Accordingly, in some embodiments, the polypeptides as described herein may comprise a mixture of polypeptides with different N-termini. In some embodiments, the N-termini differ in length by 1, 2, 3, 4, or 5 amino acids. In some embodiments, the polypeptide is substantially homogeneous, i.e., the polypeptides have the same N-terminus. In some embodiments, the signal sequence of the polypeptide comprises one or more (e.g., one, two, three, four, five, six, seven, eight, nine, ten, etc.) amino acid substitutions and/or deletions. In some embodiments, the signal sequence of the polypeptide comprises amino acid substitutions and/or deletions that allow one cleavage site to be dominant, thereby resulting in a substantially homogeneous polypeptide with one N-terminus.

In some embodiments, the bispecific agent that specifically binds MET and one or more WNT proteins comprises: a first polypeptide comprising SEQ ID NO:28 and a second polypeptide comprising SEQ ID NO:47, SEQ ID NO:48, SEQ ID NO:49, SEQ ID NO:50, SEQ ID NO:51, or SEQ ID NO:52. In some embodiments, the bispecific agent comprises: a first polypeptide comprising SEQ ID NO:28 and a second polypeptide comprising SEQ ID NO:47 or SEQ ID NO:48. In some embodiments, the bispecific agent comprises: a first polypeptide comprising SEQ ID NO:28 and a second polypeptide comprising SEQ ID NO:49 or SEQ ID NO:51. In some embodiments, the bispecific agent comprises: a first polypeptide comprising SEQ ID NO:28 and a second polypeptide comprising SEQ ID NO:50 or SEQ ID NO:52. In some embodiments, the bispecific agent comprises: a first polypeptide comprising SEQ ID NO:28 and a second polypeptide comprising SEQ ID NO:52. In some embodiments, the bispecific agent that specifically binds MET and one or more WNT proteins comprises: a first polypeptide comprising SEQ ID NO:29 and a second polypeptide comprising SEQ ID NO:47, SEQ ID NO:48, SEQ ID NO:49, SEQ ID NO:50, SEQ ID NO:51, or SEQ ID NO:52. In some embodiments, the bispecific agent comprises: a first polypeptide comprising SEQ ID NO:29 and a second polypeptide comprising SEQ ID NO:47 or SEQ ID NO:48. In some embodiments, the bispecific agent comprises: a first polypeptide comprising SEQ ID NO:29 and a second polypeptide comprising SEQ ID NO:49 or SEQ ID NO:51. In some embodiments, the bispecific agent comprises: a first polypeptide comprising SEQ ID NO:29 and a second polypeptide comprising SEQ ID NO:50 or SEQ ID NO:52. In some embodiments, the bispecific agent comprises: a first polypeptide comprising SEQ ID NO:29 and a second polypeptide comprising SEQ ID NO:52. In some embodiments, the bispecific agent that specifically binds MET and one or more WNT proteins comprises: a first polypeptide comprising SEQ ID NO:39 and a second polypeptide comprising SEQ ID NO:47, SEQ ID NO:48, SEQ ID NO:49, SEQ ID NO:50, SEQ ID NO:51, or SEQ ID NO:52. In some embodiments, the bispecific agent comprises: a first polypeptide comprising SEQ ID NO:39 and a second polypeptide comprising SEQ ID NO:47 or SEQ ID NO:48. In some embodiments, the bispecific agent comprises: a first polypeptide comprising SEQ ID NO:39 and a second polypeptide comprising SEQ ID NO:49 or SEQ ID NO:51. In some embodiments, the bispecific agent comprises: a first polypeptide comprising SEQ ID NO:39 and a second polypeptide comprising SEQ ID NO:50 or SEQ ID NO:52. In some embodiments, the bispecific agent comprises: a first polypeptide comprising SEQ ID NO:39 and a second polypeptide comprising SEQ ID NO:52.

In some embodiments, the bispecific agent comprises SEQ ID NO:55 or SEQ ID NO:56. In some embodiments, the bispecific agent comprises SEQ ID NO:56. In some embodiments, the bispecific agent comprises SEQ ID NO:87.

In some embodiments, the MET-binding agent is a bispecific agent comprising: (a) a first binding site that specifically binds human MET, and (b) a second binding site that binds one or more components of the WNT pathway, wherein the first binding site comprises (a) a heavy chain CDR1 comprising ASYAWS (SEQ ID NO: 1), a heavy chain CDR2 comprising YISYSGGTDYNPSLKS (SEQ ID NO:2), and a heavy chain CDR3 comprising KGAY (SEQ ID NO:3), and (b) a light chain CDR1 comprising SASSSVSSSYLY (SEQ ID NO:4), a light chain CDR2 comprising STSNLAS (SEQ ID NO:5), and a light chain CDR3 comprising HQWSSYPYT (SEQ ID NO:6). In some embodiments, the MET-binding agent is a bispecific agent comprising: (a) a first binding site that specifically binds human MET, and (b) a second binding site that binds one or more WNT proteins, wherein the first binding site comprises (a) a heavy chain CDR1 comprising ASYAWS (SEQ ID NO:1), a heavy chain CDR2 comprising YISYSGGTDYNPSLKS (SEQ ID NO:2), and a heavy chain CDR3 comprising KGAY (SEQ ID NO:3), and (b) a light chain CDR1 comprising SASSSVSSSYLY (SEQ ID NO:4), a light chain CDR2 comprising STSNLAS (SEQ ID NO:5), and a light chain CDR3 comprising HQWSSY-PYT (SEQ ID NO:6).

In some embodiments, the MET-binding agent is a bispecific agent comprising (a) a first binding site that specifically binds human MET and (b) a second binding site that binds one or more components of the WNT pathway, wherein the first binding site comprises a heavy chain CDR1 comprising GYTFTSYWLH (SEQ ID NO:78), a heavy chain CDR2 comprising GMIDPSNSDTRFNPNFKD (SEQ ID NO:79), and a heavy chain CDR3 comprising TYGSYVSPLDY (SEQ ID NO:81), SYGSYVSPLDY (SEQ ID NO:82), ATYGSYVSPLDY (SEQ ID NO:83), or XYGSYVSPLDY (SEQ ID NO:80), wherein X is not R; and a light chain CDR1 comprising KSSQSLLYTSSQKNYLA (SEQ ID NO:84), a light chain CDR2 comprising WASTRES (SEQ ID NO:85), and a light chain CDR3 comprising QQYYAYPWT (SEQ ID NO:86).

In some embodiments, the MET-binding agent is a bispecific agent comprising: (a) a first binding site that specifically binds human MET, and (b) a second binding site that binds one or more components of the WNT pathway, wherein the first binding site comprises a heavy chain variable region having at least about 80% sequence identity to SEQ ID NO:7. In some embodiments, the first binding site further comprises a light chain variable region having at least about 80% sequence identity to SEQ ID NO:8. In certain embodiments, the first binding site comprises a heavy chain variable region having at least about 85%, at least about 90%, at least about 95%, at least about 97%, or at least about 99% sequence identity to SEQ ID NO:7, and a light chain variable region having at least about 85%, at least about 90%, at least about 95%, at least about 97%, or at least about 99% sequence identity to SEQ ID NO:8.

In some embodiments, the MET-binding agent is a bispecific agent that comprises (a) a first arm comprising a first binding site that specifically binds human MET, and (b) a second arm comprising a second binding site that binds one or more WNT proteins, wherein the first arm comprises a heavy chain CDR1 comprising ASYAWS (SEQ ID NO:1), a heavy chain CDR2 comprising YISYSGGTDYNPSLKS (SEQ ID NO:2), and a heavy chain CDR3 comprising KGAY (SEQ ID NO:3), and a light chain CDR1 comprising SASSSVSS-SYLY (SEQ ID NO:4), a light chain CDR2 comprising STSNLAS (SEQ ID NO:5), and a light chain CDR3 comprising HQWSSYPYT (SEQ ID NO:6); and the second arm comprises a FZD8 Fri domain. In some embodiments, the second arm comprises SEQ ID NO:28, SEQ ID NO:29, or SEQ ID NO:39.

In some embodiments, the MET-binding agent is a bispecific agent that specifically binds human MET and binds one or more components of the WNT pathway, wherein the first arm of the bispecific agent comprises a heavy chain of SEQ ID NO:12, SEQ ID NO:13, or SEQ ID NO:88, and/or a light chain of SEQ ID NO: 14. In some embodiments, the first arm of the bispecific agent comprises a heavy chain of SEQ ID NO: 13 and a light chain of SEQ ID NO:14.

In some embodiments, the MET-binding agent is a bispecific agent that specifically binds human MET and binds one or more WNT proteins, wherein the first arm of the bispecific agent comprises a heavy chain of SEQ ID NO:12, SEQ ID NO:13, or SEQ ID NO:88, and a light chain of SEQ ID NO:14, and wherein the second arm of the bispecific agent comprises a first polypeptide comprising a FZD8 Fri domain. In some embodiments, the second arm of the bispecific agent comprises a first polypeptide comprising a FZD8 Fri domain and a second polypeptide comprising a human Fc region. In some embodiments, the second arm of the bispecific agent comprises a first polypeptide comprising a FZD8 Fri domain and a second polypeptide comprising a human IgG1 Fc region. In some embodiments, the second arm of the bispecific agent comprises a first polypeptide comprising a FZD8 Fri domain and a second polypeptide comprising a human IgG2 Fc region. In some embodiments, the second arm of the bispecific agent comprises SEQ ID NO:28, SEQ ID NO:29, or SEQ ID NO:39. In some embodiments, the second arm of the bispecific agent comprises a first polypeptide comprising SEQ ID NO:28, SEQ ID NO:29, or SEQ ID NO:39 and a second polypeptide comprising SEQ ID NO:49, SEQ ID NO:50, SEQ ID NO:51, or SEQ ID NO:52.

In some embodiments, the MET-binding agent is a bispecific agent that specifically binds human MET and binds one or more WNT proteins, wherein the first arm of the bispecific agent comprises a heavy chain of SEQ ID NO: 13 and a light chain of SEQ ID NO: 14, and the second arm of the bispecific agent comprises a first polypeptide of SEQ ID NO:28 and a second polypeptide of SEQ ID NO:52. In some embodiments, the MET-binding agent is a bispecific agent that specifically binds human MET and binds one or more WNT proteins, wherein the first arm of the bispecific agent comprises a heavy chain of SEQ ID NO:13 and a light chain of SEQ ID NO:14, and the second arm of the bispecific agent comprises SEQ ID NO:56. In some embodiments, the bispecific agent is referred to as bispecific agent 315B6. Bispecific agent 315B6 comprises a (a) heavy chain encoded by the plasmid comprising SEQ ID NO:16 deposited with ATCC, 10801 University Boulevard, Manassas, Va., USA, under the conditions of the Budapest Treaty on Mar. 12, 2013 and assigned designation number PTA-13609, (b) a light chain encoded by the plasmid comprising SEQ ID NO:19 deposited with ATCC under the conditions of the Budapest Treaty on Mar. 12, 2013 and assigned designation number PTA-13610; and (c) a polypeptide encoded by the plasmid comprising SEQ ID NO:89 deposited with ATCC under the conditions of the Budapest Treaty on Mar. 12, 2013 and assigned designation number PTA-13611. Bispecific agent 315B6 comprises a (a) heavy chain comprising SEQ ID NO:13 encoded by the plasmid deposited with ATCC and assigned designation number PTA-13609, (b) a light chain comprising SEQ ID NO:14 encoded by the plasmid deposited with ATCC and assigned designation number PTA-13610; and (c) a polypeptide comprising SEQ ID NO:56 encoded by the plasmid deposited with ATCC and assigned designation number PTA-13611.

In some embodiments, the bispecific agent comprises a heavy chain comprising the heavy chain variable region encoded by the plasmid deposited with ATCC designated PTA-13609 and a light chain comprising the light chain variable region encoded by the plasmid deposited with ATCC designated PTA-13610. In some embodiments, the bispecific agent comprises a polypeptide encoded by the plasmid deposited with ATCC designated PTA-13611.

In some embodiments, the MET-binding agent is a bispecific agent that specifically binds human MET and binds one or more WNT proteins, wherein the first arm of the bispecific agent comprises a heavy chain of SEQ ID NO:88 and a light chain of SEQ ID NO: 14, and wherein the second arm of the bispecific agent comprises a first polypeptide of SEQ ID NO:28 and a second polypeptide of SEQ ID NO:50. In some embodiments, the MET-binding agent is a bispecific agent that specifically binds human MET and binds one or more WNT proteins, wherein the first arm of the bispecific agent comprises a heavy chain of SEQ ID NO:88 and a light chain of SEQ ID NO: 14, and wherein the second arm of the bispecific agent comprises SEQ ID NO:87.

In some embodiments, the MET-binding agent is a bispecific agent that specifically binds human MET and binds one or more WNT proteins, wherein the first arm of the bispecific agent comprises a heavy chain variable region having at least about 80% sequence identity to SEQ ID NO:7 and a light chain variable region having at least about 80% sequence identity to SEQ ID NO:8, and the second arm of the bispecific agent comprises a FZD8 Fri domain. In certain embodiments, the first arm of the bispecific agent comprises a heavy chain variable region having at least about 85%, at least about 90%, at least about 95%, at least about 97%, or at least about 99% sequence identity to SEQ ID NO:7 and a light chain variable region having at least about 85%, at least about 90%, at least about 95%, at least about 97%, or at least about 99% sequence identity to SEQ ID NO:8, and the second arm of the bispecific agent comprises a FZD8 Fri domain. In certain embodiments, the first arm of the bispecific agent comprises a heavy chain variable region having at least about 95% sequence identity to SEQ ID NO:7 and a light chain variable region having at least about 95% sequence identity to SEQ ID NO:8, and the second arm of the bispecific agent comprises a FZD8 Fri domain. In certain embodiments, the first arm of the bispecific agent comprises a heavy chain variable region comprising SEQ ID NO:7 and a light chain variable region comprising SEQ ID NO:8, and the second arm of the bispecific agent comprises a FZD8 Fri domain. In certain embodiments, the first arm of the bispecific agent comprises a heavy chain variable region of SEQ ID NO:7 and a light chain variable region of SEQ ID NO:8, and the second arm of the bispecific agent comprises a FZD8 Fri domain.

In some embodiments, the MET-binding agent is a bispecific agent, wherein the first arm of the bispecific arm comprises a first CH3 domain and the second arm of the bispecific agent comprises a second CH3 domain, and each of the CH3 domains is modified to promote formation of heterodimers or heteromultimers. In some embodiments, the first and second CH3 domains are modified using a knobs-into-holes technique. In some embodiments, the first and second CH3 domains comprise changes or substitutions in amino acids that result in altered electrostatic interactions. In some embodiments, the first and second CH3 domains comprise changes in amino acids that result in altered hydrophobic/hydrophilic interactions.

In some embodiments, the MET-binding agent is a bispecific agent that comprises two heavy chain constant regions selected from the group consisting of: (a) a first human IgG1 constant region, wherein the amino acids at positions corresponding to positions 253 and 292 of SEQ ID NO:74 are substituted with glutamate or aspartate, and a second human IgG1 constant region, wherein the amino acids at positions corresponding to positions 240 and 282 of SEQ ID NO:74 are substituted with lysine; (b) a first human IgG2 constant region, wherein the amino acids at positions corresponding to positions 249 and 288 of SEQ ID NO:75 are substituted with glutamate or aspartate, and a second human IgG2 constant region wherein the amino acids at positions corresponding to positions 236 and 278 of SEQ ID NO:75 are substituted with lysine; (c) a first human IgG3 constant region, wherein the amino acids at positions corresponding to positions 300 and 339 of SEQ ID NO:76 are substituted with glutamate or aspartate, and a second human IgG3 constant region wherein the amino acids at positions corresponding to positions 287 and 329 of SEQ ID NO:76 are substituted with lysine; and (d) a first human IgG4 constant region, wherein the amino acids at positions corresponding to positions 250 and 289 of SEQ ID NO:77 are substituted with glutamate or aspartate, and a second IgG4 constant region wherein the amino acids at positions corresponding to positions 237 and 279 of SEQ ID NO:78 are substituted with lysine.

In some embodiments, the bispecific agent comprises a first human IgG1 constant region with amino acid substitutions at positions corresponding to positions 253 and 292 of SEQ ID NO:74, wherein the amino acids are replaced with glutamate or aspartate, and a second human IgG1 constant region with amino acid substitutions at positions corresponding to positions 240 and 282 of SEQ ID NO:74, wherein the amino acids are replaced with lysine. In some embodiments, the bispecific agent comprises a first human IgG2 constant region with amino acid substitutions at positions corresponding to positions 249 and 288 of SEQ ID NO:75, wherein the amino acids are replaced with glutamate or aspartate, and a second human IgG2 constant region with amino acid substitutions at positions corresponding to positions 236 and 278 of SEQ ID NO:75, wherein the amino acids are replaced with lysine. In some embodiments, the bispecific agent comprises a first human IgG3 constant region with amino acid substitutions at positions corresponding to positions 300 and 339 of SEQ ID NO:76, wherein the amino acids are replaced with glutamate or aspartate, and a second human IgG2 constant region with amino acid substitutions at positions corresponding to positions 287 and 329 of SEQ ID NO:76, wherein the amino acids are replaced with lysine. In some embodiments, the bispecific agent comprises a first human IgG4 constant region with amino acid substitutions at positions corresponding to positions 250 and 289 of SEQ ID NO:77, wherein the amino acids are replaced with glutamate or aspartate, and a second human IgG4 constant region with amino acid substitutions at positions corresponding to positions 237 and 279 of SEQ ID NO:77, wherein the amino acids are replaced with lysine.

In some embodiments, the bispecific agent comprises a first human IgG2 constant region with amino acid substitutions at positions corresponding to positions 249 and 288 of SEQ ID NO:75, wherein the amino acids are replaced with glutamate, and a second human IgG2 constant region with amino acid substitutions at positions corresponding to positions 236 and 278 of SEQ ID NO:75, wherein the amino acids are replaced with lysine. In some embodiments, the bispecific agent comprises a first human IgG2 constant region with amino acid substitutions at positions corresponding to positions 249 and 288 of SEQ ID NO:75, wherein the amino acids are replaced with asparate, and a second human IgG2 constant region with amino acid substitutions at positions corresponding to positions 236 and 278 of SEQ ID NO:75, wherein the amino acids are replaced with lysine.

In certain embodiments, a MET-binding agent binds MET and/or one or more components of the WNT pathway with a dissociation constant ($K_D$) of about 1 µM or less, about 100 nM or less, about 40 nM or less, about 20 nM or less, about 10 nM or less, about 1 nM or less, or about 0.1 nM or less. In some embodiments, a MET-binding agent binds MET and/or one or more components of the WNT pathway with a $K_D$ of about 20 nM or less. In some embodiments, a MET-binding agent binds MET and/or one or more components of the WNT pathway with a $K_D$ of about 10 nM or less. In some embodiments, a MET-binding agent binds MET and/or one or more components of the WNT pathway with a $K_D$ of about 1 nM or less. In some embodiments, a MET-binding agent binds MET and/or one or more components of the WNT pathway with a $K_D$ of about 0.1 nM or less. In some embodiments, a MET-binding agent binds both human MET and mouse MET with a $K_D$ of about 100 nM or less. In some embodiments, a MET-binding agent binds both human MET and mouse MET with a $K_D$ of about 50 nM or less. In some embodiments, a MET-binding agent binds human MET and does not bind mouse MET. In some embodiments, a MET-binding agent binds one or more human WNT proteins with a $K_D$ of about 100 nM or less. In some embodiments, a MET-binding agent binds one or more human WNT proteins with a $K_D$ of about 50 nM or less. In some embodiments, a MET-binding agent binds one or more human WNT proteins with a $K_D$ of about 20 nM or less. In some embodiments, the dissociation constant of the binding agent (e.g., an antibody or bispecific agent) to MET is the dissociation constant determined using a MET fusion protein comprising at least a portion of MET immobilized on a Biacore chip. In some embodiments, the dissociation constant of the binding agent (e.g., an antibody or bispecific agent) to a WNT protein is the dissociation constant determined using a WNT-fusion protein comprising at least a portion of a WNT protein immobilized on a Biacore chip.

In some embodiments, the MET-binding agent is a bispecific agent that comprises a first binding site that specifically binds MET and a second binding site that specifically binds one or more components of the WNT pathway. In some embodiments, a MET-binding agent binds both MET and one or more components of the WNT pathway (e.g., WNT proteins or FZD proteins) with a $K_D$ of about 100 nM or less. In some embodiments, a MET-binding agent binds both MET and one or more components of the WNT pathway with a $K_D$ of about 50 nM or less. In some embodiments, a MET-binding agent binds both MET and one or more components of the WNT pathway with a $K_D$ of about 20 nM or less. In some embodiments, a MET-binding agent binds both MET and one or more components of the WNT pathway with a $K_D$ of about 10 nM or less. In some embodiments, a MET-binding agent or antibody binds both MET and one or more components of the WNT pathway with a $K_D$ of about 1 nM or less.

In some embodiments, the MET-binding agent is a bispecific agent that comprises a first binding site with a binding affinity that is weaker than the binding affinity of the second binding site. For example, in some embodiments, the bispecific agent may bind MET with a $K_D$ ranging from about 0.1 nM to 1 nM and may bind one or more components of the WNT pathway with a $K_D$ ranging from about 1 nM to 10 nM. Or the bispecific agent may bind MET with a $K_D$ ranging from about 1 nM to 10 nM and may bind one or more components of the WNT pathway with a $K_D$ ranging from about 0.1 nM to 1 nM. In some embodiments, the bispecific agent may bind one or more components of the WNT pathway with a $K_D$ ranging from about 0.1 nM to 1 nM and may bind MET with a $K_D$ ranging from about 1 nM to 10 nM. Or the bispecific agent may bind one or more components of the WNT pathway with a $K_D$ ranging from about 1 nM to 10 nM and may bind MET with a $K_D$ ranging from about 0.1 nM to 1 nM. In some embodiments, the difference in affinity between the two binding sites may be about 2-fold or more, about 3-fold or more, about 5-fold or more, about 8-fold or more, about 10-fold or more, about 15-fold or more, about 30-fold or more, about 50-fold or more, or about 100-fold or more. In some embodiments, at least one amino acid residue in at least one CDR of the antigen-binding site for MET is substituted with a different amino acid so that the affinity of the MET-binding site is altered. In some embodiments, the affinity of the MET-binding site is increased. In some embodiments, the affinity of the MET-binding site is decreased. In some embodiments, the affinities of both the MET and one or more components of the WNT pathway binding sites are altered. Modulation of the affinities of the two binding sites may affect the biological activity of the bispecific agent. For example, decreasing the affinity of the binding site for MET or one or more components of the WNT pathway may have a desirable effect, for example decreased toxicity of the binding agent or an increased therapeutic index of the binding agent.

By way of non-limiting example, the bispecific agent may comprise (a) a first binding site that binds human MET with a $K_D$ between about 0.1 nM and about 10 nM, and (b) a second binding site that specifically binds one or more human WNT proteins with a $K_D$ between about 0.1 nM and about 20 nM, between about 0.5 nM and about 20 nM, between about 1.0 nM and 10 nM.

In certain embodiments, a MET-binding agent binds MET and one or more components of the WNT pathway (e.g., WNT proteins or FZD proteins) with a half maximal effective concentration ($EC_{50}$) of about 1 µM or less, about 100 nM or less, about 40 nM or less, about 20 nM or less, about 10 nM or less, about 1 nM or less, or about 0.1 nM or less. In certain embodiments, a MET-binding agent binds MET and one or more components of the WNT pathway (e.g., WNT proteins or FZD proteins) with a half maximal effective concentration ($EC_{50}$) of about 1 µM or less, about 100 nM or less, about 40 nM or less, about 20 nM or less, about 10 nM or less, about 1 nM or less, or about 0.1 nM or less.

In certain embodiments, the MET-binding agent comprises an antibody. In some embodiments, the antibody is a recombinant antibody. In some embodiments, the antibody is a monoclonal antibody. In some embodiments, the antibody is a chimeric antibody. In some embodiments, the antibody is a humanized antibody. In some embodiments, the antibody is a human antibody. In certain embodiments, the antibody is an IgA, IgD, IgE, IgG, or IgM antibody. In certain embodiments, the antibody is an IgG1 antibody. In certain embodiments, the antibody is an IgG2 antibody. In certain embodiments, the antibody is an antibody fragment comprising an antigen-binding site. In some embodiments, the antibody is a bispecific antibody. In some embodiments, the antibody is a monovalent antibody. In some embodiments, the antibody is a monospecific antibody. In some embodiments, the antibody is a multispecific antibody. In some embodiments, the antibody is conjugated to a cytotoxic moiety. In some embodiments, the antibody is isolated. In some embodiments, the antibody is substantially pure.

The binding agents of the present invention can be assayed for specific binding by any method known in the art. The immunoassays which can be used include, but are not limited to, competitive and non-competitive assay systems using techniques such as Biacore analysis, FACS analysis, immunofluorescence, immunocytochemistry, Western blot analysis, radioimmunoassay, ELISA, "sandwich" immunoassay, immunoprecipitation assay, precipitation reaction, gel diffusion precipitin reaction, immunodiffusion assay, agglutination assay, complement-fixation assay, immunoradiometric assay, fluorescent immunoassay, homogeneous time-resolved fluorescence assay (HTRF), and protein A immunoassay. Such assays are routine and well-known in the art (see, e.g., Ausubel et al., Editors, 1994-present, *Current Protocols in Molecular Biology*, John Wiley & Sons, Inc., New York, N.Y.).

For example, the specific binding of an agent to human MET and/or to a component of the WNT pathway (e.g., FZD proteins or WNT proteins) may be determined using ELISA. An ELISA assay comprises preparing antigen, coating wells of a 96 well microtiter plate with antigen, adding the binding agent conjugated to a detectable compound such as an enzymatic substrate (e.g. horseradish peroxidase or alkaline phosphatase) to the well, incubating for a period of time, and detecting the presence of the binding agent bound to the antigen. In some embodiments, the binding agent is not conjugated to a detectable compound, but instead a secondary antibody that recognizes the binding agent (e.g., an anti-Fc antibody) and is conjugated to a detectable compound is added to the well. In some embodiments, instead of coating the well with the antigen, the binding agent can be coated to the well and a secondary antibody conjugated to a detectable compound can be added following the addition of the antigen to the coated well. One of skill in the art would be knowledgeable as to the parameters that can be modified to increase the signal detected as well as other variations of ELISAs known in the art.

In another example, the specific binding of an agent to human MET and/or to a component of the WNT pathway (e.g., FZD proteins or WNT proteins) may be determined using FACS. A FACS screening assay may comprise generating a cDNA construct that expresses an antigen as a fusion protein, transfecting the construct into cells, expressing the antigen on the surface of the cells, mixing the binding agent with the transfected cells, and incubating for a period of time. The cells bound by the binding agent may be identified by using a secondary antibody conjugated to a detectable compound (e.g., PE-conjugated anti-Fc antibody) and a flow cytometer. One of skill in the art would be knowledgeable as to the parameters that can be modified to optimize the signal detected as well as other variations of FACS that may enhance screening (e.g., screening for blocking antibodies).

The binding affinity of a binding agent to an antigen (e.g., MET or a component of the WNT pathway) and the off-rate of a binding agent-target interaction can be determined by competitive binding assays. One example of a competitive binding assay is a radioimmunoassay comprising the incubation of labeled antigen/target (e.g., $^{3}$H or $^{125}$I), or fragment or variant thereof, with the binding agent of interest in the presence of increasing amounts of unlabeled antigen followed by the detection of the antibody bound to the labeled antigen/target. The affinity of the binding agent for the antigen/target and the binding off-rates can be determined from the data by Scatchard plot analysis. In some embodiments, Biacore kinetic analysis is used to determine the binding on and off rates of binding agents that bind an antigen (e.g., MET or a component of the WNT pathway). In some embodiments, Biacore kinetic analysis comprises analyzing the binding and dissociation of binding agents from chips with immobilized antigen/target (e.g., MET or a component of the WNT pathway) on their surface. In some embodiments, Biacore kinetic analysis comprises analyzing the binding and dissociation of an antigen or target (e.g., MET or a component of the WNT pathway) from chips with immobilized binding agent on their surface.

The invention provides polypeptides that specifically bind MET, bind at least one component of the WNT pathway, or bind MET and at least one component of the WNT pathway. In some embodiments, a polypeptide binds human MET. In some embodiments, a polypeptide binds one or more components of the human WNT pathway. In some embodiments, a polypeptide binds human MET and mouse MET. In some embodiments, a polypeptide binds human MET and does not bind mouse MET. In some embodiments, a polypeptide binds one or more components of the human WNT pathway. In some embodiments, a polypeptide binds one or more human FZD proteins. In some embodiments, a polypeptide binds one or more human WNT proteins. In some embodiments, a polypeptide binds human MET and does not bind mouse MET. In some embodiments, a polypeptide binds MET and one or more components of the human WNT pathway. In some embodiments, a polypeptide binds MET and one or more human FZD proteins. In some embodiments, a polypeptide binds MET and one or more human WNT proteins.

In some embodiments, a MET-binding agent comprises a polypeptide comprising a sequence selected from the group consisting of: SEQ ID NO:7. SEQ ID NO:8, SEQ ID NO:9, SEQ ID NO:10, SEQ ID NO: 11, SEQ ID NO:12, SEQ ID NO:13, SEQ ID NO:14, SEQ ID NO:28, SEQ ID NO:29, SEQ ID NO:39, SEQ ID NO:55, SEQ ID NO:56, SEQ ID NO:87, and SEQ ID NO:88. In some embodiments, the MET-binding agent further comprises a polypeptide comprising a sequence selected from the group consisting of: SEQ ID NO:47, SEQ ID NO:48, SEQ ID NO:49, SEQ ID NO:50, SEQ ID NO:51, and SEQ ID NO:52.

In certain embodiments, a MET-binding agent competes for specific binding to MET with an antibody or a bispecific agent that comprises a heavy chain variable region comprising SEQ ID NO:7 and a light chain variable region comprising SEQ ID NO:8. In certain embodiments, a MET-binding agent competes with antibody 73R009 for specific binding to human MET. In certain embodiments, a MET-binding agent competes with a monovalent version of antibody 73R009 for specific binding to human MET. In some embodiments, a MET-binding agent competes with a bispecific agent comprising the heavy chain variable region and the light chain variable region of antibody 73R009 for specific binding to human MET. In some embodiments, a MET-binding agent competes for specific binding to MET with a MET-binding agent described herein in an in vitro competitive binding assay. In some embodiments, the MET is human MET. In some embodiments, the MET is mouse MET.

In certain embodiments, a MET-binding agent binds the same epitope, or essentially the same epitope, on MET as an antibody or bispecific agent of the invention. In another embodiment, a MET-binding agent is an antibody that binds an epitope on MET that overlaps with the epitope on MET bound by an antibody or bispecific agent of the invention. In certain embodiments, a MET-binding agent binds the same epitope, or essentially the same epitope, on MET as antibody 73R009. In another embodiment, the MET-binding agent is an antibody or binding agent that binds an epitope on MET that overlaps with the epitope on MET bound by antibody 73R009. In certain embodiments, a MET-binding agent binds the same epitope, or essentially the same epitope, on MET as bispecific agent 315B6. In another embodiment, the MET-binding agent is an antibody or binding agent that binds an epitope on MET that overlaps with the epitope on MET bound by bispecific agent 315B6.

In certain embodiments, the MET-binding agent is an agent that competes for specific binding to MET with the antibody 73R009 or a monovalent version of 73R009 (e.g., in a competitive binding assay). In certain embodiments, the MET-binding agent is an agent that competes for specific binding to MET with bispecific agent 315B6 (e.g., in a competitive binding assay).

In certain embodiments, a binding agent competes with bispecific agent 315B6 for specific binding to one or more WNT proteins. In some embodiments, a binding agent or antibody competes for specific binding to one or more WNT proteins with an agent described herein in an in vitro competitive binding assay. In some embodiments, the one or more WNT proteins are human WNT proteins.

In certain embodiments, a binding agent (e.g., an antibody) binds the same target, or essentially the same target, on one or more WNT proteins as a bispecific agent of the invention. In some embodiments, a binding agent binds a target on one or more WNT proteins that overlaps with the target on one or more WNT proteins bound by a bispecific agent of the invention. In certain embodiments, a binding agent binds the same target, or essentially the same target, on one or more WNT proteins as bispecific agent 315B6. In another embodiment, the binding agent binds a target on one or more WNT proteins that overlaps with the target on WNT bound by bispecific agent 315B6.

In certain embodiments, the binding agent is an agent that competes for specific binding to one or more WNT proteins with the bispecific agent 315B6 (e.g., in a competitive binding assay).

In certain embodiments, the binding agent is an agent that competes for specific binding to MET and/or one or more WNT proteins with the bispecific agent 315B6 (e.g., in a competitive binding assay).

In certain embodiments, the MET-binding agent (e.g., an antibody or bispecific agent) described herein binds MET and modulates MET activity. In some embodiments, the MET-binding agent is a MET antagonist and inhibits MET activity. MET activity may be inhibited by several different mechanisms, including but not limited to, inhibition or blockage of the MET/HGF interaction, inhibition or blockage of MET dimerization, increase in MET shedding, increase in MET internalization, and/or increase in MET degradation. In some embodiments, the MET-binding agent is a MET antagonist and inhibits tumor growth. In some embodiments, the MET-binding agent is a MET antagonist and inhibits angiogenesis. In some embodiments, the MET-binding agent is a MET antagonist and inhibits EMT.

In certain embodiments, a MET-binding agent (e.g., an antibody or bispecific agent) described herein binds one or more human WNT proteins and modulates WNT pathway activity. In some embodiments, a MET-binding agent is a WNT pathway antagonist and inhibits WNT pathway activity. In some embodiments, a MET-binding agent is a WNT pathway antagonist and inhibits β-catenin activity. In some embodiments, a MET-binding agent is a WNT pathway antagonist and inhibits tumor growth. In some embodiments, a MET-binding agent is a WNT pathway antagonist and induces differentiation of tumor cells. In some embodiments, a MET-binding agent is a WNT pathway antagonist and induces differentiation of cancer stem cells. In some embodiments, a MET-binding agent is a WNT pathway antagonist and induces expression of differentiation markers on tumor cells. In some embodiments, a MET-binding agent is a WNT pathway antagonist and induces expression of differentiation markers on cancer stem cells.

In certain embodiments, a MET-binding agent (e.g., an antibody or bispecific agent) described herein is a bispecific agent that binds human MET and modulates MET activity. In certain embodiments, a MET-binding agent described herein is a bispecific agent that binds one or more components of the human WNT pathway and modulates WNT activity. In certain embodiments, a MET-binding agent described herein is a bispecific agent that binds human MET and one or more components of the human WNT pathway and modulates both MET activity and WNT pathway activity. In some embodiments, the bispecific agent is a MET antagonist and a WNT pathway antagonist and inhibits both MET activity and WNT pathway activity. In some embodiments, the bispecific agent is a MET antagonist and a WNT pathway antagonist and inhibits MET signaling and WNT pathway signaling. In some embodiments, the bispecific agent is a MET antagonist and a WNT pathway antagonist and inhibits tumor growth.

In certain embodiments, the MET-binding agent (e.g., an antibody or a bispecific agent) is an antagonist of MET. In some embodiments, the MET-binding agent is an antagonist of MET and inhibits MET activity. In certain embodiments, the MET-binding agent inhibits MET activity by at least about 10%, at least about 20%, at least about 30%, at least about 50%, at least about 75%, at least about 90%, or about 100%. In certain embodiments, a MET-binding agent that inhibits human MET activity comprises antibody 73R009. In certain embodiments, a MET-binding agent that inhibits human MET activity comprises a monovalent version of antibody 73R009. In certain embodiments, a MET-binding agent that inhibits human MET activity comprises the heavy chain variable region and the light chain variable region of antibody 73R009. In certain embodiments, a MET-binding agent that inhibits human MET activity is bispecific agent 315B6.

In certain embodiments, the MET-binding agent is an antagonist of the WNT pathway. In some embodiments, the MET-binding agent is an antagonist of the WNT pathway and inhibits WNT pathway activity. In certain embodiments, the MET-binding agent inhibits WNT pathway activity by at least about 10%, at least about 20%, at least about 30%, at least about 50%, at least about 75%, at least about 90%, or about 100%. In certain embodiments, a MET-binding agent that inhibits human WNT pathway activity comprises antibody 73R009. In certain embodiments, a MET-binding agent that inhibits human WNT pathway activity comprises a monovalent version of antibody 73R009. In certain embodiments, a MET-binding agent that inhibits human WNT pathway activity comprises the heavy chain variable region and the light chain variable region of antibody 73R009. In certain embodiments, a MET-binding agent that inhibits human WNT pathway activity is a bispecific agent comprising the antigen-binding site of antibody 73R009. In certain embodiments, a MET-binding agent that inhibits human WNT pathway activity is bispecific agent 315B6.

In certain embodiments, the MET-binding agent inhibits binding of MET to hepatocyte growth factor (HGF). In certain embodiments, the MET-binding agent inhibits binding of MET to HGF by at least about 10%, at least about 25%, at least about 50%/, at least about 75%, at least about 90%, or at least about 95%. In certain embodiments, a MET-binding agent that inhibits binding of human MET to HGF is antibody 73R009. In certain embodiments, a MET-binding agent that inhibits binding of human MET to HGF is a monovalent version of antibody 73R009. In certain embodiments, a MET-binding agent that inhibits binding of human MET to HGF is a bispecific agent comprising the antigen-binding site of antibody 73R009. In certain embodiments, a MET-binding agent that inhibits binding of human MET to HGF is a bispecific agent comprising the heavy chain variable region and the light chain variable region of antibody 73R009. In certain embodiments, a MET-binding agent that inhibits binding of human MET to HGF is bispecific agent 315B6.

In certain embodiments, the MET-binding agent (e.g., a bispecific agent) inhibits binding of one or more WNT proteins to one or more FZD proteins. In some embodiments, the MET-binding agent (e.g., a bispecific agent) inhibits binding of one or more WNT proteins to FZD1, FZD2, FZD3, FZD4, FZD5, FZD6, FZD7, FZD8, FZD9, and/or FZD10. In some embodiments, the MET-binding agent (e.g., a bispecific agent) inhibits binding of one or more WNT proteins to FZD8. In certain embodiments, the MET-binding agent inhibits binding of one or more WNT proteins to at least one FZD receptor by at least about 10%0/, at least about 25%, at least about 50%, at least about 75%, at least about 90%, or at least about 95%. In certain embodiments, a MET-binding agent that inhibits binding of one or more human WNT proteins to at least one FZD receptor is bispecific agent 315B6.

In vivo and in vitro assays for determining whether a MET-binding agent (or candidate MET-binding agent) inhibits MET activation are known in the art. For example, binding of human HGF to MET results in tyrosine phosphorylation of MET and activation of the MET signaling pathway. Therefore, human cells that are responsive to HGF may be used to assess the inhibition of HGF-induced MET activation by analyzing phosphorylation of MET and phosphorylation of downstream MET pathway components such as mitogen activate protein kinase (MAPK) and AKT. Assays to determine whether a MET-binding agent (or candidate MET-binding agent) inhibits MET dimerization, promotes MET degradation, and/or promotes MET "shedding" are also known in the art.

In vivo and in vitro assays for determining whether a MET-binding agent (or candidate MET-binding agent) inhibits WNT pathway activation or signaling are known in the art. For example, cell-based, luciferase reporter assays utilizing a TCF/Luc reporter vector containing multiple copies of the TCF-binding domain upstream of a firefly luciferase reporter gene may be used to measure β-catenin signaling levels in vitro (Gazit et al., 1999, Oncogene, 18; 5959-66; TOPflash, Millipore, Billerica Mass.). The level of β-catenin signaling in the presence of one or more WNT proteins (e.g., WNT(s) expressed by transfected cells or provided by WNT-conditioned media) in the presence of a binding agent is compared to the level of signaling without the binding agent present. In addition to the TCF/Luc reporter assay, the effect of a binding agent (or candidate agent) on β-catenin signaling may be measured in vitro or in vivo by measuring the effect of the agent on the level of expression of β-catenin-regulated genes, such as c-myc (He et al., 1998, *Science,* 281:1509-12), cyclin D1 (Tetsu et al., 1999, *Nature,* 398:422-6), and/or fibronectin (Gradl et al. 1999, *Mol. Cell Biol.,* 19:5576-87). In certain embodiments, the effect of a binding agent on β-catenin signaling may also be assessed by measuring the effect of the agent on the phosphorylation state of Dishevelled-1, Dishevelled-2, Dishevelled-3, LRP5, LRP6, and/or β-catenin.

In certain embodiments, the MET-binding agents have one or more of the following effects: inhibit proliferation of tumor cells, inhibit tumor growth, reduce the tumorigenicity of a tumor, reduce the frequency of cancer stem cells in a tumor, reduce the tumorigenicity of a tumor by reducing the frequency of cancer stem cells in the tumor, trigger cell death of tumor cells, induce cells in a tumor to differentiate, differentiate tumorigenic cells to a non-tumorigenic state, induce expression of differentiation markers in the tumor cells, prevent metastasis of tumor cells, inhibit angiogenesis, decrease survival of tumor cells, or any combination of the above.

In certain embodiments, the MET-binding agents are capable of inhibiting tumor growth. In certain embodiments, the MET-binding agents are capable of inhibiting tumor growth in vivo (e.g., in a xenograft mouse model, and/or in a human having cancer). In certain embodiments, tumor growth is inhibited at least about two-fold, about three-fold, about five-fold, about ten-fold, about 50-fold, about 100-fold, or about 1000-fold as compared to an untreated tumor.

In certain embodiments, the MET-binding agents are capable of reducing the tumorigenicity of a tumor. In certain embodiments, the MET-binding agent is capable of reducing the tumorigenicity of a tumor comprising cancer stem cells in an animal model, such as a mouse xenograft model. In certain embodiments, the MET-binding agent is capable of reducing the tumorigenicity of a tumor by decreasing the number or frequency of cancer stem cells in the tumor. In certain embodiments, the number or frequency of cancer stem cells in a tumor is reduced by at least about two-fold, about three-fold, about five-fold, about ten-fold, about 50-fold, about 100-fold, or about 1000-fold. In certain embodiments, the reduction in the number or frequency of cancer stem cells is determined by limiting dilution assay using an animal model. Additional examples and guidance regarding the use of limiting dilution assays to determine a reduction in the number or frequency of cancer stem cells in a tumor can be found, e.g., in International Publication Number WO 2008/042236; U.S. Patent Publication No. 2008/0064049; and U.S. Patent Publication No. 2008/0178305.

In certain embodiments, the MET-binding agents described herein have a circulating half-life in mice, cynomolgus monkeys, or humans of at least about 2 hours, at least about 5 hours, at least about 10 hours, at least about 24 hours, at least about 3 days, at least about 1 week, or at least about 2 weeks. In certain embodiments, the MET-binding agent is an IgG (e.g., IgG1 or IgG2) antibody that has a circulating half-life in mice, cynomolgus monkeys, or humans of at least about 2 hours, at least about 5 hours, at least about 10 hours, at least about 24 hours, at least about 3 days, at least about 1 week, or at least about 2 weeks. In certain embodiments, the MET-binding agent is an agent comprising at least one IgG (e.g., IgG1 or IgG2) constant region that has a circulating half-life in mice, cynomolgus monkeys, or humans of at least about 2 hours, at least about 5 hours, at least about 10 hours, at least about 24 hours, at least about 3 days, at least about 1 week, or at least about 2 weeks. Methods of increasing (or decreasing) the half-life of agents such as polypeptides, soluble receptors, and/or antibodies are known in the art. For example, known methods of increasing the circulating half-life of IgG antibodies include the introduction of mutations in the Fc region which increase the pH-dependent binding of the antibody to the neonatal Fc receptor (FcRn) at pH 6.0 (see, e.g., U.S. Patent Publication Nos. 2005/0276799, 2007/0148164, and 2007/0122403). Known methods of increasing the circulating half-life of antibody fragments lacking the Fc region include such techniques as PEGylation.

In some embodiments, the binding agents described herein are antibodies. Polyclonal antibodies can be prepared by any known method. In some embodiments, polyclonal antibodies are produced by immunizing an animal (e.g., a rabbit, rat, mouse, goat, or donkey) with an antigen of interest (e.g., a purified peptide fragment, full-length recombinant protein, or fusion protein) by multiple subcutaneous or intraperitoneal injections. The antigen can be optionally conjugated to a carrier such as keyhole limpet hemocyanin (KLH) or serum albumin. The antigen (with or without a carrier protein) is diluted in sterile saline and usually combined with an adjuvant (e.g., Complete or Incomplete Freund's Adjuvant) to form a stable emulsion. After a sufficient period of time, polyclonal antibodies are recovered from the immunized animal, usually from blood or ascites. The polyclonal antibodies can be purified from serum or ascites according to standard methods in the art including, but not limited to, affinity chromatography, ion-exchange chromatography, gel electrophoresis, and dialysis.

In some embodiments, the binding agents are monoclonal antibodies. Monoclonal antibodies can be prepared using hybridoma methods known to one of skill in the art (see e.g., Kohler and Milstein, 1975, *Nature,* 256:495-497). In some embodiments, using the hybridoma method, a mouse, hamster, or other appropriate host animal, is immunized as described above to elicit from lymphocytes the production of antibodies that specifically bind the immunizing antigen. In some embodiments, lymphocytes can be immunized in vitro. In some embodiments, the immunizing antigen can be a human protein or a portion thereof. In some embodiments, the immunizing antigen can be a mouse protein or a portion thereof.

Following immunization, lymphocytes are isolated and fused with a suitable myeloma cell line using, for example, polyethylene glycol. The hybridoma cells are selected using specialized media as known in the art and unfused lymphocytes and myeloma cells do not survive the selection process. Hybridomas that produce monoclonal antibodies directed specifically against a chosen antigen may be identified by a variety of methods including, but not limited to, immunoprecipitation, immunoblotting, and in vitro binding assays (e.g., flow cytometry, FACS, ELISA, and radioimmunoassay). The hybridomas can be propagated either in vitro culture using standard methods (J. W. Goding, 1996, *Monoclonal Antibodies: Principles and Practice*, 3$^{rd}$ *Edition*, Academic Press, San Diego, Calif.) or in vivo as ascites tumors in an animal. The monoclonal antibodies can be purified from the culture medium or ascites fluid according to standard methods in the art including, but not limited to, affinity chromatography, ion-exchange chromatography, gel electrophoresis, and dialysis.

In certain embodiments, monoclonal antibodies can be made using recombinant DNA techniques as known to one skilled in the art. The polynucleotides encoding a monoclonal antibody are isolated from mature B-cells or hybridoma cells, such as by RT-PCR using oligonucleotide primers that specifically amplify the genes encoding the heavy and light chains of the antibody, and their sequence is determined using standard techniques. The isolated polynucleotides encoding the heavy and light chains are then cloned into suitable expression vectors which produce the monoclonal antibodies when transfected into host cells such as *E. coli*, simian COS cells, Chinese hamster ovary (CHO) cells, or myeloma cells that do not otherwise produce immunoglobulin proteins.

In certain other embodiments, recombinant monoclonal antibodies, or fragments thereof, can be isolated from phage display libraries expressing variable domains or CDRs of a desired species (see e.g., McCafferty et al., 1990, *Nature*, 348:552-554; Clackson et al., 1991, *Nature*, 352:624-628; and Marks et al., 1991, *J. Mol. Biol.*, 222:581-597). In some embodiments, recombinant monoclonal antibodies, or fragments thereof, can be isolated from mammalian cell display libraries expressing variable domains or CDRs of a desired species (see e.g., U.S. patent publication No. 2011/0287979).

The polynucleotide(s) encoding a monoclonal antibody can be modified, for example, by using recombinant DNA technology to generate alternative antibodies or alternative bispecific agents. In some embodiments, the constant domains of the light and heavy chains of, for example, a mouse monoclonal antibody can be substituted for those regions of, for example, a human antibody to generate a chimeric antibody, or for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, etc. of a monoclonal antibody.

In some embodiments, the binding agent is a humanized antibody. Typically, humanized antibodies are human immunoglobulins in which residues from the CDRs are replaced by residues from a CDR of a non-human species (e.g., mouse, rat, rabbit, hamster, etc.) that have the desired specificity, affinity, and/or binding capability using methods known to one skilled in the art. In some embodiments, the Fv framework region residues of a human immunoglobulin are replaced with the corresponding residues in an antibody from a non-human species that has the desired specificity, affinity, and/or binding capability. In some embodiments, a human-ized antibody can be further modified by the substitution of additional residues either in the Fv framework region and/or within the replaced non-human residues to refine and optimize antibody specificity, affinity, and/or capability. In general, a humanized antibody will comprise substantially all of at least one, and typically two or three, variable domain regions containing all, or substantially all, of the CDRs that correspond to the non-human immunoglobulin whereas all, or substantially all, of the framework regions are those of a human immunoglobulin consensus sequence. In some embodiments, a humanized antibody can also comprise at least a portion of an immunoglobulin constant region or domain (Fc), typically that of a human immunoglobulin. In certain embodiments, such humanized antibodies are used therapeutically because they may reduce antigenicity and HAMA (human anti-mouse antibody) responses when administered to a human subject. One skilled in the art would be able to obtain a functional humanized antibody with reduced immunogenicity following known techniques (see e.g., U.S. Pat. Nos. 5,225,539; 5,585,089; 5,693,761; and 5,693,762).

In certain embodiments, the binding agent is a human antibody. Human antibodies can be directly prepared using various techniques known in the art. In some embodiments, human antibodies may be generated from immortalized human B lymphocytes immunized in vitro or from lymphocytes isolated from an immunized individual. In either case, cells that produce an antibody directed against a target antigen can be generated and isolated (see, e.g., Cole et al., 1985, *Monoclonal Antibodies and Cancer Therapy*, Alan R. Liss, p. 77; Boerner et al., 1991, *J. Immunol.*, 147:86-95; and U.S. Pat. Nos. 5,750,373; 5,567,610; and 5,229,275). In some embodiments, the human antibody can be selected from a phage library, where that phage library expresses human antibodies (Vaughan et al., 1996, *Nature Biotechnology*, 14:309-314; Sheets et al., 1998, *PNAS*, 95:6157-6162; Hoogenboom and Winter, 1991, *J. Mol. Biol.*, 227:381; Marks et al., 1991, *J. Mol. Biol.*, 222:581). Alternatively, phage display technology can be used to produce human antibodies and antibody fragments in vitro, from immunoglobulin variable domain gene repertoires from unimmunized donors. Techniques for the generation and use of antibody phage libraries are also described in U.S. Pat. Nos. 5,969,108; 6,172,197; 5,885,793; 6,521,404; 6,544,731; 6,555,313; 6,582,915; 6,593,081; 6,300,064; 6,653,068; 6,706,484; and 7,264,963; and Rothe et al., 2008, *J. Mol. Bio.*, 376:1182-1200. Once antibodies are identified, affinity maturation strategies known in the art, including but not limited to, chain shuffling (Marks et al., 1992, *Bio/Technology*, 10:779-783) and site-directed mutagenesis, may be employed to generate high affinity human antibodies.

In some embodiments, human antibodies can be made in transgenic mice that contain human immunoglobulin loci. Upon immunization these mice are capable of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

This invention also encompasses bispecific agents and bispecific antibodies. Bispecific agents are capable of specifically recognizing and binding at least two different targets or epitopes. The different targets can either be within the same molecule (e.g., two targets on a single protein) or on different molecules (e.g., one target on a protein and a second target on a second protein). In some embodiments, a bispecific agent or bispecific antibody has enhanced potency as compared to an individual agent or antibody or to a mixture of two agents. In some embodiments, a bispecific agent or bispecific antibody has reduced toxicity as compared to an individual agent or to a combination of more than one agent. It is known to those of skill in the art that any binding agent may have unique pharmacokinetics (PK) (e.g., circulating half-life). In some embodiments, a bispecific agent or bispecific antibody has the ability to synchronize the PK of two active binding agents wherein the two individual binding agents have different PK profiles. In some embodiments, a bispecific agent or bispecific antibody has the ability to concentrate the actions of two binding agents in a common area (e.g., a tumor and/or tumor environment). In some embodiments, a bispecific agent or bispecific antibody has the ability to concentrate the actions of two binding agents to a common target (e.g., a tumor or a tumor cell). In some embodiments, a bispecific agent or bispecific antibody has the ability to target the actions of two binding agents to more than one biological pathway or function.

In certain embodiments, a bispecific antibody specifically binds MET and a second target. In certain embodiments, a bispecific antibody specifically binds MET and one or more components of the WNT pathway. In some embodiments, a bispecific antibody specifically binds human MET and one or more human WNT proteins. In some embodiments, a bispecific antibody specifically binds human MET and one or more human FZD proteins. In some embodiments, the bispecific antibody is a monoclonal human. In some embodiments, the bispecific antibody is a humanized antibody. In some embodiments, the bispecific antibody is a human antibody. In some embodiments, the bispecific antibody is a chimeric antibody. In some embodiments, the bispecific antibody reduces cancer stem cell number or frequency. In some embodiments, the bispecific antibody has decreased toxicity and/or side effects. In some embodiments, the bispecific antibody has decreased toxicity and/or side effects as compared to a mixture of the two individual antibodies or the antibodies as single agents. In some embodiments, the bispecific antibody has an increased therapeutic index. In some embodiments, the bispecific antibody has an increased therapeutic index as compared to a mixture of the two individual antibodies or the antibodies as single agents.

In some embodiments, a bispecific antibody can specifically recognize and bind human MET as well as a second antigen target, such as an effector molecule on a leukocyte (e.g., CD2, CD3, CD28, CD80, or CD86) or a Fc receptor (e.g., CD64, CD32, or CD16) so as to focus cellular defense mechanisms to the cell expressing MET. In some embodiments, a bispecific antibody can be used to direct cytotoxic agents to cells which express a particular target antigen. These antibodies possess an antigen-binding site (e.g., to human MET) and a second site which binds a cytotoxic agent or a radionuclide chelator, such as EOTUBE, DPTA, DOTA, or TETA.

Techniques for making bispecific antibodies are known by those skilled in the art, see for example, Millstein et al., 1983, Nature, 305:537-539; Brennan et al., 1985, Science, 229:81; Suresh et al., 1986, Methods in Enzymol., 121:120; Traunecker et al., 1991, EMBO J., 10:3655-3659; Shalaby et al., 1992, J. Exp. Med., 175:217-225; Kostelny et al., 1992, J. Immunol., 148:1547-1553; Gruber et al., 1994, J. Immunol., 152:5368; U.S. Pat. No. 5,731,168; International Publication No. WO 2009/089004; and U.S. Patent Publication No. 2011/0123532. In some embodiments, the bispecific antibodies comprise heavy chain constant regions with modifications in the amino acids which are part of the interface between the two heavy chains. In some embodiments, the bispecific antibodies can be generated using a "knobs-into-holes" strategy (see, e.g., U.S. Pat. No. 5,731,168: Ridgway et. al. 1996. Prot. Engin., 9:617-621). At times the "knobs" and "holes" terminology is replaced with the terms "protuberances" and "cavities". In some embodiments, the bispecific antibodies may comprise variant hinge regions incapable of forming disulfide linkages between the heavy chains (see, e.g., WO 2006/028936). In some embodiments, the modifications may comprise changes in amino acids that result in altered electrostatic interactions. In some embodiments, the modifications may comprise changes in amino acids that result in altered hydrophobic/hydrophilic interactions.

Bispecific antibodies can be intact antibodies or antibody fragments comprising antigen-binding sites. Antibodies with more than two valencies are also contemplated. For example, trispecific antibodies can be prepared (Tutt et al., 1991, J. Immunol., 147:60). Thus, in certain embodiments the antibodies to MET and/or one or more components of the WNT pathway are multispecific.

In certain embodiments, the antibodies (or other polypeptides) described herein may be monospecific. In certain embodiments, each of the one or more antigen-binding sites that an antibody contains is capable of binding (or binds) a homologous epitope on different proteins.

In certain embodiments, the binding agent comprises an antibody fragment. Antibody fragments may have different functions or capabilities than intact antibodies; for example, antibody fragments can have increased tumor penetration. Various techniques are known for the production of antibody fragments including, but not limited to, proteolytic digestion of intact antibodies. In some embodiments, antibody fragments include a F(ab')2 fragment produced by pepsin digestion of an antibody molecule. In some embodiments, antibody fragments include a Fab fragment generated by reducing the disulfide bridges of an F(ab')2 fragment. In other embodiments, antibody fragments include a Fab fragment generated by the treatment of the antibody molecule with papain and a reducing agent. In certain embodiments, antibody fragments are produced using recombinant techniques. In some embodiments, antibody fragments include Fv or single chain Fv (scFv) fragments. Fab, Fv, and scFv antibody fragments can be expressed in and secreted from E. coli or other host cells, allowing for the production of large amounts of these fragments. In some embodiments, antibody fragments are isolated from antibody phage libraries as discussed herein. For example, methods can be used for the construction of Fab expression libraries (Huse et al., 1989, Science, 246: 1275-1281) to allow rapid and effective identification of monoclonal Fab fragments with the desired specificity for MET and/or one or more components of the WNT pathway or derivatives, fragments, analogs or homologs thereof. In some embodiments, antibody fragments are linear antibody fragments. In certain embodiments, antibody fragments are monospecific or bispecific. In certain embodiments, the binding agent is a scFv. Various techniques can be used for the production of single-chain antibodies specific to MET or one or more components of the WNT pathway.

It can further be desirable, especially in the case of antibody fragments, to modify an antibody in order to alter (e.g., increase or decrease) its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

Heteroconjugate antibodies are also within the scope of the present invention. Heteroconjugate antibodies are composed of two covalently joined antibodies. Such antibodies have, for example, been proposed to target immune cells to unwanted cells (see, e.g., U.S. Pat. No. 4,676,980). It is also contemplated that the heteroconjugate antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

For the purposes of the present invention, it should be appreciated that modified agents can comprise any type of region that provides for the association of the agent with the target (i.e., human MET or a human WNT protein). In some embodiments, the region is a variable region that may comprise or be derived from any type of mammal that can be induced to mount a humoral response and generate immunoglobulins against the desired antigen. As such, a variable region of modified antibodies can be, for example, of human, murine, non-human primate (e.g. cynomolgus monkeys, macaques, etc.) or rabbit origin. In some embodiments, both a variable and a constant region of a modified immunoglobulin are human. In other embodiments, variable regions of compatible antibodies (usually derived from a non-human source) can be engineered or specifically tailored to improve the binding properties or reduce the immunogenicity of the molecule. In this respect, variable regions useful in the present invention can be humanized or otherwise altered through the inclusion of imported amino acid sequences.

In certain embodiments, variable domains in both the heavy and light chains are altered by at least partial replacement of one or more CDRs and, if necessary, by partial framework region replacement and sequence modification and/or alteration. Although the CDRs may be derived from an antibody of the same class or even subclass as the antibody from which the framework regions are derived, it is envisaged that the CDRs may be derived from an antibody of different class and often from an antibody from a different species. It may not be necessary to replace all of the CDRs with all of the CDRs from the donor variable region to transfer the antigen binding capacity of one variable domain to another. Rather, it may only be necessary to transfer those residues that are required to maintain the activity of the antigen-binding site.

Alterations to a variable region notwithstanding, those skilled in the art will appreciate that the modified antibodies of this invention will comprise antibodies (e.g., full-length antibodies or immunoreactive fragments thereof) or bispecific agents in which at least a fraction of one or more of the constant region domains has been deleted or otherwise altered so as to provide desired biochemical characteristics such as increased tumor localization or increased serum half-life when compared with an antibody of approximately the same immunogenicity comprising a native or unaltered constant region. In some embodiments, the constant region of the modified antibodies will comprise a human constant region. Modifications to the constant region compatible with this invention comprise additions, deletions or substitutions of one or more amino acids in one or more domains. The modified antibodies and/or bispecific agents disclosed herein may comprise alterations or modifications to one or more of the three heavy chain constant domains (CH1, CH2 or CH3) and/or to the light chain constant domain (CL). In some embodiments, one or more domains are partially or entirely deleted from the constant regions of the modified antibodies. In some embodiments, the modified antibodies will comprise domain deleted constructs or variants wherein the entire CH2 domain has been removed (ΔCH2 constructs). In some embodiments, the omitted constant region domain is replaced by a short amino acid spacer (e.g., 10 amino acid residues) that provides some of the molecular flexibility typically imparted by the absent constant region.

In some embodiments, the modified antibodies or bispecific agents are engineered to fuse the CH3 domain directly to the hinge region of the antibody. In other embodiments, a peptide spacer is inserted between the hinge region and the modified CH2 and/or CH3 domains. For example, constructs may be expressed wherein the CH2 domain has been deleted and the remaining CH3 domain (modified or unmodified) is joined to the hinge region with a 5-20 amino acid spacer. Such a spacer may be added to ensure that the regulatory elements of the constant domain remain free and accessible or that the hinge region remains flexible. However, it should be noted that amino acid spacers may, in some cases, prove to be immunogenic and elicit an unwanted immune response against the construct. Accordingly, in certain embodiments, any spacer added to the construct will be relatively non-immunogenic so as to maintain the desired biological qualities of the modified antibodies.

In some embodiments, the modified antibodies or bispecific agents may have only a partial deletion of a constant domain or substitution of a few or even a single amino acid. For example, the mutation of a single amino acid in selected areas of the CH2 domain may be enough to substantially reduce Fc binding and thereby increase cancer cell localization and/or tumor penetration. Similarly, it may be desirable to simply delete the part of one or more constant region domains that control a specific effector function (e.g. complement Clq binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies and/or bispecific agents may be modified through the mutation or substitution of one or more amino acids that enhances the profile of the resulting construct. In this respect it may be possible to disrupt the activity provided by a conserved binding site (e.g., Fc binding) while substantially maintaining the configuration and immunogenic profile of the modified antibody. In certain embodiments, the modified antibodies and/or bispecific agents comprise the addition of one or more amino acids to the constant region to enhance desirable characteristics such as decreasing or increasing effector function or provide for more cytotoxin or carbohydrate attachment sites.

It is known in the art that the constant region mediates several effector functions. For example, binding of the Cl component of complement to the Fc region of IgG or IgM antibodies (bound to antigen) activates the complement system. Activation of complement is important in the opsonization and lysis of cell pathogens. The activation of complement also stimulates the inflammatory response and can also be involved in autoimmune hypersensitivity. In addition, the Fc region of an antibody or a Fc-fusion proteins can bind a cell expressing a Fc receptor (FcR). There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell cytotoxicity or ADCC), release of inflammatory mediators, placental transfer, and control of immunoglobulin production.

In certain embodiments, the modified antibodies and/or bispecific agents provide for altered effector functions that, in turn, affect the biological profile of the administered antibody. For example, in some embodiments, the deletion or inactivation (through point mutations or other means) of a constant region domain may reduce Fc receptor binding of the circulating modified antibody thereby increasing cancer cell localization and/or tumor penetration. In other embodiments, the constant region modifications increase the serum half-life of the antibody and/or bispecific agent. In other embodiments, the constant region modifications reduce the serum half-life of the antibody and/or bispecific agent. In some embodiments, the constant region is modified to eliminate disulfide linkages or oligosaccharide moieties. Modifications to the constant region in accordance with this invention may easily be made using well known biochemical or molecular engineering techniques known to those of skill in the art.

In certain embodiments, an antibody and/or bispecific agent does not have one or more effector functions. For instance, in some embodiments, the antibody or bispecific agent has no ADCC activity, and/or no complement-dependent cytotoxicity (CDC) activity. In certain embodiments, the antibody and/or bispecific agent does not bind an Fc receptor, and/or complement factors. In certain embodiments, the antibody and/or bispecific agent has no effector function.

The present invention further embraces variants and equivalents which are substantially homologous to the chimeric, humanized, and human antibodies, or antibody fragments thereof, or bispecific agents, described herein. These can contain, for example, conservative substitution mutations, i.e. the substitution of one or more amino acids by similar amino acids. For example, conservative substitution refers to the substitution of an amino acid with another amino acid within the same general class such as, for example, one acidic amino acid with another acidic amino acid, one basic amino acid with another basic amino acid or one neutral amino acid by another neutral amino acid. What is intended by a conservative amino acid substitution is well known in the art and described herein.

Thus, the present invention provides methods for producing an antibody or bispecific agent that binds MET and/or one or more components of the WNT pathway, including bispecific agents that specifically bind both MET and one or more WNT proteins. In some embodiments, the method for producing an antibody that binds MET or one or more components of the WNT pathway comprises using hybridoma techniques. In some embodiments, the method of generating an agent that binds MET or one or more components of the WNT pathway or a bispecific agent that binds MET and one or more components of the WNT pathway comprises screening a human phage display library. In some embodiments, the method of generating an agent that binds MET or one or more components of the WNT pathway or a bispecific agent that binds MET and one or more components of the WNT pathway comprises screening a mammalian cell display library. The present invention further provides methods of identifying an agent that binds MET and/or one or more components of the WNT pathway. In some embodiments, the agent is identified by FACS screening for binding to MET or a fragment thereof. In some embodiments, the agent is identified by FACS screening for binding to one or more components of the WNT pathway or a fragment thereof. In some embodiments, the agent is identified by FACS screening for binding to both MET and one or more components of the WNT pathway or a fragment thereof. In some embodiments, the agent is identified by screening using ELISA for binding to MET. In some embodiments, the agent is identified by screening using ELISA for binding to one or more components of the WNT pathway. In some embodiments, the agent is identified by screening using ELISA for binding to MET and one or more components of the WNT pathway. In some embodiments, the agent is identified by FACS screening for blocking of binding of human MET to human hepatocyte growth factor. In some embodiments, the agent is identified by FACS screening for blocking of binding of one or more WNT proteins to a human FZD protein. In some embodiments, the agent is identified by screening for inhibition or blocking of WNT pathway signaling. In some embodiments, the agent is identified by screening for inhibition or blocking of MET activity.

In certain embodiments, the antibodies and/or bispecific agents described herein are isolated. In certain embodiments, the antibodies and/or bispecific agents described herein are substantially pure.

In some embodiments of the present invention, the MET-binding agents are polypeptides. The polypeptides can be recombinant polypeptides, natural polypeptides, or synthetic polypeptides comprising an antibody, or fragment thereof, that bind MET and/or one or more components of the WNT pathway. The polypeptides can be recombinant polypeptides, natural polypeptides, or synthetic polypeptides comprising a soluble receptor, or fragment thereof, that bind one or more components of the WNT pathway. It will be recognized in the art that some amino acid sequences of the binding agents described herein can be varied without significant effect on the structure or function of the protein. Thus, the invention further includes variations of the polypeptides which show substantial activity or which include regions of an antibody, or fragment thereof, against human MET and/or one or more components of the WNT pathway. In some embodiments, amino acid sequence variations of MET-binding polypeptides include deletions, insertions, inversions, repeats, and/or other types of substitutions.

In some embodiments, the polypeptides described herein are isolated. In some embodiments, the polypeptides described herein are substantially pure.

The polypeptides, analogs and variants thereof, can be further modified to contain additional chemical moieties not normally part of the polypeptide. The derivatized moieties can improve or otherwise modulate the solubility, the biological half-life, and/or absorption of the polypeptide. The moieties can also reduce or eliminate undesirable side effects of the polypeptides and variants. An overview for chemical moieties can be found in *Remington: The Science and Practice of Pharmacy*, 22$^{st}$ Edition, 2012, Pharmaceutical Press, London.

The polypeptides described herein can be produced by any suitable method known in the art. Such methods range from direct protein synthesis methods to constructing a DNA sequence encoding polypeptide sequences and expressing those sequences in a suitable host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g., Zoeller et al., 1984, *PNAS*, 81:5662-5066 and U.S. Pat. No. 4,588,585.

In some embodiments, a DNA sequence encoding a polypeptide of interest may be constructed by chemical synthesis using an oligonucleotide synthesizer. Oligonucleotides can be designed based on the amino acid sequence of the desired polypeptide and selecting those codons that are favored in the host cell in which the recombinant polypeptide of interest will be produced. Standard methods can be applied to synthesize a polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis, or another method), the polynucleotide sequences encoding a particular polypeptide of interest can be inserted into an expression vector and operatively linked to an expression control sequence appropriate for expression of the protein in a desired host. Proper assembly can be confirmed by nucleotide sequencing, restriction enzyme mapping, and/or expression of a biologically active polypeptide in a suitable host. As is well-known in the art, in order to obtain high expression levels of a transfected gene in a host, the gene must be operatively linked to transcriptional and translational expression control sequences that are functional in the chosen expression host.

In certain embodiments, recombinant expression vectors are used to amplify and express DNA encoding antibodies or fragments thereof or bispecific agents that bind human MET and/or one or more components of the WNT pathway. For example, recombinant expression vectors can be replicable DNA constructs which have synthetic or cDNA-derived DNA fragments encoding a polypeptide chain of a MET-binding agent, such as an anti-MET antibody or bispecific agent comprising an anti-MET antibody and a FZD soluble receptor, or fragment thereof, operatively linked to suitable transcriptional and/or translational regulatory elements derived from mammalian, microbial, viral, or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences. Regulatory elements can include an operator sequence to control transcription. The ability to replicate in a host, usually conferred by an origin of replication, and a selection gene to facilitate recognition of transformants can additionally be incorporated. DNA regions are "operatively linked" when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. In some embodiments, structural elements intended for use in yeast expression systems include a leader sequence enabling extracellular secretion of translated protein by a host cell. In other embodiments, in situations where recombinant protein is expressed without a leader or transport sequence, it can include an N-terminal methionine residue. This residue can optionally be subsequently cleaved from the expressed recombinant protein to provide a final product.

The choice of an expression control sequence and an expression vector depends upon the choice of host. A wide variety of expression host/vector combinations can be employed. Useful expression vectors for eukaryotic hosts include, for example, vectors comprising expression control sequences from SV40, bovine papilloma virus, adenovirus, and cytomegalovirus. Useful expression vectors for bacterial hosts include known bacterial plasmids, such as plasmids from E. coli, including pCR1, pBR322, pMB9, and their derivatives, and wider host range plasmids, such as M13 and other filamentous single-stranded DNA phages.

The binding agents (e.g., polypeptides) of the present invention can be expressed from one or more vectors. For example, in some embodiments, a heavy chain polypeptide is expressed by one vector and a light chain polypeptide is expressed by a second vector. In some embodiments, a heavy chain polypeptide and a light chain polypeptide are expressed by one vector. In some embodiments, a heavy chain polypeptide is expressed by one vector, a light chain polypeptide is expressed by a second vector and a polypeptide comprising a soluble receptor is expressed by a third vector. In some embodiments, a heavy chain polypeptide and a light chain polypeptide are expressed by one vector and a polypeptide comprising a soluble receptor is expressed by a second vector. In some embodiments, three polypeptides are expressed from one vector. Thus, in some embodiments, a heavy chain polypeptide, a light chain polypeptide, and a polypeptide comprising a soluble receptor are expressed by a single vector.

Suitable host cells for expression of a MET-binding polypeptide or agent (or a MET, WNT, or FZD protein to use as an antigen) include prokaryotes, yeast cells, insect cells, or higher eukaryotic cells under the control of appropriate promoters. Prokaryotes include gram-negative or gram-positive organisms, for example E. coli or Bacillus. Higher eukaryotic cells include established cell lines of mammalian origin as described below. Cell-free translation systems may also be employed. Appropriate cloning and expression vectors for use with bacterial, fungal, yeast, and mammalian cellular hosts are described in Pouwels et al., 1985, *Cloning Vectors: A Laboratory Manual*, Elsevier, New York, N.Y. Additional information regarding methods of protein production, including antibody production, can be found, e.g., in U.S. Patent Publication No. 2008/0187954; U.S. Pat. Nos. 6,413,746; 6,660,501; and International Patent Publication No. WO 04/009823.

Various mammalian cell culture systems may be used to express recombinant polypeptides. Expression of recombinant proteins in mammalian cells may be desirable because these proteins are generally correctly folded, appropriately modified, and biologically functional. Examples of suitable mammalian host cell lines include, but are not limited to, COS-7 (monkey kidney-derived), L-929 (murine fibroblast-derived), C127 (murine mammary tumor-derived), 3T3 (murine fibroblast-derived), CHO (Chinese hamster ovary-derived), HeLa (human cervical cancer-derived), BHK (hamster kidney fibroblast-derived), HEK-293 (human embryonic kidney-derived) cell lines and variants of these cell lines. Mammalian expression vectors can comprise non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences.

Expression of recombinant proteins in insect cell culture systems (e.g., baculovirus) also offers a robust method for producing correctly folded and biologically functional proteins. Baculovirus systems for production of heterologous proteins in insect cells are well-known to those of skill in the art (see, e.g., Luckow and Summers, 1988, *Bio/Technology*, 6:47).

Thus, the present invention provides cells comprising the binding agents described herein. In some embodiments, the cells produce the binding agents described herein. In certain embodiments, the cells produce an antibody. In some embodiments, the cells produce a MET-binding agent, such as an anti-MET antibody. In some embodiments, the cells produce a bispecific agent that binds MET. In some embodiments, the cells produce a bispecific agent that binds MET and one or more components of the WNT pathway. In some embodiments, the cells produce a bispecific agent that binds MET and one or more FZD proteins. In some embodiments, the cells produce a bispecific agent that binds MET and one or more WNT proteins. In certain embodiments, the cells produce antibody 73R009. In certain embodiments, the cells produce a bispecific agent which comprises an antigen-binding site from antibody 73R009. In certain embodiments, the cells produce a bispecific agent which comprises an antigen-binding site from antibody 73R009 and a FZD Fri domain. In certain embodiments, the cells produce a bispecific agent which comprises an antigen-binding site from antibody 73R009 and a FZD8 Fri domain. In certain embodiments, the cells produce the bispecific agent 315B6.

The proteins produced by a transformed host can be purified according to any suitable method. Standard methods include chromatography (e.g., ion exchange, affinity, and sizing column chromatography), centrifugation, differential solubility, or by any other standard technique for protein purification. Affinity tags such as hexa-histidine, maltose binding domain, influenza coat sequence, and glutathione-S-transferase can be attached to the protein to allow easy purification by passage over an appropriate affinity column. Affinity chromatography used for purifying immunoglobulins can include Protein A, Protein G, and Protein L chromatography. Isolated proteins can be physically characterized using such techniques as proteolysis, size exclusion chromatography (SEC), mass spectrometry (MS), nuclear magnetic resonance (NMR), isoelectric focusing (IEF), high performance liquid chromatography (HPLC), and x-ray crystallography. The purity of isolated proteins can be determined using techniques known to those of skill in the art, including but not limited to, SDS-PAGE, SEC, capillary gel electrophoresis, IEF, and capillary isoelectric focusing (cIEF).

In some embodiments, supernatants from expression systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. In some embodiments, an anion exchange resin can be employed, for example, a matrix or substrate having pendant diethylaminoethyl (DEAE) groups. The matrices can be acrylamide, agarose, dextran, cellulose, or other types commonly employed in protein purification. In some embodiments, a cation exchange step can be employed. Suitable cation exchangers include various insoluble matrices comprising sulfopropyl or carboxymethyl groups. In some embodiments, a hydroxyapatite media can be employed, including but not limited to, ceramic hydroxyapatite (CHT). In certain embodiments, one or more reverse-phase HPLC steps employing hydrophobic RP-HPLC media, e.g., silica gel having pendant methyl or other aliphatic groups, can be employed to further purify a recombinant protein (e.g., a MET-binding agent). Some or all of the foregoing purification steps, in various combinations, can be employed to provide a homogeneous recombinant protein.

In some embodiments, heterodimeric proteins such as bispecific agents described herein are purified according the any of the methods described herein. In some embodiments, bispecific agents are isolated and/or purified using at least one chromatography step. In some embodiments, the at least one chromatography step comprises affinity chromatography. In some embodiments, the at least one chromatography step further comprises anion exchange chromatography. In some embodiments, the isolated and/or purified antibody product comprises at least 90% heterodimeric agent. In some embodiments, the isolated and/or purified product comprises at least 95%, 96%, 97%, 98% or 99% heterodimeric agent. In some embodiments, the isolated and/or purified product comprises about 100% heterodimeric agent.

In some embodiments, recombinant protein produced in bacterial culture can be isolated, for example, by initial extraction from cell pellets, followed by one or more concentration, salting-out, aqueous ion exchange, or size exclusion chromatography steps. HPLC can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying antibodies and other proteins also include, for example, those described in U.S. Patent Publication Nos. 2008/0312425, 2008/0177048, and 2009/0187005.

In certain embodiments, a MET-binding agent is a polypeptide that is not an antibody. A variety of methods for identifying and producing non-antibody polypeptides that bind with high affinity to a protein target are known in the art. See, e.g., Skerra, 2007, *Curr. Opin. Biotechnol.,* 18:295-304; Hosse et al., 2006, *Protein Science,* 15:14-27; Gill et al., 2006, *Curr. Opin. Biotechnol.,* 17:653-658; Nygren, 2008, *FEBS J.,* 275:2668-76; and Skerra, 2008, *FEBS J.,* 275:2677-83. In certain embodiments, phage or mammalian cell display technology may be used to produce and/or identify a MET-binding polypeptide that is not an antibody. In certain embodiments, the polypeptide comprises a protein scaffold of a type selected from the group consisting of protein A, protein G, a lipocalin, a fibronectin domain, an ankyrin consensus repeat domain, and thioredoxin.

In certain embodiments, a MET-binding agent can be used in any one of a number of conjugated (i.e. an immunoconjugate or radioconjugate) or non-conjugated forms. In certain embodiments, the agent can be used in a non-conjugated form to harness the subject's natural defense mechanisms including complement-dependent cytotoxicity and antibody-dependent cellular toxicity to eliminate malignant or cancer cells.

In some embodiments, a MET-binding agent (e.g., an antibody or bispecific agent) is conjugated to a cytotoxic agent. In some embodiments, the cytotoxic agent is a chemotherapeutic agent including, but not limited to, methotrexate, adriamicin, doxorubicin, melphalan, mitomycin C, chlorambucil, daunorubicin or other intercalating agents. In some embodiments, the cytotoxic agent is an enzymatically active toxin of bacterial, fungal, plant, or animal origin, or fragments thereof, including, but not limited to, diphtheria A chain, non-binding active fragments of diphtheria toxin, exotoxin A chain, ricin A chain, abrin A chain, modeccin A chain, alpha-sarcin, Aleurites fordii proteins, dianthin proteins, Phytolaca americana proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. In some embodiments, the cytotoxic agent is a radioisotope to produce a radioconjugate or a radioconjugated antibody. A variety of radionuclides are available for the production of radioconjugated antibodies including, but not limited to, $^{90}$Y, $^{125}$I, $^{131}$I, $^{123}$I, $^{111}$In, $^{131}$In, $^{105}$Rh, $^{153}$Sm, $^{67}$Cu, $^{67}$Ga, $^{166}$Ho, $^{177}$Lu, $^{186}$Re, $^{188}$Re and $^{212}$Bi. In some embodiments, conjugates of a binding agent described herein and one or more small molecule toxins, such as calicheamicins, maytansinoids, trichothecenes, and CC1065, and the derivatives of these toxins that have toxin activity, can also be used. In some embodiments, a binding agent described herein is conjugated to a maytansinoid. In some embodiments, a binding agent described herein is conjugated to mertansine (DM1). Conjugates of a binding agent described herein and a cytotoxic agent can be made using a variety of bifunctional protein-coupling agents including, but not limited to, N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

III. Polynucleotides

In certain embodiments, the invention encompasses polynucleotides comprising polynucleotides that encode a polypeptide (or a fragment of a polypeptide) that specifically binds MET, one or more components of the WNT pathway, or both MET and one or more components of the WNT pathway. The term "polynucleotides that encode a polypeptide" encompasses a polynucleotide which includes only coding sequences for the polypeptide, as well as a polynucleotide which includes additional coding and/or non-coding sequences. For example, in some embodiments, the invention provides a polynucleotide comprising a polynucleotide sequence that encodes an antibody to human MET or encodes a fragment of such an antibody (e.g., a fragment comprising the antigen-binding site). In some embodiments, the invention provides a polynucleotide comprising a polynucleotide sequence that encodes a polypeptide that binds one or more human FZD proteins or encodes a fragment of such a polypeptide (e.g., a fragment comprising the binding site). In some embodiments, the invention provides a polynucleotide comprising a polynucleotide sequence that encodes a polypeptide that binds one or more human WNT proteins or encodes a fragment of such a polypeptide (e.g., a fragment comprising the binding site). The polynucleotides of the invention can be in the form of RNA or in the form of DNA. DNA includes cDNA, genomic DNA, and synthetic DNA; and can be double-stranded or single-stranded, and if single-stranded can be the coding strand or non-coding (anti-sense) strand.

In certain embodiments, the polynucleotide comprises a polynucleotide encoding a polypeptide comprising a sequence selected from the group consisting of: SEQ ID NO:12, SEQ ID NO:13, SEQ ID NO:14, SEQ ID NO:55, SEQ ID NO:56, SEQ ID NO:87, and SEQ ID NO:88. In some embodiments, the polynucleotide comprises a polynucleotide sequence selected from the group consisting of: SEQ ID NO:15, SEQ ID NO:16, SEQ ID NO:17, SEQ ID NO:18, SEQ ID NO:19, SEQ ID NO:20, SEQ ID NO:89, and SEQ ID NO:90. In some embodiments, the polynucleotide comprises the complement of a polynucleotide sequence selected from the group consisting of: SEQ ID NO: 15, SEQ ID NO: 16, SEQ ID NO: 17, SEQ ID NO: 18, SEQ ID NO: 19, SEQ ID NO:20, SEQ ID NO:89, and SEQ ID NO:90.

In certain embodiments, the polynucleotide comprises a polynucleotide having a nucleotide sequence at least about 80% identical, at least about 85% identical, at least about 90% identical, at least about 95% identical, and in some embodiments, at least about 96%, 97%, 98% or 99% identical to a polynucleotide comprising a sequence selected from the group consisting of: SEQ ID NO: 15, SEQ ID NO:16, SEQ ID NO:17, SEQ ID NO:18, SEQ ID NO:19, SEQ ID NO:20, SEQ ID NO:89, and SEQ ID NO:90. Also provided is a polynucleotide that comprises a polynucleotide that hybridizes to SEQ ID NO:15, SEQ ID NO:16, SEQ ID NO:17, SEQ ID NO:18, SEQ ID NO:19, SEQ ID NO:20, SEQ ID NO:89, or SEQ ID NO:90. Also provided is a polynucleotide that comprises a polynucleotide that hybridizes to the complement of SEQ ID NO:15, SEQ ID NO:16, SEQ ID NO:17, SEQ ID NO:18, SEQ ID NO:19, and SEQ ID NO:20 or hybridizes to a complement of SEQ ID NO:15, SEQ ID NO:16, SEQ ID NO: 17, SEQ ID NO:18, SEQ ID NO:19, SEQ ID NO:20, SEQ ID NO:89, or SEQ ID NO:90. In certain embodiments, the hybridization is under conditions of high stringency.

The binding agents of the present invention can be encoded by one or more polynucleotides. For example, in some embodiments, a heavy chain polypeptide is encoded by one polynucleotide and a light chain polypeptide is encoded by a second polynucleotide. In some embodiments, a heavy chain polypeptide and a light chain polypeptide are encoded by one polynucleotide. In some embodiments, a heavy chain polypeptide is encoded by one polynucleotide, a light chain polypeptide is encoded by a second polynucleotide and a polypeptide comprising a soluble receptor is encoded by a third polynucleotide. In some embodiments, a heavy chain polypeptide and a light chain polypeptide are encoded by one polynucleotide and a polypeptide comprising a soluble receptor is encoded by a second polynucleotide. In some embodiments, three polypeptides are encoded from one polynucleotide. Thus, in some embodiments, a heavy chain polypeptide, a light chain polypeptide, and a polypeptide comprising a soluble receptor are encoded by a single polynucleotide.

In certain embodiments, the polynucleotides comprise the coding sequence for the mature polypeptide fused in the same reading frame to a polynucleotide which aids, for example, in expression and secretion of a polypeptide from a host cell (e.g., a leader sequence which functions as a secretory sequence for controlling transport of a polypeptide from the cell). The polypeptide having a leader sequence is a preprotein and can have the leader sequence cleaved by the host cell to form the mature form of the polypeptide. The polynucleotides can also encode for a proprotein which is the mature protein plus additional 5' amino acid residues. A mature protein having a prosequence is a proprotein and is an inactive form of the protein. Once the prosequence is cleaved an active mature protein remains.

In certain embodiments, the polynucleotides comprise the coding sequence for the mature polypeptide fused in the same reading frame to a marker sequence that allows, for example, for purification of the encoded polypeptide. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) is used. In some embodiments, the marker sequence is a FLAG tag, a peptide of sequence DYKDDDDK (SEQ ID NO:73) which can be used in conjunction with other affinity tags.

The present invention further relates to variants of the hereinabove described polynucleotides encoding, for example, fragments, analogs, and/or derivatives.

In certain embodiments, the present invention provides polynucleotides comprising polynucleotides having a nucleotide sequence at least about 80% identical, at least about 85% identical, at least about 90% identical, at least about 95% identical, and in some embodiments, at least about 96%, 97%, 98% or 99% identical to a polynucleotide encoding a polypeptide comprising a MET-binding agent (e.g., an antibody or bispecific agent), or fragment thereof, described herein.

As used herein, the phrase a polynucleotide having a nucleotide sequence at least, for example, 95% "identical" to a reference nucleotide sequence is intended to mean that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the 5' or 3' terminal positions of the reference nucleotide sequence or anywhere between those terminal positions, interspersed either individually among nucleotides in the reference sequence or in one or more contiguous groups within the reference sequence.

The polynucleotide variants can contain alterations in the coding regions, non-coding regions, or both. In some embodiments, a polynucleotide variant contains alterations which produce silent substitutions, additions, or deletions, but does not alter the properties or activities of the encoded polypeptide. In some embodiments, a polynucleotide variant comprises silent substitutions that results in no change to the amino acid sequence of the polypeptide (due to the degeneracy of the genetic code). Polynucleotide variants can be produced for a variety of reasons, for example, to optimize codon expression for a particular host (i.e., change codons in the human mRNA to those preferred by a bacterial host such as *E. coli*). In some embodiments, a polynucleotide variant comprises at least one silent mutation in a non-coding or a coding region of the sequence.

In some embodiments, a polynucleotide variant is produced to modulate or alter expression (or expression levels) of the encoded polypeptide. In some embodiments, a polynucleotide variant is produced to increase expression of the encoded polypeptide. In some embodiments, a polynucleotide variant is produced to decrease expression of the encoded polypeptide. In some embodiments, a polynucleotide variant has increased expression of the encoded polypeptide as compared to a parental polynucleotide sequence. In some embodiments, a polynucleotide variant has decreased expression of the encoded polypeptide as compared to a parental polynucleotide sequence.

In some embodiments, at least one polynucleotide variant is produced (without changing the amino acid sequence of the encoded polypeptide) to increase production of a heterodimeric or heteromultimeric molecule. In some embodiments, at least one polynucleotide variant is produced (without changing the amino acid sequence of the encoded polypeptide) to increase production of a bispecific agent.

In certain embodiments, the polynucleotides are isolated. In certain embodiments, the polynucleotides are substantially pure.

Vectors and cells comprising the polynucleotides described herein are also provided. In some embodiments, an expression vector comprises a polynucleotide. In some embodiments, a host cell comprises an expression vector comprising the polynucleotide. In some embodiments, a host cell comprises a polynucleotide.

IV. Methods Of Use And Pharmaceutical Compositions

The MET-binding agents (including antibodies and bispecific agents) of the invention that bind MET or MET and one or more components of the WNT pathway are useful in a variety of applications including, but not limited to, therapeutic treatment methods, such as the treatment of cancer. In certain embodiments, the agents are useful for inhibiting MET activity, inhibiting WNT pathway activity, inhibiting tumor growth, reducing tumor volume, reducing the frequency of cancer stem cells in a tumor, reducing the tumorigenicity of a tumor, inducing differentiation of tumor cells, inducing differentiation of cancer stem cells, inducing expression of differentiation markers on tumor cells, inducing expression of differentiation markers on cancer stem cells, inhibiting angiogenesis, and/or inhibiting EMT. The methods of use may be in vitro, ex vivo, or in vivo. In certain embodiments, a MET-binding agent is an antagonist of human MET. In certain embodiments, a MET-binding agent is an antagonist of one or more components of the WNT pathway. In certain embodiments, a MET-binding agent is an antagonist of both MET and one or more components of the WNT pathway.

The present invention provides methods for inhibiting growth of a tumor using the MET-binding agents described herein. In certain embodiments, the method of inhibiting growth of a tumor comprises contacting a tumor cell with a MET-binding agent (e.g., an antibody or a bispecific agent) in vitro. For example, an immortalized cell line or a cancer cell line is cultured in medium to which is added an antibody or a bispecific agent described herein to inhibit tumor cell growth. In some embodiments, tumor cells are isolated from a patient sample such as, for example, a tissue biopsy, pleural effusion, or blood sample and cultured in medium to which is added a binding agent to inhibit tumor cell growth.

In some embodiments, the method of inhibiting growth of a tumor comprises contacting a tumor or tumor cells with a MET-binding agent (e.g., an antibody or a bispecific agent) in vivo. In certain embodiments, contacting a tumor or tumor cell with a MET-binding agent is undertaken in an animal model. For example, an antibody or bispecific agent described herein may be administered to an immunocompromised host animal (e.g., NOD/SCID mice) that has a tumor xenograft. In some embodiments, tumor cells and/or cancer stem cells are isolated from a patient sample such as, for example, a tissue biopsy, pleural effusion, or blood sample and injected into an immunocompromised host animal (e.g., NOD/SCID mice) that is then administered a binding agent to inhibit tumor cell growth. In some embodiments, the MET-binding agent is administered at the same time or shortly after introduction of tumorigenic cells into the animal to prevent tumor growth ("preventative model"). In some embodiments, the MET-binding agent is administered as a therapeutic after tumors have grown to a specified size ("therapeutic model"). In certain embodiments, the MET-binding agent is a bispecific agent described herein that specifically binds human MET and one or more components of the WNT pathway. In certain embodiments, the MET-binding agent is a bispecific agent described herein that specifically binds human MET and one or more WNT proteins.

In certain embodiments, the method of inhibiting growth of a tumor in a subject comprises administering to the subject a therapeutically effective amount of a MET-binding agent described herein. In certain embodiments, the subject is a human. In certain embodiments, the subject has a tumor or had a tumor that was removed. In certain embodiments, the tumor comprises cancer stem cells. In certain embodiments, the frequency of cancer stem cells in the tumor is reduced by administration of the MET-binding agent. The invention also provides a method of reducing the frequency of cancer stem cells in a tumor, comprising contacting the tumor with an effective amount of a MET-binding agent (e.g., an antibody or a bispecific agent) described herein. In some embodiments, a method of reducing the frequency of cancer stem cells in a tumor in a subject, comprises administering to the subject a therapeutically effective amount of a MET-binding agent described herein. In certain embodiments, the MET-binding agent is a bispecific agent described herein that specifically binds human MET and one or more components of the WNT pathway. In certain embodiments, the MET-binding agent is a bispecific agent described herein that specifically binds human MET and one or more WNT proteins.

The present invention further provides methods for inhibiting angiogenesis in a subject comprising administering a therapeutically effective amount of a MET-binding agent described herein to the subject. In some embodiments, the angiogenesis is tumor angiogenesis.

The present invention further provides methods for inhibiting epithelial-mesenchymal transition (EMT) of tumor cells comprising contacting tumor cells with an effective amount of a MET-binding agent described herein. The present invention further provides methods for inhibiting EMT of tumor cells in a subject comprising administering a therapeutically effective amount of a MET-binding agent described herein to the subject.

In some embodiments, the tumor is a solid tumor. In certain embodiments, the tumor is a tumor selected from the group consisting of colorectal tumor, colon tumor, pancreatic tumor, lung tumor, ovarian tumor, liver tumor, breast tumor, kidney tumor, prostate tumor, gastrointestinal tumor, melanoma, cervical tumor, bladder tumor, glioblastoma, and head and neck tumor. In certain embodiments, the tumor is a colorectal tumor or a colon tumor. In certain embodiments, the tumor is an ovarian tumor. In some embodiments, the tumor is a lung tumor. In certain embodiments, the tumor is a pancreatic tumor. In certain embodiments, the tumor is a breast tumor, including triple negative breast tumors. In some embodiments, the tumor is a glioblastoma.

The present invention further provides methods for treating cancer in a subject comprising administering a therapeutically effective amount of a MET-binding agent described herein to the subject. In some embodiments, the MET-binding agent binds MET, and inhibits or reduces cancer growth. In some embodiments, the MET-binding agent binds one or more components of the WNT pathway, and inhibits or reduces cancer growth. In some embodiments, the MET-binding agent is a bispecific agent that binds MET and one or more components of the WNT pathway, and inhibits or reduces cancer growth. In some embodiments, the MET-binding agent is a bispecific agent that binds MET and one or more components of the WNT pathway and provides dual inhibition of cancer involved signaling pathways. In some embodiments, the MET-binding agent binds MET, interferes with MET/HGF interactions, and inhibits or reduces cancer growth. In some embodiments, the MET-binding agent binds MET, blocks binding of MET to HGF, and inhibits or reduces cancer growth. In some embodiments, the MET-binding agent hinds MET, inhibits angiogenesis, and inhibits or reduces cancer growth. In some embodiments, the MET-binding agent binds one or more components of the WNT pathway, interferes with WNT/FZD interactions, and inhibits or reduces cancer growth. In some embodiments, the MET-binding agent binds both MET and one or more components of the WNT pathway, interferes with MET/HGF interactions and with WNT/FZD interactions, and inhibits or reduces cancer growth. In some embodiments, the MET-binding agent binds one or more WNT proteins and reduces the frequency of cancer stem cells in the cancer.

The present invention provides methods of treating cancer in a subject (e.g., a subject in need of treatment) comprising administering a therapeutically effective amount of a MET-binding agent described herein to the subject. In certain embodiments, the subject is a human. In certain embodiments, the subject has a cancerous tumor. In certain embodiments, the subject has had a tumor removed. The invention also provides a bispecific agent or antibody for use in a method of treating cancer, wherein the bispecific agent or antibody is an agent or antibody described herein. The invention also provides the use of a bispecific agent or antibody described herein for the manufacture of a medicament for the treatment of cancer.

In certain embodiments, the cancer is a cancer selected from the group consisting of colorectal cancer, pancreatic cancer, lung cancer, ovarian cancer, liver cancer, breast cancer, kidney cancer, prostate cancer, gastrointestinal cancer, melanoma, cervical cancer, bladder cancer, glioblastoma, and head and neck cancer. In certain embodiments, the cancer is ovarian cancer. In certain embodiments, the cancer is colorectal cancer or colon cancer. In certain embodiments, the cancer is pancreatic cancer. In certain embodiments, the cancer is breast cancer, including triple negative breast cancer. In certain embodiments, the cancer is prostate cancer. In certain embodiments, the cancer is lung cancer, including non-small cell lung cancer and small cell lung cancer.

In some embodiments, the subject's cancer/tumor may be refractory to certain treatment(s). As a non-limiting example, the subject's cancer (or tumor) may be chemorefractory. In some embodiments, the subject's cancer may be resistant to EGFR inhibitors.

Methods of treating a disease or disorder in a subject, wherein the disease or disorder is characterized by an increased level of stem cells and/or progenitor cells are further provided. In some embodiments, the treatment methods comprise administering a therapeutically effective amount of a MET-binding agent, polypeptide, or antibody described herein to the subject.

In certain embodiments of any of the methods described herein, the MET-binding agent is a bispecific agent that specifically binds human MET and one or more components of the WNT pathway. In some embodiments, the bispecific agent comprises a first binding site that specifically binds human MET and a second binding site that specifically binds one or more components of the human WNT pathway, wherein the first binding site comprises a heavy chain CDR1 comprising ASYAWS (SEQ ID NO:1), a heavy chain CDR2 comprising YISYSGGTDYNPSLKS (SEQ ID NO:2), and a heavy chain CDR3 comprising KGAY (SEQ ID NO:3), and a light chain CDR1 comprising SASSSVSSSYLY (SEQ ID NO:4), a light chain CDR2 comprising STSNLAS (SEQ ITD NO:5), and a light chain CDR3 comprising HQWSSYPYT (SEQ ID NO:6). In some embodiments, the bispecific agent comprises a first binding site that specifically binds human MET and a second binding site that specifically binds one or more components of the human WNT pathway, wherein the first antigen-binding site comprises a heavy chain CDR1 comprising GYTFTSYWLH (SEQ ID NO:78), a heavy chain CDR2 comprising GMIDPSNSDTRFNPNFKD (SEQ ID NO:79), and a heavy chain CDR3 comprising TYGSYVS- PLDY (SEQ ID NO:81), SYGSYVSPLDY (SEQ ID NO:82), ATYGSYVSPLDY (SEQ ID NO:83), or XYGSYVSPLDY (SEQ ID NO:80), wherein X is not R; and a light chain CDR1 comprising KSSQSLLYTSSQKNYLA (SEQ ID NO:84), a light chain CDR2 comprising WASTRES (SEQ ID NO:85), and a light chain CDR3 comprising QQYYAYPWT (SEQ ID NO:86).

In certain embodiments of any of the methods described herein, the MET-binding agent is a bispecific agent that comprises a heavy chain variable region having at least about 80% sequence identity to SEQ ID NO:7 and a light chain variable region having at least about 80% sequence identity to SEQ ID NO:8.

In some embodiments of any of the methods described herein, the MET-binding agent is an antibody. In some embodiments, the anti-MET antibody comprises the heavy chain variable region and the light chain variable region of antibody 73R009. In some embodiments, the anti-MET antibody is antibody 73R009. In some embodiments, the anti-MET antibody is a monovalent version of antibody 73R009. In some embodiments, the anti-MET antibody is an antibody comprising a heavy chain variable region encoded by the plasmid deposited with ATCC as PTA-13609 and a light chain variable region encoded by the plasmid deposited with ATCC as PTA-13610. In some embodiments, the MET-binding agent is a bispecific agent comprising an antigen-binding site from antibody 73R009. In some embodiments, the MET-binding agent is a bispecific agent comprising a heavy chain variable region encoded by the plasmid deposited with ATCC as PTA-13609 and a light chain variable region encoded by the plasmid deposited with ATCC as PTA-13610. In some embodiments, the MET-binding agent is a bispecific agent comprising a first arm comprising the heavy chain variable region and the light chain variable region of antibody 73R009 and a second arm comprising a FZD8 Fri domain. In some embodiments, the MET-binding agent is a bispecific agent comprising a first arm comprising the heavy chain variable region and the light chain variable region of antibody 73R009 and a second arm comprising a FZD8 Fri domain and a human Fc region. In some embodiments, the MET-binding agent is bispecific agent 315B6. In some embodiments, the MET-binding agent is a bispecific agent comprising SEQ ID NO:7, SEQ ID NO:8, and SEQ ID NO:28. In some embodiments, the MET-binding agent is a bispecific agent comprising SEQ ID NO:7, SEQ ID NO:8, and SEQ ID NO:29. In some embodiments, the MET-binding agent is a bispecific agent comprising SEQ ID NO:7, SEQ ID NO:8, and SEQ ID NO:39. In some embodiments, the MET-binding agent is a bispecific agent comprising SEQ ID NO:13, SEQ ID NO:14, and SEQ ID NO:56. In some embodiments, the MET-binding agent is a bispecific agent, wherein a first arm of the bispecific agent comprises SEQ ID NO:13 and SEQ ID NO:14; and a second arm of the bispecific agent comprises SEQ ID NO:56.

In certain embodiments, the methods further comprise a step of determining the level of MET expression in the tumor or cancer. In some embodiments, the level of expression of MET in a tumor or cancer is compared to the level of expression of MET in a reference sample. As used herein, a "reference sample" includes but is not limited to, normal tissue, non-cancerous tissue of the same tissue type, tumor tissue of the same tissue type, and tumor tissue of a different tissue type. Thus, in some embodiments, the level of expression of MET in a tumor or cancer is compared to the level of expression of MET in normal tissue. In some embodiments, the level of expression of MET in a tumor or cancer is compared to the level of expression of MET in non-cancerous tissue of the same tissue type. In some embodiments, the level of expression of MET in a tumor or cancer is compared to the level of expression of MET in tumors or cancers of the same tissue type. In some embodiments, the level of expression of MET in a tumor or cancer is compared to the level of expression of MET in tumors or cancers of a different tissue type. In some embodiments, the level of expression of MET in a tumor or cancer is compared to a pre-determined level of MET. In some embodiments, determining the level of MET expression is done prior to treatment. In some embodiments, determining the level of MET expression is by immunohistochemistry. In some embodiments, the subject is administered a MET-binding agent described herein if the tumor or cancer has an elevated level of MET expression as compared to the expression of MET in normal tissue or non-cancerous tissue of the same tissue type. For example, in some embodiments, the subject is administered a MET-binding agent (e.g., bispecific agent 315B6) if the tumor or cancer has an elevated level of MET expression as compared to the level of MET expression in a reference sample. In some embodiments, the subject is administered a MET-binding agent described herein if the tumor or cancer has an elevated level of MET expression as compared to the pre-determined level of MET.

In addition, the present invention provides methods of identifying a human subject for treatment with a MET-binding agent, comprising determining if the subject has a tumor that has an elevated level of MET expression as compared to expression of MET in a reference sample. In some embodiments, the reference sample is normal tissue or non-cancerous tissue of the same tissue type. In some embodiments, the reference sample is tumor/cancer tissue of the same tissue type. In some embodiments, the reference sample is tumor/cancer tissue of a different tissue type. In some embodiments, the level of expression of MET in a tumor or cancer is compared to a pre-determined level of MET. In some embodiments, if the tumor has an elevated level of MET expression the subject is selected for treatment with an agent that specifically binds MET. In some embodiments, if selected for treatment, the subject is administered a MET-binding agent described herein. In certain embodiments, the subject has had a tumor removed. For example, in some embodiments, the expression level of MET in a tumor is determined, if the tumor has an elevated level of MET expression as compared to the level of MET in a reference sample or a pre-determined level, the subject is selected for treatment with an agent that specifically binds MET. If selected for treatment, the subject is administered a MET-binding agent described herein. In some embodiments, the MET-binding agent is antibody 73R009 or a monovalent version thereof. In some embodiments, the MET-binding agent is an anti-MET/FZD-Fc bispecific agent. In some embodiments, the MET-binding agent is an anti-MET/FZD8-Fc bispecific agent. In some embodiments, the MET-binding agent is bispecific agent 315B6.

The present invention provides methods of selecting a human subject for treatment with a MET-binding agent, comprising determining if the subject has a tumor that has an elevated expression level of MET. In some embodiments, the methods of selecting a human subject for treatment with a MET-binding agent comprise determining if the subject has a tumor that has an elevated expression level of MET, wherein if the tumor has an elevated expression level of MET, the subject is selected for treatment with an agent that specifically binds MET. The present invention provides methods of selecting a human subject for treatment with a MET-binding agent, comprising determining if the subject has a tumor that has a high expression level of MET. In some embodiments, the methods of selecting a human subject for treatment with a MET-binding agent comprise determining if the subject has a tumor that has a high expression level of MET, wherein if the tumor has a high expression level of MET the subject is selected for treatment with an agent that specifically binds MET. In some embodiments, the "elevated" or "high" expression level is in comparison to the expression level of MET in normal tissue of the same tissue type. In some embodiments, the "elevated" or "high" expression level is in comparison to the expression level of MET in other tumors of the same tissue type. In some embodiments, the "elevated" or "high" expression level is in comparison to the expression level of MET in a reference sample. In some embodiments, the "elevated" or "high" expression level is in comparison to a pre-determined level of MET. In some embodiments, if selected for treatment, the subject is administered a MET-binding agent described herein. In certain embodiments, the subject has had a tumor removed. In some embodiments, the MET-binding agent is an anti-MET antibody. In some embodiments, the anti-MET antibody is antibody 73R009 or a monovalent version thereof. In some embodiments, the MET-binding agent is an anti-MET/FZD-Fc bispecific agent. In some embodiments, the MET-binding agent is an anti-MET/FZD8-Fc bispecific agent. In some embodiments, the anti-MET/FZD-Fc bispecific agent is 315B6.

The present invention also provides methods of treating cancer in a human subject, comprising: (a) selecting a subject for treatment based, at least in part, on the subject having a cancer that has an elevated or high expression level of MET, and (b) administering to the subject a therapeutically effective amount of a MET-binding agent described herein.

Methods for determining the level of MET expression in a cell, tumor, or cancer are known by those of skill in the art. For nucleic acid expression these methods include, but are not limited to, PCR-based assays, microarray analyses, and nucleotide sequencing (e.g., NextGen sequencing). For protein expression, these methods include, but are not limited to, Western blot analysis, protein arrays, ELISAs, immunohistochemistry (IHC) assays, and FACS analysis.

Methods for determining whether a tumor or cancer has an elevated or high level of MET expression can use a variety of samples. In some embodiments, the sample is taken from a subject having a tumor or cancer. In some embodiments, the sample is a fresh tumor/cancer sample. In some embodiments, the sample is a frozen tumor/cancer sample. In some embodiments, the sample is a formalin-fixed paraffin-embedded sample. In some embodiments, the sample is processed to a cell lysate. In some embodiments, the sample is processed to DNA or RNA.

The present invention further provides pharmaceutical compositions comprising the binding agents described herein. In certain embodiments, the pharmaceutical compositions further comprise a pharmaceutically acceptable vehicle. These pharmaceutical compositions find use in inhibiting tumor growth and/or treating cancer in a subject (e.g., a human patient).

In certain embodiments, the invention provides pharmaceutical compositions comprising bispecific agents, wherein at least about 90%, at least about 95%, at least about 98%, at least about 99% of the agents in the composition are bispecific agents or heterodimeric agents. In certain embodiments, the bispecific agents are IgG (e.g., IgG2 or IgG1) based agents. In certain embodiments, the bispecific agents are IgG2-based agents. In certain embodiments, less than about 10%, less than about 5%, less than about 2%, or less than about 1% of the total agents in the composition are monospecific agents or homodimeric agents. In certain embodiments, the agents in the composition are at least about 98% heterodimeric.

In certain embodiments, formulations are prepared for storage and use by combining a purified antibody or agent of the present invention with a pharmaceutically acceptable vehicle (e.g., a carrier or excipient). Suitable pharmaceutically acceptable vehicles include, but are not limited to, non-toxic buffers such as phosphate, citrate, and other organic acids; salts such as sodium chloride; antioxidants including ascorbic acid and methionine; preservatives such as octadecyldimethylbenzyl ammonium chloride, hexamethonium chloride, benzalkonium chloride, benzethonium chloride, phenol, butyl or benzyl alcohol, alkyl parabens, such as methyl or propyl paraben, catechol, resorcinol, cyclohexanol, 3-pentanol, and m-cresol; low molecular weight polypeptides (e.g., less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such c sucrose, mannitol, trehalose or sorbitol; salt-forming counter-ions such as sodium; metal complexes such as Zn-protein complexes; and non-ionic surfactants such as TWEEN or polyethylene glycol (PEG). (*Remington: The Science and Practice of Pharmacy*, $22^{st}$ Edition, 2012, Pharmaceutical Press, London).

The pharmaceutical compositions of the present invention can be administered in any number of ways for either local or systemic treatment. Administration can be topical by epidermal or transdermal patches, ointments, lotions, creams, gels, drops, suppositories, sprays, liquids, and powders; pulmonary by inhalation or insufflation of powders or aerosols, including by nebulizer, intratracheal, and intranasal; oral; or parenteral including intravenous, intraarterial, intratumoral, subcutaneous, intraperitoneal, intramuscular (e.g., injection or infusion), or intracranial (e.g., intrathecal or intraventricular).

The therapeutic formulation can be in unit dosage form. Such formulations include tablets, pills, capsules, powders, granules, solutions or suspensions in water or non-aqueous media, or suppositories. In solid compositions such as tablets the principal active ingredient is mixed with a pharmaceutical carrier. Conventional tableting ingredients include corn starch, lactose, sucrose, sorbitol, talc, stearic acid, magnesium stearate, dicalcium phosphate or gums, and diluents (e.g., water). These can be used to form a solid preformulation composition containing a homogeneous mixture of a compound of the present invention, or a non-toxic pharmaceutically acceptable salt thereof. The solid preformulation composition is then subdivided into unit dosage forms of a type described above. The tablets, pills, etc. of the formulation or composition can be coated or otherwise compounded to provide a dosage form affording the advantage of prolonged action. For example, the tablet or pill can comprise an inner composition covered by an outer component. Furthermore, the two components can be separated by an enteric layer that serves to resist disintegration and permits the inner component to pass intact through the stomach or to be delayed in release. A variety of materials can be used for such enteric layers or coatings, such materials include a number of polymeric acids and mixtures of polymeric acids with such materials as shellac, cetyl alcohol and cellulose acetate.

The MET-binding agents described herein can also be entrapped in microcapsules. Such microcapsules are prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions as described in Remington: The Science and Practice of Pharmacy, 22$^{st}$ Edition, 2012, Pharmaceutical Press, London.

In certain embodiments, pharmaceutical formulations include a MET-binding agent (e.g., an antibody or a bispecific agent) of the present invention complexed with liposomes. Methods to produce liposomes are known to those of skill in the art. For example, some liposomes can be generated by reverse phase evaporation with a lipid composition comprising phosphatidylcholine, cholesterol, and PEG-derivatized phosphatidylethanolamine (PEG-PE) Liposomes can be extruded through filters of defined pore size to yield liposomes with the desired diameter.

In certain embodiments, sustained-release preparations can be produced. Suitable examples of sustained-release preparations include semi-permeable matrices of solid hydrophobic polymers containing a MET-binding agent (e.g., an antibody or a bispecific agent), where the matrices are in the form of shaped articles (e.g., films or microcapsules). Additional examples of sustained-release matrices include polyesters, hydrogels such as poly(2-hydroxyethyl-methacrylate) or poly(vinyl alcohol), polylactides, copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

In certain embodiments, in addition to administering a MET-binding agent described herein (e.g., an antibody or bispecific agent), a method or treatment further comprises administering at least one additional therapeutic agent. An additional therapeutic agent can be administered prior to, concurrently with, and/or subsequently to, administration of the MET-binding agent. Pharmaceutical compositions comprising a MET-binding agent and the additional therapeutic agent(s) are also provided. In some embodiments, the at least one additional therapeutic agent comprises 1, 2, 3, or more additional therapeutic agents.

Combination therapy with at least two therapeutic agents often uses agents that work by different mechanisms of action, although this is not required. Combination therapy using agents with different mechanisms of action may result in additive or synergetic effects. Combination therapy may allow for a lower dose of each agent than is used in monotherapy, thereby reducing toxic side effects and/or increasing the therapeutic index of at least one of the agents. Combination therapy may decrease the likelihood that resistant cancer cells will develop. In some embodiments, combination therapy comprises a therapeutic agent that primarily affects (e.g., inhibits or kills) non-tumorigenic cells and a therapeutic agent that primarily affects (e.g., inhibits or kills) tumorigenic CSCs.

Useful classes of therapeutic agents include, for example, anti-tubulin agents, auristatins, DNA minor groove binders, DNA replication inhibitors, alkylating agents (e.g., platinum complexes such as cisplatin, mono(platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, purine antimetabolites, puromycins, radiation sensitizers, steroids, taxanes, topoisomerase inhibitors, vinca alkaloids, or the like. In certain embodiments, the second therapeutic agent is an alkylating agent, an anti-metabolite, an anti-mitotic, a topoisomerase inhibitor, or an angiogenesis inhibitor. In some embodiments, the second therapeutic agent is a platinum complex such as carboplatin or cisplatin. In some embodiments, the additional therapeutic agent is a platinum complex in combination with a taxane.

Therapeutic agents that may be administered in combination with the MET-binding agents include chemotherapeutic agents. Thus, in some embodiments, the method or treatment involves the administration of a MET-binding agent of the present invention in combination with a chemotherapeutic agent or cocktail of multiple different chemotherapeutic agents. In some embodiments, the method or treatment involves the administration of a bispecific agent of the present invention that binds MET and one or more WNT proteins in combination with a chemotherapeutic agent or cocktail of multiple different chemotherapeutic agents.

Chemotherapeutic agents useful in the instant invention include, but are not limited to, alkylating agents such as thiotepa and cyclophosphamide (CYTOXAN); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytosine arabinoside, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenishers such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); taxoids, e.g. paclitaxel (TAXOL) and docetaxel (TAXOTERE); chlorambucil; gemcitabine; 6-thioguanine; mercaptopurine; platinum analogs such as cisplatin and carboplatin; vinblastine; platinum; etoposide (VP-16); ifosfamide; mitomycin C; mitoxantrone: vincristine; vinorelbine; navelbine; novantrone; teniposide; daunomycin; aminopterin; ibandronate; CPT11; topoisomerase inhibitor RFS 2000; difluoromethylornithine (DMFO); retinoic acid; esperamicins; capecitabine (XELODA); and pharmaceutically acceptable salts, acids or derivatives of any of the above. Chemotherapeutic agents also include anti-hormonal agents that act to regulate or inhibit hormone action on tumors such as anti-estrogens including, for example, tamoxifen, raloxifene, aromatase inhibiting 4(5)-imidazoles, 4-hydroxytamoxifen, trioxifene, keoxifene, LY117018, onapristone, and toremifene (FARESTON); and anti-androgens such as flutamide, nilutamide, bicalutamide, leuprolide, and goserelin; and pharmaceutically acceptable salts, acids or derivatives of any of the above. In certain embodiments, the second therapeutic agent is cisplatin. In certain embodiments, the second therapeutic agent is carboplatin. In certain embodiments, the second therapeutic agent is paclitaxel.

In certain embodiments, the chemotherapeutic agent is a topoisomerase inhibitor. Topoisomerase inhibitors are chemotherapeutic agents that interfere with the action of a topoisomerase enzyme (e.g., topoisomerase I or II). Topoisomerase inhibitors include, but are not limited to, doxorubicin HCl, daunorubicin citrate, mitoxantrone HCl, actinomycin D, etoposide, topotecan HCl, teniposide (VM-26), and irinotecan, as well as pharmaceutically acceptable salts, acids, or derivatives of any of these. In certain embodiments, the second therapeutic agent is irinotecan.

In certain embodiments, the chemotherapeutic agent is an anti-metabolite. An anti-metabolite is a chemical with a structure that is similar to a metabolite required for normal biochemical reactions, yet different enough to interfere with one or more normal functions of cells, such as cell division. Anti-metabolites include, but are not limited to, gemcitabine, fluorouracil, capecitabine, methotrexate sodium, ralitrexed, pemetrexed, tegafur, cytosine arabinoside, thioguanine, 5-azacytidine, 6-mercaptopurine, azathioprine, 6-thioguanine, pentostatin, fludarabine phosphate, and cladribine, as well as pharmaceutically acceptable salts, acids, or derivatives of any of these. In certain embodiments, the second therapeutic agent is gemcitabine.

In certain embodiments, the chemotherapeutic agent is an anti-mitotic agent, including, but not limited to, agents that bind tubulin. In some embodiments, the agent is a taxane. In certain embodiments, the agent is paclitaxel or docetaxel, or a pharmaceutically acceptable salt, acid, or derivative of paclitaxel or docetaxel. In certain embodiments, the agent is paclitaxel (TAXOL), docetaxel (TAXOTERE), albumin-bound paclitaxel (ABRAXANE), DHA-paclitaxel, or PG-paclitaxel. In certain alternative embodiments, the anti-mitotic agent comprises a vinca alkaloid, such as vincristine, binblastine, vinorelbine, or vindesine, or pharmaceutically acceptable salts, acids, or derivatives thereof. In some embodiments, the anti-mitotic agent is an inhibitor of kinesin Eg5 or an inhibitor of a mitotic kinase such as Aurora A or Plk1. In certain embodiments, where the chemotherapeutic agent administered in combination with a MET-binding agent is an anti-mitotic agent, the cancer or tumor being treated is breast cancer or a breast tumor.

In some embodiments, an additional therapeutic agent comprises an agent such as a small molecule. For example, treatment can involve the combined administration of a MET-binding agent (e.g. an antibody or bispecific agent) of the present invention with a small molecule that acts as an inhibitor against additional tumor-associated proteins including, but not limited to, EGFR, ErbB2, HER2, and/or MET. In certain embodiments, the additional therapeutic agent is a small molecule that inhibits a cancer stem cell pathway. In some embodiments, the additional therapeutic agent is a small molecule inhibitor of the NOTCH pathway. In some embodiments, the additional therapeutic agent is a small molecule inhibitor of the WNT pathway. In some embodiments, the additional therapeutic agent is a small molecule inhibitor of the BMP pathway. In some embodiments, the additional therapeutic agent is a small molecule that inhibits $\beta$-catenin signaling.

In some embodiments, an additional therapeutic agent comprises a biological molecule, such as an antibody. For example, treatment can involve the combined administration of a MET-binding agent (e.g. an antibody or bispecific agent) of the present invention with other antibodies against additional tumor-associated proteins including, but not limited to, antibodies that bind EGFR, ErbB2, and/or HER2. In certain embodiments, the additional therapeutic agent is an antibody that is an anti-cancer stem cell marker antibody. In some embodiments, the additional therapeutic agent is an antibody that binds a component of the NOTCH pathway. In some embodiments, the additional therapeutic agent is an antibody that binds a component of the WNT pathway. In certain embodiments, the additional therapeutic agent is an antibody that inhibits a cancer stem cell pathway. In some embodiments, the additional therapeutic agent is an antibody inhibitor of the NOTCH pathway. In some embodiments, the additional therapeutic agent is an antibody inhibitor of the WNT pathway. In some embodiments, the additional therapeutic agent is an antibody inhibitor of the BMP pathway. In some embodiments, the additional therapeutic agent is an antibody that inhibits $\beta$-catenin signaling. In certain embodiments, the additional therapeutic agent is an antibody that is an angiogenesis inhibitor or modulator (e.g., an anti-VEGF or VEGF receptor antibody). In certain embodiments, the additional therapeutic agent is bevacizumab (AVASTIN), trastuzumab (HERCEPTIN), panitumumab (VECTIBIX), or cetuximab (ERBITUX). Combined administration can include co-administration, either in a single pharmaceutical formulation or using separate formulations, or consecutive administration in either order but generally within a time period such that all active agents can exert their biological activities simultaneously.

Furthermore, treatment with a MET-binding agent described herein can include combination treatment with other biologic molecules, such as one or more cytokines (e.g., lymphokines, interleukins, tumor necrosis factors, and/or growth factors) or can be accompanied by surgical removal of tumors, cancer cells, or any other therapy deemed necessary by a treating physician.

In certain embodiments, the treatment involves the administration of a MET-binding agent (e.g. an antibody or bispecific agent) of the present invention in combination with radiation therapy. Treatment with a MET-binding agent can occur prior to, concurrently with, or subsequent to administration of radiation therapy. Dosing schedules for such radiation therapy can be determined by the skilled medical practitioner.

It will be appreciated that the combination of a MET-binding agent and an additional therapeutic agent may be administered in any order or concurrently. Treatment with a MET-binding agent (e.g., an antibody or a bispecific agent) can occur prior to, concurrently with, or subsequent to administration of chemotherapies. Combined administration can include co-administration, either in a single pharmaceutical formulation or using separate formulations, or consecutive administration in either order but generally within a time period such that all active agents can exert their biological activities simultaneously. Preparation and dosing schedules for such chemotherapeutic agents can be used according to manufacturers' instructions or as determined empirically by the skilled practitioner. Preparation and dosing schedules for such chemotherapy are also described in *The Chemotherapy*

*Source Book*, 4$^{th}$ Edition, 2008, M. C. Perry, Editor, Lippincott, Williams & Wilkins, Philadelphia, Pa.

In some embodiments, the MET-binding agent will be administered to patients that have previously undergone treatment with therapeutic agents. In certain other embodiments, the MET-binding agent and an additional therapeutic agent will be administered substantially simultaneously or concurrently. For example, a subject may be given a MET-binding agent (e.g., an antibody or bispecific agent) while undergoing a course of treatment with a second therapeutic agent (e.g., chemotherapy). In certain embodiments, a MET-binding agent will be administered within 1 year of the treatment with a second therapeutic agent. In certain alternative embodiments, a MET-binding agent will be administered within 10, 8, 6, 4, or 2 months of any treatment with a second therapeutic agent. In certain other embodiments, a MET-binding agent will be administered within 4, 3, 2, or 1 weeks of any treatment with a second therapeutic agent. In some embodiments, a MET-binding agent will be administered within 5, 4, 3, 2, or 1 days of any treatment with a second therapeutic agent. It will further be appreciated that the two (or more) agents or treatments may be administered to the subject within a matter of hours or minutes (i.e., substantially simultaneously).

For the treatment of a disease, the appropriate dosage of a MET-binding agent (e.g., an antibody or bispecific agent) of the present invention depends on the type of disease to be treated, the severity and course of the disease, the responsiveness of the disease, whether the MET-binding agent is administered for therapeutic or preventative purposes, previous therapy, the patient's clinical history, and so on, all at the discretion of the treating physician. The MET-binding agent can be administered one time or as a series of treatments spread over several days to several months, or until a cure is effected or a diminution of the disease state is achieved (e.g., reduction in tumor size). Optimal dosing schedules can be calculated from measurements of drug accumulation in the body of the patient and will vary depending on the relative potency of an individual antibody or agent. The administering physician can determine optimum dosages, dosing methodologies, and repetition rates. In certain embodiments, dosage of a MET-binding agent is from about 0.01 µg to about 100 mg/kg of body weight, from about 0.1 µg to about 100 mg/kg of body weight, from about 1 µg to about 100 mg/kg of body weight, from about 1 mg to about 100 mg/kg of body weight, about 1 mg to about 80 mg/kg of body weight from about 10 mg to about 100 mg/kg of body weight, from about 10 mg to about 75 mg/kg of body weight, or from about 10 mg to about 50 mg/kg of body weight. In certain embodiments, the dosage of the MET-binding agent is from about 0.1 mg to about 20 mg/kg of body weight. In certain embodiments, dosage can be given once or more daily, weekly, monthly, or yearly. In certain embodiments, the MET-binding agent is given once every week, once every two weeks, once every three weeks, or once every month.

In some embodiments, a MET-binding agent (e.g., an antibody or bispecific agent) may be administered at an initial higher "loading" dose, followed by one or more lower doses. In some embodiments, the frequency of administration may also change. In some embodiments, a dosing regimen may comprise administering an initial dose, followed by additional doses (or "maintenance" doses) once a week, once every two weeks, once every three weeks, or once every month. For example, a dosing regimen may comprise administering an initial loading dose, followed by a weekly maintenance dose of, for example, one-half of the initial dose. Or a dosing regimen may comprise administering an initial loading dose, followed by maintenance doses of, for example one-half of the initial dose every other week. Or a dosing regimen may comprise administering three initial doses for 3 weeks, followed by maintenance doses of, for example, the same amount every other week. Or a dosing regimen may comprise administering an initial dose followed by additional doses every 3 weeks or once a month. The treating physician can estimate repetition rates for dosing based on measured residence times and concentrations of the drug in bodily fluids or tissues. The progress of therapy can be monitored by conventional techniques and assays.

As is known to those of skill in the art, administration of any therapeutic agent may lead to side effects and/or toxicities. In some cases, the side effects and/or toxicities are so severe as to preclude administration of the particular agent at a therapeutically effective dose. In some cases, drug therapy must be discontinued, and other agents may be tried. However, many agents in the same therapeutic class often display similar side effects and/or toxicities, meaning that the patient either has to stop therapy, or if possible, suffer from the unpleasant side effects associated with the therapeutic agent.

Side effects from therapeutic agents may include, but are not limited to, hives, skin rashes, itching, nausea, vomiting, decreased appetite, diarrhea, chills, fever, fatigue, muscle aches and pain, headaches, low blood pressure, high blood pressure, hypokalemia, bone effects, low blood counts, bleeding, and cardiovascular problems.

Thus, one aspect of the present invention is directed to methods of treating cancer in a patient comprising administering a MET-binding agent described herein using an intermittent dosing regimen, which may reduce side effects and/or toxicities associated with administration of the agent. As used herein, "intermittent dosing" refers to a dosing regimen using a dosing interval of more than once a week, e.g., dosing once every 2 weeks, once every 3 weeks, once every 4 weeks, etc. In some embodiments, a method for treating cancer in a human patient comprises administering to the patient an effective dose of a MET-binding agent (e.g., an antibody or a bispecific agent) described herein according to an intermittent dosing regimen. In some embodiments, a method for treating cancer in a human patient comprises administering to the patient an effective dose of a MET-binding agent (e.g., an antibody or a bispecific agent) according to an intermittent dosing regimen, and increasing the therapeutic index of the MET-binding agent. In some embodiments, the intermittent dosing regimen comprises administering an initial dose of a MET-binding agent (e.g., an antibody or a bispecific agent) to the patient, and administering subsequent doses of the MET-binding agent about once every 2 weeks. In some embodiments, the intermittent dosing regimen comprises administering an initial dose of a MET-binding agent (e.g., an antibody or a bispecific agent) to the patient, and administering subsequent doses of the MET-binding agent about once every 3 weeks. In some embodiments, the intermittent dosing regimen comprises administering an initial dose of a MET-binding agent (e.g., an antibody or a bispecific agent) to the patient, and administering subsequent doses of the MET-binding agent about once every 4 weeks.

In some embodiments, the subsequent doses in an intermittent dosing regimen are about the same amount or less than the initial dose. In other embodiments, the subsequent doses are a greater amount than the initial dose. As is known by those of skill in the art, doses used will vary depending on the clinical goals to be achieved. In some embodiments, the initial dose is about 0.25 mg/kg to about 20 mg/kg. In some embodiments, the initial dose is about 0.5, 1, 2, 3, 4, 5, 6, 7, 8, 9, 10, 11, 12, 13, 14, 15, 16, 17, 18, 19, or 20 mg/kg. In certain embodiments, the initial dose is about 0.5 mg/kg. In certain embodiments, the initial dose is about 1 mg/kg. In certain embodiments, the initial dose is about 2.5 mg/kg. In certain embodiments, the initial dose is about 5 mg/kg. In certain embodiments, the initial dose is about 7.5 mg/kg. In certain embodiments, the initial dose is about 10 mg/kg. In certain embodiments, the initial dose is about 12.5 mg/kg. In certain embodiments, the initial dose is about 15 mg/kg. In certain embodiments, the initial dose is about 20 mg/kg. In some embodiments, the subsequent doses are about 0.25 mg/kg to about 15 mg/kg. In certain embodiments, the subsequent doses are about 0.5, 1, 2, 3, 4, 5, 6, 7, 8, 9, 10, 11, 12, 13, 14 or 15 mg/kg. In certain embodiments, the subsequent doses are about 0.5 mg/kg. In certain embodiments, the subsequent doses are about 1 mg/kg. In certain embodiments, the subsequent doses are about 2.5 mg/kg. In certain embodiments, the subsequent doses are about 5 mg/kg. In some embodiments, the subsequent doses are about 7.5 mg/kg. In some embodiments, the subsequent doses are about 10 mg/kg. In some embodiments, the subsequent doses are about 12.5 mg/kg.

Thus the present invention provides methods for reducing toxicity of a MET-binding agent (e.g., an antibody or a bispecific agent) described herein in a human patient that comprise administering to the patient the MET-binding agent using an intermittent dosing regimen. Also provided are methods for reducing side effects of a MET-binding agent (e.g., an antibody or a bispecific agent) in a human patient that comprise administering to the patient the MET-binding agent using an intermittent dosing regimen. Also provided are methods for increasing the therapeutic index of a MET-binding agent (e.g., an antibody or a bispecific agent) in a human patient that comprise administering to the patient the MET-binding agent using an intermittent dosing regimen.

The choice of delivery method for the initial and subsequent doses is made according to the ability of the animal or human patient to tolerate introduction of the MET-binding agent into the body. Thus, in any of the aspects and/or embodiments described herein, the administration of the MET-binding agent (e.g., an antibody or a bispecific agent) may be by intravenous injection or intravenously. In some embodiments, the administration is by intravenous infusion. In any of the aspects and/or embodiments described herein, the administration of the MET-binding agent may be by a non-intravenous route.

V. Kits Comprising Met/Wnt-Binding Agents

The present invention provides kits that comprise the MET-binding agents (e.g., antibodies or bispecific agents) described herein and that can be used to perform the methods described herein. In certain embodiments, a kit comprises at least one purified antibody against MET or at least one purified bispecific agent that binds MET and one or more components of the WNT pathway in one or more containers. In some embodiments, the kits contain all of the components necessary and/or sufficient to perform a detection assay, including all controls, directions for performing assays, and any necessary software for analysis and presentation of results. One skilled in the art will readily recognize that the disclosed MET-binding agents of the present invention can be readily incorporated into one of the established kit formats which are well known in the art.

Further provided are kits comprising a MET-binding agent (e.g., an antibody or bispecific agent), as well as at least one additional therapeutic agent. In certain embodiments, the second (or more) therapeutic agent is a chemotherapeutic agent. In certain embodiments, the second (or more) therapeutic agent is an angiogenesis inhibitor.

Embodiments of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, may be practiced without departing from the scope of the present disclosure.

EXEMPLARY EMBODIMENTS

Embodiment 1. A bispecific agent comprising: a) a first binding site that specifically binds human MET, and b) a second binding site that specifically binds one or more components of the WNT pathway.

Embodiment 2. The bispecific agent of embodiment 1, wherein the first binding site comprises an antigen-binding site of an antibody that specifically binds human MET.

Embodiment 3. The bispecific agent of embodiment 1 or embodiment 2, wherein the first binding site comprises a heavy chain CDR1 comprising ASYAWS (SEQ ID NO:1), a heavy chain CDR2 comprising YISYSGGTDYNPSLKS (SEQ ID NO:2), and a heavy chain CDR3 comprising KGAY (SEQ ID NO:3); and a light chain CDR1 comprising SASSSVSSSYLY (SEQ ID NO:4), a light chain CDR2 comprising STSNLAS (SEQ ID NO:5), and a light chain CDR3 comprising HQWSSYPYT (SEQ ID NO:6).

Embodiment 4. The bispecific agent of any one of embodiments 1-3, wherein the second binding site comprises an antigen-binding site of an antibody that specifically binds one or more components of the WNT pathway.

Embodiment 5. The bispecific agent of any one of embodiments 1-4, which is a bispecific antibody.

Embodiment 6. The bispecific agent of any one of embodiments 1-5, wherein the second binding site specifically binds one or more human WNT proteins.

Embodiment 7. The bispecific agent of embodiment 6, wherein the one or more WNT proteins is selected from the group consisting of: WNT1, WNT2, WNT2b, WNT3, WNT3a, WNT7a, WNT7b, WNT8a, WNT8b, WNT10a, and WNT100b.

Embodiment 8. The bispecific agent of any one of embodiments 1-5, wherein the second binding site specifically binds one or more Frizzled (FZD) proteins.

Embodiment 9. The bispecific agent of embodiment 8, wherein the second binding site specifically binds one or more FZD proteins selected from the group consisting of: FZD1, FZD2, FZD5, FZD7, and FZD8.

Embodiment 10. The bispecific agent of any one of embodiments 1, 2, 3, 6, or 7, which comprises a soluble FZD receptor.

Embodiment 11. The bispecific agent of embodiment 10, wherein the soluble receptor comprises a Fri domain of a human FZD protein.

Embodiment 12. The bispecific agent of embodiment 10, wherein the human FZD protein is human FZD8.

Embodiment 13. The bispecific agent of embodiment 11, wherein the Fri domain of the human FZD protein comprises a sequence selected from the group consisting of: SEQ ID NO:21. SEQ ID NO:22. SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, and SEQ ID NO:41.

Embodiment 14. The bispecific agent of embodiment 13, wherein the Fri domain of the human FZD protein comprises SEQ ID NO:28, SEQ ID NO:29, or SEQ ID NO:39.

Embodiment 15. The bispecific agent of any one of embodiments 10-14, wherein the Fri domain of the human FZD protein is directly linked to a heterologous polypeptide.

Embodiment 16. The bispecific agent of any one of embodiments 10-14, wherein the Fri domain of the human FZD protein is connected to a heterologous polypeptide by a linker.

Embodiment 17. The bispecific agent of embodiment 15 or embodiment 16, wherein the heterologous polypeptide comprises a human Fc region.

Embodiment 18. The bispecific agent of any one of embodiments 15-17, wherein the heterologous polypeptide comprises SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:42, SEQ ID NO:43, SEQ ID NO:91, or SEQ ID NO:92.

Embodiment 19. The bispecific agent of embodiment 10, wherein the soluble FZD receptor comprises: (a) a first polypeptide consisting essentially of SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, or SEQ ID NO:41; and (b) a second polypeptide comprising SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52; wherein the first polypeptide is directly linked to the second polypeptide.

Embodiment 20. The bispecific agent of embodiment 10, wherein the soluble FZD receptor comprises: (a) a first polypeptide comprising SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, or SEQ ID NO:41; and (b) a second polypeptide comprising SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52; wherein the first polypeptide is connected to the second polypeptide by a linker.

Embodiment 21. The bispecific agent of embodiment 19 or embodiment 20, wherein the first polypeptide consists of SEQ ID NO:28.

Embodiment 22. The bispecific agent of embodiment 21, wherein the second polypeptide consists of SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52.

Embodiment 23. The bispecific agent of embodiment 19 or embodiment 20, wherein the first polypeptide consists of SEQ ID NO:29.

Embodiment 24. The bispecific agent embodiment 23, wherein the second polypeptide consists of SEQ ID NO:44, SEQ ID NO:45, SEQ ID NO:46, SEQ ID NO:47, SEQ ID NO:48, SEQ ID NO:49, SEQ ID NO:50, SEQ ID NO:5 I, or SEQ ID NO:52.

Embodiment 25. The bispecific agent of embodiment 10, wherein the soluble FZD receptor comprises SEQ ID NO:53 or SEQ ID NO:56.

Embodiment 26. The bispecific agent of embodiment 10, wherein the soluble FZD receptor comprises SEQ ID NO:56.

Embodiment 27. A bispecific agent of any one of embodiments 1-26, wherein the first binding site comprises a heavy chain variable region having at least about 90% sequence identity to SEQ ID NO:7 and a light chain variable region having at least about 90% sequence identity to SEQ ID NO:8.

Embodiment 28. The bispecific agent of embodiment 27, wherein the first binding site comprises a heavy chain variable region having at least 95% sequence identity to SEQ ID NO:7 and a light chain variable regions have at least 95% sequence identity to SEQ ID NO:8.

Embodiment 29. The bispecific agent of embodiment 27, wherein the first antigen-binding site comprises a heavy chain variable region comprising SEQ ID NO:7 and a light chain variable region comprising SEQ ID NO:8.

Embodiment 30. The bispecific agent of any one of embodiments 1-29, which comprises a first CH3 domain and a second CH3 domain, each of which is modified to promote formation of heterodimers.

Embodiment 31. The bispecific agent of embodiment 30, wherein the first and second CH3 domains are modified based upon electrostatic effects.

Embodiment 32. The bispecific agent of any one of embodiments 1-31, which comprises a first human IgG2 constant region with amino acid substitutions at positions corresponding to positions 249 and 288 of SEQ ID NO:75, wherein the amino acids are replaced with glutamate or aspartate, and a second human IgG2 constant region with amino acid substitutions at positions corresponding to positions 236 and 278 of SEQ ID NO:75, wherein the amino acids are replaced with lysine.

Embodiment 33. The bispecific agent according to any one of embodiments 1-31, which comprises a first human IgG2 constant region with amino acid substitutions at positions corresponding to positions 236 and 278 of SEQ ID NO:75, wherein the amino acids are replaced with lysine, and a second human IgG2 constant region with amino acid substitutions at positions corresponding to positions 249 and 288 of SEQ ID NO:75, wherein the amino acids are replaced with glutamate or aspartate.

Embodiment 34. The bispecific agent of embodiment 30, wherein the first and second CH3 domains are modified using a knobs-into-holes technique.

Embodiment 35. A bispecific agent that specifically binds human MET and specifically binds one or more components of the WNT pathway, which comprises a heavy chain of SEQ ID NO:13 and a light chain of SEQ ID NO: 14.

Embodiment 36. The bispecific agent of any one of embodiments 1-35, which binds human MET with a $K_D$ of about 100 nM or less and binds one or more components of the WNT pathway with a $K_D$ of about 100 nM or less.

Embodiment 37. A bispecific agent which is 315B6.

Embodiment 38. The bispecific agent of any one of embodiments 1-37, which inhibits binding of MET to hepatocyte growth factor.

Embodiment 39. The bispecific agent of any one of embodiments 1-38, which facilitates internalization of MET.

Embodiment 40. The bispecific agent of any one of embodiments 1-39, which stimulates degradation of MET.

Embodiment 41. The bispecific agent of any one of embodiments 1-38, which inhibits dimerization of MET.

Embodiment 42. The bispecific agent of any one of embodiments 1-41, which inhibits activation of MET.

Embodiment 43. The bispecific agent of any one of embodiments 1-42, which inhibits binding of one or more WNT proteins to at least one FZD.

Embodiment 44. The bispecific agent of embodiment 43, wherein the FZD is selected from the group consisting of FZD1, FZD2, FZD5, FZD7, and FZD8.

Embodiment 45. The bispecific agent of embodiment 44, wherein the FZD is FZD8.

Embodiment 46. The bispecific agent of any one of embodiments 1-45, which inhibits WNT signaling.

Embodiment 47. The bispecific agent of any one of embodiments 1-46, which inhibits canonical WNT signaling.

Embodiment 48. The bispecific agent of any one of embodiments 1-47, which inhibits the growth of a tumor or tumor cells.

Embodiment 49. The bispecific agent of any one of embodiments 1-48, which induces expression of differentiation markers in a tumor.

Embodiment 50. The bispecific agent of any one of embodiments 1-49, which induces cells in a tumor to differentiate.

Embodiment 51. The bispecific agent of any one of embodiments 1-50, which reduces the frequency of cancer stem cells in a tumor.

Embodiment 52. The bispecific agent of any one of embodiments 1-51, which inhibits epithelial-mesenchymal transition (EMT).

Embodiment 53. An isolated antibody that specifically binds human MET, which comprises: a heavy chain CDR comprising ASYAWS (SEQ ID NO:1), a heavy chain CDR2 comprising YISYSGGTDYNPSLKS (SEQ ID NO:2), and a heavy chain CDR3 comprising KGAY (SEQ ID NO:3); and a light chain CDR1 comprising SASSSVSSSYLY (SEQ ID NO:4), a light chain CDR2 comprising STSNLAS (SEQ ID NO:5), and a light chain CDR3 comprising HQWSSYPYT (SEQ ID NO:6).

Embodiment 54. An isolated antibody that specifically binds human MET, which comprises: (a) a heavy chain variable region having at least about 90% sequence identity to SEQ ID NO:7; and (b) a light chain variable region having at least about 90% sequence identity to SEQ ID NO:8.

Embodiment 55. The antibody of embodiment 54, which comprises: (a) a heavy chain variable region having at least about 95% sequence identity to SEQ ID NO:7; and (b) a light chain variable region having at least about 95% sequence identity to SEQ ID NO:8.

Embodiment 56. The antibody of embodiment 54, which comprises: (a) a heavy chain variable region comprising SEQ ID NO:7; and (b) a light chain variable region comprising SEQ ID NO:8.

Embodiment 57. An isolated antibody that specifically binds human MET, which comprises: (a) a heavy chain comprising SEQ ID NO:12; and (b) a light chain comprising SEQ ID NO: 14.

Embodiment 58. The antibody of any one of embodiments 53-57, which is a monoclonal antibody, a recombinant antibody, a monovalent antibody, a chimeric antibody, a humanized antibody, a human antibody, a bispecific antibody, an IgG1 antibody, an IgG2 antibody, or antibody fragment comprising an antigen-binding site.

Embodiment 59. The antibody of any one of embodiments 53-57, which is a monovalent antibody.

Embodiment 60. The antibody of any one of embodiments 53-57, which is a bispecific antibody.

Embodiment 61. The antibody of any one of embodiments 53-60, which inhibits binding of MET to hepatocyte growth factor.

Embodiment 62. A polypeptide comprising a sequence selected from the group consisting of: SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:55, SEQ ID NO:56, SEQ ID NO:87, and SEQ ID NO:88.

Embodiment 63. A cell comprising the bispecific agent, antibody, or polypeptide of any one of embodiments 1-62.

Embodiment 64. A cell producing the bispecific agent, antibody, or polypeptide of any one of embodiments 1-62.

Embodiment 65. An isolated polynucleotide molecule comprising a polynucleotide that encodes a bispecific agent, antibody, or polypeptide of any one of embodiments 1-62.

Embodiment 66. An isolated polynucleotide molecule comprising a polynucleotide sequence selected from the group consisting of: SEQ ID NO: 15, SEQ ID NO:16, SEQ ID NO:17, SEQ ID NO: 18, SEQ ID NO:19, SEQ ID NO:20, SEQ ID NO:89, and SEQ ID NO:90.

Embodiment 67. A vector comprising the polynucleotide of embodiment 65 or embodiment 66.

Embodiment 68. A cell comprising the polynucleotide of embodiment 65 or embodiment 66 or the vector of embodiment 67.

Embodiment 69. A pharmaceutical composition comprising the bispecific agent or antibody of any one of embodiments 1-61 and a pharmaceutically acceptable carrier.

Embodiment 70. A method of inhibiting growth of a tumor, wherein the method comprises contacting the tumor with an effective amount of a bispecific agent of any one of embodiments 1-52 or an antibody of any one of embodiments 53-61.

Embodiment 71. A method of inhibiting growth of a tumor in a subject, comprising administering to the subject a therapeutically effective amount of a bispecific agent of any one of embodiments 1-52 or an antibody of any one of embodiments 53-61.

Embodiment 72. A method of reducing the frequency of cancer stem cells in a tumor in a subject, comprising administering to the subject a therapeutically effective amount of a bispecific agent of any one of embodiments 1-52 or an antibody of any one of embodiments 53-61.

Embodiment 73. A method of inhibiting EMT in a tumor in a subject, comprising administering to the subject a therapeutically effective amount of a bispecific agent of any one of embodiments 1-52 or an antibody of any one of embodiments 53-61.

Embodiment 74. A method of inhibiting angiogenesis in a subject, comprising administering to the subject a therapeutically effective amount of a bispecific agent of any one of embodiments 1-52 or an antibody of any one of embodiments 53-61.

Embodiment 75. The method of embodiment 74, wherein the angiogenesis is tumor angiogenesis.

Embodiment 76. The method of any one of embodiments 70-75, wherein the tumor is selected from the group consisting of colorectal tumor, colon tumor, ovarian tumor, pancreatic tumor, lung tumor, liver tumor, breast tumor, kidney tumor, prostate tumor, gastrointestinal tumor, melanoma, cervical tumor, bladder tumor, glioblastoma, and head and neck tumor.

Embodiment 77. A method of treating cancer in a subject, comprising administering to the subject a therapeutically effective amount of a bispecific agent of any one of embodiments 1-52 or an antibody of any one of embodiments 53-61.

Embodiment 78. The method of embodiment 77, wherein the cancer is selected from the group consisting of colorectal cancer, colon cancer, ovarian cancer, pancreatic cancer, lung cancer, liver cancer, breast cancer, kidney cancer, prostate cancer, gastrointestinal cancer, melanoma, cervical cancer, bladder cancer, glioblastoma, head and neck cancer, lymphoma and leukemia.

Embodiment 79. The method of any one of embodiments 79-78, which further comprises administering at least one additional therapeutic agent.

Embodiment 80. The method of embodiment 79, wherein the additional therapeutic agent is a chemotherapeutic agent.

Embodiment 81. The method of embodiment 79, wherein the additional therapeutic agent is a second antibody.

Embodiment 82. The method of any one of embodiments 70 or 72-81, wherein the subject is human.

Embodiment 83. A method for the production of a bispecific agent or an antibody, comprising expressing at least one polynucleotide of embodiment 65 or embodiment 66 in a cell.

Embodiment 84. The method of embodiment 83, wherein the cell is a prokaryotic cell or a eukaryotic cell.

Embodiment 85. The method of embodiment 83 or embodiment 84, further comprising isolating the bispecific agent or antibody from the cell or the cell culture supernatant.

Embodiment 86. A bispecific agent comprising (a) a first antigen-binding site that binds human MET with a $K_D$ between about 0.1 nM and about 5.0 nM and (b) a second binding site that specifically binds one or more components of the WNT pathway with a $K_D$ between about 0.1 nM and about 20 nM.

Embodiment 87. A pharmaceutical composition comprising the bispecific agent of embodiment 86 and a pharmaceutically acceptable carrier.

Embodiment 88. A method of treating cancer in a subject, comprising administering to the subject a therapeutically effective amount of the bispecific agent of embodiment 86.

Embodiment 89. A method of identifying a human subject for treatment with a bispecific agent that specifically binds MET and specifically binds one or more components of the WNT pathway, comprising: determining if the subject has a tumor that has an elevated expression level of MET as compared to a reference sample or a pre-determined level of MET.

Embodiment 90. A method of identifying a human subject for treatment with a bispecific agent that specifically binds MET and specifically binds one or more components of the WNT pathway, comprising: (a) obtaining a tumor sample from the subject, and (b) determining if the tumor has an elevated expression level of MET as compared to a reference sample or a pre-determined level of MET.

Embodiment 91. A method of identifying a human subject for treatment with a bispecific agent that specifically binds MET and specifically binds one or more components of the WNT pathway, comprising: determining if the subject has a tumor that has an elevated expression level of MET as compared to a reference sample or a pre-determined level of MET, wherein if the tumor has an elevated expression level of MET the subject is selected for treatment with the bispecific agent.

Embodiment 92. A method of identifying a human subject for treatment with a bispecific agent that specifically binds MET and specifically binds one or more components of the WNT pathway, comprising: (a) obtaining a tumor sample from the subject, and (b) determining if the tumor has an elevated expression level of MET as compared to a reference sample or a pre-determined level of MET, wherein if the tumor has an elevated expression level of MET the subject is selected for treatment with the bispecific agent.

Embodiment 93. A method of selecting a human subject for treatment with a bispecific agent that specifically binds MET and specifically binds one or more components of the WNT pathway, comprising: determining if the subject has a tumor that has an elevated expression level of MET as compared to a reference sample or a pre-determined level of MET.

Embodiment 94. A method of selecting a human subject for treatment with a bispecific agent that specifically binds MET and specifically binds one or more components of the WNT pathway, comprising: (a) obtaining a tumor sample from the subject, and (b) determining if the tumor has an elevated expression level of MET as compared to a reference sample or a pre-determined level of MET.

Embodiment 95. A method of selecting a human subject for treatment with a bispecific agent that specifically binds MET and specifically binds one or more components of the WNT pathway, comprising: determining if the subject has a tumor that has an elevated expression level of MET as compared to a reference sample or a pre-determined level of MET, wherein if the tumor has an elevated expression level of MET the subject is selected for treatment with the bispecific agent.

Embodiment 96. A method of selecting a human subject for treatment with a bispecific agent that specifically binds MET and specifically binds one or more components of the WNT pathway, comprising: (a) obtaining a tumor sample from the subject, and (b) determining if the tumor has an elevated expression level of MET as compared to a reference sample or a pre-determined level of MET, wherein if the tumor has an elevated expression level of MET the subject is selected for treatment with the bispecific agent.

Embodiment 97. The method of any one of embodiments 89-96, wherein the bispecific agent is a bispecific agent of any one of embodiments 1-52.

Embodiment 98. The method of any one of embodiments 89-97, wherein the tumor is selected from the group consisting of colorectal tumor, colon tumor, ovarian tumor, pancreatic tumor, lung tumor, liver tumor, breast tumor, kidney tumor, prostate tumor, gastrointestinal tumor, melanoma, cervical tumor, bladder tumor, glioblastoma, and head and neck tumor.

Embodiment 99. The method of embodiment 98, wherein the tumor is a lung tumor.

Embodiment 100. The method of embodiment 98, wherein the tumor is a pancreatic tumor.

Embodiment 101. The method any one of embodiments 89-100, wherein the expression level of MET is determined in a sample by a PCR-based assay, microarray analysis, or immunohistochemistry.

Embodiment 102. The method of embodiment 101, wherein the sample is a fresh tumor sample, a frozen tumor sample, or a formalin-fixed paraffin-embedded sample.

Embodiment 103. Use of the bispecific agent of any one of embodiments 1-52 or an antibody of any one of embodiments 53-61 for the manufacture of a medicament for the treatment of cancer.

Embodiment 104. A bispecific agent or an antibody for use in a method of treating cancer, wherein the bispecific agent is a bispecific agent of any one of embodiments 1-52 or the antibody is an antibody of any one of embodiments 53-61.

EXAMPLES

Example 1

Binding Affinities of MET-Binding Agents

The $K_D$ of monovalent version of 73R009, monovalent anti-MET antibody 5D5, and anti-MET/FZD8-Fc bispecific agent 315B6 were determined using a Biacore 2000 system from Biacore LifeSciences (GE Healthcare). A goat anti-human antibody (Invitrogen H10500) was coupled to a carboxymethyl-dextran (CM5) SPR chip using standard amine-based chemistry (NHS/EDC) and blocked with ethanolamine. Antibodies were diluted to a concentration of 10 μg/ml in HBS-P-BSA (0.01M HEPES pH7.4, 0.15M NaCl, 0.005% v/v Polysorbate 20, 100 ug/ml BSA) and captured onto the chip via the anti-human antibody. Human MET was serially diluted 2-fold from 300 nM to 37.5 nM in HBS-P-BSA and injected sequentially over the captured anti-MET antibodies. MET association and dissociation was measured at each concentration. After each antigen injection 5 μl of 100 mM $H_3PO_4$ was injected to remove the antigen-antibody complex and a subsequent injection performed. Kinetic data were collected over time and were fit using the simultaneous global fit equation to yield affinity constants ($K_D$ values) for each agent.

Bivalent "parental" antibody 73R009 had an affinity constant ($K_D$) for human MET of 1.1 nM, monovalent version of 73R009 had a $K_D$ for human MET of 1.4 nM, monovalent antibody 5D5 had a $K_D$ for human MET of 7.2 nM, and bispecific agent 315B6 had a $K_D$ for human MET of 1.8 nM. Thus, the monovalent anti-MET antibody 73R009 and the bispecific agent 315B6 both demonstrated binding affinity very similar to the parental antibody despite the fact the parental antibody is bivalent. In addition, the bispecific agent 315B6 appeared to have stronger affinity for human MET than anti-MET antibody 5D5.

The anti-MET/FZD8-Fc bispecific agent 315B6 has been shown to not bind mouse MET.

Anti-MET/FZD8-Fc bispecific agent 315B6 comprises (a) a heavy chain encoded by the plasmid deposited with ATCC, 10801 University Boulevard, Manassas, Va., USA, under the conditions of the Budapest Treaty on Mar. 12, 2013 and assigned designation number PTA-13609, (b) a light chain encoded by the plasmid deposited with ATCC under the conditions of the Budapest Treaty on Mar. 12, 2013 and assigned designation number PTA-13610, and (c) a fusion protein encoded by the plasmid deposited with ATCC under the conditions of the Budapest Treaty on Mar. 12, 2013 and assigned designation number PTA-13611.

Example 2

Inhibition of binding of hepatocyte growth factor to MET

A full-length human MET (FL-MET) construct was generated using standard recombinant DNA techniques. HEK-293T cells were transiently transfected with the MET construct and a GFP plasmid at a plasmid MET: GFP ratio of 2:1. After 24 hours, transfected cells were harvested and suspended in ice cold PBS containing 2% FBS. The transfected cells were incubated on ice in the presence of 10, 5, 2.5, 1.25, 0.625, 0.3, or 0.16 μg/ml of monovalent anti-MET antibody 5D5, monovalent version of anti-MET antibody 73R009, or anti-MET/FZD8-Fc bispecific agent 315B6 for 1 hour. 30 ng of hepatocyte growth factor (HGF) conjugated to biotin was added to each sample and incubated on ice for an additional 40 minutes. Cells were washed with PBS containing 2% FBS, PE-conjugated streptavidin was added, and the cells were incubated for 1 hour. Transfected cells were incubated with no HGF as a negative control and with HGF but no antibody or binding agent as a positive control. After final incubation, cells were stained with 5 μg/ml DAPI and analyzed on a FACSCanto II instrument (BD Biosciences, San Jose, Calif.) and the data was processed using FlowJo software.

As shown in FIG. 1, the positive controls showed that approximately 20% of the transfected cells expressed MET and were bound by human HGF (FIG. 1A). Inhibition of HGF binding to MET by the binding agents was compared to the positive control of 20% binding. The monovalent anti-MET antibody 5D5 reduced binding of HGF to MET by approximately 70% at the highest concentration of 10 μg/ml with a dose-dependent response down to a reduction of 28% at the lowest concentration of 0.16 μg/ml (FIG. 1B). In contrast, the monovalent version of anti-MET antibody 73R009 reduced binding of HGF to MET by approximately 72% at the highest concentration of 10 μg/ml with a dose-dependent response down to a reduction of approximately 56% at the lowest concentration of 0.16 μg/ml (FIG. 1C). Similarly, the bispecific anti-MET/FZD8-Fc agent reduced binding of HGF to MET by approximately 80% at the highest concentration of 10 μg/ml with a dose-dependent response down to a reduction of approximately 56% at the lowest concentration of 0.16 μg/ml (FIG. 1D).

These results showed that both the monovalent version of anti-MET antibody 73R009 and the bispecific anti-MET/FZD8-Fc agent 351B6 were strong blockers of HGF binding to MET. In addition, both appeared to have a greater ability to block binding of HGF to MET than anti-MET antibody 5D5 and were able to block binding at lower concentrations.

Example 3

Inhibition of HGF-induced MET activity

MET activation in human cells can be characterized by analyzing MET phosphorylation and downstream activation of mitogen-activated protein kinase (MAPK) and AKT after HGF stimulation.

A549 cells were seeded into 12-well plates at $1.5 \times 10^5$ cells/well in DMEM medium containing 10% FBS and grown overnight. Cells were transferred to serum-free medium and after approximately 18 hours the cells were pre-treated for one hour with monovalent version of anti-MET antibody 73R009, bispecific anti-MET/FZD8-Fc agent 5D5/FZD, and bispecific anti-MET/FZD8-Fc agent 315B6 at concentrations of 50, 10, 2, and 0.4 μg/ml. Subsequently the cells were stimulated with 50 ng/ml human HGF (EMD Millipore, Billerica Mass.) for 15 minutes. Cells were lysed and cell lysate supernatants were collected. Cell lysates were resolved by SDS-PAGE using 4-12% NuPAGE Novex gels (Invitrogen/Life Technologies, Grand Island, N.Y.), transferred to nitrocellulose membranes, and analyzed by Western blot techniques. Antibodies used were anti-human MET (anti-Met (L41G3) mAb, Cell Signaling Technology, Danvers, Mass.); anti-phospho-MET (anti-phospho-MET (Tyr1234/1235) mAb, Cell Signaling Technology, Danvers, Mass.); anti-phospho-AKT (anti-phospho-AKT (Ser473) mAb, Cell Signaling Technology, Danvers, Mass.); anti-phospho-MAPK (anti-phospho-p44/42 MAPK (Erk1/2) (Thr202/Tyr204), Cell Signaling Technology, Danvers, Mass.); and anti-actin (anti-beta actin antibody, Abcam, Cambridge, Mass.).

As shown in FIG. 2, bispecific anti-MET/FZD8-Fc agent 315B6 reduced the amount of phosphorylated MET to a greater extent than the bispecific anti-MET/FZD agent 5D5/FZD or the monovalent version of anti-MET antibody 73R009. At the highest concentration, it appeared that 315B6 reduced the amount of phosphorylated AKT to a greater extent than the other agents also. These studies demonstrated that the bispecific anti-MET/FZD8-Fc agent 315B6 was able to inhibit and/or block HGF-induced MET activation and was able to inhibit and/or block MET activation to a greater extent than the bispecific anti-MET/FZD agent 5D5/FZD or the monovalent version of anti-MET antibody 73R009.

Example 4

Inhibition of WNT Signaling

STF-293 cells were cultured in DMEM supplemented with antibiotics and 10% FCS. The STF-293 cells are HEK-293 cells stably integrated with an 8×TCF Luc reporter vector and a *Renilla* luciferase reporter. The 8×TCF Luc reporter contains seven copies of the TCF binding site linked to a promoter upstream of a firefly luciferase reporter gene to measure canonical WNT signaling levels (Gazit et al., 1999, Oncogene 18:5959-66). The *Renilla* luciferase reporter (Promega; Madison, Wis.) is used as an internal control for transfection efficiency. Anti-MET/FZD bispecific agent 315B6 and control agents anti-MFT monovalent agent 5D5/FLAG and monovalent agent FZD8/FLAG were serially diluted 5-fold from 20 ug/ml to 0.0064 ug/ml, added to the appropriate wells, and incubated overnight. The cells were then incubated in the presence or absence of WNT3A-conditioned medium that had been prepared from L cells that stably express WNT3a or control conditioned media from L cells not over-expressing WNT3A. After overnight incubation, luciferase levels were measured using a dual luciferase assay kit (Promega; Madison, Wis.) with firefly luciferase activity normalized to *Renilla* luciferase activity.

As shown in FIG. 3, anti-MET/FZD8-Fc bispecific agent 315B6 inhibited WNT pathway signaling. The inhibition was similar to the monovalent FZD8/FLAG agent and as expected the anti-MET 5D5/FLAG agent had no ability to inhibit WNT pathway signaling. Thus, in combination with the results presented in Example 3, the anti-MET/FZD8-Fc bispecific agent 315B6 has demonstrated the ability to inhibit both MET-induced and WNT-induced signaling and/or activation.

Example 5

Inhibition of Lung Tumor Growth In Vivo

OMP-LU45 tumors were selected based on the high level of MET expression observed in microarray analysis. Dissociated OMP-LU45 lung tumor cells ($1 \times 10^5$ cells) were injected in to 6-8 week old NOD/SCID mice. Tumors were allowed to grow for 26 days until they reached an average volume of 90 mm$^3$. The mice were randomized (n=10 per group) and treated with a monovalent anti-MET antibody (5D5/FLAG), a control antibody, a monovalent FZD8-Fc (FZD8Fc/FLAG), a bivalent FZD8-Fc (54F28), or an anti-MET/FZD8Fc bispecific agent, either as single agents or in combination with taxol. Protein agents were dosed at 25 mg/kg once a week, and taxol was dosed at 15 mg/ml once a week. Administration of the protein agents and taxol was performed via injection into the intraperitoneal cavity. Tumor growth was monitored and tumor volumes were measured with electronic calipers at the indicated time points. Data are expressed as mean±S.E.M.

When used as a monotherapy, all of the agents had minimal or no detectable effect on LU45 tumor growth as compared to the control antibody (FIG. 4A). In contrast, the MET/FZD8-Fc bispecific agent in combination with taxol significantly inhibited OMP-LU45 tumor growth and this inhibition of tumor growth was greater than inhibition observed with any of the other agents in combination with taxol (FIG. 4B).

It is understood that the examples and embodiments described herein are for illustrative purposes only and that various modifications or changes in light thereof will be suggested to persons skilled in the art and are to be included within the spirit and purview of this application.

All publications, patents, patent applications, internet sites, and accession numbers/database sequences including both polynucleotide and polypeptide sequences cited herein are hereby incorporated by reference herein in their entirety for all purposes to the same extent as if each individual publication, patent, patent application, internet site, or accession number/database sequence was specifically and individually indicated to be so incorporated by reference.

Following are the sequences disclosed in the application:

```
73R009 Heavy chain CDR1
                                                          (SEQ ID NO: 1)
ASYAWS 73R009 Heavy chain CDR2
                                                          (SEQ ID NO: 2)
YISYSGGTDYNPSLKS 73R009 Heavy chain CDR3
                                                          (SEQ ID NO: 3)
KGAY 73R009 Light chain CDR1
                                                          (SEQ ID NO: 4)
SASSSVSSSYLY 73R009 Light chain CDR2
                                                          (SEQ ID NO: 5)
STSNLAS 73R009 Light chain CDR3
                                                          (SEQ ID NO: 6)
HQWSSYPYT 73R009 Heavy chain variable region amino acid sequence
                                                          (SEQ ID NO: 7)
QVQLQESGPGLVKPSETLSLTCTVTGTTITASYAWSWIRQPPGKGLEWMGYISYSGGTDY

NPSLKSRITISRDTFKNQFSLKLSSVTAADTATYYCARKGAYWGQGTLVTVSS

73R009 Light chain variable region amino acid sequence
                                                          (SEQ ID NO: 8)
DIVLTQSPATLSASPGEKVTLTCSASSSVSSSYLYWYQQKPGQAPKLLIYSTSNLASGVP

ARFSGSGSGTSYSLTISSLEPEDFATYYCHQWSSYPYTEGGGTKLEIK
```

73R009 Heavy chain amino acid sequence with predicted signal sequence
underlined
(SEQ ID NO: 9)
MKHLWFFLLLVAAPRWVLSQVQLQESGPGLVKPSETLSLTCTVTGTTITASYAWSWIRQP

PGKGLEWMGYISYSGGTDYNPSLKSRITISRDTFKNQFSLKLSSVTAADTATYYCARKGA

YWGQGTLVTVSSASTKGPSVFPLAPCSRSTSESTAALGCLVKDYFPEPVTVSWNSGALTS

GVHTFPAVLQSSGLYSLSSVVTVPSSNFGTQTYTCNVDHKPSNTKVDKTVERKCCVECPP

CPAPPVAGPSVFLEPPKPKDTLMISRTPEVTCVVVDVSHEDPEVQFNWYVDGVEVHNAKT

KPREEQFNSTFRVVSVLTVVHQDWLNGKEYKCKVSNKGLPAPIEKTISKTKGQPREPQVY

TLPPSREEMTKNQVSLTCLVKGFYPSDIAVEWESNGQPENNYKTTPPMLDSDGSFFLYSK

LTVDKSRWQQGNVFSCSVMHEALHNHYTQKSLSLSPGK

73R009 (13A variant) Heavy chain amino acid sequence with predicted
signal sequence underlined
(SEQ ID NO: 10)
MKHLWEELLLVAAPRWVLSQVQLQESGPGLVKPSETLSLTCTVTGTTITASYAWSWIRQP

PGKGLEWMGYISYSGGTDYNPSLKSRITISRDTFKNQFSLKLSSVTAADTATYYCARKGA

YWGQGTLVTVSSASTKGPSVFPLAPCSRSTSESTAALGCLVKDYFPEPVTVSWNSGALTS

GVHTFPAVLQSSGLYSLSSVVTVPSSNFGTQTYTCNVDHKPSNTKVDKTVERKCCVECPP

CPAPPVAGPSVFLFPPKPKDTLMISRTPEVTCVVVDVSHEDPEVQFNWYVDGVEVHNAKT

KPREEQFNSTERVVSVLTVVHQDWLNGKEYKCKVSNKGLPAPIEKTISKTKGQPREPQVY

TLPPSREKMTKNQVSLTCLVKGFYPSDIAVEWESNGQPENNYKTTPPMLKSDGSFFLYSK

LTVDKSRWQQGNVFSCSVMHEALHNHYTQKSLSLSPGK

738009 Light chain amino acid sequence with predicted signal sequence
underlined
(SEQ ID NO: 11)
MKHLWFFLLLVAAPRWVLSDIVLTQSPATLSASPGEKVTLTCSASSSVSSSYLYWYQQKP

GQAPKLLIYSTSNLASGVPARFSGSGSGTSYSLTISSLEPEDFATYYCHQWSSYPYTFGG

GTKLEIKRTVAAPSVFIFPPSDEQLKSGTASVVCLLMIFYPREAKVQWKVDNALQSGNSQ

ESVTEQDSKDSTYSLSSTLTLSKADYEKHKVYACEVTHQGLSSPVTKSFNRGEC

73R009 Heavy chain amino acid sequence without predicted signal
sequence
(SEQ ID NO: 12)
QVQLQESGPGLVKPSETLSLTCTVTGTTITASYAWSWIRQPPGKGLEWMGYISYSGGTDY

NPSLKSRITISRDTEKNQFSLKLSSVTAADTATYYCARKGAYWGQGTLVTVSSASTKGPS

VFPLAPCSRSTSESTAALGCLVKDYFPEPVTVSWNSGALTSGVHTFPAVLQSSGLYSLSS

VVTVPSSNEGTQTYTCNVDHKPSNTKVDKTVERKCCVECPPCPAPPVAGPSVFLEPPKPK

DTLMISRTPEVTCVVVDVSHEDPEVQFNWYVDGVEVHNAKTKPREEQFNSTERVVSVLTV

VHQDWLNGKEYKCKVSNKGLPAPIEKTISKTKGQPREPQVYTLPPSREEMTKNQVSLTCL

VKGFYPSDIAVEWESNGQPENNYKTTPPMLDSDGSFELYSKLTVDKSRWQQGNVFSCSVM

HEALHNHYTQKSLSLSPGK

73R009 (13A variant) Heavy chain amino acid sequence without
predicted signal sequence
(SEQ ID NO: 13)
QVQLQESGPGLVKPSETLSLTCTVTGTTITASYAWSWIRQPPGKGLEWMGYISYSGGTDY

NPSLKSRITISRDTEKNQFSLKLSSVTAADTATYYCARKGAYWGQGTLVTVSSASTKGPS

VFPLAPCSRSTSESTAALGCLVKDYFPEPVTVSWNSGALTSGVHTFPAVLQSSGLYSLSS

VVTVPSSNEGTQTYTCNVDHKPSNTKVDKTVERKCCVECPPCPAPPVAGPSVELFPPKPK

DTLMISRTPEVTCVVVDVSHEDPEVQFNWYVDGVEVHNAKTKPREEQFNSTFRVVSVLTV

-continued

VHQDWLNGKEYKCKVSNKGLPAPIEKTISKTKGQPREPQVYTLPPSREKMTKNQVSLTCL

VKGFYPSDIAVEWESNGQPENNYKTTPPMLKSDGSFELYSKLTVDKSRWQQGNVFSCSVM

HEALHNHYTQKSLSLSPGK

73R009 Light chain amino acid sequence without predicted signal
sequence
(SEQ ID NO: 14)
DIVLTQSPATLSASPGEKVTLTCSASSSVSSSYLYWYQQKPGQAPKLLIYSTSNLASGVP

ARFSGSGSGTSYSLTISSLEPEDFATYYCHQWSSYPYTFGGGTKLEIKRTVAAPSVFIFP

PSDEQLKSGTASVVCLLNNEYPREAKVQWKVDNALQSGNSQESVTEQDSKDSTYSLSSTL

TLSKADYEKHKVYACEVTHQGLSSPVTKSFNRGEC

73R009 Heavy chain nucleotide sequence
(SEQ ID NO: 15)
ATGAAGCATCTGTGGTTTTTCCTGCTGCTCGTGGCTGCTCCCCGGTGGGTCCTGTCTCAG

GTCCAATTGCAAGAGTCAGGACCAGGGCTTGTGAAGCCCTCAGAGACTCTGTCACTCACT

TGTACCGTGACCGGAACTACCATCACTGCCTCCTACGCCTGGAGCTGGATCAGGCAGCCT

CCGGGAAAAGGCCTGGAATGGATGGGTTACATCTCCTATTCAGGCGGAACCGACTACAAT

CCTAGCCTGAAGTCTCGCATCACCATTTCACGCGATACCTTCAAGAACCAATTCAGCCTT

AAACTCTCCAGCGTGACCGCTGCAGACACTGCCACCTACTACTGCGCAAGAAAGGGAGCC

TATTGGGGTCAGGGGACCCTTGTGACCGTGAGCTCAGCCTCTACCAAGGGCCCTAGCGTC

TTCCCTCTGGCCCCCTGCTCCCGGTCCACCAGCGAGAGCACAGCCGCCCTGGGCTGCCTG

GTCAAGGACTACTTCCCCGAACCTGTGACAGTGTCCTGGAACTCCGGCGCTCTGACCAGC

GGCGTGCACACCTTCCCAGCTGTCCTCCAGTCCTCCGGACTCTACTCCCTCCTCCGTG

GTGACAGTGCCCTCCTCCAACTTCGGCACCCAGACCTACACCTGCAACGTCGATCACAAG

CCCAGCAACACCAAGGTTGATAAGACAGTTGAGCGCAAATGTTGTGTCGAGTGCCCTCCT

TGCCCAGCCCCTCCTGTGGCTGGACCTTCCGTCTTCCTCTTCCCCCCTAAACCCAAAGAC

ACCCTCATGATCTCCCGGACCCCTGAGGTCACATGCGTGGTGGTGGACGTGAGCCACGAA

GACCCCGAGGTCCAGTTCAACTGGTATGTGGACGGCGTGGAGGTGCATAATGCCAAGACA

AAGCCACGGGAGGAGCAGTTCAACAGCACATTCCGGGTGGTCAGCGTCCTCACCGTTGTG

CACCAGGACTGGCTGAACGGCAAGGAGTACAAGTGCAAAGTCTCCAACAAAGGCCTCCCT

GCCCCCATCGAGAAAACCATCTCCAAAACCAAAGGGCAGCCCAGGGAACCACAGGTGTAC

ACCCTGCCCCCITCCCGGGAGGARATGACCAAGAACCAAGTCAGCCTGACCTGCCTGGTC

AAAGGCTTCTACCCCTCCGACATCGCCGTGGAGTGGGAGAGCAATGCGCAGCCTGAGAAC

AACTACAAGACCACACCTCCCATGCTGGAYTCCGACGGCTCCTTCTTCCTCTACTCCAAA

CTCACCGTGGACAAGAGCAGGTGGCAGCAGGGGAACGTCTTCTCCTGCTCCGTGATGCAT

GAGGCTCTGCACAACCACTACACACAGAAGTCCCTCTCCCTGTCTCCTGGAAAA

Wherein R = A or G
Wherein Y = C or T

73R009 (13A variant) Heavy chain nucleotide sequence
(SEQ ID NO: 16)
ATGAAGCATCTGTGGTTTTTCCTGCTGCTCGTGGCTGCTCCCCGGTGGGTCCTGTCTCAG

GTCCAATTGCAAGAGTCAGGACCAGGGCTTGTGAAGCCCTCAGAGACTCTGTCACTCACT

TGTACCGTGACCGGAACTACCATCACTGCCTCCTACGCCTGGAGCTGGATCAGGCAGCCT

CCGGGAAAAGGCCTGGAATGGATGGGTTACATCTCCTATTCAGGCGGAACCGACTACAAT

CCTAGCCTGAAGTCTCGCATCACCATTTCACGCGATACCTTCAAGAACCAATTCAGCCTT

```
AAACTCTCCAGCGTGACCGCTGCAGACACTGCCACCTACTACTGCGCAAGAAAGGGAGCC

TATTGGGGTCAGGGGACCCTTGTGACCGTGAGCTCAGCCTCTACCAAGGGCCCTAGCGTC

TTCCCTCTGGCCCCCTGCTCCCGGTCCACCAGCGAGAGCACAGCCGCCCTGGGCTGCCTG

GTCAAGGACTACTTCCCCGAACCTGTGACAGTGTCCTGGAACTCCGGCGCTCTGACCAGC

GGCGTGCACACCTTCCCAGCTGTCCTCCAGTCCTCCGGACTCTACTCCCTCTCCTCCGTG

GTGACAGTGCCCTCCTCCAACTTCGGCACCCAGACCTACACCTGCAACGTCGATCACAAG

CCCAGCAACACCAAGGTTGATAAGACAGTTGAGCGCAAATGTTGTGTCGAGTGCCCTCCT

TGCCCAGCCCCTCCTGTGGCTGGACCTTCCGTCTTCCTCTTCCCCCCTAAACCCAAAGAC

ACCCTCATGATCTCCCGGACCCCTGAGGTCACATGCGTGGTGGTGGACGTGAGCCACGAA

GACCCCGAGGTCCAGTTCAACTGGTATGTGGACGGCGTGGAGGTGCATAATGCCAAGACA

AAGCCACGGGAGGAGCAGTTCAACAGCACATTCCGGGTGGTCAGCGTCCTCACCGTTGTG

CACCAGGACTGGCTGAACGGCAAGGAGTACAAGTGCAAAGTCTCCAACAAAGGCCTCCCT

GCCCCCATCGAGAAACCATCTCCAAAACCAAAGGGCAGCCCAGGGAACCACAGGTGTAC

ACCCTGCCCCCTTCCCGGGAGAAGATGACCAAGAACCAAGTCAGCCTGACCTGCCTGGTC

AAAGGCTTCTACCCCTCCGACATCGCCGTGGAGTGGGAGAGCAATGGGCAGCCTGAGAAC

AACTACAAGACCACACCTCCCATGCTGAAGTCCGACGGCTCCTTCTTCCTCTACTCCAAA

CTCACCGTGGACAAGAGCAGGTGGCAGCAGGGGAACGTCTTCTCCTGCTCCGTGATGCAT

GAGGCTCTGCACAACCACTACACACAGAAGTCCCTCTCCCTGTCTCCTGGAAAA

73R009 Heavy chain nucleotide sequence without predicted signal
sequence
                                                        (SEQ ID NO: 17)
CAGGTCCAATTGCAAGAGTCAGGACCAGGGCTTGTGAAGCCCTCAGAGACTCTGTCACTC

ACTTGTACCGTGACCGGAACTACCATCACTGCCTCCTACGCCTGGAGCTGGATCAGGCAG

CCTCCGGGAAAAGGCCTGGAATGGATGGGTTACATCTCCTATTCAGGCGGAACCGACTAC

AATCCTAGCCTGAAGTCTCGCATCACCATTTCACGCGATACCTTCAAGAACCAATTCAGC

CTTAAACTCTCCAGCGTGACCGCTGCAGACACTGCCACCTACTACTGCGCAAGAAAGGGA

GCCTATTGGGGTCAGGGGACCCTTGTGACCGTGAGCTCAGCCTCTACCAAGGGCCCTAGC

GTCTTCCCTCTGGCCCCCTGCTCCCGGTCCACCAGCGAGAGCACAGCCGCCCTGGGCTGC

CTGGTCAAGGACTACTTCCCCGAACCTGTGACAGTGTCCTGGAACTCCGGCGCTCTGACC

AGCGGCGTGCACACCTTCCCAGCTGTCCTCCAGTCCTCCGGACTCTACTCCCTCTCCTCC

GTGGTGACAGTGCCCTCCTCCAACTTCGGCACCCAGACCTACACCTGCAACGTCGATCAC

AAGCCCAGCAACACCAAGGTTGATAAGACAGTTGAGCGCAAATGTTGTGTCGAGTGCCCT

CCTTGCCCAGCCCCTCCTGTGGCTGGACCTTCCGTCTTCCTCTTCCCCCCTAAACCCAAA

GACACCCTCATGATCTCCCGGACCCCTGAGGTCACATGCGTGGTGGTGGACGTGAGCCAC

GAAGACCCCGAGGTCCAGTTCAACTGGTATGTGGACGGCGTGGAGGTGCATAATGCCAAG

ACAAAGCCACGGGAGGAGCAGTTCAACAGCACATTCCGGGTGGTCAGCGTCCTCACCGTT

GTGCACCAGGACTGGCTGAACGGCAAGGAGTACAAGTGCAAAGTCTCCAACAAAGGCCTC

CCTGCCCCCATCGAGAAACCATCTCCAAAACCAAAGGGCAGCCCAGGGAACCACAGGTG

TACACCCTGCCCCCTTCCCGGGAGGARATGACCAAGAACCAAGTCAGCCTGACCTGCCTG

GTCAAAGGCTTCTACCCCTCCGACATCGCCGTGGAGTGGGAGAGCAATGGGCAGCCTGAG
```

-continued

AACAACTACAAGACCACACCTCCCATGCTGGAYTCCGACGGCTCCTTCTTCCTCTACTCC

AAACTCACCGTGGACAAGAGCAGGTGGCAGCAGGGGAACGTCTTCTCCTGCTCCGTGATG

CATGAGGCTCIGCACAACCACTACACACAGAAGTCCCTCTCCCTGTCTCCTGGAAAA

Wherein R = A or G
Wherein Y = C or T

73R009 (13A variant) Heavy chain nucleotide sequence without
predicted signal sequence (SEQ ID NO: 18)
CAGGTCCAATTGCAAGAGTCAGGACCAGGGCTTGTGAAGCCCTCAGAGACTCTGTCACTC

ACTTGTACCGTGACCGGAACTACCATCACTGCCTCCTACGCCTGGAGCTGGATCAGGCAG

CCTCCGGGAAAAGGCCTGGAATGGATGGGTTACATCTCCTATTCAGGCGGAACCGACTAC

AATCCTAGCCTGAAGTCTCGCATCACCATTTCACGCGATACCTTCAAGAACCAATTCAGC

CTTAAACTCTCCAGCGTGACCGCTGCAGACACTGCCACCTACTACTGCGCAAGAAAGGGA

GCCTATTGGGGTCAGGGGACCCTTGTGACCGTGAGCTCAGCCTCTACCAAGGGCCCTAGC

GTCTTCCCTCTGGCCCCCTGCTCCCGGTCCACCAGCGAGAGCACAGCCGCCCTGGGCTGC

CTGGTCAAGGACTACTTCCCCGAACCTGTGACAGTGTCCTGGAACTCCGGCGCTCTGACC

AGCGGCGTGCACACCTTCCCAGCTGTCCTCCAGTCCTCCGGACTCTACTCCCTCTCCTCC

GTGGTGACAGTGCCCTCCTCCAACTTCGGCACCCAGACCTACACCTGCAACGTCGATCAC

AAGCCCAGCAACACCAAGGTTGATAAGACAGTTGAGCGCAAATGTTGTGTCGAGTGCCCT

CCTTGCCCAGCCCCTCCTGTGGCTGGACCTTCCGTCTTCCTCTTCCCCCCTAAACCCAAA

GACACCCTCATGATCTCCCGGACCCCTGAGGTCACATGCGTGGTGGTGGACGTGAGCCAC

GAAGACCCCGAGGTCCAGTTCAACTGGTATGTGGACGGCGTGGAGGTGCATAATGCCAAG

ACAAAGCCACGGGAGGAGCAGTTCAACAGCACATTCCGGGTGGTCAGCGTCCTCACCGTT

GTGCACCAGGACTGGCTGAACGGCAAGGAGTACAAGTGCAAAGTCTCCAACAAAGGCCTC

CCTGCCCCCATCGAGAAAACCATCTCCAAAACCAAAGGGCAGCCCAGGGAACCACAGGTG

TACACCCTGCCCCCTTCCCGGGAGAAGATGACCAAGAACCAAGTCAGCCTGACCTGCCTG

GTCAAAGGCTTCTACCCCTCCGACATCGCCGTGGAGTGGGAGAGCAATGGGCAGCCTGAG

AACAACTACAAGACCACACCTCCCATGCTGAAGTCCGACGGCTCCTTCTTCCTCTACTCC

AAACTCACCGTGGACAAGAGCAGGTGGCAGCAGGGGAACGTCTTCTCCTGCTCCGTGATG

CATGAGGCTCTGCACAACCACTACACACAGAAGTCCCTCTCCCTGTCTCCTGGAAAA

73R009 Light chain nucleotide sequence (SEQ ID NO: 19)
ATGAAGCACCTCTGGTTCTTCCTTCTTCTTGTGGCCGCTCCCCGCTGGGTCCTCAGCGAT

ATCGTGCTGACCCAGTCACCCGCCACCCTCTCAGCTTCACCTGGCGAGAAGGTCACTCTG

ACTTGCTCTGCCTCATCTAGCGTGTCATCTTCATATCTGTACTGGTATCAGCAAAAACCG

GGACAAGCCCCGAAGCTCCTGATCTACAGCACCAGCAACCTTGCATCCGGAGTGCCTGCC

AGGTTTAGCGGGTCCGGGTCCGGTACCTCATATTCACTGACCATTTCTTCTCTTGAACCC

GAAGATTTCGCTACCTACTACTGTCATCAGTGGTCTAGCTACCCATACACTTTCGGCGGA

GGAACCAAACTGGAGATTAAGCGTACGGTGGCAGCCCCTTCTGTCTTTATCTTCCCTCCA

TCCGACGAGCAGCTCAAATCAGGAACCGCTTCTGTCGTGTGCCTGCTTAACAATTTCTAC

CCACGGGAAGCCAAGGTGCAGTGGAAGGTGGACAATGCCCTGCAATCAGGTAATTCCCAA

GAGTCAGTGACTGAACAGGATAGCAAGGACAGCACCTATTCACTCTCCAGCACTCTGACC

CTGTCCAAGGCTGACTACGAAAAGCATAAGGTGTACGCATGCGAGGTGACCCACCAGGGT

CTGAGCAGCCCCGTCACCAAGTCTTTCAACAGAGGGGAGTGT

73R009 Light chain nucleotide sequence without predicted signal
sequence
(SEQ ID NO: 20)
GATATCGTGCTGACCCAGTCACCCGCCACCCTCTCAGCTTCACCTGGCGAGAAGGTCACT

CTGACTTGCTCTGCCTCATCTAGCGTGTCATCTTCATATCTGTACTGGTATCAGCAAAAA

CCCGGACAAGCCCCGAAGCTCCTGATCTACAGCACCAGCAACCTTGCATCCGGAGTGCCT

GCCAGGTTTAGCGGGTCCGGGTCCGGTACCTCATATTCACTGACCATTTCTTCTCTTGAA

CCCGAAGATTTCGCTACCTACTACTGTCATCAGTGGTCTAGCTACCCATACACTTTCGGC

GGAGGAACCAAACTGGAGATTAAGCGTACGGTGGCAGCCCCTTCTGTCTTTATCTTCCCT

CCATCCGACGAGCAGCTCAAATCAGGAACCGCTTCTGTCGTGTGCCTGCTTAACAATTTC

TACCCACGGGAAGCCAAGGTGCAGTGGAAGGTGGACAATGCCCTGCAATCAGGTAATTCC

CAAGAGTCAGTGACTGAACAGGATAGCAAGGACAGCACCTATTCACTCTCCAGCACTCTG

ACCCTGTCCAAGGCTGACTACGAAAAGCATAAGGTGTACGCATGCGAGGTGACCCACCAG

GGTCTGAGCAGCCCCGTCACCAAGTCTTTCAACAGAGGGGAGTGT

Human FZD1 Fri domain amino acid sequence
(SEQ ID NO: 21)
QQPPPPPQQQQSGQQYNGERGISVPDHGYCQPISIPLCTDIAYNQTIMPNLLGHTNQEDA

GLEVHQFYPLVKVQCSAELKFFLCSMYAPVCTVLEQALPPCRSLCERARQGCEALMNKFG

FQWPDTLKCEKFPVHGAGELCVGQNTSDKGT

Human FZD2 Fri domain amino acid sequence
(SEQ ID NO: 22)
QFHGEKGISIPDHGFCQPISIPLCTDIAYNQTIMPNLLGHTNQEDAGLEVHQFYPLVKVQ

CSPELRFFLCSMYAPVCTVLEQAIPPCRSICERARQGCEALMNKFGFQWPERLRCEHFPR

HGAEQICVGQNHSEDG

Human FZD3 Fri domain amino acid sequence
(SEQ ID NO: 23)
HSLFSCEPITLRMCQDLPYNTTFMPNLLNHYDQQTAALAMEPFHPMVNLDCSRDF

RPFLCALYAPICMEYGRVTLPCRRLCQRAYSECSKLMEMFGVPWPEDMECSRFPDCDEPY

PRLVDL

Human FZD4 Fri domain amino acid sequence
(SEQ ID NO: 24)
FGDEEERRCDPIRISMCQNLGYNVTKMPNLVGHELQTDAELQLTTFTPLIQYGCSSQLQF

FLCSVYVPMCTEKINIPIGPCGGMCLSVKRRCEPVLKEFGFAWPESLNCSKFPPQNDHNH

MCMEGPGDEEV

Human FZD5 Fri domain amino acid sequence
(SEQ ID NO: 25)
ASKAPVCQEITVPMCRGIGYNLTHMPNQFNHDTQDEAGLEVHQFWPLVEIQCSPDLRFFL

CSMYTPICLPDYHKPLPPCRSVCERAKAGCSPLMRQYGFAWPERMSCDRLPVLGRDAEVL

CMDYNRSEATT

Human FZD6 Fri domain amino acid sequence
(SEQ ID NO: 26)
HSLFTCEPITVPRCMKMAYNMTFFPNLMGHYDQSIAAVEMEHFLPLANLECSPNIETFLC

KAFVPTCIEQIHVVPPCRKLCEKVYSDCKKLIDTFGIRWPEELECDRLQYCDETVPVTFD

PHTEFLG

```
Human FZD7 Fri domain amino acid sequence
                                                           (SEQ ID NO: 27)
QPYHGEKGISVPDHGFCQPISIPLCTDIAYNQTILPNLLGHTNQEDAGLEVHQFYPLVKV

QCSPELRFFLCSMYAPVCTVLDQAIPPCRSLCERARQGCEALMNKFGFQWPERLRCENFP

VHGAGEICVGQNTSDGSG

Human FZD8 Fri domain amino acid sequence
                                                           (SEQ ID NO: 28)
ASAKELACQEITVPLCKGIGYNYTYMPNQFNHDTQDEAGLEVHQFWPLVEIQCSPDLKFF

LCSMYTPICLEDYKKPLPPCRSVCERAKAGCAPLMRQYGFAWPDRMRCDRLPEQGNPDTL

CMDYNRTDLTT

Human FZD8 Fri domain amino acid sequence (variant)
                                                           (SEQ ID NO: 29)
ASAKELACQEITVPLCKGIGYNYTYMPNQFNHDTQDEAGLEVHQFWPLVEIQCSPDLKFF

LCSMYTPICLEDYKKPLPPCRSVCERAKAGCAPLMRQYGFAWPDRMRCDRLPEQGNPDTL

CMDYNRTDL

Human FZD9 Fri domain amino acid sequence
                                                           (SEQ ID NO: 30)
LEIGRFDPERGRGAAPCQAVEIPMCRGIGYNLTRMPNLLGHTSQGEAAAELAEFAPLVQY

GCHSHLRFFLCSLYAPMCTDQVSTPIPACRPMCEQARLRCAPIMEQFNEGWPDSLDCARL

PTRNDPHALCMEAPENA

Human FZD10 Fri domain amino acid sequence
                                                           (SEQ ID NO: 31)
ISSMDMERPGDGKCQPIEIPMCKDIGYNMTRMPNLMGHENQREAAIQLHEFAPLVEYGCH

GHLRFFLCSLYAPMCTEQVSTPIPACRVMCEQARLKCSPIMEQFNFKWPDSLDCRKLPNK

NDPNYLCMEAPNNG

Human FZD1 amino acids 116-227
                                                           (SEQ ID NO: 32)
CQPISIPLCTDIAYNQTIMPNLLGHTNQEDAGLEVHQFYPLVKVQCSAELKFFLCSMYAP

VCTVLEQALPPCRSLCERARQGCEALMNKFGFQWPDTLKCEKFPVHGAGELC

Human FZD2 amino acids 39-150
                                                           (SEQ ID NO: 33)
CQPISIPLCTDIAYNQTIMPNLLGHTNQEDAGLEVHQFYPLVKVQCSPELRFFLCSMYAP

VCTVLEQAIPPCRSICERARQGCEALMNKFGFQWPERLRCEHFPRHGAEQIC

Human FZD3 amino acids 28-133
                                                           (SEQ ID NO: 34)
CEPITLRMCQDLPYNTTFMPNLLNHYDQQTAALAMEPFHPMVNLDCSRDFRPFLCALYAP

ICMEYGRVTLPCRRLCQRAYSECSKLMEMFGVPWPEDMECSRFPDC

Human FZD4 amino acids 48-161
                                                           (SEQ ID NO: 35)
CDPIRISMCQNLGYNVTKMPNLVGHELQTDAELQLTTFTPLIQYGCSSQLQFFLCSVYVP

MCTEKINIPIGPCGGMCLSVKRRCEPVLKEFGFAWPESLNCSKEPPQNDHNHMC

Human FZD5 amino acids 33-147
                                                           (SEQ ID NO: 36)
CQEITVPMCRGIGYNLTHMPNQFNHDTQDEAGLEVHQFWPLVEIQCSPDLRFFLCSMYTP

ICLPDYHKPLPPCRSVCERAKAGCSPLMRQYGFAWPERMSCDRLPVLGRDAEVLC

Human FZD6 amino acids 24-129
                                                           (SEQ ID NO: 37)
CEPITVPRCMKMAYNMTFFPNLMGHYDQSIAAVEMEHFLPLANLECSPNIETFLCKAFVP

TCIEQIHVVPPCRKLCEKVYSDCKKLIDTFGIRWPEELECDRLQYC
```

Human FZD7 amino acids 49-160
(SEQ ID NO: 38)
CQPISIPLCTDIAYNQTILPNLLGHTNQEDAGLEVHQFYPLVKVQCSPELRFFLCSMYAP

VCTVLDQAIPPCRSLCERARQGCEALMNKFGFQWPERLRCENFPVHGAGEIC

Human FZD8 amino acids 35-148
(SEQ ID NO: 39)
CQEITVPLCKGIGYNYTYMPNQFNHDTQDEAGLEVHQFWPLVEIQCSPDLKFFLCSMYTP

ICLEDYKKPLPPCRSVCERAKAGCAPLMRQYGFAWPDRMRCDRLPEQGNPDTLC

Human FZD9 amino acids 39-152
(SEQ ID NO: 40)
CQAVEIPMCRGIGYNLTRMPNLLGHTSQGEAAAELAEFAPLVQYGCHSHLRFFLCSLYAP

MCTDQVSTPIPACRPMCEQARLRCAPIMEQFNFGWPDSLDCARLPTRNDPHALC

Human FZD10 amino acids 34-147
(SEQ ID NO: 41)
CQPIEIPMCKDIGYNMTRMPNLMGHENQREAAIQLHEFAPLVEYGCHGHLRFFLCSLYAP

MCTEQVSTPIPACRVMCEQARLKCSPIMEQFNFKWPDSLDCRKLPNKNDPNYLC

Human IgG$_1$ Fc region
(SEQ ID NO: 42)
DKTHTCPPCPAPELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPAPIEKTISKAK

GQPREPQVYTLPPSRDELTIMQVSLTCLVKGFYPSDIAVEWESNGQPENNYKTTPPVLDS

DGSFFLYSKLTVDKSRWQQGNVFSCSVMHEALHNHYTQKSLSLSPGK

Human IgG$_1$ Fc region (variant)
(SEQ ID NO: 43)
DKTHTCPPCPAPELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPAPIEKTISKAK

GQPREPQVYTLPPSREEMTKNQVSLTCLVKGFYPSDIAVEWESNGQPENNYKTTPPVLDS

DGSFFLYSKLTVDKSRWQQGNVFSCSVMHEALHNHYTQKSLSLSPGK

Human IgG$_2$ Fc region
(SEQ ID NO: 44)
CVECPPCPAPPVAGPSVFLFPPKPKDTLMISRTPEVTCVVVDVSHEDPEVQFNWYVDGVE

VHNAKTKPREEQFNSTFRVVSVLTVVHQDWLNGKEYKCKVSNKGLPAPIEKTISKTKGQP

REPQVYTLPPSREEMTKNQVSLTCLVKGFYPSDIAVEWESNGQPENNYKTTPPMLDSDGS

FFLYSKLTVDKSRWQQGNVFSCSVMHEALHNHYTQKSLSLSPCK

Human IgG$_2$ Fc region
(SEQ ID NO: 45)
TKVDKTVERKCCVECPPCPAPPVAGPSVFLFPPKPKDTLMISRTPEVTCVVVDVSHEDPE

VQFNWYVDGVEVHNAKTKPREEQENSTFRVVSVLTVVHQDWLNGKEYKCKVSNKGLPAPI

EKTISKTKGQPREPQVYTLPPSREEMTKNQVSLTCLVKGFYPSDIAVEWESNGQPENNYK

TTPPMLDSDGSFFLYSKLTVDKSRWQQGNVFSCSVMHEALHNHYTQKSLSLSPGK

Human IgG$_2$ Fc region variant
(SEQ ID NO: 46)
TKVDKTVERKSCVECPPCPAPPVAGPSVFLFPPKPKDTLMISRTPEVTCVVVDVSHEDPE

VQFNWYVDGVEVHNAKTKPREEQENSTFRVVSVLTVVHQDWLNGKEYKCKVSNKGLPAPI

EKTISKTKGQPREPQVYTLPPSREEMTKNQVSLTCLVKGFYPSDIAVEWESNGQPENNYK

TTPPMLDSDGSFFLYSKLTVDKSRWQQGNVFSCSVMHEALHNHYTQKSLSLSPGK

Human IgG$_2$ Fc region (Variant 13A)
(SEQ ID NO: 47)
CVECPPCPAPPVAGPSVFLFPPKPKDTLMISRTPEVTCVVVDVSHEDPEVQFNWYVDGVE

VHNAKTKPREEQENSTFRVVSVLTVVHQDWLNGKEYKCKVSNKGLPAPIEKTISKTKGQP

REPQVYTLPPSREKMTKNQVSLTCLVKGFYPSDIAVEWESNGQPENNYKTTPPMLKSDGS

FFLYSKLTVDKSRWQQGNVFSCSVMHEALHNHYTQKSLSLSPGK

Human IgG$_2$ Fc region (Variant 13B)
(SEQ ID NO: 48)
CVECPPCPAPPVAGPSVFLFPPKPKDTLMISRTPEVTCVVVDVSHEDPEVQFNWYVDGVE

VHNAKTKPREEQFNSTFRVVSVLTVVHQDWLNGKEYKCKVSNKGLPAPIEKTISKTKGQP

REPQVYTLPPSREEMTKNQVSLTCLVEGFYPSDIAVEWESNGQPENNYKTTPPMLDSDGS

FFLYSELTVDKSRWQQGNVESCSVMHEALHNHYTQKSLSLSPGK

Human IgG$_2$ Fc region (Variant 13A)
(SEQ ID NO: 49)
TKVDKTVERKCCVECPPCPAPPVAGPSVFLFPPKPKDTLMISRTPEVTCVVVDVSHEDPE

VQFNWYVDGVEVHNAKTKPREEQFNSTFRVVSVLTVVHQDWLNGKEYKCKVSNKGLPAPI

EKTISKTKGQPREPQVYTLPPSREKMTKNQVSLTCLVKGFYPSDIAVEWESNGQPENNYK

TTPPMLKSDGSFFLYSKLTVDKSRWQQGNVFSCSVMHEALHNHYTQKSLSLSPGK

Human IgG$_2$ Fc region variant (Variant 13A)
(SEQ ID NO: 50)
TKVDKTVERKSCVECPPCPAPPVAGPSVFLFPPKPKDTLMISRTPEVTCVVVDVSHEDPE

VQFNWYVDGVEVHNAKTKPREEQFNSTFRVVSVLTVVHQDWLNGKEYKCKVSNKGLPAPI

EKTISKTKGQPREPQVYTLPPSREKMTKNQVSLTCLVKGFYPSDIAVEWESNGQPENNYK

TTPPMLKSDGSFFLYSKLTVDKSRWQQGNVFSCSVMHEALHNHYTQKSLSLSPGK

Human IgG$_2$ Fc region (Variant 13B)
(SEQ ID NO: 51)
TKVDKTVERKCCVECPPCPAPPVAGPSVFLFPPKPKDTLMISRTPEVTCVVVDVSHEDPE

VQFNWYVDGVEVHNAKTKPREEQFNSTFRVVSVLTVVHQDWLNGKEYKCKVSNKGLPAPI

EKTISKTKGQPREPQVYTLPPSREEMTKNQVSLTCLVEGFYPSDIAVEWESNGQPENNYK

TTPPMLDSDGSFFLYSELTVDKSRWQQGNVFSCSVMHEALHNHYTQKSLSLSPGK

Human IgG$_2$ Fc region variant (Variant 13B)
(SEQ ID NO: 52)
TKVDKTVERKSCVECPPCPAPPVAGPSVFLFPPKPKDTLMISRTPEVTCVVVDVSHEDPE

VQFNWYVDGVEVHNAKTKPREEQENSTFRVVSVLTVVHQDWLNGKEYKCKVSNKGLPAPI

EKTISKTKGQPREPQVYTLPPSREEMTKNQVSLTCLVEGFYPSDIAVEWESNGQPENNYK

TTPPMLDSDGSFFLYSELTVDKSRWQQGNVFSCSVMHEALHNHYTQKSLSLSPGK

FZD8-Fc variant 54F28 amino acid sequence (without predicted
signal sequence)
(SEQ ID NO: 53)
ASAKELACQEITVPLCKGIGYNYTYMPNQFNHDTQDEAGLEVHQFWPLVEIQCSPDLKFF

LCSMYTPICLEDYKKPLPPCRSVCERAKAGCAPLMRQYGFAWPDRMRCDRLPEQGNPDTL

CMDYNRTDLTTEPKSSDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDWLNGKEYKCKVS

NKALPAPIEKTISKAKGQPREPQVYTLPPSRDELTKNQVSLTCLVKGFYPSDIAVEWESN

GQPENNYKTTPPVLDSDGSFFLYSKLTVDKSRWQQGNVFSCSVMHEALHNHYTQKSLSLS

PGK

FZD8-Fc variant 54F28 amino acid sequence with signal sequence
(SEQ ID NO: 54)
MEWGYLLEVTSLLAALLLLQRSPFVHAASAKELACQEITVPLCKGIGYNYTYMPNQFNHD

TQDEAGLEVHQFWPLVEIQCSPDLKFFLCSMYTPICLEDYKKPLPPCRSVCERAKAGCAP

LMRQYGFAWPDRMRCDRLPEQGNPDTLCMDYNRTDLTTEPKSSDKTHTCPPCPAPELLGG

PSVFLEPPKPKDTLMISRTPEVTCVVVDVSHEDPEVKFNWYVDGVEVHNAKTKPREEQYN

```
STYRVVSVLTVLHQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFFLYSKLTVDKSRW

QQGNVESCSVMHEALHNHYTQKSLSLSPGK
```

FZD8-Fc variant (13B variant) amino acid sequence with signal
sequence
(SEQ ID NO: 55)
```
MEWGYLLEVTSLLAALLLLQRSPIVHAASAKELACQEITVPLCKGIGYNYTYMPNQFNHD

TQDEAGLEVHQFWPLVEIQCSPDLKFFLCSMYTPICLEDYKKPLPPCRSVCERAKAGCAP

LMRQYGFAWPDRMRCDRLPEQGNPDTLCMDYNRTDLTTTKVDKTVERKSCVECPPCPAPP

VAGPSVFLEPPKPKDTLMISRTPEVTCVVVDVSHEDPEVQFNWYVDGVEVHNAKTKPREE

QFNSTERVVSVLTVVHQDWLNGKEYKCKVSNKGLPAPIEKTISKTKGQPREPQVYTLPPS

REEMTKNQVSLTCLVEGFYPSDIAVEWESNGQPENNYKTTPPMLDSDGSFFLYSELTVDK

SRWQQGNVFSCSVMHEALHNHYTQKSLSLSPGK
```

FZD8-Fc variant (13B variant) amino acid sequence without signal
sequence
(SEQ ID NO: 56)
```
ASAKELACQEITVPLCKGIGYNYTYMPNQFNHDTQDEAGLEVHQFWPLVEIQCSPDLKFF

LCSMYTPICLEDYKKPLPPCRSVCERAKAGCAPLMRQYGFAWPDRMRCDRLPEQGNPDTL

CMDYNRTDLTTTKVDKTVERKSCVECPPCPAPPVAGPSVFLPPPKPKDTLMISRTPEVTC

VVVDVSHEDPEVQFNWYVDGVEVHNAKTKPREEQFNSTERVVSVLTVVHQDWLNGKEYKC

KVSNKGLPAPIEKTISKTKGQPREPQVYTLPPSREEMTKNQVSLTCLVEGFYPSDIAVEW

ESNGQPENNYKTTPPMLDSDGSFFLYSELTVDKSRWQQGNVFSCSVMHEALHNHYTQKSL

SLSPGK
```

Human WNT1 C-terminal cysteine rich domain (aa 288-370)
(SEQ ID NO: 57)
```
DLVYFEKSPNFCTYSGRLGTAGTAGRACNSSSPALDGCELLCCGRGHRTRTQRVTERCNC

TFHWCCHVSCRNCTHTRVLHECL
```

Human WNT2 C-terminal cysteine rich domain (aa 267-360)
(SEQ ID NO: 58)
```
DLVYFENSPDYCIRDREAGSLGTAGRVCNLTSRGMDSCEVMCCGRGYDTSHVTRMTKCGC

KFHWCCAVRCQDCLEALDVHTCKAPKNADWTTAT
```

Human Wnt2b C-terminal cysteine rich domain (aa 298-391)
(SEQ ID NO: 59)
```
DLVYFDNSPDYCVLDKAAGSLGTAGRVCSKTSKGTDGCEIMCCGRGYDTTRVTRVTQCEC

KFHWCCAVRCKECRNTVDVHTCKAPKKAEWLDQT
```

Human WNT3 C-terminal cysteine rich domain (aa 273-355)
(SEQ ID NO: 60)
```
DLVYYENSPNFCEPNPETGSFGTRDRTCNVTSHGIDGCDLLCCGRGHNTRTEKRKEKCHC

IFHWCCYVSCQECIRIYDVHTCK
```

Human WNT3a C-terminal cysteine rich domain (aa 270-352)
(SEQ ID NO: 61)
```
DLVYYEASPNECEPNPETGSEGTRDRTCNVSSHGIDGCDLLCCGRGHNARAERRREKCRC

VFHWCCYVSCQECTRVYDVHTCK
```

Human WNT7a C-terminal cysteine rich domain (aa 267-359)
(SEQ ID NO: 62)
```
DLVYIEKSPNYCEEDPVTGSVGTQGRACNKTAPQASGCDLMCCGRGYNTHQYARVWQCNC

KFHWCCYVKCNTCSERTEMYTCK
```

-continued

Human WNT7b C-terminal cysteine rich domain (aa 267-349)
(SEQ ID NO: 63)
DLVYIEKSPNYCEEDAATGSVGTQGRLCNRTSPGADGCDTMCCGRGYNTHQYTKVWQCNC

KFHWCCFVKCNTCSERTEVETCK

Human WNT8a C-terminal cysteine rich domain (aa 248-355)
(SEQ ID NO: 64)
ELIFLEESPDYCTCNSSLGIYGTEGRECLQNSHNTSRWERRSCGRLCTECGLQVEERKTE

VISSCNCKFQWCCTVKCDQCRHVVSKYYCARSPGSAQSLGRVWFGVYI

Human WNT8b C-terminal cysteine rich domain (aa 245-351)
(SEQ ID NO: 65)
ELVHLEDSPDYCLENKTLGLLGTEGRECLRRGRALGRWELRSCRRLCGDCGLAVEERRAE

TVSSCNCKFHWCCAVRCEQCRRRVTKYFCSRAERPRGGAAHKPGRKP

Human WNT10a C-terminal cysteine rich domain (aa 335-417)
(SEQ ID NO: 66)
DLVYFEKSPDFCEREPRLDSAGTVGRLCNKSSAGSDGCGSMCCGRGHNILRQTRSERCHC

RFHWCCFVVCEECRITEWVSVCK

Human WNT10b C-terminal cysteine rich domain (aa 307-389)
(SEQ ID NO: 67)
ELVYFEKSPDFCERDPTMGSPGTRGRACNKTSRLLDGCGSLCCGRGHNVLRQTRVERCHC

RFHWCCYVLCDECKVTEWVNVCK

Linker
(SEQ ID NO: 68)
ESGGGGVT

Linker
(SEQ ID NO: 69)
LESGGGGVT

Linker
(SEQ ID NO: 70)
GRAQVT

Linker
(SEQ ID NO: 71)
WRAQVT

Linker
(SEQ ID NO: 72)
ARGRAQVT

FLAG peptide
(SEQ ID NO: 73)
DYKDDDDK

Human IgG1 Heavy chain constant region
(SEQ ID NO: 74)
ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFFLYSKLTVDKSRW

QQGNVFSCSVMHEALHNHYTQKSLSLSPGK

Human IgG2 Heavy chain constant region
(SEQ ID NO: 75)
ASTKGPSVFPLAPCSRSTSESTAALGCLVKDYFPEPVTVSWNSGALTSGVHTFPAVLQSS

GLYSLSSVVTVPSSNFGTQTYTCNVDHKPSNTKVDKTVERKCCVECPPCPAPPVAGPSVF

LFPPKPKDTLMISRTPEVTCVVVDVSHEDPEVQFNWYVDGVEVHNAKTKPREEQFNSTFR

VVSVLTVVHQDWLNGKEYKCKVSNKGLPAPIEKTISKTKGQPREPQVYTLPPSREEMTKN

QVSLTCLVKGFYPSDIAVEWESNGQPENNYKTTPPMLDSDGSFFLYSKLTVDKSRWQQGN

VFSCSVMHEALHNHYTQKSLSLSPGK

Human IgG3 Heavy chain constant region
(SEQ ID NO: 76)
ASTKGPSVFPLAPCSRSTSGGTAALGCLVKDYFPEPVTVSWNSGALTSGVHTFPAVLQSS

GLYSLSSVVTVPSSSLGTQTYTCNVNHKPSNTKVDKRVELKTPLGDTTHTCPRCPEPKSC

DTPPPCPRCPEPKSCDTPPPCPRCPEPKSCDTPPPCPRCPAPELLGGPSVFLFPPKPKDT

LMISRTPEVTCVVVDVSHEDPEVQFKWYVDGVEVHNAKTKPREEQYNSTERVVSVLTVLH

QDWLNGKEYKCKVSNKALPAPIEKTISKTKGQPREPQVYTLPPSREEMTKNQVSLTCLVK

GFYPSDIAVEWESSGQPENNYNTTPPMLDSDGSFFLYSKLTVDKSRWQQGNIFSCSVMHE

ALHNRFTQKSLSLSPGK

Human IgG4 Heavy chain constant region
(SEQ ID NO: 77)
ASTKGPSVFPLAPCSRSTSESTAALGCLVKDYFPEPVTVSWNSGALTSGVHTFPAVLQSS

GLYSLSSVVTVPSSSLGTKTYTCNVDHKPSNTKVDKRVESKYGPPCPSCPAPEFLGGPSV

FLFPPKPKDTLMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYTLPPSQEEMTK

NQVSLTCLVKGFYPSDIAVEWESNGQPENNYKTTPPVLDSDGSFFLYSRLTVDKSRWQEG

NVFSCSVMHEALHNHYTQKSLSLSLGK

MET antibody Heavy chain CDR1
(SEQ ID NO: 78)
GYTFTSYWLH

MET antibody Heavy chain CDR2
(SEQ ID NO: 79)
GMIDPSNSDTRFNPNFKD

MET Heavy chain CDR3
(SEQ ID NO: 80)
XYGSYVSPLDY wherein X is not R

MET Heavy chain CDR3
(SEQ ID NO: 81)
TYGSYVSPLDY

MET Heavy chain CDR3
(SEQ ID NO: 82)
SYGSYVSPLDY

MET Heavy chain CDR3
(SEQ ID NO: 83)
ATYGSYVSPLDY

MET Light chain CDR1
(SEQ ID NO: 84)
KSSQSLLYTSSQKNYLA

MET Light chain CDR2
(SEQ ID NO: 85)
WASTRES

MET Light chain CDR3
(SEQ ID NO: 86)
QQYYAYPWT

FZD8-Fc variant (13A variant) amino acid sequence without signal sequence
(SEQ ID NO: 87)
ASAKELACQEITVPLCKGIGYNYTYMPNQFNHDTQDEAGLEVHQFWPLVEIQCSPDLKFF

LCSMYTPICLEDYKKPLPPCRSVCERAKAGCAPLMRQYGFAWPDRMRCDRLPEQGNPDTL

CMDYNRTDLTTTKVDKTVERKSCVECPPCPAPPVAGPSVFLFPPKPKDTLMISRTPEVTC

VVVDVSHEDPEVQFNWYVDGVEVHNAKTKPREEQFNSTERVVSVLTVVHQDWLNGKEYKC

KVSNKGLPAPIEKTISKTKGQPREPQVYTLPPSREKMTKNQVSLTCLVKGFYPSDIAVEW

ESNGQPENNYKTTPPMLKSDGSFFLYSKLTVDKSRWQQGNVFSCSVMHEALHNHYTQKSL

SLSPGK

73R009 (13B variant) Heavy chain amino acid sequence without
predicted signal sequence
(SEQ ID NO: 88)
QVQLQESGPGLVKPSETLSLTCTVTGTTITASYAWSWIRQPPGKGLEWMGYISYSGGTDY

NPSLKSRITISRDTEKNQFSLKLSSVTAADTATYYCARKGAYWGQGTLVTVSSASTKGPS

VFPLAPCSRSTSESTAALGCLVKDYFPEPVTVSWNSGALTSGVHTFPAVLQSSGLYSLSS

VVTVPSSNFGTQTYTCNVDHKPSNTKVDKTVERKCCVECPPCPAPPVAGPSVFLFPPKPK

DTLMISRTPEVTCVVVDVSHEDPEVQFNWYVDGVEVHNAKTKPREEQFNSTERVVSVLTV

VHQDWLNGKEYKCKVSNKGLPAPIEKTISKTKGQPREPQVYTLPPSREEMTKNQVSLTCL

VEGFYPSDIAVEWESNGQPENNYKTTPPMLDSDGSFELYSELTVDKSRWQQGNVESCSVM

HEALHNHYTQKSLSLSPGK

FZD8-Fc variant (13B variant) nucleotide sequence with signal
sequence
(SEQ ID NO: 89)
ATGGAGTGGGGTTATCTTTTAGAAGTGACCTCGCTGCTAGCCGCCTTGCTACTGCTGCAG

CGCTCTCCGATCGTGCACGCCGCCTCGGCCAAGGAGCTGGCATGCCAAGAGATCACCGTG

CCGCTATGCAAGGGCATCGGCTACAACTACACCTACATGCCCAATCAATTCAACCACGAC

ACGCAAGACGAGGCGGGCCTGGAGGTGCACCAGTTCTGGCCGCTGGTGGAGATCCAGTGC

TCGCCCGATCTCAAGTTCTTCCTGTGCAGCATGTACACGCCCATCTGCCTAGAGGACTAC

AAGAAGCCGCTGCCGCCCTGCCGCTCGGTGTGCGAGCGCGCCAAGGCCGGCTGCGCGCCG

CTCATGCGCCAGTACGGCTTCGCCTGGCCCGACCGCATGCGCTGCGACCGGCTGCCCGAG

CAAGGCAACCCTGACACGCTGTGCATGGACTACAACCGCACCGACCTAACCACCACCAAA

GTTGACAAGACTGTTGAGCGAAAGAGCTGCGTTGAGTGCCCTCCATGTCCTGCACCTCCT

GTGGCTGGCCCTTCTGTGTTCCTGTTCCCTCCAAAACCTAAAGACACTCTAATGATCTCT

CGGACTCCTGAGGTGACTTGCGTGGTTGTGGACGTGTCCCACGAGGACCCTGAGGTGCAG

TTTAATTGGTACGTGGACGGAGTCGAGGTGCACAATGCAAAGACCAAGCCTCGGGAGGAA

CAGTTCAACTCCACCTTCCGGGTGGTTTCTGTGTTGACCGTTGTGCACCAAGACTGGCTG

AACGGCAAAGAATACAAGTGCAAGGTGTCCAACAAGGGCCTGCCTGCCCCTATCGAAAAG

ACCATCAGCAAGACCAAGGGCCAGCCTCGCGAGCCTCAGGTGTACACCCTGCCTCCCAGC

CGGGAAGAAATGACCAAGAACCAGGTGTCCCTGACCTGTCTGGTGGAGGGCTTCTACCCT

TCCGACATCGCCGTTGAGTGGGAGTCTAACGGACAGCCGGAGAACAACTACAAGACTACG

CCTCCAATGCTGGACTCCGACGGCTCCTTCTTCCTGTACTCCGAACTGACCGTGGACAAG

TCCCGGTGGCAGCAGGGCAACGTGTTCTCATGCTCCGTAATGCACGAAGCCTTACACAAT

CACTACACTCAAAAGTCCCTATCCTTATCTCCTGGCAAGTAG

FZD8-Fc variant (13B variant) nucleotide sequence without signal
sequence
(SEQ ID NO: 90)
CGCTCTCCGATCGTGCACGCCGCCTCGGCCAAGGAGCTGGCATGCCAAGAGATCACCGTG

CCGCTATGCAAGGGCATCGGCTACAACTACACCTACATGCCCAATCAATTCAACCACGAC

ACGCAAGACGAGGCGGGCCTGGAGGTGCACCAGTTCTGGCCGCTGGTGGAGATCCAGTGC

TCGCCCGATCTCAAGTTCTTCCTGTGCAGCATGTACACGCCCATCTGCCTAGAGGACTAC

-continued

```
AAGAAGCCGCTGCCGCCCTGCCGCTCGGTGTGCGAGCGCGCCAAGGCCGGCTGCGCGCCG

CTCATGCGCCAGTACGGCTTCGCCTGGCCCGACCGCATGCGCTGCGACCGGCTGCCCGAG

CAAGGCAACCCTGACACGCTGTGCATGGACTACAACCGCACCGACCTAACCACCACCAAA

GTTGACAAGACTGTTGAGCGAAAGAGCTGCGTTGAGTGCCCTCCATGTCCTGCACCTCCT

GTGGCTGGCCCTTCTGTGTTCCTGTTCCCTCCAAAACCTAAAGACACTCTAATGATCTCT

CGGACTCCTGAGGTGACTTGCGTGGTTGTGGACGTGTCCCACGAGGACCCTGAGGTGCAG

TTTAATTGGTACGTGGACGGAGTCGAGGTGCACAATGCAAAGACCAAGCCTCGGGAGGAA

CAGTTCAACTCCACCTTCCGGGTGGTTTCTGTGTTGACCGTTGTGCACCAAGACTGGCTG

AACGGCAAAGAATACAAGTGCAAGGTGTCCAACAAGGGCCTGCCTGCCCCTATCGAAAAG

ACCATCAGCAAGACCAAGGGCCAGCCTCGCGAGCCTCAGGTGTACACCCTGCCTCCCAGC

CGGGAAGAAATGACCAAGAACCAGGTGTCCCTGACCTGTCTGGTGGAGGGCTTCTACCCT

TCCGACATCGCCGTTGAGTGGGAGTCTAACGGACAGCCGGAGAACAACTACAAGACTACG

CCTCCAATGCTGGACTCCGACGGCTCCTTCTTCCTGTACTCCGAACTGACCGTGGACAAG

TCCCGGTGGCAGCAGGGCAACGTGTTCTCATGCTCCGTAATGCACGAAGCCTTACACAAT

CACTACACTCAAAAGTCCCTATCCTTATCTCCTGGCAAGTAG
```

Human IgG₁ Fc region
(SEQ ID NO: 91)
KSSDKTHTCPPCPAPELLGGPSVFLEPPKPKDTLMISRTPEVTCVVVDVSHEDPEVKFNW
YVDGVEVHNAKTKPREEQYNSTYRVVSVLTVLHQDWLNGKEYKCKVSNKALPAPIEKTIS
KAKGQPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPGK Human IgG₁ Fc region
(SEQ ID NO: 92)
EPKSSDKTHTCPPCPAPELLGGPSVFLEPPKPKDTLMISRTPEVTCVVVDVSHEDPEVKF
NWYVDGVEVHNAKTKPREEQYNSTYRVVSVLTVLHQDWLNGKEYKCKVSNKALPAPIEKT
ISKAKGQPREPQVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLSPGK Human MET
(SEQ ID NO: 93)
MKAPAVLAPGILVLLFTLVQRSNGECKEALAKSEMNVNMKYQLPNFTAETPIQNVILHEH
HIFLGATNYIYVLNEEDLQKVAEYKTGPVLEHPDCFPCQDCSSKANLSGGVWKDNINMAL
VVDTYYDDQLISCGSVNRGTCQRHVEPHNHTADIQSEVHCIFSPQIEEPSQCPDCVVSAL
GAKVLSSVKDRFINFFVGNTINSSYFPDHPLHSISVRRLKETKDGEMELTDQSYIDVLPE
FRDSYPIKYVHAFESNNFIYFLTVQRETLDAQTFHTRIIRFCSINSGLHSYMEMPLECIL
TEKRKKRSTKKEVFNILQAAYVSKPGAQLARQIGASLNDDILFGVFAQSKPDSAEPMDRS
AMCAFPIKYVNDFFNKIVNKNNVRCLQHFYGPNHEHCFNRTLLRNSSGCEARRDEYRTEF
TTALQRVDLFMGQFSEVLLTSISTFIKGDLTIANLGTSEGRFMQVVVSRSGPSTPHVNFL
LDSHPVSPEVIVEHTLNQNGYTLVITGKKITKIPLNGLGCRHFQSCSQCLSAPPFVQCGW
CHDKCVRSEECLSGTWTQQICLPAIYKVFPNSAPLEGGTRLTICGWDFGFRRNNKFDLKK
TRVLLGNESCTLTLSESTMNTLKCTVGPAMNKHFNMSIIISNGHGTTQYSTFSYVDPVIT
SISPKYGPMAGGTLLTLTGNYLNSGNSRHISIGGKTCTLKSVSNSILECYTPAQTISTEF
AVKLKIDLANRETSIFSYREDPIVYEIHPTKSFISGGSTITGVGKNLNSVSVPRMVINVH
EAGRNFTVACQHRSNSEIICCTTPSLQQLNLQLPLKTKAFFMLDGILSKYFDLIYVHNPV -continued

FKPFEKPVMISMGNENVLEIKGNDIDPEAVKGEVLKVGNKSCENIHLHSEAVLCTVPNDL

LKLNSELNIEWKQAISSTVLGKVIVQPDQNFTGLIAGVVSISTALLLLLGFFLWLKKRKQ

IKDLGSELVRYDARVHTPHLDRLVSARSVSPTTEMVSNESVDYRATFPEDQFPNSSQNGS

CRQVQYPLTDMSPILTSGDSDISSPLLQNTVHIDLSALNPELVQAVQHVVIGPSSLIVHF

NEVIGRGHFGCVYHGTLLDNDGKKIHCAVKSLNRITDIGEVSQFLTEGIIMKDFSHPNVL

SLLGICLRSEGSPLVVLPYMKHGDLRNFIRNETHNPTVKDLIGFGLQVAKGMKYLASKKF

VHRDLAARNCMLDEKFTVKVADFGLARDMYDKEYYSVHNKTGAKLPVKWMALESLQTQKF

TTKSDVWSEGVLLWELMTRGAPPYPDVNTEDITVYLLQGRRLLQPEYCPDPLYEVMLKCW

HPKAEMRPSFSELVSRISAIFSTFIGEHYVHVNATYVNVKCVAPYPSLLSSEDNADDEVD

TRPASFWETS

---

What is claimed is:

1. A bispecific agent comprising:
   a) a first binding site comprising an antigen-binding site of an antibody that specifically binds human MET, wherein the antigen-binding site comprises a heavy chain CDR1 comprising ASYAWS (SEQ ID NO:1), a heavy chain CDR2 comprising YISYSGGTDYNPSLKS (SEQ ID NO:2), and a heavy chain CDR3 comprising KGAY (SEQ ID NO:3); and a light chain CDR1 comprising SASSSVSSSYLY (SEQ ID NO:4), a light chain CDR2 comprising STSNLAS (SEQ ID NO:5), and a light chain CDR3 comprising HQWSSYPYT (SEQ ID NO:6); and
   b) a second binding site that specifically binds one or more components of the WNT pathway, wherein the second binding site comprises a soluble human frizzled 8 (FZD8) receptor.

2. The bispecific agent of claim 1, wherein the second binding site comprises the Fri domain of human FZD8.

3. The bispecific agent of claim 2, wherein the Fri domain of human FZD8 comprises SEQ ID NO:28, SEQ ID NO:29, or SEQ ID NO:39.

4. The bispecific agent of claim 2, wherein the Fri domain of human FZD8 is linked to a heterologous polypeptide.

5. The bispecific agent of claim 4, wherein the heterologous polypeptide comprises a human Fc region.

6. The bispecific agent of claim 1, wherein the soluble FZD8 receptor comprises SEQ ID NO:56.

7. The bispecific agent of claim 1, wherein the first binding site comprises a heavy chain variable region comprising SEQ ID NO: FZD7 and a light chain variable region comprising SEQ ID NO: FZD8.

8. The bispecific agent of claim 1, wherein the second binding site comprises a polypeptide encoded by the plasmid deposited with ATCC designated PTA-13611.

9. The bispecific agent of claim 1, wherein the first binding site comprises a heavy chain variable region encoded by the plasmid deposited with ATCC designated PTA-13609 and a light chain variable region encoded by the plasmid deposited with ATCC designated PTA-13610; and the second binding site comprises a polypeptide encoded by the plasmid deposited with ATCC designated PTA-13611.

10. The bispecific agent of claim 1, which comprises a first human IgG2constant region with amino acid substitutions, at positions corresponding to positions 249 and 288 of SEQ ID NO: 75, wherein the amino acids are replaced with glutamate or aspartate, and a second human IgG2 constant region with amino acid substitutions at positions corresponding to positions 236 and 278 of SEQ ID NO: 75, wherein the amino acids are replaced with lysine.

11. A pharmaceutical composition comprising the bispecific agent of claim 1 and a pharmaceutically acceptable carrier.

12. A cell producing the bispecific agent of claim 1.

13. A method of inhibiting growth of a lung tumor in a subject, comprising administering to the subject a therapeutically effective amount of a bispecific agent of claim 1.

14. A method of treating lung cancer in a subject, comprising administering to the subject a therapeutically effective amount of a bispecific agent of claim 1.

15. The method of claim 14, which further comprises administering at least one additional therapeutic agent.

16. An isolated antibody that specifically binds human MET, which comprise:

a heavy chain CDR1 comprising ASYAWS (SEQ ID NO. 1), a heavy chain CDR2comprising YISYSGGT-DYNPSLKS (SEQ ID NO: 2) and a heavy chain CDR3 comprising KGAY (SEQ ID NO: 3); and a light chain CDR1 comprising SASSSVSSSYLY (SEQ ID NO: 4), a light chain CDR2 comprising STSNLAS (SEQ ID NO: 5), and a light chain CDR 3 comprising HQWSSYPYT (SEQ ID NO:6).

17. The antibody of claim 16, which comprises a heavy chain variable region comprising SEQ ID NO: 7 and a light chain variable region comprising SEQ ID NO:8.

18. The antibody of claim 16, which is a monoclonal antibody, a recombinant antibody, a monovalent antibody, a chimeric antibody, a humanized antibody, a human antibody, a bispecific antibody, an IgG1 antibody, an IgG2 antibody, or an antibody fragment comprising an antigen-binding site.

19. The antibody of claim 18, which is a monoclonal antibody.

20. The antibody of claim 18, which is a humanized antibody.

21. The antibody of claim 18, which is a bispecific antibody.

* * * * *

UNITED STATES PATENT AND TRADEMARK OFFICE
CERTIFICATE OF CORRECTION

PATENT NO. : 9,168,300 B2
APPLICATION NO. : 14/212177
DATED : October 27, 2015
INVENTOR(S) : Gurney et al.

Page 1 of 1

It is certified that error appears in the above-identified patent and that said Letters Patent is hereby corrected as shown below:

Claims
In column 207, lines 6-7, (Claim 7), please replace "SEQ ID NO: FZD7" with --SEQ ID NO: 7--
In column 207, line 8, (Claim 7), please replace "SEQ ID NO: FZD8" with --SEQ ID NO: 8--
In column 207, line 19, (Claim 10), please replace "IgG2constant" with --IgG2 constant--
In column 207, line 19, (Claim 10), please replace "substitutions, at" with --substitutions at--
In column 208, lines 8-9, (Claim 16), please replace "SEQ ID NO. 1" with --SEQ ID NO: 1--
In column 208, line 9, (Claim 16), please replace "CDR2comprising" with --CDR2 comprising--

Signed and Sealed this
Fifteenth Day of March, 2016

Michelle K. Lee
*Director of the United States Patent and Trademark Office*